US011896678B2

(12) United States Patent
Goldstein et al.

(10) Patent No.: US 11,896,678 B2
(45) Date of Patent: Feb. 13, 2024

(54) COMPOSITIONS AND METHODS FOR TREATMENT OF PEROXISOME PROLIFERATOR-ACTIVATED RECEPTOR GAMMA (PPARG) ACTIVATED CANCER

(71) Applicants: THE BROAD INSTITUTE, INC., Cambridge, MA (US); DANA-FARBER CANCER INSTITUTE, INC., Boston, MA (US)

(72) Inventors: Jonathan Goldstein, Cambridge, MA (US); Matthew Meyerson, Boston, MA (US); Craig Strathdee, Cambridge, MA (US)

(73) Assignees: Dana-Farber Cancer Institute, Inc., Boston, MA (US); The Broad Institute, Inc., Cambridge, MA (US)

( * ) Notice: Subject to any disclaimer, the term of this patent is extended or adjusted under 35 U.S.C. 154(b) by 1020 days.

(21) Appl. No.: 16/498,860

(22) PCT Filed: Mar. 28, 2018

(86) PCT No.: PCT/US2018/024970
§ 371 (c)(1),
(2) Date: Sep. 27, 2019

(87) PCT Pub. No.: WO2018/183580
PCT Pub. Date: Oct. 4, 2018

(65) Prior Publication Data
US 2020/0179534 A1 Jun. 11, 2020

Related U.S. Application Data

(60) Provisional application No. 62/478,380, filed on Mar. 29, 2017.

(51) Int. Cl.
| | | |
|---|---|---|
| *A61K 45/06* | (2006.01) | |
| *G01N 33/574* | (2006.01) | |
| *A61K 48/00* | (2006.01) | |
| *A61K 38/46* | (2006.01) | |
| *C12N 5/09* | (2010.01) | |
| *C12N 9/22* | (2006.01) | |
| *C12N 15/11* | (2006.01) | |

(52) U.S. Cl.
CPC ........ *A61K 48/0025* (2013.01); *A61K 38/465* (2013.01); *A61K 45/06* (2013.01); *C12N 5/0693* (2013.01); *C12N 9/22* (2013.01); *C12N 15/11* (2013.01); *G01N 33/57492* (2013.01); *C12N 2310/20* (2017.05); *C12N 2800/80* (2013.01); *G01N 2333/70567* (2013.01)

(58) Field of Classification Search
None
See application file for complete search history.

(56) References Cited

U.S. PATENT DOCUMENTS

| 2006/0159669 A1 | 7/2006 | Nagy et al. |
| 2014/0170753 A1 | 6/2014 | Zhang |

FOREIGN PATENT DOCUMENTS

| EP | 2081599 A2 | 7/2009 | |
| WO | 2005077126 A2 | 8/2005 | |
| WO | WO-2005077126 A2 * | 8/2005 | ............. A61K 31/00 |
| WO | 2007144679 A2 | 12/2007 | |

OTHER PUBLICATIONS

Kawahara et al., Peroxisome Proliferator-Activated Receptor γ (PPARγ)-Independent Specific Cytotoxicity against Immature Adipocytes Induced by PPARγ Antagonist T0070907. Biol. Pharm. Bull. (2013), 36(9): 1428-1434 (Year: 2013).*
Guo Shu Master's Thesis, Investigation of Transcription Factors Regulating Urothelial Differentiation and Signaling Pathways involved in Urothelial Cancer Cells, Aug. 2015 (Year: 2015).*
The Cancer Genome Atlas Research Network, Comprehensive molecular characterization of urothelial bladder carcinoma. Nature (2014), 507: 315-332 (Year: 2014).*
Nakajima et al., Inhibition of peroxisome proliferator-activated receptor g activity suppresses pancreatic cancer cell motility. Cancer Sci (2008), 99: 1892-1900 (Year: 2008).*
Zheng et al., Applications of bacillus Calmette-Guerin and recombinant bacillus Calmette-Guerin in vaccine development and tumor immunotherapy. Expert Rev Vaccines (2015), 14(9): 1255-1275 (Year: 2015).*
Ward et al., Multiplex PCR and Next Generation Sequencing for the Non-Invasive Detection of Bladder Cancer. PLOS One. (2016), DOI:10.1371/journal.pone.0149756, pp. 1-11 and Supplemental material (Year: 2016).*
Lee et al., Clinical experience of MRI in two dogs with muscle-invasive transitional cell carcinoma of the urinary bladder. J. Vet. Med . Sci. (2016), 78: 1351-1354 (Year: 2016).*
Chaffer et al., PPARγ-independent induction of growth arrest and apoptosis in prostate and bladder carcinoma. BMC Cancer (2006) , 6:53 (Year: 2006).*
Jonathan T. Goldstein et al: "Genomic Activation of PPARG Reveals a Candidate Therapeutic Axis in Bladder Cancer", Cancer Research, vol. 77, No. 24, Sep. 18, 2017 (Sep. 18, 2017), pp. 6987-6998, XP055552822, US ISSN: 0008-5472, DOI: 10.1158/0008-5472.CAN-17-1701 the whole document.
Extended European Search Report dated Nov. 20, 2020 for related European Patent Application No. 18778213.1 corresponding to International Application No. PCT/US2018/024970.
International Search Report dated Sep. 5, 2018 for related Application No. PCT/US18/24970.

(Continued)

*Primary Examiner* — Samuel C Woolwine
*Assistant Examiner* — Catherine Konopka
(74) *Attorney, Agent, or Firm* — Withers Bergman LLP; Richard B. Emmons; Christopher R. Cowles

(57) ABSTRACT

The present disclosure provides compositions and methods for the treatment of PPARG activated cancer. For example, the present disclosure provides PPARG signaling modulators for the treatment of bladder cancer. In particular, therapeutic and/or prophylactic compositions and uses of PPARG inverse-agonists are described.

15 Claims, 51 Drawing Sheets

Specification includes a Sequence Listing.

(56) References Cited

OTHER PUBLICATIONS

Weinstein et al. "Comprehensive molecular characterization of urothelial bladder carcinoma" Nature. Mar. 20, 2014, vol. 507, No. 7492, pp. 315-322.
Goldstein et al. "Genomic activation of PPARG reveals a candidate therapeutic axis in bladder cancer" Supplementary data [online] Jan. 1, 2017 [Retrieved on Jun. 7, 2018].
International Preliminary Report on Patentability dated Oct. 1, 2019 for related Application No. PCT/US18/24970.
1 Examination Report in corresponding EP application No. 18778213.1 dated Dec. 5, 2022.

* cited by examiner

| Cell Line | Pathway Alteration | Proliferation (% of DMSO control) | | | |
|---|---|---|---|---|---|
| | | GW9662 | SR2595 | T0070907 | SR10221 |
| HT-1197 | RXRA p.S427F | 109 | 81 | 56 | 71 |
| 5637 | PPARG amplified | 93.0 | 116.9 | 51.4 | 72.8 |
| UM-UC-9 | PPARG amplified | 108.4 | 97.2 | 19.3 | 19.8 |
| RT112/84 | PPARG signature | 98.2 | 101.3 | 69.1 | 80.3 |
| UM-UC-1 | PPARG signature | 96.4 | 84.4 | 46.9 | 62.0 |
| Cal29 | PPARG signature | 96.8 | 86.2 | 55.4 | 74.4 |
| SW1710 | Not altered | 98.6 | 90.8 | 95.7 | 80.9 |
| KU19.19 | Not altered | 85.3 | 90.7 | 94.6 | 90.7 |
| UM-UC-3 | Not altered | 92.4 | 101.8 | 90.8 | 95.8 |

FIG. 12

500nM Drug
T0070907 = 56% growth inhibition at 1/2 confluency
TSR10221 = 50% growth inhibition at 1/2 confluency

COMPOSITIONS AND METHODS FOR TREATMENT OF PEROXISOME PROLIFERATOR-ACTIVATED RECEPTOR GAMMA (PPARG) ACTIVATED CANCER

CROSS-REFERENCE TO RELATED APPLICATION

This application is a national stage application, filed under 35 U.S.C. § 371, of International Application No. PCT/US18/24970, filed Mar. 28, 2018, which claims the benefit of priority of U.S. Provisional Application No. 62/478,380, filed Mar. 29, 2017, the entire contents of which are hereby incorporated by reference.

STATEMENT REGARDING FEDERALLY SPONSORED RESEARCH

This invention was made with government support under Grant No. 5R35CA197568, awarded by the National Institutes of Health. The government has certain rights in the invention.

FIELD OF THE DISCLOSURE

The present disclosure provides compositions and methods for the treatment of Peroxisome proliferator-activated receptor gamma (PPARG) activated cancer. More particularly, the present disclosure provides inverse-agonists of PPARG activated cancer for the treatment of breast cancer, esophageal cancer, pancreatic cancer, colorectal cancer, hepatocellular cancer, and bladder cancer.

SEQUENCE LISTING

The instant application contains a Sequence Listing which has been filed electronically in ASCII format and is hereby incorporated by reference in its entirety. Said ASCII copy, created on Nov. 22, 2019, is named "52199_502N01US_SeqListing.txt" and is 194 kB in size.

BACKGROUND OF THE DISCLOSURE

It is estimated that approximately 7.5 million people worldwide die from cancer every year. Peroxisome proliferator-activated receptor gamma (PPARG) activated cancers (e.g., breast cancer, esophageal cancer, pancreatic cancer, colorectal cancer, hepatocellular cancer, bladder cancer, and the like) represent a significant class of cancers. For example, bladder cancer is the fifth most commonly diagnosed cancer type in the United States. About half of all bladder cancer patients are diagnosed with non-invasive/superficial urothelial carcinoma of the bladder and respond well to existing chemotherapy regimens, with a 5-year survival rate of 96%. Patients diagnosed with invasive disease have a poorer prognosis, with a 5-year survival rate of 70% or less, depending upon extent of invasion beyond the bladder. Currently, there are no FDA-approved targeted therapeutics available to these patients. Accordingly, there is an urgent need for compositions and methods for treating PPARG activated cancers such as bladder cancer.

SUMMARY OF THE DISCLOSURE

The present disclosure relates, at least in part, to the discovery of Peroxisome proliferator-activated receptor gamma (PPARG) signaling as a therapeutic target for the treatment of various PPARG activated cancers such as, for example, breast cancer, esophageal cancer, pancreatic cancer, colorectal cancer, hepatocellular cancer, and bladder cancer. As described herein, the present disclosure provides PPARG signaling modulators (e.g., inverse-agonists) that are able to down regulate PPARG signaling in PPARG activated cancers, thereby decreasing cellular proliferation associated with PPARG activated cancers (e.g., breast cancer, esophageal cancer, pancreatic cancer, colorectal cancer, hepatocellular cancer, bladder cancer, and the like). It is also contemplated within the scope of the disclosure that molecular genetic methodologies (e.g., CRISPR/Cas, RNAi, and the like) that allow editing of gene sequences and mutations that provoke PPARG activated cancers can also be used as therapeutic modalities to down regulate PPARG signaling in PPARG activated cancers, thereby blocking the increased cellular proliferation associated with PPARG activated cancers. In particular, the present disclosure provides inverse-agonists that are able to reverse up-regulation of PPARG signaling in PPARG activated cancers, thereby providing a therapeutic modality capable of treating PPARG activated cancers such as, for example, bladder cancer.

In an aspect, the present disclosure provides a method of treating a subject having a peroxisome proliferator-activated receptor gamma (PPARG) activated cancer that includes a step of administering a therapeutically effective amount of a PPARG signaling modulator to the subject.

In an embodiment, the PPARG signaling modulator is an antagonist or an inverse-agonist of PPARG signaling. In an embodiment, the PPARG signaling modulator is an inverse-agonist of PPARG signaling. In an embodiment, the inverse-agonist is selected from the group consisting of T0070907, T0070907 analogs, SR10221, SR10221 analogs, and combinations thereof.

In an embodiment, the PPARG activated cancer is associated with a mutation in PPARG and/or retinoid X receptor alpha (RXRA). In an embodiment, the mutation in PPARG is T447M, PPARG focal gene amplification, or a PPARG missense mutation. In an embodiment, the mutation in RXRA is S427F/Y.

In an embodiment, the PPARG activated cancer is associated with an up-regulated peroxisome proliferator-activated receptor (PPAR) signaling pathway. In an embodiment, the up-regulated PPAR signaling pathway is associated with increased expression of one or more genes selected from the group consisting of Uroplakin 1A (UPK1A), Uroplakin 1B (UPK1B), Uroplakin (UPK2), Keratin 20 (KRT20), GATA Binding Protein 3 (GATA3), Nuclear Receptor Corepressor 1 (NCOR1), Nuclear Receptor Corepressor 2 (NCOR2), Fatty Acid Binding Protein 4 (FABP4), Forkhead Box A1 (FOXA1), CD36 Molecule (CD36), Acyl-CoA Oxidase 1 (ACOX1), 3-Hydroxy-3-Methylglutaryl-CoA Synthase 2 (HMGCS2), Acyl-CoA Synthetase Long-Chain Family Member 5 (ACSL5), Arachidonate 5-Lipoxygenase (ALOX5), and Acyl-CoA Synthetase Long-Chain Family Member 1 (ACSL1).

In an embodiment, the PPARG activated cancer is breast cancer, esophageal cancer, pancreatic cancer, colorectal cancer, hepatocellular cancer, or bladder cancer. In an embodiment, the bladder cancer is luminal or non-luminal bladder cancer, basal bladder cancer, muscle-invasive bladder cancer, or non-muscle-invasive bladder cancer.

In an embodiment, the step of administering the inverse-agonist to the subject decreases proliferation of one or more PPARG activated cancer cells within the subject. The subject may be a human or non-human mammal (e.g., a bovine, a canine, an equine, a feline, an ovine, a primate, and the like).

In an embodiment, the PPARG signaling modulator is a CRISPR-Cas system, optionally a CRISPR-Cas system that replaces a T447M mutation in PPARG, a focal gene amplification of PPARG, a CRISPR-Cas system that replaces a S427F/Y mutation in RXRA, or any combination thereof. In an embodiment, the PPARG signaling modulator is an inhibitory nucleic acid, optionally an antisense oligonucleotide or RNAi agent.

In an aspect, the present disclosure provides a method of treating a subject diagnosed with a peroxisome proliferator-activated receptor gamma (PPARG) activated cancer that includes the steps of: performing an assay to determine the identity of an amino acid at position 447 of PPARG and/or position 427 of retinoid X receptor alpha (RXRA), wherein a PPARG reference amino acid at position 447 is threonine (T) and a RXRA reference amino acid at position 427 is serine (S); detecting the presence of a PPARG amino acid variation relative to the PPARG reference amino acid, wherein the PPARG amino acid variation is methionine (M) and/or a RXRA amino acid variation relative to the RXRA reference amino acid, where the RXRA amino acid variation is phenylalanine (F) or tyrosine (Y); and administering a therapeutically effective amount of a PPARG signaling modulator to the subject having a PPARG T447M variation and/or a RXRA S427F/Y variation.

In an embodiment, the PPARG signaling modulator is an antagonist or an inverse-agonist of PPARG signaling. In an embodiment, the PPARG signaling modulator is an inverse-agonist of PPARG signaling. In an embodiment, the inverse-agonist is selected from the group consisting of T0070907, T0070907 analogs, SR10221, SR10221 analogs, and combinations thereof.

In an embodiment, the PPARG activated cancer is associated with an up-regulated peroxisome proliferator-activated receptor (PPAR) signaling pathway. In an embodiment, the up-regulated PPAR signaling pathway is associated with increased expression of one or more genes selected from the group consisting of Uroplakin 1A (UPK1A), Uroplakin 1B (UPK1B), Uroplakin (UPK2), Keratin 20 (KRT20), GATA Binding Protein 3 (GATA3), Nuclear Receptor Corepressor 1 (NCOR1), Nuclear Receptor Corepressor 2 (NCOR2), Fatty Acid Binding Protein 4 (FABP4), Forkhead Box A1 (FOXA1), CD36 Molecule (CD36), Acyl-CoA Oxidase 1 (ACOX1), 3-Hydroxy-3-Methylglutaryl-CoA Synthase 2 (HMGCS2), Acyl-CoA Synthetase Long-Chain Family Member 5 (ACSL5), Arachidonate 5-Lipoxygenase (ALOX5), and Acyl-CoA Synthetase Long-Chain Family Member 1 (ACSL1).

In an embodiment, the PPARG activated cancer is breast cancer, esophageal cancer, pancreatic cancer, colorectal cancer, hepatocellular cancer, or bladder cancer. In an embodiment, the bladder cancer is luminal and non-luminal bladder cancer, basal bladder cancer, muscle-invasive bladder cancer, or non-muscle-invasive bladder cancer.

In an embodiment, the step of administering the inverse-agonist to the subject decreases proliferation of one or more PPARG activated cancer cells within the subject. In an embodiment, the subject is a human or non-human mammal (e.g., a bovine, a canine, an equine, a feline, an ovine, a primate, and the like).

In an embodiment, the method can further include a step of administering one or more chemotherapeutic agents. In an embodiment, the one or more chemotherapeutic agents are selected from the group consisting of an alkylating agent, an anti-metabolite, an anti-microtubule agent, and a topoisomerase inhibitor.

In an embodiment, the PPARG signaling modulator is a CRISPR-Cas system, optionally a CRISPR-Cas system that replaces a T447M mutation in PPARG, a focal gene amplification of PPARG, a CRISPR-Cas system that replaces a S427F/Y mutation in RXRA, or any combination thereof.

In an embodiment, the PPARG signaling modulator is an inhibitory nucleic acid, optionally an antisense oligonucleotide or RNAi agent.

In an aspect, the present disclosure provides a method of diagnosing a human subject as having a peroxisome proliferator-activated receptor gamma (PPARG) activated cancer amenable to being treated with a modulator of PPAR signaling that includes the steps of: performing an assay to determine the identity of an amino acid at position 447 of PPARG and/or position 427 of retinoid X receptor alpha (RXRA), wherein a PPARG reference amino acid at position 447 is serine (S) and a RXRA reference amino acid at position 427 is threonine (T); detecting the presence of a PPARG amino acid variation relative to the PPARG reference amino acid, wherein the PPARG amino acid variation is methionine (M) and/or a RXRA amino acid variation relative to the RXRA reference amino acid, wherein the RXRA amino acid variation is phenylalanine (F) or tyrosine (Y); and determining that the human subject has a PPARG activated cancer amenable to being treated with a modulator of PPAR signaling.

In an embodiment, the PPARG signaling modulator is an antagonist or an inverse-agonist of PPARG signaling. In an embodiment, the inverse-agonist is T0070907 or SR10221.

In an embodiment, the PPARG activated cancer is breast cancer, esophageal cancer, pancreatic cancer, colorectal cancer, hepatocellular cancer, or bladder cancer. In an embodiment, the bladder cancer is luminal and non-luminal bladder cancer, basal bladder cancer, muscle-invasive bladder cancer, or non-muscle-invasive bladder cancer.

In an embodiment, the assay is selected from the group consisting of dynamic allele-specific hybridization, molecular beacons, SNP microarrays, PCR, quantitative PCR, Taqman, SNPlex, and a metabolite assay.

In an aspect, the present disclosure provides a cell line, comprising a cancer cell having a recombinant Fatty Acid Binding Protein 4 (FABP4) gene with a reporter gene inserted into the 3' untranslated region (UTR).

In an embodiment, the reporter gene is selected from the group consisting of green fluorescent protein (GFP), red fluorescent protein (RFP), yellow fluorescent protein (YFP), and luciferase. In an embodiment, the luciferase is selected from the group consisting of *Renilla* luciferase, firefly luciferase, and NanoLuc™ In an embodiment, the cancer cell is a PPARG activated cancer cell. In an embodiment, the PPARG activated cancer cell is a breast cancer cell or a bladder cancer cell. In an embodiment, the bladder cancer cell is selected from the group consisting of a RT112/84 cell, a UM-UC-9 cell, a RT112 cell, a 5637 cell, a HT-1197 cell, a RT4 cell, a KMBC2 cell, a CAL29 cell, a TCCSUP cell, a SW780 cell, and a UM-UC-1 cell. In an embodiment, the cell line has a wide dynamic range.

In an aspect, the present disclosure provides a method of identifying PPAR signaling modulators that includes the steps of: contacting the cell line of claim 36 with an agent; and identifying the agent as a PPAR signaling modulator when the basal activity of the FABP4 reporter gene is decreased.

In an embodiment, the PPAR signaling modulator is an antagonist or an inverse-agonist.

In an aspect, the present disclosure provides a method of altering expression of at least one gene product in a peroxisome proliferator-activated receptor gamma (PPARG) activated cancer cell that includes the steps of: introducing into a PPARG activated cancer cell containing and expressing a DNA molecule having a target sequence and encoding the at least one gene product in an engineered, non-naturally occurring Clustered Regularly Interspaced Short Palindromic Repeats (CRISPR)-CRISPR associated (Cas) system having one or more vectors including a) a first regulatory element operable in a eukaryotic cell operably linked to at least one nucleotide sequence encoding a CRISPR-Cas system guide RNA that hybridizes with the target sequence, and b) a second regulatory element operable in a eukaryotic cell operably linked to a nucleotide sequence encoding a Type-II Cas9 protein, where components (a) and (b) are located on the same or different vectors of the system, wherein the guide RNA is comprised of a chimeric RNA and includes a guide sequence and a trans-activating cr (tracr) sequence, whereby the guide RNA targets the target sequence and the Cas9 protein cleaves the DNA molecule, whereby expression of the at least one gene product is altered; and, wherein the Cas9 protein and the guide RNA do not naturally occur together.

In an embodiment, the expression of two or more gene products is altered. In an embodiment, the two or more gene products comprise a PPARG T447M variant and a RXRA S427F/Y variant.

In an embodiment, the CRISPR-Cas system further comprises one or more nuclear localization signal(s) (NLSs).

In an embodiment, the Cas9 protein is codon optimized for expression in the PPARG activated cancer cell.

In an embodiment, the expression of the one or more gene products is decreased.

In an embodiment, the one or more vectors are viral vectors.

In an embodiment, the PPARG activated cancer cell is a cell in vitro.

In an aspect, the present disclosure provides a method of treating a subject having a peroxisome proliferator-activated receptor gamma (PPARG) activated cancer, the method involving administering a therapeutically effective amount of a PPARG signaling modulator and a therapeutic agent to the subject.

In an embodiment, the therapeutic agent is Atezolizumab, Avelumab, a *Bacillus* Calmette-Guerin (BCG) therapy (e.g., a *Bacillus* of Calmette and Guérin (BCG) strain of *Mycobacterium bovis* live, attenuated culture preparation, e.g., TheraCys® and/or TICE® BCG), Cisplatin, Doxorubicin Hydrochloride, Durvalumab, Nivolumab, Pembrolizumab, Platinol®, Platinol®-AQ, Thiotepa, an anti-PD-1 antibody, and/or an anti-PD-L1 antibody, and/or a combination thereof.

Definitions

Unless defined otherwise, all technical and scientific terms used herein have the meaning commonly understood by a person skilled in the art to which this disclosure belongs. The following references provide one of skill with a general definition of many of the terms used in this disclosure: The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term about.

An "agent" refers to any small compound, antibody, nucleic acid molecule, or peptide or fragment thereof.

An "agonist" as used herein is a molecule that initiates or enhances the biological function of a protein. The agonist can thereby bind to a target protein (e.g. a nuclear receptor) to elicit its functions. The agonist can enhance the biological function of the protein directly or indirectly. Agonists that increase expression of certain genes are envisioned within the scope of particular embodiments of the disclosure. Suitable agonists will be evident to those of skill in the art. For example, receptors may be activated by either endogenous (e.g., neurotransmitters, signaling peptides, hormones, and the like) or exogenous (e.g., synthetic peptides, small molecules, and the like) agonists, thereby resulting in a biological response or function. For the present disclosure it is not necessary that the agonist enhances the function of the target protein directly. Rather, agonists are also envisioned which stabilize or enhance the function of one or more proteins upstream in a pathway that eventually leads to activation of targeted protein. Alternatively, the agonist can inhibit the function of a negative transcriptional regulator of the target protein, wherein the transcriptional regulator acts upstream in a pathway that eventually represses transcription of the target protein.

An "antagonist" may refer to a molecule that interferes with the activity or binding of another molecule, for example, by competing for the one or more binding sites of an agonist, but does not induce an active response.

An "inverse-agonist" is an agent that binds to the same molecule as an agonist for that molecule (e.g., a nuclear receptor) and inhibits the constitutive activity of the molecule. Inverse-agonists exert the opposite pharmacological effect of a receptor agonist, not merely an absence of the agonist effect, as is seen with antagonist.

By "alkylating agent" is meant a cytotoxic agent that transfers an alkyl group to a nucleophilic group on a molecule. Examples of alkylating agents include, for example, nitrogen mustards (e.g., mechlorethamine, chlorambucil, cyclophosphamide (Cytoxan®), ifosfamide, and melphalan), alkyl sulfonates (e.g., busulfan), triazines (e.g., dacarbazine (DTIC), temozolomide (Temodar®)), Nitrosoureas (including streptozocin, carmustine (BCNU), and lomustine), and ethylenimines (e.g., thiotepa and altretamine). In addition, platinum drugs (e.g., cisplatin, carboplatin, and oxalaplatin) are often considered alkylating agents because they kill cancer cells in a similar way. Exemplary alkylating agents include, but are not limited to cisplatin, temozolomide, mechlorethamine, cyclophosphamide, chlorambucil, melphalan, ifosfamide, thiotepa, hexamethylmelamine, busulfan, altretamine, procarbazine, dacarbazine carmustine, lomustine, streptozocin, carboplatin, and oxaliplatin.

By "ameliorate" is meant decrease, suppress, attenuate, diminish, arrest, or stabilize the development or progression of a disease.

By "analog" is meant a molecule that is not identical, but has analogous functional or structural features.

By "bladder cancer" is meant a disease or disorder of the bladder characterized by excess proliferation or reduced apoptosis within the urothelium of the urinary bladder. Illustrative bladder cancers may include, but are not limited to, luminal and non-luminal bladder cancer, basal bladder cancer, muscle-invasive bladder cancer, and non-muscle-invasive bladder cancer. Bladder cancer may be further characterized as one of the following subtypes: basal squamous, neuronal, luminal-papillary, luminal-infiltrated, and/or luminal.

By "biologic sample" is meant any tissue, cell, fluid, or other material derived from an organism or collected from the environment.

By "chemotherapeutic agent" is meant one or more chemical agents used in the treatment or control of proliferative diseases, including cancer. Chemotherapeutic agents include cytotoxic and cytostatic agents.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

Any compositions or methods provided herein can be combined with one or more of any of the other compositions and methods provided herein.

As used herein, a "cytotoxic agent" refers to any agent capable of destroying cells, preferably dividing cells such as cancer cells.

By "effective amount" is meant the amount of an agent required to ameliorate the symptoms of a disease relative to an untreated patient. The effective amount of active agent(s) used to practice the present disclosure for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

As used herein, the term "immunotherapeutic agent" refers to any agent, compound, or biologic which is capable of modulating the host's immune system. For example, an immunotherapeutic agent is capable of causing a stimulation of the immune system against a tumor cell.

By "marker" is meant any protein or polynucleotide having an alteration in expression level or activity that is associated with a disease or disorder.

By "marker profile" is meant a characterization of the expression or expression level of two or more polypeptides or polynucleotides such as, for example, Uroplakin 1A (UPK1A), Uroplakin 1B (UPK1B), Uroplakin (UPK2), Keratin 20 (KRT20), GATA Binding Protein 3 (GATA3), Nuclear Receptor Corepressor 1 (NCOR1), Nuclear Receptor Corepressor 2 (NCOR2), Fatty Acid Binding Protein 4 (FABP4), Forkhead Box A1 (FOXA1), CD36 Molecule (CD36), Acyl-CoA Oxidase 1 (ACOX1), 3-Hydroxy-3-Methylglutaryl-CoA Synthase 2 (HMGCS2), Acyl-CoA Synthetase Long-Chain Family Member 5 (ACSL5), Arachidonate 5-Lipoxygenase (ALOX5), and Acyl-CoA Synthetase Long-Chain Family Member 1 (ACSL1),.

By "neoplasia" is meant a disease or disorder characterized by excess proliferation or reduced apoptosis. Illustrative neoplasms for which the disclosure can be used include, but are not limited to, breast cancer, esophageal cancer, pancreatic cancer, colorectal cancer, hepatocellular cancer, bladder cancer, luminal and non-luminal bladder cancer, basal bladder cancer, muscle-invasive bladder cancer, and non-muscle-invasive bladder cancer, pancreatic cancer, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, glioblastoma multiforme, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma).

Nucleic acid molecules useful in the methods of the disclosure include any nucleic acid molecule that encodes a polypeptide of the disclosure or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (e.g., Wahl, G. M. and S. L. Berger (1987) *Methods Enzymol.* 152:399; Kimmel, A. R. (1987) *Methods Enzymol.* 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 μg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (*Proc. Natl. Acad. Sci., USA* 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

As used herein, "obtaining" as in "obtaining an agent" includes synthesizing, purchasing, or otherwise acquiring the agent.

By "Peroxisome proliferator-activated receptor gamma (PPARG) activated cancer" is meant a disease or disorder characterized by excess proliferation or reduced apoptosis that is driven by up-regulation of Peroxisome proliferator-activated receptor (PPAR) signaling. Illustrative examples of PPARG activated cancer may include, but are not limited to, breast cancer, bladder cancer, pancreatic cancer, esophageal cancer, colorectal cancer, and hepatocellular cancer.

Unless specifically stated or obvious from context, as used herein, the term "or" is understood to be inclusive. Unless specifically stated or obvious from context, as used herein, the terms "a", "an", and "the" are understood to be singular or plural.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

By "reduces" is meant a negative alteration of at least 10%, 25%, 50%, 75%, or 100%.

By "reference" is meant a standard of comparison. For example, the PPARG or RXRA polypeptide or polynucleotide level present in a patient sample may be compared to the level of said polypeptide or polynucleotide present in a corresponding healthy cell or tissue or in a neoplastic cell or tissue that lacks a propensity to display over-proliferation or to metastasize.

By "subject" is meant a mammal, including, but not limited to, a human or non-human mammal, such as a bovine, canine equine, feline, ovine, or primate.

A "therapeutically effective amount" is an amount sufficient to effect beneficial or desired results, including clinical results. An effective amount can be administered in one or more administrations.

As used herein, the terms "treat," treating," "treatment," and the like refer to reducing or ameliorating a disorder and/or symptoms (e.g., PPARG activated cancer, bladder cancer, and the like) associated therewith. It will be appreciated that, although not precluded, treating a disorder or condition does not require that the disorder, condition or symptoms associated therewith be completely eliminated.

The recitation of a listing of chemical groups in any definition of a variable herein includes definitions of that variable as any single group or a combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

Other features and advantages of the disclosure will be apparent to those skilled in the art from the following detailed description and claims

BRIEF DESCRIPTION OF THE DRAWINGS

FIG. 1A depicts an amino acid map of RXRA depicting mutation, insertion, and deletion sites relative to specific protein domains, as well as the relative frequencies of occurrence of these mutations within the provisional TGCA muscle-invasive bladder cancer dataset (data is available from the Broad Institute TCGA Genome Data Analysis Center. Analysis-ready standardized TCGA data from Broad GDAC Firehose 2016_01_28 run on the world wide web at doi.org/10.7908/C11GOKM9.). FIG. 1B shows enrichment of gene expression in bladder cancer cohort possessing RXRA p.S427F/Y mutations relative to patients without RXRA mutations. FIG. 1C shows a heatmap of gene copy number for 3p25 region in 101 of 412 samples from TCGA bladder cancer cohort sorted by PPARG copy number. FIG. 1D shows a mutation analysis of RXRA across TCGA bladder cancer cohort. FIG. 1E depicts a heat map of gene expression (RSEM) sorted by correlation (Pearson) to PPARG across 412 patients from TCGA bladder cancer cohort (REF) keeping only genes with Pearson correlation >0.5 or <−0.5. FIG. 1F shows gene expression correlation between PPARG and GATA3 across TCGA bladder cancer cohort (REF) in RSEM (log 2) normalized.

FIG. 1G shows a heatmap of gene expression (RSEM) across bladder cancer cell lines in CCLE indicating luminal differentiation markers and PPARG target genes from using data (Entrez_20120929) grouped by Euclidean distance. FIG. 1H shows Western blots of PPARG, FABP4, and VCL in several urinary tract cell lines. FIG. 1I shows immunoblot analysis of lysates from bladder cancer cell lines treated for 7 days with vehicle (DMSO), antagonist (GW9662 @ 100 nM), and inverse-agonist (T0070907 @ 100 nM).

FIG. 2A shows a gene expression heat map (RSEM) of key differentially expressed genes when comparing ectopic expression of wild-type plus parental SW780 cells to mutant alleles of both RXRA and PPARG FIG. 2B shows a gene set enrichment analysis of all significant (P<0.01) differentially expressed genes from FIG. 2A. FIG. 2C depicts a Western immunoblot analysis of lysates from SW780 cells ectopically expressing RXRA and PPARG wild-type and activating mutant alleles. FIG. 2D shows a Western immunoblot analysis of lysates from SW780 cells ectopically expressing a variety of RXRA mutant alleles, and shows that RXRA S427F, S427Y, but not other RXRA alleles, up-regulated PPAR target genes ACSL5 and HMGCS2 in SW780 cells. FIG. 2E shows RNA expression (RSEM) of selected genes that were differentially expressed when comparing parental SW780 cells, cells with ectopic expression of wild-type RXRA and PPARG, and cells expressing mutant alleles of RXRA and PPARG. FIG. 2F shows Heatmap of Cancer Cell Line Encyclopedia gene-centric RMA-normalized mRNA expression data (26) across bladder cancer cell lines indicating luminal differentiation markers and PPARG target genes. The samples were grouped by hierarchical clustering of columns using the Morpheus software package (see e.g., the World Wide Web at (www)software.broadinstitute.org/morpheus/).

FIG. 3A shows PPARG sgRNA's 3 and 6 knockout PPARG protein in 5637 cells. The left panel of FIG. 3A depicts a Western immunoblot of PPARG and loading control VCL, while the right panel shows a bar graph depicting quantification of PPARG Western blot signal after normalization to VCL, reported as ratio of integrated fluorescence intensity K counts and was performed using LICOR Odyssey Application Software version 3.0.30. FIGS. 3B-D depict a CRISPR/Cas9 competition screen performed to measure relative proliferation of cells harboring sgRNA targeting PPARG (yellow), non-essential control of PPARG intron (cyan), and essential control gene KIF11 (red). Cells lines were infected with lentivirus encoding both fluorescent marker and sgRNA prior to pooling cells for assay. Cell lines included HT-1997 (FIG. 3B; RXRA p.S427F), Cal 29 (FIG. 3C; PPARG-activated) and SW1710 (FIG. 3D; not altered, neutral control).

FIG. 4A depicts a genome engineering scheme to generate NanoLuc™ reporter cell line in PPARG-activated RT112/84 cells by inserting NanoLuciferase™ gene into the 3'UTR of FABP4, a canonical PPARG target gene. FIG. 4B shows representative data from dose-response testing of select tool compounds in RT 112/84 FABP4-NLucP assayed after overnight treatment. FIG. 4C shows representative data from dose-response testing of select tool compounds in RT112/84 FABP4-NLucP assayed after overnight treatment in the presence of an agonist, Rosiglitazone, at the EC50. FIG. 4D shows a representation of the effects of ligand-dependent modulation on the PPARG interactome. In the basal state for PPARG-activated bladder cancer cells, PPARG is moderately activated (middle). Agonist activation further increases interactions with co-activators, induces histone acetylation, chromatin remodeling, and induces transactivation of target genes by the PPARG complex (top), while inverse-agonists induce interactions with co-repressors, resulting in repression of transactivation through recruitment of corepressors and histone deactylases (bottom). PPARG antagonists block the effects of either agonists or antagonists.

FIG. 6A shows the proliferation assay measuring dose-dependent effect of PPARG modulators on cell number in UM-UC-9 cells using high content imaging to count fluorescently-labeled nuclei after 9 days of treatment. FIG. 6B shows a graph depicting results of a kinetic proliferation assay measuring the effect of 100 nmol/L modulator on growth rate over time in UM-UC-9 with graphical representation of percent of control calculation. Fluorescently labeled nuclei were counted using IncuCyte Zoom every 2 hours (n ¼ 4 replicates per condition). Data are represented as mean±SD. FIGS. 6C-I show kinetic proliferation assay measuring the effect of 100 nM modulator on growth rate over time in UM-UC-1 (FIG. 6C), 5637 (FIG. 6D), Cal29 (FIG. 6E), HT-1197 (FIG. 6F), SW1710 (FIG. 6G), KU19.19 (FIG. 6H), and UM-UC-3 (FIG. 6I).

FIG. 7A shows that RXRA S427 is located at the dimerization domain with PPARG. FIG. 7B shows that the RXRA S427F/Y mutation created favorable hydrophobic interactions with the C-terminus of PPARG and locked into the active conformation. FIG. 7C shows RXRA p.S427F/Y mutation created favorable hydrophobic interactions with the c-terminus of PPARG and locked into the active conformation.

FIG. 8A is a graph depicting dose-response testing of panel of PPARG modulators in RT112/84 FABP4-NLucP reporter assay under unstimulated conditions to evaluate activity of agonists and inverse agonists. FIG. 8B is a graph depicting antagonist mode dose-response testing of panel of PPARG modulators in the RT112/84 FABP4-NLucP reporter assay performed by combined dosing of the PPARG agonist, rosiglitazone at the EC50, 20 nmol/L, in combination with a dose-response for test compounds, as indicated. FIG. 8C is a graph showing dose-response testing of a panel of PPARG modulators in competitive ligand-binding TR-FRET biochemical assay. FIGS. 8D-8E show that PPARG inverse-agonists induce a repressive complex by blocking interactions with coactivators and inducing interactions with corepressor NCOR2. A TR-FRET assay was used to evaluate the ligand-dependent interactions between Terbium-labeled PPARG ligand binding domain (PPARG-LBD) and fluorescein-labeled peptides derived from nuclear receptor coregulators, as indicated. FIG. 8D is a graph showing dose-response testing of a panel of PPARG modulators in an inverse agonist biochemical model evaluating PPARG LBD-SMRT (NCOR2) corepressor interactions. FIG. 8E is a graph showing dose-response testing of a panel of PPARG modulators in an agonist biochemical model evaluating in a PPARG-LBD—TRAP220 (MED1) coactivator peptide interaction assay to measure agonist-induced interactions, or inverse-agonist induced decrease in interactions.

FIG. 12 shows a table summarizing the results of cell proliferation assays showing that PPARG inverse-agonists inhibited proliferation of PPARG activated bladder cancer cell lines. It should be noted that bladder cancer cell lines were treated with vehicle or GW9662, SR2595, SR10221, or T0070907 at 100 nmol/L in long-term kinetic proliferation assays lasting 6-12 days. Data reported as percent of DMSO control, calculated by determining the relative number of cells for treatment versus DMSO control at the time point where DMSO control reached 50% confluence (see FIG. 4B for graphical representation) by counting fluorescently labeled nuclei (IncuCyte Zoom). Significant differences in cell number for test sample relative to DMSO control were calculated using two-way ANOVA with Dunnett multiple comparison test.

FIGS. 13A-D show the proliferation assay measuring dose-dependent effect of PPARG modulators on cell number in pancreatic cancer cells (TCCPAN2 cells; FIG. 13A), pancreatic cancer cells (KP-2 cells; FIG. 13B), pancreatic cancer cells (HUP-T4 cells; FIG. 13C), and colorectal cancer cells (LS1034 cells; FIG. 13D) using high content imaging to count fluorescently-labeled nuclei. FIGS. 13A-D show kinetic proliferation assay measuring the effect of 500 nM modulator on growth rate over time.

DETAILED DESCRIPTION OF THE DISCLOSURE

Figure 1A:
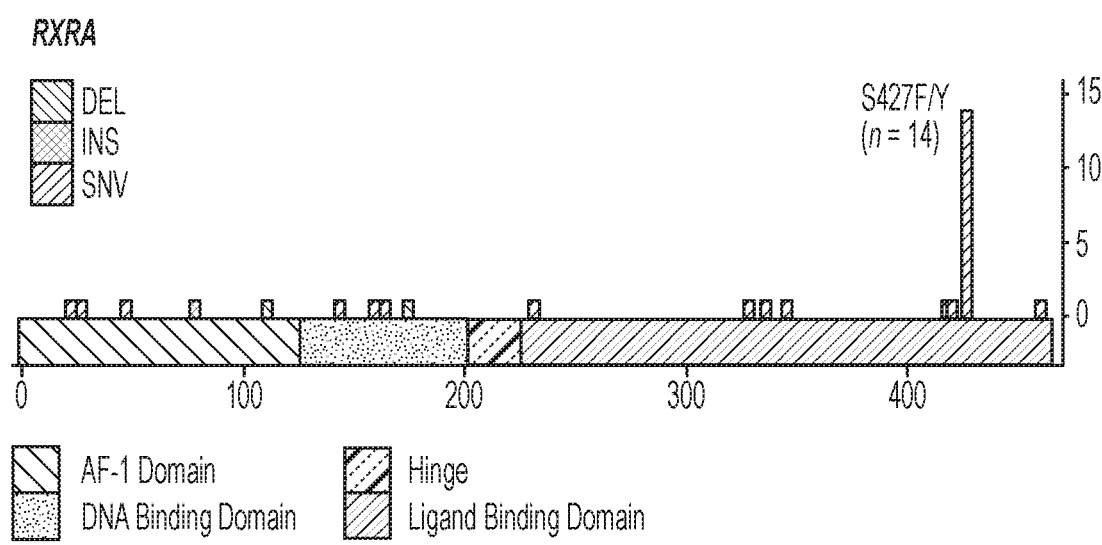
FIGS. 1A-I show that somatic alterations in Peroxisome proliferator-activated receptor gamma (PPARG) and retinoid X receptor alpha (RXRA) are hallmarks of luminal bladder cancer.

The present disclosure is based, at least in part, on the discovery of Peroxisome proliferator-activated receptor gamma (PPARG) signaling as a therapeutic target for the treatment of various PPARG activated cancers such as, for example, bladder cancer. For example, as described herein, the present disclosure provides PPARG signaling modulators that are able to down regulate PPARG signaling in PPARG activated cancers, thereby decreasing cellular proliferation associated with PPARG activated cancers (e.g., bladder cancer). It is also contemplated within the scope of the disclosure, that molecular genetic methodologies (e.g., CRISPR/Cas9, RNAi, and the like) that allow correction of mutations that generate PPARG activated cancers can also be used as therapeutic modalities to down regulate PPARG signaling in PPARG activated cancers, thereby blocking the increased cellular proliferation associated with PPARG activated cancers. In particular, the present disclosure provides inverse-agonists that are able to reverse up regulation of PPARG signaling in PPARG activated cancers, thereby providing a therapeutic modality capable of treating PPARG activated cancers such as, for example, bladder cancer.

The present disclosure analyzed large-scale cancer genome datasets derived from patients with muscle-invasive bladder cancer to identify novel therapeutic targets and identified the presence of p.S427F/Y hotspot mutations in the Retinoid X Receptor Alpha (RXRA) gene, which occur in ~5% of bladder cancer samples (2, 3), but which have been observed only sporadically in other cancers. RXRA is a well characterized ligand-activated nuclear receptor that serves as a requisite heterodimer partner for ~30 nuclear receptors (RARA, RARB, VDR, TR, PPARA, PPARG, PPARD, LXRs, PXR, etc.) (4), suggesting that recurrent mutations in RXRA could impact the formation and/or function of these heterodimers and change the expression of their downstream target genes.

Previous reports have shown that patient samples containing p.S427F/Y mutations in RXRA are associated with enhanced expression of genes involved in adipogenesis and lipid metabolism, including ACOX1, ACSL1, ACSL5, FABP4, and HMGS2 (Supplementary Information Figure S2.6 in (2)). These genes are targets of Peroxisome Proliferator Activated Receptor Gamma (PPARG), a member of the PPAR subfamily of nuclear receptors. PPARG is a master regulator of adipocyte differentiation and controls expression of a large set of genes involved in lipid and glucose homeostasis. In contrast to PPARG's well-characterized activity in adipocytes, however, relatively little is known about its function in the urinary bladder and in the pathogenesis of bladder cancer.

Pharmacological evidence has suggested a role for PPARG and potentially PPARA in the development of bladder cancer in rodents (5-7). However, rosiglitazone, a highly selective PPARG agonist that is approved for the treatment of type 2 diabetes, has not been shown to increase the hazard ratio for development of bladder cancer in humans (8). In contrast, other studies using a less-selective PPARG agonist, pioglitazone, have reported an increase in risk of development of bladder cancer, with long-term use (9-12), including a recent meta-analysis of the largest case cohort study to date for PPARG modulators in bladder cancer containing 689,616 person years of data (8). In addition, PPARG/PPARA dual agonists in the "glitizar" class have resulted in significant pre-clinical toxicity issues, notably including the development of bladder cancer (5, 13).

Recently, several immune checkpoint blockade drugs have been FDA-approved for treatment of urothelial carcinoma, including atezolizumab, an anti-PD-L1 antibody, in 2016 (35); nivolumab and pembrolizumab, anti-PD-1 antibodies, in 2017 (36); and avelumab and durvalumab, anti-PD-L1 antibodies, in 2017 (37, 38). These approvals mark the first new drugs for metastatic bladder cancer in over 20 years. However, the objective response rates (defined using RECIST v1.1) were relatively low in these clinical trials, with 15%-20% overall response rate and 26%-28% response rate in PD-L1-positive patients (35, 36). Beyond checkpoint inhibitors, a number of therapies targeting specific genetic alterations, including FGFR3 alterations, mTOR pathway alterations, and DNA repair deficiencies associated with ERCC2 alterations (39-42), are under clinical evaluation.

The techniques herein explored large-scale cancer genome datasets derived from patients with muscle-invasive bladder cancer with the purpose of identifying novel therapeutic targets. Hotspot mutations (p.S427F/Y) in the retinoid X receptor alpha (RXRA) gene are present in approximately 5% of bladder cancer samples (2, 3). RXRA is a well-characterized ligand-activated nuclear receptor that serves as a requisite heterodimer partner for approximately 30 nuclear receptors, including PPARA, PPARG, PPARD, RARA, RARB, VDR, TR, LXR, and PXR (4), suggesting that recurrent mutations in RXRA could impact the formation and/or function of these heterodimers and change the expression of their downstream target genes. Previous reports have shown that cancer samples containing RXRA p.S427F/Y mutations are associated with enhanced expression of genes involved in adipogenesis and lipid metabolism, including ACOX1, ACSL1, ACSL5, FABP4, and HMGS2 (2). These genes are targets of PPARG, a member of the PPAR subfamily of nuclear receptors.

Figure 1B:
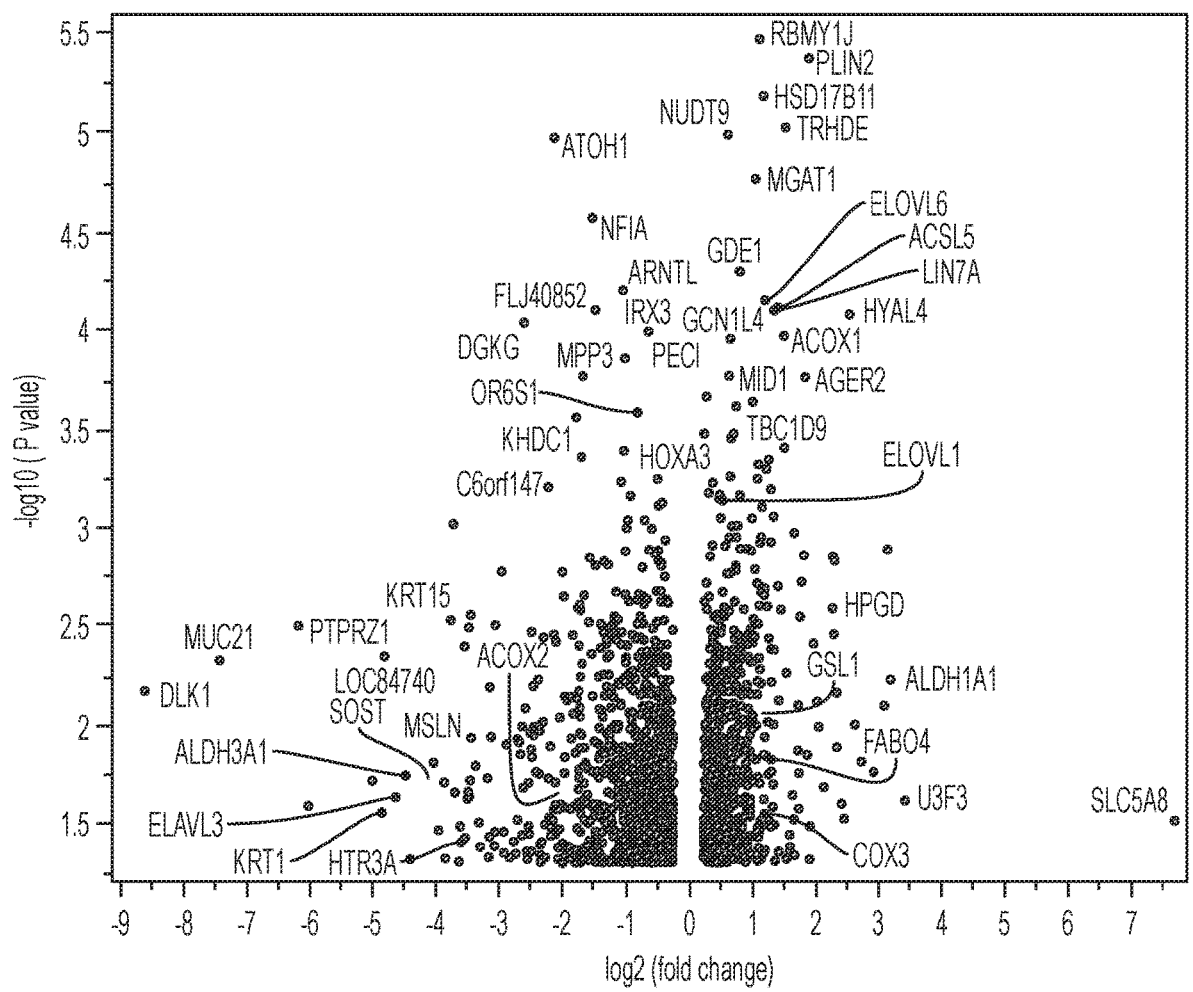
Figure 1C:
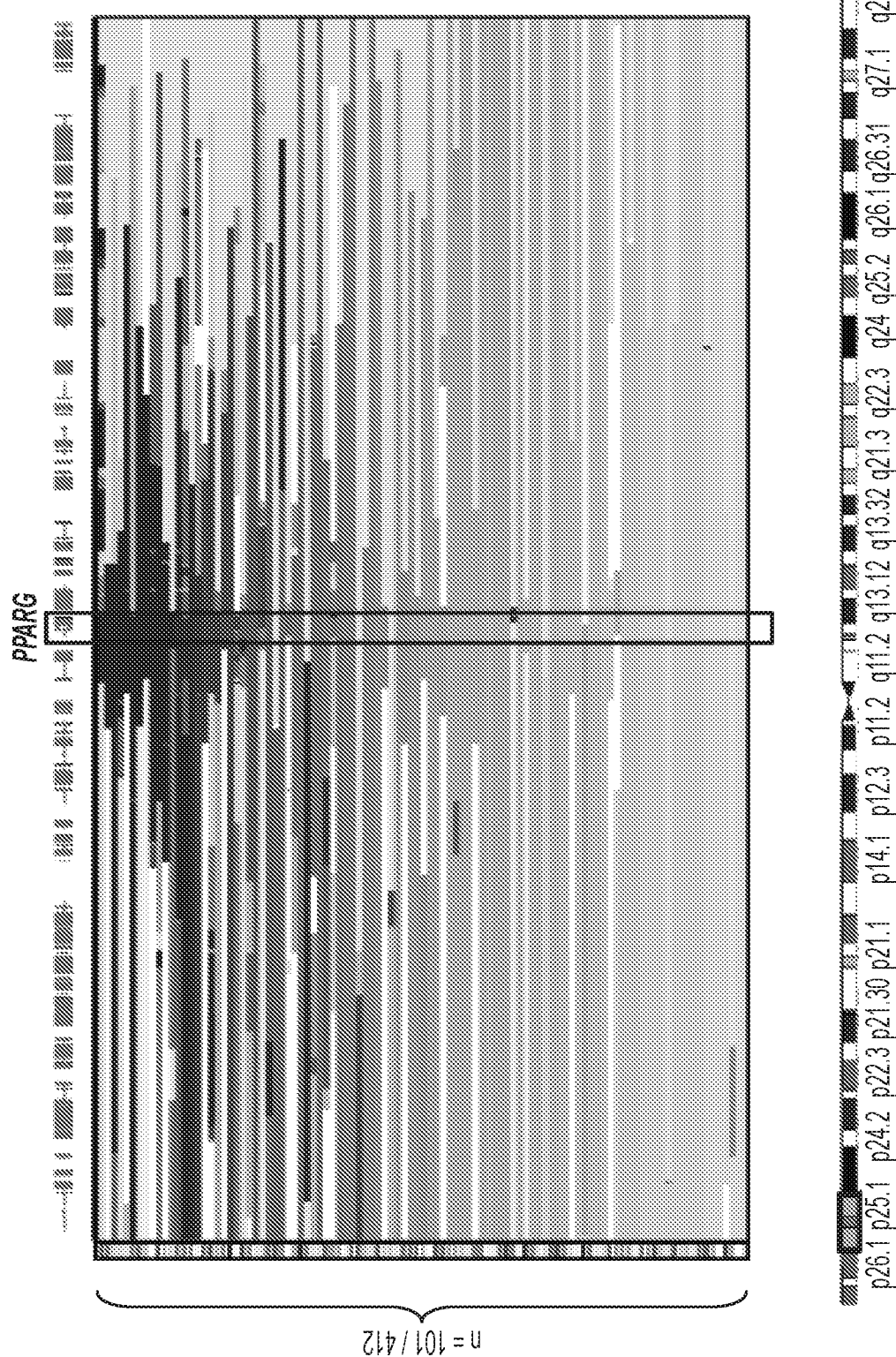
Figure 1D:
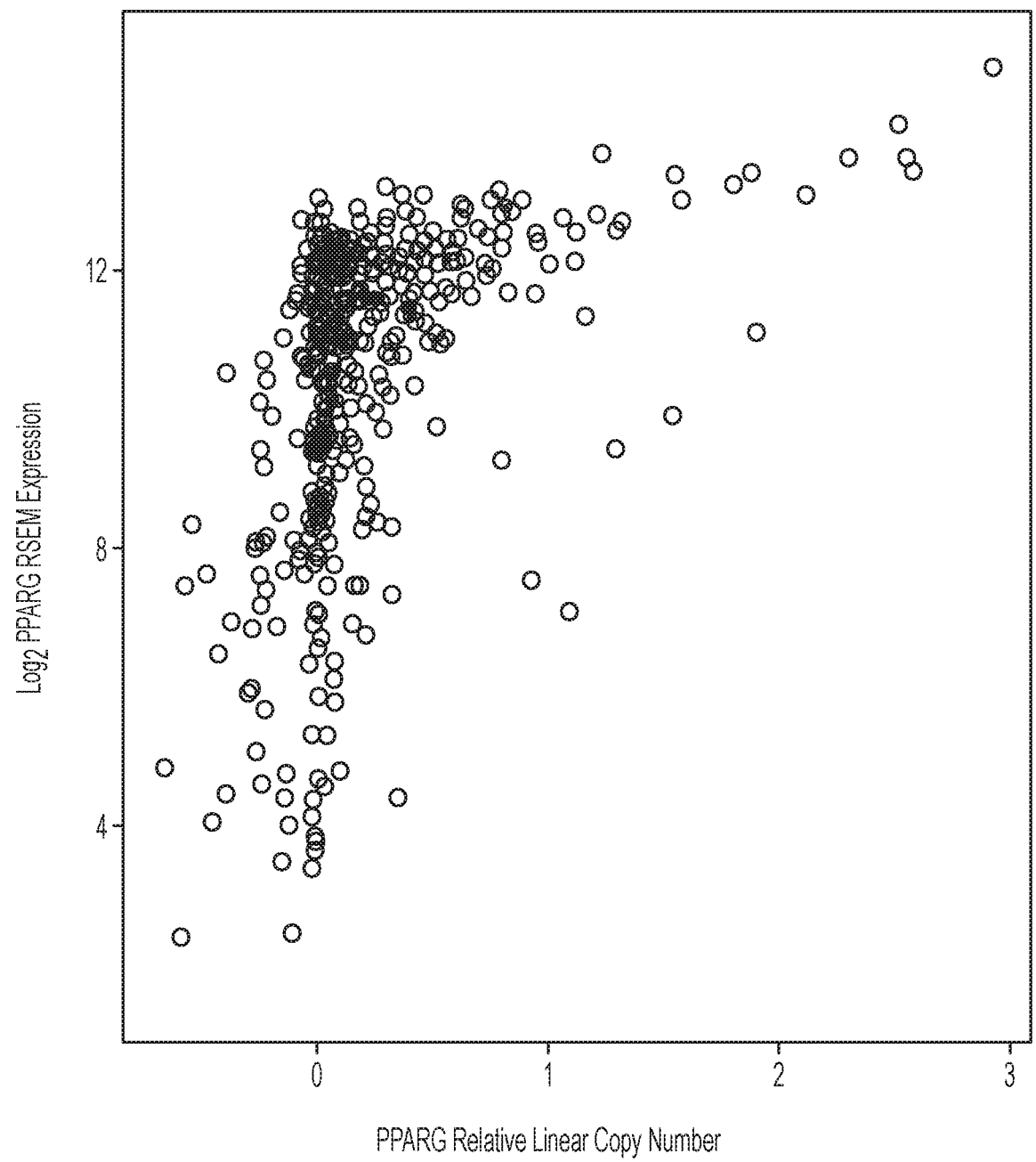
Figure 1E:
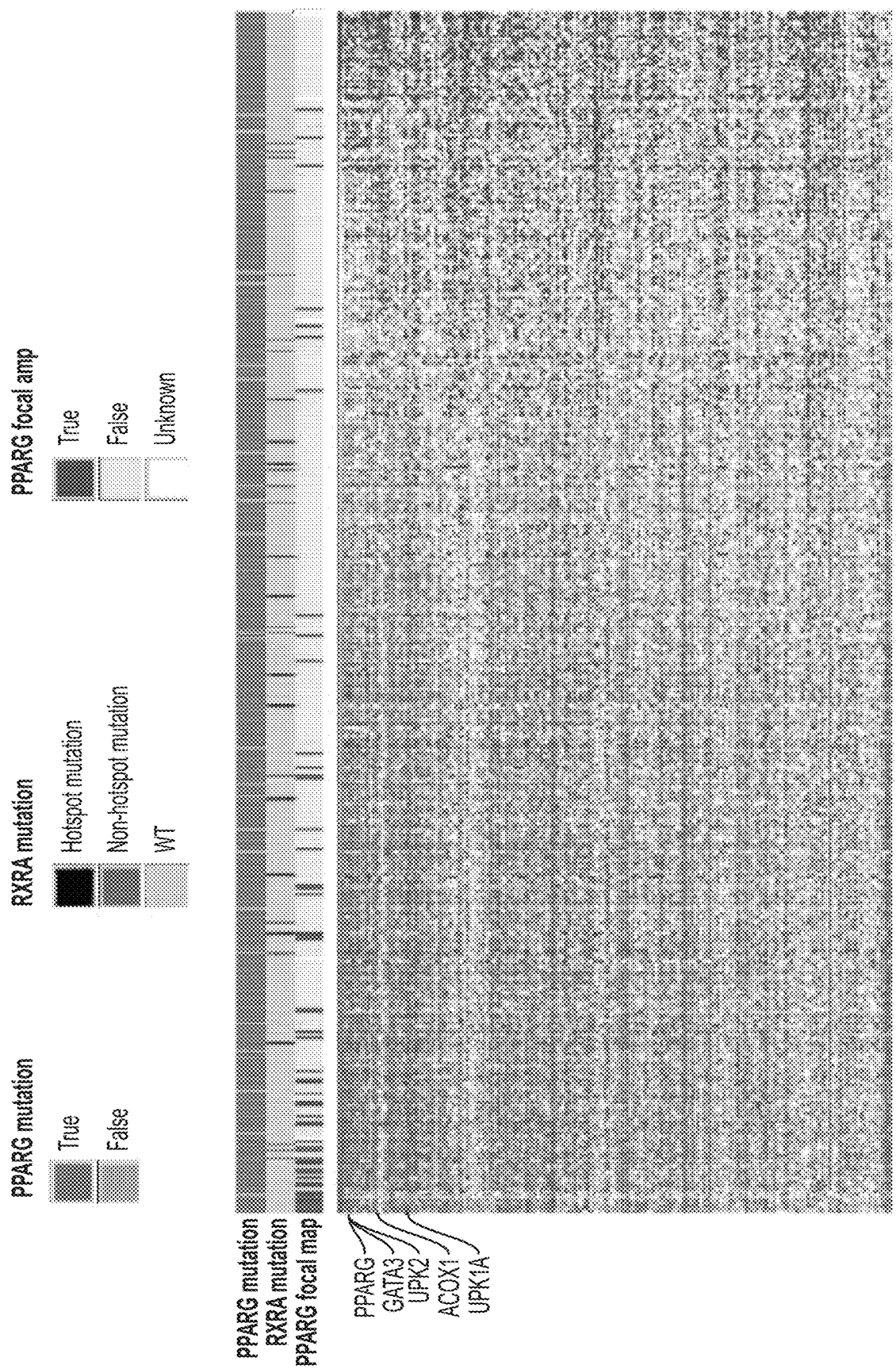

Interestingly, the PPARG gene is focally amplified in 15% of bladder cancer samples (FIG. 1C; ref. 43). This amplification is strongly correlated with expression of PPARG (FIG. 1D) as well as expression of PPARG target genes and luminal differentiation markers such as GATA3, UPK2, ACOX1, and UPK1A (FIG. 1E; refs. 22-45). PPARG is a master regulator of adipocyte differentiation and controls expression of a large set of genes involved in lipid and glucose homeostasis (43). In contrast to PPARG's well-characterized activity in adipocytes, however, little is known about its function in the urinary bladder and in the pathogenesis of bladder cancer.

The potential risk of bladder cancer upon activation of the PPAR subfamily of nuclear receptors is controversial, and was first suggested following rodent toxicity studies testing antidiabetic PPAR agonists in which numerous glitazar-class PPARA/PPARG dual agonist compounds were associated with an increased incidence of bladder cancer (5). In terms of more selective PPARG agonists, also antidiabetic drugs with insulin sensitizing activity, the carcinogenic effect in rodents was also observed with pioglitazone, which has weak PPARA activity (46), but not with rosiglitazone, which is highly selective for PPARG (5, 6). In a more sensitive, chemically-induced model using the carcinogen, 4-hydroxybutyl (butyl) nitrosamine (OH-BBN), rosiglitazone was found to potentiate urinary bladder carcinogenesis in rats compared with OH-BBN alone (47). It was originally hypothesized that the effects of PPARA/PPARG dual agonists on promoting bladder cancer was rodent-specific due to indirectly causing calcium crystal formation in the bladder, resulting in urolithiasis (48). Numerous studies have since examined the incidence of bladder cancer in humans following the clinical use of these compounds, with some detecting an increased risk and others concluding there is no increased risk (9, 11). The most comprehensive retrospective study to date showed an increase in the hazard ratio for bladder cancer with long-term, high-dose treatment with pioglitazone (8).

Without being bound be theory, the present disclosure postulates that activation of PPARG is oncogenic in the transitional epithelial cells of the bladder. This was evaluated by investigating the biological impact of ectopic expression of mutant alleles of RXRA and PPARG, pharmacologic ablation of RXRA/PPARG signaling using small-molecule perturbagens, and genetic ablation of RXRA and PPARG using CRISPR/Cas9 gene knockouts. The results herein demonstrate an oncogenic role for PPARG in the development of luminal bladder cancer, revealing a novel axis that could be exploited for the development of targeted therapies for this disease.

Again without being bound by theory, the present disclosure also postulates that the RXRA/PPARG signaling pathway activity inhibits the host immune response. In other words, RXRA/PPARG signaling activation enables cells to evade detection by the host immunosurveillance system. According to the techniques herein, inverse agonists can help RXRA/PPARG cancers be detected by the immune system.

Based on combined genetic and pharmacologic evidence, the present disclosure hypothesized that activation of PPARG can be oncogenic in cells of the bladder. As described herein, this hypothesis was validated by evaluating the biological impact of (i) ectopic expression of mutant alleles of RXRA and PPARG found in bladder cancer, (ii) genetic ablation of RXRA and PPARG using CRISPR/Cas9, and (iii) pharmacologic ablation of RXRA/PPARG signaling using small molecule perturbagens. The results described herein demonstrate an oncogenic role for PPARG in the development of luminal bladder cancer, unveiling a novel axis for development of targeted therapies for this disease.

Peroxisome Proliferator-Activated Receptor (PPAR)

PPARs are a group of nuclear receptor proteins that function as transcription factors that regulate the expression of downstream target genes (see e.g., Michalik et al. (2006) International Union of Pharmacology. LXI. Peroxisome proliferator-activated receptors; *Pharmacol. Rev.* 58 (4):

726-41). PPARs play an essential role in many eukaryotic processes, including: regulation of cellular differentiation, development, and metabolism (carbohydrate, lipid, protein).

PPARs are modular in structure and may contain one or more of the following protein domains: an N-terminal region, a DNA-binding domain (DBD), a flexible hinge region, a ligand binding domain (LBD), and/or a C-terminal region (CTR). Generally, PPAR DBDs contain two zinc finger motifs, which bind to specific sequences of DNA known as peroxisome proliferator hormone response elements when the receptor is activated (see below). The LBD has an extensive secondary structure consisting of 13 alpha helices and a beta sheet (see e.g., Zoete et al. (2007). *Biochim. Biophys. Acta.* 1771 (8): 915-25). Natural and synthetic ligands bind to the LBD, either activating or repressing the receptor, depending on their three dimensional structure and specific nature of their interaction with the LBD.

To date, three main subtypes of PPARs have been identified: PPAR Alpha (PPARA), PPAR Gamma (PPARG), and PPAR Delta (PPARD), each of which is encoded by a different gene. Additionally, the PPARG subtype includes three additional subtypes: Gamma1, Gamma2, and Gamma3. These three PPARG subtypes are alternate transcriptional splicing variants of the PPARG gene, each of which is characterized by cell/tissue type patterns of expression. PPARG1 is widely expressed in a variety of tissues/organs including, but not limited to, heart, muscle, kidney, pancreas, spleen, and colon. PPARG2 is primarily expressed in adipose tissue. PPARG3 is generally expressed in white adipose tissue, large intestine, and in macrophages.

Endogenous ligands for the PPARs include free fatty acids and eicosanoids. For example, PPARA may be activated by leukotriene B4, a leukotriene involved in inflammation. PPARG may be activated by PGJ2 (e.g., a cyclopentenone prostaglandin having the ability to suppress inflammation responses and both the growth and survival of cells, particularly cancerous cells) as well as several members of the 5-HETE family of arachidonic acid metabolites including 5-oxo-15(S)-HETE and 5-oxo-ETE (see e.g., O'Flaherty et al. (2205) *Biochim. Biophys. Acta* 1736:228-236). In contrast, PPARA, PPARD, and PPARG may be activated to various degrees by members of the 15-Hydroxyicosatetraenoic acid family of arachidonic acid metabolites, including, but not limited to, 15(S)-HETE, 15(R)-HETE, and 15-HpETE (see e.g., Naruhn et al. (2010) *Mol. Pharmacol.* 77-171-184).

The function of PPARs may be modified by the precise shape of their ligand-binding domain induced by ligand binding, as well as by coactivator and corepressor proteins, which may stimulate or inhibit receptor function, respectively (see e.g., Yu S, Reddy JK (2007) Biochim. *Biophys. Acta.* 1771 (8): 936-51).

Peroxisome Proliferator-Activated Receptor Gamma (PPARG)

PPARG is a nuclear receptor that interacts with retinoid X receptor (RXRA) to form a heterodimeric transcription factor complex that binds to specific enhancer regions on the DNA of target genes termed peroxisome proliferator hormone response elements (PPREs). The consensus PPRE DNA sequence is AGGTCANAGGTCA (SEQ ID NO: 1), where N is any nucleotide. In general, a PPARG/RXRA heterodimer can bind the PPRE sequence in the promotor region of a gene, thereby increasing or decreasing transcription of the target gene, depending on the gene (i.e., expression of some target genes can be increased, while expression of other target genes can be decreased).

PPARG is known to interact with several co-regulatory proteins including, but not limited to, nuclear receptor co-repressor 1 (NCOR1) and nuclear receptor co-repressor 2 (NCOR2).

NCOR1 and NCOR2 are transcriptional coregulatory protein that contains several nuclear receptor interacting domains. Functionally, NCOR1 and NCOR2 appear to recruit histone deacetylases to DNA promoter regions and assists nuclear receptors in the down regulation of target gene expression.

By "PPARG nucleic acid molecule" is meant a polynucleotide encoding a PPARG polypeptide. An exemplary PPARG nucleic acid molecule is provided at NCBI Accession No. NM_138712.3, and reproduced below:

>NM_138712.3

(SEQ ID NO: 2)

ggcgcccgcgcccgccccgcgccgggcccggctcggcccgacccgg ctccgccgcgggcaggcggggcccagcgcactcggagcccgagcccg agccgcagccgccgcctggggcgcttgggtcggcctcgaggacaccg gagaggggcgccacgccgccgtggccgcagatttgaaagaagccaac actaaaccacaaatatacaacaaggccattttctcaaacgagagtca gcctttaacgaaatgaccatggttgacacagagatgccattctggcc caccaactttgggatcagctccgtggatctctccgtaatggaagacc actcccactcctttgatatcaagcccttcactactgttgacttctcc agcatttctactccacattcgaagacattccattcacaagaacaga tccagtggttgcagattacaagtatgacctgaaacttcaagagtacc aaagtgcaatcaaagtggagcctgcatctccaccttattattctgag aagactcagctctacaataagcctcatgaagagccttccaactccct catggcaattgaatgtcgtgtctgtggagataaagcttctggatttc actatggagttcatgcttgtgaaggatgcaagggtttcttccggaga acaatcagattgaagcttatctatgacagatgtgatcttaactgtcg gatccacaaaaaagtagaaataaatgtcagtactgtcggtttcaga aatgccttgcagtggggatgtctcataatgccatcaggtttgggcgg atgccacaggccgagaaggagaagctgttggcggagatctccagtga tatcgaccagctgaatccagagtccgctgacctccgggccctggcaa aacatttgtatgactcatacataaagtccttcccgctgaccaaagca aaggcgagggcgatcttgacaggaaagacaacagacaaatcaccatt cgttatctatgacatgaattccttaatgatgggagaagataaaatca agttcaaacacatcacccccctgcaggagcagagcaaagaggtggcc atccgcatctttcagggctgccagtttcgctccgtggaggctgtgca ggagatcacagagtatgccaaaagcattcctggttttgtaaatcttg acttgaacgaccaagtaactctcctcaaatatggagtccacgagatc atttacacaatgctggcctccttgatgaataaagatggggttctcat atccgagggccaaggcttcatgacaagggagtttctaaagagcctgc gaaagccttttggtgactttatggagcccaagtttgagtttgctgtg aagttcaatgcactggaattagatgacagcgacttggcaatatttat

```
tgctgtcattattctcagtggagaccgcccaggtttgctgaatgtga agcccattgaagacattcaagacaacctgctacaagccctggagctc cagctgaagctgaaccaccctgagtcctcacagctgtttgccaagct gctccagaaaatgacagacctcagacagattgtcacggaacacgtgc agctactgcaggtgatcaagaagacggagacagacatgagtcttcac ccgctcctgcaggagatctacaaggacttgtactagcagagagtcct gagccactgccaacatttcccttcttccagttgcactattctgaggg aaaatctgacacctaagaaatttactgtgaaaaagcattttaaaaag aaaaggttttagaatatgatctattttatgcatattgtttataaaga cacatttacaatttacttttaatattaaaaattaccatattatgaaa ttgctgatagta
```

By "PPARG polypeptide" is meant a polypeptide or fragment thereof having at least about 85% amino acid identity to NCBI Accession No. NP_005028.4 and having DNA binding activity, as reproduced below:

```
>NP_619726.2
                                         (SEQ ID NO: 3)
MTMVDTEMPFWPTNFGISSVDLSVMEDHSHSFDIKPFTTVDFSSIST

PHYEDIPFTRTDPVVADYKYDLKLQEYQSAIKVEPASPPYYSEKTQL

YNKPHEEPSNSLMAIECRVCGDKASGFHYGVHACEGCKGFFRRTIRL

KLIYDRCDLNCRIHKKSRNKCQYCRFQKCLAVGMSHNAIRFGRMPQA

EKEKLLAEISSDIDQLNPESADLRALAKHLYDSYIKSFPLTKAKARA

ILTGKTTDKSPFVIYDMNSLMMGEDKIKFKHITPLQEQSKEVAIRIF

QGCQFRSVEAVQEITEYAKSIPGFVNLDLNDQVTLLKYGVHEIIYTM

LASLMNKDGVLISEGQGFMTREFLKSLRKPFGDFMEPKFEFAVKFNA

LELDDSDLAIFIAVIILSGDRPGLLNVKPIEDIQDNLLQALELQLKL

NHPESSQLFAKLLQKMTDLRQIVTEHVQLLQVIKKTETDMSLHPLLQ

EIYKDLY
```

By "NCOR1 nucleic acid molecule" is meant a polynucleotide encoding a NCOR1 polypeptide. An exemplary NCOR1 nucleic acid molecule is provided at NCBI Accession No. NM_006311.3, and reproduced below:

```
>NM_006311.3
                                         (SEQ ID NO: 4)
gcgggctggggggagggagaggggttgagtcaagatggcggccaaggtggcgaagcagca gccgcggcggcggcggctggagtgagcgtccgactcgccgcgccgaacgaggtcccg gtgtagggccgcgcgccgtggccgcgtcccactcctcaggccggggcgcacgtcggctcc cacgcttagccagctcccggtggtttcctagaaacatgattgtttattggcattgatctc acagtctggtgaggacttctttactgataatgtcaagttcaggttatcctcccaaccaag gagcattcagcacagaacaaagtcgttatcctcctcactctgtccagtatacatttccca acacccgccaccagcaggagttcgcagtccctgattatcgttcctctcatcttgaagtga gtcaggcatcacagcttttgcagcaacagcagcagcaacagcttcgaaggcgaccttcct tgctttcagaatttcacccaggttctgacaggcctcaagaaaggagaactagttatgaac cgtttcatccaggcccatccccagtggatcatgattcactggaatcgaagcgaccacgtc tggaacaggtttctgattctcattttcagcgtgtcagtgctgcggttttgcctttagtgc acccgctgccagaagggctgagggcttctgcagatgctaagaaggatccagcattcggag gcaaacatgaagctccatcctctccaatttcggggcaaccatgtggagatgatcaaaatg cttcaccttcaaaactctcaaaggaagagttaatacagagtatggatcgtgtagatcgag aaattgcaaaagtagaacagcagatccttaaactgaaaaagaaacaacaacagcttgaag aagaggcagctaaacctcctgagcctgagaagcccgtgtcccctcctcctgtggagcaga aacaccgcagtattgtccaaattatttatgatgagaatcggaaaaaagcagaagaagctc ataaaatttttgaaggtcttggcccaaaagttgaactgccactgtataaccagccatcag ataccaaggtgtaccatgagaacatcaagacaaaccaggtgatgaggaaaaaactcattt tattttttaaaagaagaaatcatgcaagaaaacaaagggaacaaaaaatctgccagcgtt atgatcagctcatggaggcatgggagaaaaagtggacagaatagaaaataatcctcgga ggaaagctaaagaaagcaaaacaagggaatactatgaaaagcagtttccagaaattcgaa aacaaagagaacagcaagaaagatttcagcgagttgggcagaggggagctggtctttcag ccaccattgctaggagtgagcatgagatttctgaaattattgatgggctctctgagcagg
```

-continued

```
agaataatgagaaacaaatgcggcagctctctgtgattccacctatgatgtttgatgcag aacaaagacgagtcaagttcattaacatgaatgggcttatggaggaccctatgaaagtgt ataaagataggcagtttatgaatgtttggactgaccatgaaaaggagatctttaaggaca agtttatccagcatccaaaaaactttggactaattgcatcatacttggagaggaagagtg ttcctgattgtgttttgtattactatttaaccaagaaaaatgagaattataaagccctcg tcagaaggaattatgggaaacgcagaggcagaaaccagcaaattgctcgaccctcgcaag aagaaaagtagaagaaaagaagaggataaagcagaaaaacagaaaaaaaagaagaag aaaagaaagatgaagaggaaaaagatgaaaagaagactccaaagaaaataccaaggaaa aggacaagatagatggtacagcagaagaaactgaggaaagagagcaagccacaccccggg ggcgaaagactgccaacagtcagggccgccgtaagggccggatcaccaggtccatgacaa acgaagctgcagctgccagtgctgcagccgcagcggctactgaagagcccccaccacctc tgccaccgccaccagaagggatttctacagagcctgtggagacctctcgatggacagaag aagaaatggaagttgctaaaaaaggtctagtagaacatggtcgtaactgggcagcaattg ctaaaatggtgggaacgaaaagtgaagctcaatgtaaaaacttctattttaactataaaa ggcgacacaatcttgacaacctcttacagcagcataaacagaaaacttcacgaaaacctc gtgaagagcgagatgtgtctcaatgtgaaagtgtcgcttccactgtttctgctcaggagg atgaagatattgaagcctccaatgaagaagaaaatccagaagacagcgaagttgaagctg tcaagcccagcgaggacagtcctgaaaatgctacttctcgaggaaacacagaacctgcgg ttgagcttgagcccaccacggaaactgcacccagtacatctccctccttagcagttccaa gtacaaaaccagctgaagatgaaagtgtggagacccaggtgaatgacagcatcagtgctg agacagcagagcagatggatgtagatcagcaggagcacagtgctgaagagggttctgttt gtgatccccacccgctaccaaagctgactctgtggacgttgaagtgagggtgccagaaa accatgcatctaaagttgaaggtgataataccaaagaaagagacttggatagagccagtg agaaggtggaacctagagatgaagatttggtggtagctcagcaaataaatgcccaaggc ccgagcccagtcagacaatgattccagtgccacgtgcagcgctgatgaggatgtggatg gagagccagagaggcagagaatgtttcctatggactcaaagccttcactgttaaacccca ctggatctatactcgtctcatctccgttaaaaccaaatccactggatctgccacagcttc agcatcgagctgctgttatcccaccaatggtatcctgcacccatgtaacataccaattg gaacccagtgagcggctatgctctctaccagcgacacattaaagcaatgcatgagtcag cactcctggaggagcagcggcagagacaagaacagatagatttggaatgtagaagttcta caagtccatgtggcacatccaagagtccaaacagagagtgggaagtccttcagcctgctc cacatcaagtgataactaatctccctgaaggcgttcggcttccgacaactcgaccaacca ggccaccgccccctctcatcccgtcatccaaaaccacagtggcttcagaaaaaccatctt ttataatgggaggctccatctcacagggaacaccaggcacttatttgacttctcataatc aggcttcctacactcaagaaacacccaagccgtcagtgggatctatctctcttggactgc cacggcaacaggaatctgccaaatcagctactttgccctacatcaagcaggaagaattt ctccccgaagccaaaactcacaacctgagggtctgttggtcagggcccaacatgaaggtg tagtcagaggtaccgcaggagccatacaagaaggaagtataactcggggaactccaacca gcaaaatttcagtggagagcattccatccctacggggctctatcactcagggcaccccgg ctctgccccagactggcataccaacagaggctttggtgaaggggtccatttcgagaatgc ccattgaagacagcagtcctgagaaaggcagagaggaagctgcatccaaaggccatgtta
```

-continued

```
tttatgaaggcaaaagtggacatatcttgtcatatgataatattaagaatgcccgagaag
ggactaggagtccaagaacagctcatgaaatcagtttaaagagaagctatgaatcagtgg
aaggaaatataaagcaagggatgtcaatgagggagtctcctgtatcagcaccgttagagg
ggctgatatgccgagcattacccagggggagtcctcattctgacctcaaagaaaggactg
tattgtctggctccataatgcaggggacaccaagagcaacaactgaaagctttgaagatg
gccttaaatatcccaaacaaattaaaagggaaagtcctcccatacgagcatttgaaggtg
ccattaccaaaggaaaaccatatgatggcatcaccaccatcaaagaaatggggcgttcca
ttcatgagattccaaggcaagatattttaactcaggaaagtcggaaaactccagaagtgg
tccagagcacacggccgataattgagggttccatttcccagggcacaccaataaagtttg
acaacaactcaggtcaatctgccatcaaacacaatgtcaaatccttaatcacggggccta
gcaaactatcccgtggaatgcctccgctggaaattgtgccagagaacataaaagtggtag
aacggggaaaatatgaggatgtgaaagcaggcgagaccgtgcgttcccggcacacgtcag
tggtaagctctggcccctccgttcttaggtccacactgcatgaagctcccaaagcacaac
tgagccctgggatttatgatgacaccagtgcacggaggaccctgtgagttatcaaaaca
ccatgtccagaggctcacccatgatgaacagaacttctgatgttacaatttcttctaaca
agtctaccaatcatgaaaggaaatcgacactgacccctacccagagggaaagtatcccag
cgaagtctccagtgcctggggtggaccctgtcgtgagccacagtccgtttgatccccatc
acagaggcagcactgcaggcgaggtttatcggagccacctgcccacgcacttggatccag
ccatgccttttcacagggctttggatcctgcagcggctgcttacctgtttcagagacagc
tttcaccaactccaggttacccaagtcagtatcagctttacgcaatggagaacacaagac
agacaatcttaaatgattacattacctcacaacagatgcaagtgaacttgcgtccagatg
tggccagaggactctccccaagagagcagccactgggtctcccatacccagcaacgagag
gaatcattgacctgaccaatatgcctccaacaattttagtgcctcatccaggggggaacaa
gcactcctcccatggacagaatcacttatattcctggtacacagattactttccctccca
ggccgtacaactctgcttccatgtctccaggacacccaacacaccttgcagctgctgcaa
gtgctgagagggaacgggaacgggagcgggagaaggagcgggagcgggaacggattgctg
cagcttcctccgacctctacctgcggccaggctcagaacagcctggccgacctggcagtc
atggatatgttcgctcccctttcccctttcagtaagaactcaggagaccatgttgcaacaga
gacccagtgttttccaaggaaccaatggaaccagtgtaatcacacctttggatccaactg
ctcagctacgaatcatgccactgcctgctgggggcccttcaataagccaaggcctgccag
cctcccgttacaacactgctgcggatgccctggctgctcttgtggatgctgcagcttctg
cacccagatggatgtgtccaaaacaaaagagagtaagcatgaagctgccaggttagaag
aaaatttgagaagcaggtcagcagcagttagtgaacagcagcagctagagcagaaaaccc
tggaggtggagaagagatctgttcagtgtttatacacttcttcagccttccaagtggca
agccccagcctcattcttcagtagtttattctgaggctgggaaagataaagggcctcctc
caaaatccagatatgaggaagagctaaggaccagagggaagactaccattactgcagcta
acttcatagacgtgatcatcacccggcaaattgcctcggacaaggatgcgagggaacgtg
gctctcaaagttcagactcttctagtagcttatcttctcacaggtatgaaacacctagcg
atgctattgaggtgataagtcctgccagctcacctgcgccacccaggagaaactgcaga
cctatcagccagaggttgttaaggcaaatcaagcggaaaatgatcctaccagacaatatg
```

-continued

```
aaggaccattacatcactatcgaccacagcaggaatcaccatctccccaacaacagctgc
cccttcttcacaggcagagggaatggggcaagtgcccaggacccatcggctgatcacac
ttgctgatcacatctgtcaaattatcacacaagattttgctagaaatcaagtttcctcgc
agactccccagcagcctcctacttctacattccagaactcaccttctgctttggtatcta
cacctgtgaggactaaaacatcaaaccgttacagcccagaatcccaggctcagtctgtcc
atcatcaaagaccaggttcaagggtctctccagaaaatcttgtggacaaatccaggggaa
gtaggcctggaaaatccccagagaggagtcacgtctcttcggagccctacgagcccatct
cccccacccaggttccggttgtgcatgagaaacaggacagcttgctgctcttgtctcaga
ggggcgcagagcctgcagagcagaggaatgatgcccgctcaccagggagtataagctact
tgccttcattcttccaccaagcttgaaaatacatcacccatggttaaatcaaagaagcagg
agattttcgtaagttgaactcctctggtggaggtgactctgatatggcagctgctcagc
caggaactgagatctttaatctgccagcagttactacgtcaggctcagttagctctagag
gccattcttttgctgatcctgccagtaatcttgggctggaagacattatcaggaaggctc
tcatgggaagctttgatgacaaagttgaggatcatggagttgtcatgtcccagcctatgg
gagtagtgcctggtactgccaacacctcagttgtgaccagtggtgagacacgaagagagg
aaggggacccatcacctcattcaggaggagtttgcaaaccaaagctgatcagcaagtcaa
acagcaggaaatctaagtctcctatacctgggcaaggctacttaggaacggaacggccct
cttcagtctcctctgtacattcagaaggggattaccataggcagacgccagggtgggcct
gggaagacaggccctcttcaacaggctcaactcagtttccttataaccctctgactatgc
ggatgctcagcagtactccaccaacaccgattgcatgtgctccctctgcggtgaaccaag
cagctcctcaccaacagaacaggatctgggagcgagagcctgccccactgctctcagcac
agtacgagaccctgtcggatagtgatgactgaactgcacaaagtgaggggaacagggtgc
aggagagggatctctagttttttgtggtttaattttttagtagcaggtcaaaaacctgccct
cctgtgacttattccctgagacttttcaggagagccagcccacagatgatgaagaaatga
tggaagttcatttggagagtcaaatgggaaaaaaacaaacaaaaaactgcctttgataca
ggcaattcagtggactataataatagtggagggttgagatgtagagttttttaaaaagtga
acagttgctgttcttacatctgtaaagaaaaccataatgtctttaaatcactcttctgta
aatagatgaccttttttgcagtgtatatccccttgctgtagtatctggtgtacttatgttc
aaatcagcgcatcaactttgggggtgattttttaaaaatcttttttgtctatctatcttttt
aaccctagccttctaaacaacctcatacagcccagttacataatgttggctgtcacgggc
attgtacttttatctgatattgtttcctctaaattcagctttccagtgatgtttaaaatc
ttgtgaaaatgtttagattttttaacacagaccctgtcataaaatctgtacattagggtca
aaaggtaaaagtaacaaattctgccatattgtaaatttccagtgcaggctttaatttttt
ttttcattagtagcactgaaaaaatattactgcatgggtatgttctagttcagtttata
aagttttaaaggcttatttgaggcatacctcactgttacgcacactggtaatttaaccat
gcccctaagtattccttttctcctgcatttgatgcagcccaacaaagcttttgttttgaa
ataaatttgactaccctgtccatagctacagtagattatttgtggtttaaggctcctggt
gtctcaggttccaaaggaaaagcttacatattttccccttagtttgaatatatgattggt
tgggttaaaagataatgatctgtgtagtatttagataagctttatgctgcatcctgaaaa
actcatggtgaacacagtcctttttccccatcactatggaccagcatttactctcacttt
gctcccttgggacaagagtttactgttaaatgttttcatttcacagagtctcaaggtgca
```

-continued

```
aataatttaaaagactgaattctaaactaattatggtactagagggccagttttatcttt cattaagaattgcttgctgaatttttaaagttttttttcatacaatttatcatagcatttaa gtatctttctataacatagatactaacagttttgggagaatgccactggtaactggaaag gggagaaacagatctctcaggatgataaaaattagcactttacagactttcaagtagacc taaacttttaaacaaaagtactcaaggcttttaaggaagcagctctgtgattagctactg accaagaccctcctatcactggtgtctaatccctatgttacagatgaagacacaggttta gtactttgcccatatagttaaattagtgacagagataggccataagcccacatttgtctt cagtcaaagctttcactcctgtccctgttccactcctgtatacctgaggtccccaacata aactttagatcaggcttagtggtcagcattcctagtacttggaaagttggtattttttac aacagatatatgtaaacatataaaaatttcaaatgaatgaaaaacagtgactaaatgtt ccacttcacagttttctgctgaattttttttttttcaggtactggtaatattttagagttt gttaataatttatattgccaacctaccataaaagagattatgatggtattttttctatgac cctgagggtcttaagctattctgagtcagaatacagttgaccctttgaacaacacgggttt gaactgtgtgggtccacttatacatggattttcttccacctctgccacccaagatagcaa gaccaacccccttctcatcctcagcctattcaacatgaagatgacaaggatgaagaccttc atgatgatccacttccacttaatgaatagtaaatatattttctcttccttataatcttaa caaacattttctcttctctagcttactttattgtaagaatacagtatataatacatatac aaaatatgtgtcaaaaaaaaaaaaaaaa
```

By "NCOR1 polypeptide" is meant a polypeptide or fragment thereof having at least about 85% amino acid identity to NCBI Accession No. NP_006302.2 and having DNA binding activity, as reproduced below:

>NP_006302.2

(SEQ ID NO: 5)
MSSSGYPPNQGAFSTEQSRYPPHSVQYTFPNTRHQQEFAVPDYRSSH

LEVSQASQLLQQQQQQQLRRRPSLLSEFHPGSDRPQERRTSYEPFHP

GPSPVDHDSLESKRPRLEQVSDSHFQRVSAAVLPLVHPLPEGLRASA

DAKKDPAFGGKHEAPSSPISGQPCGDDQNASPSKLSKEELIQSMDRV

DREIAKVEQQILKLKKKQQQLEEEAAKPPEPEKPVSPPPVEQKHRSI

VQIIYDENRKKAEEAHKIFEGLGPKVELPLYNQPSDTKVYHENIKTN

QVMRKKLILFFKRRNHARKQREQKICQRYDQLMEAWEKKVDRIENNP

RRKAKESKTREYYEKQFPEIRKQREQQERFQRVGQRGAGLSATIARS

EHEISEIIDGLSEQENNEKQMRQLSVIPPMMFDAEQRRVKFINMNGL

MEDPMKVYKDRQFMNVWTDHEKEIFKDKFIQHPKNFGLIASYLERKS

VPDCVLYYYLTKKNENYKALVRRNYGKRRGRNQQIARPSQEEKVEEK

EEDKAEKTEKKEEEKKDEEEKDEKEDSKENTKEKDKIDGTAEETEER

EQATPRGRKTANSQGRRKGRITRSMTNEAAAASAAAAAATEEPPPPL

PPPPEPISTEPVETSRWTEEEMEVAKKGLVEHGRNWAAIAKMVGTKS

EAQCKNFYFNYKRRHNLDNLLQQHKQKTSRKPREERDVSQCESVAST

VSAQEDEDIEASNEEENPEDSEVEAVKPSEDSPENATSRGNTEPAVE

LEPTTETAPSTSPSLAVPSTKPAEDESVETQVNDSISAETAEQMDVD

QQEHSAEEGSVCDPPPATKADSVDVEVRVPENHASKVEGDNTKERDL

DRASEKVEPRDEDLVVAQQINAQRPEPQSDNDSSATCSADEDVDGEP

ERQRMFPMDSKPSLLNPTGSILVSSPLKPNPLDLPQLQHRAAVIPPM

VSCTPCNIPIGTPVSGYALYQRHIKAMHESALLEEQRQRQEQIDLEC

RSSTSPCGTSKSPNREWEVLQPAPHQVITNLPEGVRLPTTRPTRPPP

PLIPSSKTTVASEKPSFIMGGSISQGTPGTYLTSHNQASYTQETPKP

SVGSISLGLPRQQESAKSATLPYIKQEEFSPRSQNSQPEGLLVRAQH

EGVVRGTAGAIQEGSITRGTPTSKISVESIPSLRGSITQGTPALPQT

GIPTEALVKGSISRMPIEDSSPEKGREEAASKGHVIYEGKSGHILSY

DNIKNAREGTRSPRTAHEISLKRSYESVEGNIKQGMSMRESPVSAPL

EGLICRALPRGSPHSDLKERTVLSGSIMQGTPRATTESFEDGLKYPK

QIKRESPPIRAFEGAITKGKPYDGITTIKEMGRSIHEIPRQDILTQE

SRKTPEVVQSTRPIIEGSISQGTPIKFDNNSGQSAIKHNVKSLITGP

SKLSRGMPPLEIVPENIKVVERGKYEDVKAGETVRSRHTSVVSSGPS

VLRSTLHEAPKAQLSPGIYDDTSARRTPVSYQNTMSRGSPMMNRTSD

VTISSNKSTNHERKSTLTPTQRESIPAKSPVPGVDPVVSHSPFDPHH

RGSTAGEVYRSHLPTHLDPAMPFHRALDPAAAAYLFQRQLSPTGYP

SQYQLYAMENTRQTILNDYITSQQMQVNLRPDVARGLSPREQPLGLP

YPATRGIIDLTNMPPTILVPHPGGTSTPPMDRITYIPGTQITFPPRP

YNSASMSPGHPTHLAAAASAEREREREREKEREREREIAAASSDLYLR

PGSEQPGRPGSHGYVRSPSPSVRTQETMLQQRPSVFQGTNGTSVITP

-continued

```
LDPTAQLRIMPLPAGGPSISQGLPASRYNTAADALAALVDAAASAPQ

MDVSKTKESKHEAARLEENLRSRSAAVSEQQQLEQKTLEVEKRSVQC

LYTSSAFPSGKPQPHSSVVYSEAGKDKGPPPKSRYEEELRTRGKTTI

TAANFIDVIITRQIASDKDARERGSQSSDSSSSLSSHRYETPSDAIE

VISPASSPAPPQEKLQTYQPEVVKANQAENDPTRQYEGPLHHYRPQQ

ESPSPQQQLPPSSQAEGMGQVPRTHRLITLADHICQIITQDFARNQV

SSQTPQQPPTSTFQNSPSALVSTPVRTKTSNRYSPESQAQSVHHQRP

GSRVSPENLVDKSRGSRPGKSPERSHVSSEPYEPISPPQVPVVHEKQ
```

-continued

```
DSLLLLSQRGAEPAEQRNDARSPGSISYLPSFFTKLENTSPMVKSKK

QEIFRKLNSSGGGDSDMAAAQPGTEIFNLPAVTTSGSVSSRGHSFAD

PASNLGLEDIIRKALMGSFDDKVEDHGVVMSQPMGVVPGTANTSVVT

SGETRREEGDPSPHSGGVCKPKLISKSNSRKSKSPIPGQGYLGTERP

SSVSSVHSEGDYHRQTPGWAWEDRPSSTGSTQFPYNPLTMRMLSSTP

PTPIACAPSAVNQAAPHQQNRIWEREPAPLLSAQYETLSDSDD
```

By "NCOR2 nucleic acid molecule" is meant a polynucleotide encoding a NCOR2 polypeptide. An exemplary NCOR2 nucleic acid molecule is provided at NCBI Accession No. NM_006312.5, and reproduced below:

```
>NM_006312.5
                                              (SEQ ID NO: 6)
gccggcgccctaggaggcggcggcgggaggatcgcgtcccgacccgaggccgggcctgct gcgcgccccagcccgatcggcaccgccacttgcctgagcgccccggcggcccgagcgcg ccccaagcccgggcgccaccgctgccacctccgcgaggtctccctgagtctttgaggaca cagcctcgctggaggcagtttctggtgccagtgacggggtggcccgtgagctgatgacga ggactggcttttaatccttggtggtgattaagagaaagcttattggggcctgggagcagc tccccgccgaccccaccaccatgtcgggatccacacagcctgtggcacagacgtggagg gccactgagccccgctacccgccccacagcctttcctaccagtgcagatcgcccggacg cacacggacgtcgggctcctggagtaccagcaccactcccgcgactatgcctcccacctg tcgcccggctccatcatccagcccagcggcggaggccctccctgctgtctgagttccag cccgggaatgaacggtcccaggagctccacctgcggccagagtcccactcatacctgccc gagctggggaagtcagagatggagttcattgaaagcaagcgccctcggctagagctgctg cctgacccctgctgcgaccgtcaccctgctggccacgggccagcctgcgggatctgaa gacctcaccaaggaccgtagcctgacgggcaagctggaaccggtgtctcccccccagcccc ccgcacactgaccctgagctggagctggtgccgccacggctgtccaaggaggagctgatc cagaacatggaccgcgtggaccgagagatcaccatggtagagcagcagatctctaagctg aagaagaagcagcaacagctggaggaggaggctgccaagccgcccgagcctgagaagccc gtgtcaccgccgcccatcgagtcgaagcaccgcagcctggtgcagatcatctacgacgag aaccggaagaaggctgaagctgcacatcggattctggaaggcctggggcccaggtggag ctgccgctgtacaaccagccctccgacacccggcagtatcatgagaacatcaaaataaac caggcgatgcggaagaagctaatcttgtacttcaagaggaggaatcacgctcggaaacaa tgggagcagaagttctgccagcgctatgaccagctcatggaggctgggagaagaaggtg gagcgcatcgagaacaacccccggcggcgggccaaggagagcaaggtgcgcgagtactac gagaagcagttccctgagatccgcaagcagcgcgagctgcaggagcgcatgcagagcagg gtgggccagcggggcagtgggctgtccatgtcggccgcccgcagcgagcacgaggtgtca gagatcatcgatggcctctcagagcaggagaacctggagaagcagatgcgccagctggcc gtgatcccgcccatgctgtacgacgctgaccagcagcgcatcaagttcatcaacatgaac gggcttatggccgaccccatgaaggtgtacaaagaccgccaggtcatgaacatgtggagt gagcaggagaaggagaccttccgggagaagttcatgcagcatcccaagaactttggcctg atcgcatcattcctggagaggaagacagtggctgagtgcgtcctctattactacctgact
```

-continued

```
aagaagaatgagaactataagagcctggtgagacggagctatcggcgccgcggcaagagc cagcagcagcaacaacagcagcagcagcagcagcagcagcagcagcagcccatgccc cgcagcagccaggaggagaaagatgagaaggagaaggaaaaggaggcggagaaggaggag gagaagccggaggtggagaacgacaaggaagacctcctcaaggagaagacagacgacacc tcaggggaggacaacgacgagaaggaggctgtggcctccaaaggccgcaaaactgccaac agccagggaagacgcaaaggccgcatcacccgctcaatggctaatgaggccaacagcgag gaggccatcaccccccagcagagcgccgagctggcctccatggagctgaatgagagttct cgctggacagaagaagaaatggaaacagccaagaaaggtctcctggaacacggccgcaac tggtcggccatcgcccggatggtgggctccaagactgtgtcgcagtgtaagaacttctac ttcaactacaagaagaggcagaacctcgatgagatcttgcagcagcacaagctgaagatg gagaaggagaggaacgcgcggaggaagaagaagaaagcgccggcggcggccagcgaggag gctgcattcccgcccgtggtggaggatgaggagatggaggcgtcgggcgtgagcggaaat gaggaggagatggtggaggaggctgaagccttacatgcctctgggaatgaggtgcccaga ggggaatgcagtggcccagccactgtcaacaacagctcagacaccgagagcatcccctct cctcacactgaggccgccaaggacacagggcagaatgggcccaagccccagccaccctg ggcgccgacgggccaccccagggccacccaccccaccaccggaggacatcccggccccc actgagcccaccccggcctctgaagccaccggagcccctacgcccccaccagcaccccca tcgccctctgcacctcctcctgtggtcccaaggaggagaaggaggaggagaccgcagca gcgcccccagtggaggaggggggaggagcagaagcccccgcggctgaggagctggcagtg gacacagggaaggccgaggagcccgtcaagagcgagtgcacggaggaagccgaggagggg ccggccaagggcaaggacgcggaggccgctgaggccacggccgagggggcgctcaaggca gagaagaaggagggcgggagcggcagggccaccacagccaagagctcgggcgcccccag gacagcgactccagtgctacctgcagtgcagacgaggtggatgaggccgagggcggcgac aagaaccggctgctgtccccaaggcccagcctcctcaccccgactggcgaccccgggcc aatgcctcaccccagaagccactggacctgaagcagctgaagcagcgagcggctgccatc cccccatccaggtcaccaaagtccatgagccccccgggaggacgcagctcccaccaag ccagctcccccagcccaccgccaccgcaaaacctgcagccggagagcgacgcccctcag cagcctggcagcagccccggggcaagagcaggagcccggcaccccccgccgacaaggag gccttcgcagccgaggcccagaagctgcctggggaccccccttgctggacttccggcctg cccttccccgtgccccccgtgaggtgatcaaggcctccccgcatgccccggacccctca gccttctcctacgctccacctggtcacccactgccctgggcctccatgacactgcccgg cccgtcctgccgcgcccacccaccatctccaacccgcctcccctcatctcctctgccaag caccccagcgtcctcgagaggcaaataggtgccatctcccaaggaatgtcggtccagctc cacgtcccgtactcagagcatgccaaggccccgtgggccctgtcaccatggggctgccc ctgcccatggacccaaaagctggcaccttcagcggagtgaagcaggagcagctgtcc ccacggggccaggctgggccaccggagagcctgggggtgcccacagcccaggaggcgtcc gtgctgagagggacagctctgggctcagttccgggcggaagcatcaccaaaggcattccc agcacacgggtgccctcggacagcgccatcacataccgcggctccatcacccacggcacg ccagctgacgtcctgtacaagggcaccatcaccaggatcatcggcgaggacagcccgagt cgcttggaccgcggccgggaggacagcctgcccaagggccacgtcatctacgaaggcaag aagggccacgtcttgtcctatgagggtggcatgtctgtgacccagtgctccaaggaggac
```

-continued

```
ggcagaagcagctcaggacccccccatgagacggccgcccccaagcgcacctatgacatg
atggagggccgcgtgggcagagccatctcctcagccagcatcgaaggtctcatgggccgt
gccatcccgccggagcgacacagccccaccacctcaaagagcagcaccacatccgcggg
tccatcacacaagggatccctcggtcctacgtggaggcacaggaggactacctgcgtcgg
gaggccaagctcctaaagcgggagggcacgcctccgcccccaccgccctcacgggacctg
accgaggcctacaagacgcaggccctgggcccctgaagctgaagccggcccatgagggc
ctggtggccacggtgaaggaggcgggccgctccatccatgagatcccgcgcgaggagctg
cggcacacgcccgagctgcccctggccccgcggccgctcaaggagggctccatcacgcag
ggcaccccgctcaagtacgacaccggcgcgtccaccactggctccaaaaagcacgacgta
cgctccctcatcggcagccccggccgacgttccacccgtgcacccgctggatgtgatg
gccgacgcccgggcactggaacgtgcctgctacgaggagagcctgaagagccggccaggg
accgccagcagctcgggggctccattgcgcgcggcgccccggtcattgtgcctgagctg
ggtaagccgcggcagagcccctgacctatgaggaccacggggcacccttgccggccac
ctcccacgaggttcgcccgtgaccacgcgggagcccacgccgcgcctgcaggagggcagc
cttcgtccagcaaggcatcccaggaccgaaagctgacgtcgacgcctcgtgagatcgcc
aagtccccgcacagcaccgtgcccgagcaccaccacacccatctcgccctatgagcac
ctgcttcggggcgtgagtggcgtggacctgtatcgcagccacatcccctggccttcgac
cccacctccataccccgcggcatccctctggacgcagccgctgcctactacctgccccga
cacctggccccaaccccacctacccgcacctgtacccaccctacctcatccgcggctac
cccgacacggcggcgctggagaaccggcagaccatcatcaatgactacatcacctcgcag
cagatgcaccacaacgcggccaccgccatggcccagcgagctgatatgctgaggggcctc
tcgccccgcgagtcctcgctggcactcaactacgctgcgggtccccgaggcatcatcgac
ctgtcccaagtgccacacctgcctgtgctcgtgccccgacaccaggcaccccagccacc
gccatggaccgccttgcctacctccccaccgcgccccagcccttcagcagccgccacagc
agctccccactctccccaggaggtccaacacacttgacaaaaccaaccaccacgtcctcg
tccgagcgggagcgagaccgggatcgagagcgggaccgggatcgggagcgggaaaagtcc
atcctcacgtccaccacgacggtggagcacgcacccatctggagacctggtacagagcag
agcagcggcagcagcggcggggtgggggcagcagcagccgccccgcctcccactcccat
gcccaccagcactcgcccatctcccctcggacccaggatgccctccagcagagacccagt
gtgcttcacaacacaggcatgaagggtatcatcaccgctgtggagcccagcacgcccacg
gtcctgaggtccacctccacctcctcacccgttcgcccggctgccacattcccacctgcc
acccactgccactgggcggcaccctcgatggggtctaccctaccctcatggagcccgtc
ttgctgcccaaggaggcccccgggtcgcccggccagagcggccccgagcagacaccggc
catgccttcctcgccaagcccccagcccgctccgggctggagcccgcctcctcccccagc
aagggctcggagccccggcccctagtgcctcctgtctctggccacgccaccatcgcccgc
accccctgcgaagaacctcgcacctcaccacgccagcccggacccgccggcgccacctgcc
tcggcctcggacccgcaccgggaaaagactcaaagtaaaccttttccatccaggaactg
gaactccgttctctggttaccacggcagcagctacagccccgaaggggtggagcccgtc
agccctgtgagctcacccagtctgacccacgacaaggggctcccaagcacctggaagag
ctcgacaagagccacctggaggggagctgcggcccaagcagccaggccccgtgaagctt
```

-continued

```
ggcggggaggccgcccacctcccacacctgcggccgctgcctgagagccagccctcgtcc
agcccgctgctccagaccgccccaggggtcaaaggtcaccagcgggtggtcaccctggcc
cagcacatcagtgaggtcatcacacaggactacacccggcaccacccacagcagctcagc
gcacccctgcccgcccccctctactccttccctggggccagctgccccgtcctggacctc
cgccgcccacccagtgacctctacctcccgcccccggaccatggtgccccggcccgtggc
tcccccacagcgaaggggcaagaggtctccagagccaaacaagacgtcggtcttgggt
ggtggtgaggacggtattgaacctgtgtccccaccggagggcatgacggagccagggcac
tcccggagtgctgtgtacccgctgctgtaccgggatggggaacagacggagcccagcagg
atgggctccaagtctccaggcaacaccagccagccgccagccttcttcagcaagctgacc
gagagcaactccgccatggtcaagtccaagaagcaagagatcaacaagaagctgaacacc
cacaaccggaatgagcctgaatacaatatcagccagcctgggacggagatcttcaatatg
cccgccatcaccggaacaggccttatgacctatagaagccaggcggtgcaggaacatgcc
agcaccaacatggggctggaggccataattagaaaggcactcatgggtaaatatgaccag
tgggaagagtccccgccgctcagcgccaatgcttttaaccctctgaatgccagtgccagc
ctgcccgctgctatgcccataaccgctgctgacggacggagtgaccacacactcacctcg
ccaggtggcggcgggaaggccaaggtctctggcagacccagcagccgaaaagccaagtcc
ccggccccgggcctggcatctggggaccggccaccctctgtctcctcagtgcactcggag
ggagactgcaaccgccggacgccgctcaccaaccgcgtgtgggaggacaggccctcgtcc
gcaggttccacgccattcccctacaacccctgatcatgcggctgcaggcgggtgtcatg
gcttccccaccccaccgggcctccccgcgggcagcgggcccctcgctggccccaccac
gcctgggacgaggagcccaagccactgctctgctcgcagtacgagacactctccgacagc
gagtgactcagaacagggcggggggggggcggtgtcaggtcccagcgagccacaggaac
ggccctgcaggagcagggcggctgccgactccccaaccaaggaaggagcccctgagtcc
gcctgcgcctccatccatctgtccgtccagagccggcatccttgcctgtctaaagcctta
actaagactcccgccccgggctggccctgtgcagaccttactcaggggatgtttacctgg
tgctcgggaagggaggggaaggggccgggagggggcacggcaggcgtgtggcagccaca
cgcaggcggccagggcggccagggacccaaagcaggatgaccacgcacctccacgccact
gcctcccccgaatgcatttggaaccaaagtctaaactgagctcgcagccccgcgccctc
cctccgcctcccatcccgcttagcgctctggacagatggacgcaggccctgtccagcccc
cagtgcgctcgttccggtccccacagactgccccagccaacgagattgctggaaaccaag
tcaggccaggtgggcggacaaaagggccaggtgcggcctgggggaacggatgctccgag
gactggactgttttttttcacacatcgttgccgcagcggtgggaaggaaaggcagatgtaa
atgatgtgttggtttacagggtatattttgataccttcaatgaattaattcagatgttt
tacgcaaggaaggacttacccagtattactgctgctgtgcttttgatctctgcttaccgt
tcaagaggcgtgtgcaggccgacagtcggtgaccccatcactcgcaggaccaagggggcg
gggactgctggctcacgccccgctgtgtcctccctccctcccttccttgggcagaatgaa
ttcgatgcgtattctgtggccgccatctgcgcagggtggtggtattctgtcatttacaca
cgtcgttctaattaaaaagcgaattatactccagtta
```

By "NCOR2 polypeptide" is meant a polypeptide or fragment thereof having at least about 85% amino acid identity to NCBI Accession No. NP_006303.4 and having DNA binding activity, as reproduced below:

>NP_006303.4
(SEQ ID NO: 7)
MSGSTQPVAQTWRATEPRYPPHSLSYPVQIARTHTDVGLLEYQHHSRDYA

SHLSPGSIIQPQRRRPSLLSEFQPGNERSQELHLRPESHSYLPELGKSEM

EFIESKRPRLELLPDPLLRPSPLLATGQPAGSEDLTKDRSLTGKLEPVSP

PSPPHTDPELELVPPRLSKEELIQNMDRVDREITMVEQQISKLKKKQQQL

EEEAAKPPEPEKPVSPPPIESKHRSLVQIIYDENRKKAEAAHRILEGLGP

QVELPLYNQPSDTRQYHENIKINQAMRKKLILYFKRRNHARKQWEQKFCQ

RYDQLMEAWEKKVERIENNPRRRAKESKVREYYEKQFPEIRKQRELQERM

QSRVGQRGSGLSMSAARSEHEVSEIIDGLSEQENLEKQMRQLAVIPPMLY

DADQQRIKFINMNGLMADPMKVYKDRQVMNMWSEQEKETFREKFMQHPKN

FGLIASFLERKTVAECVLYYYLTKKNENYKSLVRRSYRRRGKSQQQQQQQ

QQQQQQQQQPMPRSSQEEKDEKEKEKEAEKEEEKPEVENDKEDLLKEKT

DDTSGEDNDEKEAVASKGRKTANSQGRRKGRITRSMANEANSEEAITPQQ

SAELASMELNESSRWTEEEMETAKKGLLEHGRNWSAIARMVGSKTVSQCK

NFYFNYKKRQNLDEILQQHKLKMEKERNARRKKKAPAAASEEAAFPPVV

EDEEMEASGVSGNEEEMVEEAEALHASGNEVPRGECSGPATVNNSSDTES

IPSPHTEAAKDTGQNGPKPPATLGADGPPPGPPTPPPEDIPAPTEPTPAS

EATGAPTPPPAPPSPSAPPPVVPKEEKEEETAAAPPVEEGEEQKPPAAEE

LAVDTGKAEEPVKSECTEEAEEGPAKGKDAEAAEATAEGALKAEKKEGGS

GRATTAKSSGAPQDSDSSATCSADEVDEAEGGDKNRLLSPRPSLLTPTGD

PRANASPQKPLDLKQLKQRAAAIPPIQVTKVHEPPREDAAPTKPAPPAPP

PPQNLQPESDAPQQPGSSPRGKSRSPAPPADKEAFAAEAQKLPGDPPCWT

SGLPFPVPPREVIKASPHAPDPSAFSYAPPGHPLPLGLHDTARPVLPRPP

TISNPPPLISSAKHPSVLERQIGAISQGMSVQLHVPYSEHAKAPVGPVTM

GLPLPMDPKKLAPFSGVKQEQLSPRGQAGPPESLGVPTAQEASVLRGTAL

GSVPGGSITKGIPSTRVPSDSAITYRGSITHGTPADVLYKGTITRIIGED

SPSRLDRGREDSLPKGHVIYEGKKGHVLSYEGGMSVTQCSKEDGRSSSGP

PHETAAPKRTYDMMEGRVGRAISSASIEGLMGRAIPPERHSPHHLKEQHH

IRGSITQGIPRSYVEAQEDYLRREAKLLKREGTPPPPPPSRDLTEAYKTQ

ALGPLKLKPAHEGLVATVKEAGRSIHEIPREELRHTPELPLAPRPLKEGS

ITQGTPLKYDTGASTTGSKKHDVRSLIGSPGRTFPPVHPLDVMADARALE

RACYEESLKSRPGTASSSGGSIARGAPVIVPELGKPRQSPLTYEDHGAPF

AGHLPRGSPVTTREPTPRLQEGSLSSSKASQDRKLTSTPREIAKSPHSTV

PEHHPHPISPYEHLLRGVSGVDLYRSHIPLAFDPTSIPRGIPLDAAAAYY

LPRHLAPNPTYPHLYPPYLIRGYPDTAALENRQTIINDYITSQQMHHNAA

TAMAQRADMLRGLSPRESSLALNYAAGPRGIIDLSQVPHLPVLVPPTPGT

PATAMDRLAYLPTAPQPFSSRHSSSPLSPGGPTHLTKPTTTSSSERERDR

DRERDRDREREKSILTSTTTVEHAPIWRPGTEQSSGSSGGGGSSSRPAS

HSHAHQHSPISPRTQDALQQRPSVLHNTGMKGIITAVEPSTPTVLRSTST

SSPVRPAATFPPATHCPLGGTLDGVYPTLMEPVLLPKEAPRVARPERPRA

DTGHAFLAKPPARSGLEPASSPSKGSEPRPLVPPVSGHATIARTPAKNLA

PHHASPDPPAPPASASDPHREKTQSKPFSIQELELRSLGYHGSSYSPEGV

EPVSPVSSPSLTHDKGLPKHLEELDKSHLEGELRPKQPGPVKLGGEAAHL

PHLRPLPESQPSSSPLLQTAPGVKGHQRVVTLAQHISEVITQDYTRHHPQ

QLSAPLPAPLYSFPGASCPVLDLRRPPSDLYLPPPDHGAPARGSPHSEGG

KRSPEPNKTSVLGGGEDGIEPVSPPEGMTEPGHSRSAVYPLLYRDGEQTE

PSRMGSKSPGNTSQPPAFFSKLTESNSAMVKSKKQEINKKLNTHNRNEPE

YNISQPGTEIFNMPAITGTGLMTYRSQAVQEHASTNMGLEAIIRKALMGK

YDQWEESPPLSANAFNPLNASASLPAAMPITAADGRSDHTLTSPGGGGKA

KVSGRPSSRKAKSPAPGLASGDRPPSVSSVHSEGDCNRRTPLTNRVWEDR

PSSAGSTPFPYNPLIMRLQAGVMASPPPPGLPAGSGPLAGPHHAWDEEPK

PLLCSQYETLSDSE

Retinoid X receptor (RXR)

The RXRs represent a family of nuclear receptors having three subtypes: RXR Alpha (RXRA), RXR Beta (RXRB), and RXR Gamma (RXRG), which are encoded by RXRA, RXRB, and RXRG genes located on chromosomes 9 (band q34.3), 6 (band 21.3), and 1 (band q22-q23), respectively. 9-cis-retinoic acid (9-cis-RA) was initially identified as a candidate natural ligand, but many researchers were not able to identify endogenous 9-cis-RA in either in cells, in culture, or in vivo without addition of its isomer all-trans retinoic acid (ATRA). Other RXR ligands are polyunsaturated fatty acids, such as docosahexaenoic acid, arachidonic acid, and oleic acid, and phytanic acid, a saturated metabolite of chlorophyll.

RXR functions as a transcription factor and binds as a homodimer or heterodimer to a enhancer known as a RXR response element (RRE), which is a 6 bp sequences of DNA in the promoter regions of specific genes. The RRE is composed of two 6 bp sequences (half-sites) separated by a discrete number of bases to which the RXR homo- or hetero-dimer binds, and has the following consensus sequence 5'-PuG(G/T)TCA-(X)n-PuG(G/T)TCA-3' (SEQ ID NO: 8). The specific DNA sequence of the RRE is determined by binding site specificity of the homo- or hetero-dimer nuclear receptor partner. The consensus sequences may be reiterated directly (DR), inverted (IR), everted (ER), palindromic (pal), or disordered in relation to the dimer bound (see e.g., De Cosmo et al. (2017) *Front Endocrinol* 8:24).

As is the case with other type II nuclear receptors, the RXR heterodimer in the absence of ligand is bound to hormone response elements complexed with corepressor protein. Binding of RXR agonists results in dissociation of corepressor and recruitment of coactivator protein, which promotes transcription of downstream target genes.

By "RXRA nucleic acid molecule" is meant a polynucleotide encoding a RXRA polypeptide. An exemplary RXRA nucleic acid molecule is provided at NCBI Accession No. NM_002957.5, and reproduced below:

>NM_002957.5

(SEQ ID NO: 9)

ttgtttgggcgacttttgcaacaactcgccgcgccgcggcctccgcgcgcc gccgccgccaccgcagccgccggctccccgccgcccgggcccgggccggc cgcgccggggccgccgcgcccgccgccgctgcctgccgccgcggccgg gcatgagttagtcgcagacatggacaccaaacatttcctgccgctcgatt tctccacccaggtgaactcctccctcacctccccgacggggcgaggctcc atggctgcccctcgctgcaccgtccctggggcctggcatcggctcccc gggacagctgcattctcccatcagcaccctgagctcccccatcaacggca tgggcccgcctttctcggtcatcagctcccccatgggcccccactccatg tcggtgccaccacacccaccctgggcttcagcactggcagccccagct cagctcacctatgaaccccgtcagcagcagcgaggacatcaagcccccc tgggcctcaatggcgtcctcaaggtcccgcccacccctcaggaaacatg gcttccttcaccaagcacatctgcgccatctgcggggaccgctcctcagg caagcactatggagtgtacagctgcgaggggtgcaagggcttcttcaagc ggacggtgcgcaaggacctgacctacacctgccgcgacaacaaggactgc ctgattgacaagcggcagcggaaccggtgccagtactgccgctaccagaa gtgcctggccatgggcatgaagcgggaagccgtgcaggaggagcggcagc gtggcaaggaccggaacgagaatgaggtggagtcgaccagcagcgccaac gaggacatgccggtggagaggatcctggaggctgagctggccgtggagcc caagaccgagacctacgtggaggcaaacatggggctgaaccccagctcgc cgaacgaccctgtcaccaacatttgccaagcagccgacaaacagctttc accctggtggagtgggccaagcggatcccacacttctcagagctgcccct ggacgaccaggtcatcctgctgcgggcaggctggaatgagctgctcatcg cctccttctcccaccgctccatcgccgtgaaggacgggatcctcctggcc accgggctgcacgtccaccggaacagcgcccacagccgcagggtgggcgc catctttgacagggtgctgacggagcttgtgtccaagatgcgggacatgc agatggacaagacggagctgggctgcctgcgcgcatcgtcctctttaac cctgactccaaggggctctcgaacccggccgaggtggaggcgctgaggga gaaggtctatgcgtccttggaggcctactgcaagcacaagtaccagagc agccgggaaggttcgctaagctcttgctccgcctgccggctctgcgctcc atcgggctcaaatgcctggaacatctcttcttcttcaagctcatcgggga cacacccattgacaccttccttatggagatgctggaggcgccgcaccaaa tgacttaggcctgcgggccatcctttgtgcccaccgttctggccaccc tgcctggacgccagctgttcttctcagcctgagcctgtccctgccttc tctgcctggcctgtttggactttggggcacagcctgtcactgctctgcct aagagatgtgttgtcaccctccttatttctgttactacttgtctgtggcc cagggcagtggctttcctgaggcagcagccttcgtggcaagaactagcgt gagcccagccaggcgcctcccaccgggctctcaggacaccctgccacac cccacggggcttgggcgactacaggtcttcgggccccagccctggagct gcaggagttgggaacgggcttttgtttccgttgctgtttatcgatgctg gttttcagaattcctgtgtggccctcctgtctggagtgacatcttcatct gctctgaatactggtgcccagccagcccgtgacagcttcccccctaatcag gaggggacagctggggcgcaagctggtgtgtcatcagcaaagacctcag ccgcctcggggatgagaggggactcgtggggcaagcaagctgccctgtgc tctgagtgagggggaaggtagcccctttttccaaagataactcacagttt tgccctcgagccaatgagaacatgagctgccctctgtgcaaggtttcggg gccacctccaggctgcaggggcgggtcactcaccccctgttttctctct gccttggtgttctggtttcagactcccgactcccgttcagaccagagtg ccccggcccctccccagcctgagtcttctccttgctctgcggggtgggct gaggcttgtccttgtttcctgcagggctggccctggctcgggcagggtgg ggcatcaccacctcactggccttgctggaggcacagggctctgcggacct gcagccatctgtgaggcccgcggggatgggaggggaggagggtggcctgt tggtttccctcagaggggcaggtggcctggagagagaggggctcaggaa ctgggagcctcgtgggtggggcagatgctccgcggcctggagtggctctg ccggggcattggtgggaccctgctcaggccttctctctggctgccagtt gtgtctaaaagactcttgaatctgagaacccggagtcgcagcgccctcg ggcctgggccacacgcaggccctggtgggaccacccagcctggtattgtc cacggacacgcgttgttcacccagagccttacttgggagcctcactgaacg cctgctctggttgaaggtggggtggggcggggcttggggcctccctggc tcagcccagtgcggcctggcgctcctcccgcaggctctgcccccgggctc cggtggtgcggggccctctcaggttgaactcgcctcttttgcactggaag gccctcccttggcctgagtacttttcccgttcacgcctcagtcccgtgg acccagcctttgtcagtggcaggtgcctgaacagagggtggatgggggg ataccgaggggtcttgtcttcccagccgcagtctaggaatgatgcggg ggggtggacgccttctccatagtctttccccacctggagcagggcttcc tcagtggtgaggggagctgcctacaggttggaccgggaggcagtggcttg gagaggcagctttccagccttggtggggaagaaagtgtccattcttgcc ttcctggagctcccagccagagctgagcttaggcacccgagtggagcctg cagctgagtctgtgcccgagacaggctgtcagagattccagaagcctctc ctccccgccgccctccaccctgcctttcagcgttgtggatccctagagg tggcccctgcccgatccaccgtcctgaggcagagtgttgagcctcatac ctgtaccaggtccccggccagctgggcccctcccaggcactgccaggaag ccccagctgcccctggcgggtgtggtggaaatggcaggagggtgcaggta ctcttggggccccagcggtgggagtgcaaaagacccaacgccaacacctg gtgccttctgcagccagcgccacccatccgtgcccggaccttgggaat gcccgcggctccagaggaaaaagcccagggacggggcctccgttgcgggg ggtcggctgcttcttgggaactttgtcgtttccggcgctggctggctggc tggctggctgtaaagcactgaagccccccggccgccaacccctgaaagca gaacctggcctccctggccacagcagccttacccaccgctctacgtgtcc cgggcacttcccgcagccttcccgtccctttctcatcggccttgtagttg tacagtgctgttggtttgaaaaggtgatgtgtggggagtgcggctcatca ctgagtagagaggtagaatttctatttaaccagacctgtagtagtattac

```
caatccagttcaattaaggtgattttttgtaattattattattttggtgg gacaatctttaattttctaaagatagcactaacatcagctcattagccac ctgtgcctgtccccgccttggcccggctggatgaagcggcttccccgcag ggcccccacttcccagtggctgcttcctggggacccagggcaccccggca ccttcaggcacgctcctcagctggtcacctcccggctttgccgttcagat ggggctcctgaggctcaggagtgaagatgccacagagccgggctcccta ggctgcgtcgggcatgcttggaagctggcctgccaggaccttccaccctg gggcctgtgtcagccgccggccctccgcaccctggaagcacacggcctct gggaaggacagccctgaccttcggttttccgagcacggtgtttcccaaga attctgggctggcggcctggtggcagtgctggagatgaccccgagccct ccccgtggggcacccaggagggccctgccggaatgtgcagcctgtgggta gtcggctggtgtccctgtcgtggagctggggtgcgtgatctggtgctcgt ccacgcaggtgtgtggtgtaaacatgtatgtgctgtacagagagacgcgt gtggagagagccgcacaccagcgccacccaggaaaggcggagcggttacc agtgttttgtgtttattttaatcaagacgtttccctgttttcctataa atttgcttcgtgtaagcaagtacataaggaccctcctttggtgaaatccg ggttcgaatgaatatctcaaggcaggagatgcatctattttaagatgctt tggagcagacagctttagccgttcccaatccttagcaatgccttagctgg gacgcatagctaatactttagagaggatgacagatccataaagagagtaa agataagagaaaatgtctaaagcatctggaaaggtaaaaaaaaaaaatct attttgtacaaatgtaattttatccctcatgtatacttggatatggcgg ggggagggctgggactgtttcgtttctgcttctagagattgaggtgaaag cttcgtccgagaaacgccaggacagacgatggcagaggagagggctcctg tgacggcggcgaggcttgggaggaaaccgccgcaatgggggtgtcttccc tcggggcaggagggtgggcctgaggcttcaagggttttcttccctttcg agtaattttaaagccttgctctgttgtgtcctgttgccggctctggcct tcctgtgactgactgtgaagtggcttctccgtacgattgtctctgaaaca tcgtggcctcaggtgccagggtttgatggacagtagcattagaattgtgg aaaaggaacacgcaaagggagaagtgtgagaggagaaacaaaatatgagc gtttaaaatacatcgccattcagttcgttt
```

By "RXRA polypeptide" is meant a polypeptide or fragment thereof having at least about 85% amino acid identity to NCBI Accession No. NP_002948.1 and having DNA binding activity, as reproduced below:

```
>NP_002948.1
                                    (SEQ ID NO: 10)
MDTKHFLPLDFSTQVNSSLTSPTGRGSMAAPSLHPSLGPGIGSPGQLHSP

ISTLSSPINGMGPPFSVISSPMGPHSMSVPTTPTLGFSTGSPQLSSPMNP

VSSSEDIKPPLGLNGVLKVPAHPSGNMASFTKHICAICGDRSSGKHYGVY

SCEGCKGFFKRTVRKDLTYTCRDNKDCLIDKRQRNRCQYCRYQKCLAMGM

KREAVQEERQRGKDRNENEVESTSSANEDMPVERILEAELAVEPKTETYV

EANMGLNPSSPNDPVTNICQAADKQLFTLVEWAKRIPHFSELPLDDQVIL

LRAGWNELLIASFSHRSIAVKDGILLATGLHVHRNSAHSAGVGAIFDRVL

TELVSKMRDMQMDKTELGCLRAIVLFNPDSKGLSNPAEVEALREKVYASL

EAYCKHKYPEQPGRFAKLLLRLPALRSIGLKCLEHLFFFKLIGDTPIDTF

LMEMLEAPHQMT
```

Diagnostics

The present disclosure features diagnostic assays for the detection of PPARG cancers or the propensity to develop such cancers. In one embodiment, levels of any one or more of the following markers Uroplakin 1A (UPK1A), Uroplakin 1B (UPK1B), Uroplakin (UPK2), Keratin 20 (KRT20), GATA Binding Protein 3 (GATA3), Nuclear Receptor Corepressor 1 (NCOR1), Nuclear Receptor Corepressor 2 (NCOR2), Fatty Acid Binding Protein 4 (FABP4), Forkhead Box A1 (FOXA1), CD36 Molecule (CD36), Acyl-CoA Oxidase 1 (ACOX1), 3-Hydroxy-3-Methylglutaryl-CoA Synthase 2 (HMGCS2), Acyl-CoA Synthetase Long-Chain Family Member 5 (ACSL5), Arachidonate 5-Lipoxygenase (ALOX5), and Acyl-CoA Synthetase Long-Chain Family Member 1 (ACSL1), are measured in a subject sample and used to characterize or detect PPARG cancers or the propensity to develop such cancers. In an embodiment, expression levels of PPARG target genes including, but not limited to, ACOX1, ALOX5, ACSL1, ACSL5, FABP4, HMGS2, and/or CD36 may be assessed to indicate an active PPARG pathway. In other embodiments, levels of luminal differentiation markers in the bladder including, but not limited to PPARG, UPK1A, UPK1B, UPK2, KRT20, FOXA1, and/or GATA3 may be characterized in a subject sample and useful to select patients or patient populations. In other embodiments, levels of lipid metabolites in urine may be characterized in a subject sample and useful to select patients or patient populations.

By "UPK1A nucleic acid molecule" is meant a polynucleotide encoding a UPK1A polypeptide. An exemplary UPK1A nucleic acid molecule is provided at NCBI Accession No. NM_007000.3, and reproduced below:

```
>NM_007000.3
                                    (SEQ ID NO: 11)
cagagaggctgcagacagagaaggatgatggcgtctgcggcagcagcgga ggccgagaagggatctccagttgtggtgggcctgctagttgtgggcaata tcattattctgctgtcaggcctgtccctgtttgctgagaccatatggtg acagccgaccagtaccgtgtatacccactgatgggagtctcaggcaagga tgacgtcttcgctggtgcctggattgccatcttctgcggcttctcctct tcatggtagccagttttggtgtgggtgccgcactctgccgccgccggtcc atggtcctcacgtacctggtgctcatgctcatcgtctacatcttcgagtg cgcctcctgcatcacgtcctacacccaccgtgactacatggtgtccaacc catccctgatcaccaagcagatgctgaccttctacagcgcggacaccgac cagggcaggagctgacccgcctctgggaccgcgtcatgattgagcaaga atgctgtggcacatctggtcccatggactgggtgaacttcacgtcagcct tccgggcggccactccggaggtggtgttccctggccccactgtgctgt cgccggacgggaaacttcatcccctcaacgaggagggctgccgcctggg gcacatggactacctgttcaccaagggctgcttcgaacacatcggccacg
```

```
ccatcgacagctacacgtggggtatctcgtggtttgggtttgccatcctg
atgtggacgctcccggtcatgctgatagccatgtatttctacaccatgct
ctgagggacaggaggggaaggcaacatacacaccccggactcctccgcat
cctcctcctgcttcctccgctgggcctggatggctgcctcacctctcacc
tcccaacgtccctagcccttacgtccttccacttccaagatcttttcca
ggttcctgagccctactgtgtctcaggtgtgccctgaaaccccagggctt
gtgtgcacatatccttagcccatctttcaagggacctctccatgatccca
cctcccattcacagatacctctcttgtagctctctgacctcctccttcat
ggcaggcatcgccattcttgctgaaccgtttgtgattgccatttgagctc
tggaagcctctattgccatgagagttctgtcacggtcactttactgtccc
catcatcacccagcacgggctaagcatatactagatagtcaataaataa
ataaataatgaatgaatgaaaaaaaaaaaaaaaa
```

By "UPK1A polypeptide" is meant a polypeptide or fragment thereof having at least about 85% amino acid identity to NCBI Accession No. NP_008931.1, as reproduced below:

```
>NP_008931.1
                                              (SEQ ID NO: 12)
MASAAAAEAEKGSPVVVGLLVVGNIIILLSGLSLFAETIWVTADQYRVYP

LMGVSGKDDVFAGAWIAIFCGFSFFMVASFGVGAALCRRRSMVLTYLVLM

LIVYIFECASCITSYTHRDYMVSNPSLITKQMLTFYSADTDQGQELTRLW

DRVMIEQECCGTSGPMDWVNFTSAFRAATPEVVFPWPPLCCRRTGNFIPL

NEEGCRLGHMDYLFTKGCFEHIGHAIDSYTWGISWFGFAILMWTLPVMLI

AMYFYTML
```

By "UPK1B nucleic acid molecule" is meant a polynucleotide encoding a UPK1B polypeptide. An exemplary UPK1B nucleic acid molecule is provided at NCBI Accession No. NM_006952.3, and reproduced below:

```
>NM_006952.3
                                              (SEQ ID NO: 13)
acctgggtcgggtgcagactgcggagcgggccctaccgtgtgcgcagaaa gaggaggcgcttgccttcagcttgtgggaaatcccgaagatggccaaaga caactcaactgttcgttgcttccagggcctgctgattttggaaatgtga ttattggttgttgcggcattgccctgactgcggagtgcatcttcttgta tctgaccaacacagcctctaccactgcttgaagccaccgacaacgatga catctatgggctgcctggatcggcatatttgtgggcatctgcctcttct gcctgtctgttctaggcattgtaggcatcatgaagtccagcaggaaatt cttctggcgtatttcattctgatgtttatagtatatgcctttgaagtggc atcttgtatcacagcagcaacacaacaagactttttcacacccaacctct tcctgaagcagatgctagagaggtaccaaaacaacagccctccaaacaat gatgaccagtggaaaaacaatggagtcaccaaaacctgggacaggctcat gctccaggacaattgctgtggcgtaaatggtccatcagactggcaaaaat acacatctgcctccggactgagaataatgatgctgactatccctggcct cgtcaatgctgtgttatgaacaatcttaaagaacctctcaacctggaggc ttgtaaactaggcgtgcctggtttttatcacaatcagggctgctatgaac tgatctctggtccaatgaaccgacacgcctgggggggttgcctggtttgga tttgccattctctgctggacttttgggttctcctgggtaccatgttcta ctggagcagaattgaatattaagcataaagtgttgccaccatacctcctt ccccgagtgactctggatttggtgctggaaccagctctcctaatattc cacgttgtgccccacactaacgtgtgtgtcttacattgccaagtcagat ggtacggacttcctttaggatctcaggcttctgcagttctcatgactcct acttttcatcctagtctagcattctgcaacatttatatagactgttgaaa ggagaatttgaaaaatgcataataactacttccatccctgcttatttta atttgggaaaataaatacattcgaaggaacctgtgttatcacagtaaccc agagctgtatttggctagcaatctgcctgtatctctcactattatctaaa agaaaccttccaatgcttctgttgatctcagtattgtcaggggaacagag aagttgggaaaagattactgaaatatacctttttgcatttctttctagagt agctcccatatatggagatgggtgattctcttgatgccaccttcagatcc ttttattctccagaataattcttaacagtggttcaaatttcctttcatac cttgaagtatgtgtttagtagcctcaattctccattaattaaaagtgtgg gctgggcgtgggggctcatgcctgtaatcccagcactttgggaggccgag gtgggcagatcacctgaggtcaggagttcaagaccagcctggccaacatg gtgaaacccgtctctacaaaaatacaaaaattagccaggcgtgatggca ggtgcctgtaatcctagctacttggcaggctaacgcaggagaatcacttg accgggagacagaggttgcagtgagctgagatcgtacctattgcactcca tcctggatgaaagagccagactctgtctcaaaacaaacaaaaaagcgtgg ggacttctggggacagacaaggtgcctgttatatatttactcagtctttg ccctgaatggtctcagcttgagaccatttcaaactggagagaagcaagcc agccaatagaatggggtgatttacagggatttctgtttactgtcaaaata tttctcatctgcactatgtttccatttgtggtcctgaaggaaattcttat aactcaacatttgtctggtcttataagtaaagacagctttaaaatctgtt cactttcaaa
```

By "UPK1B polypeptide" is meant a polypeptide or fragment thereof having at least about 85% amino acid identity to NCBI Accession No. NP_008883.2, as reproduced below:

```
>NP_008883.2
                                              (SEQ ID NO: 14)
MAKDNSTVRCFQGLLIFGNVIIGCCGIALTAECIFFVSDQHSLYPLLEAT

DNDDIYGAAWIGIFVGICLFCLSVLGIVGIMKSSRKILLAYFILMFIVYA

FEVASCITAATQQDFFTPNLFLKQMLERYQNNSPPNNDDQWKNNGVTKTW

DRLMLQDNCCGVNGPSDWQKYTSAFRTENNDADYPWPRQCCVMNNLKEPL

NLEACKLGVPGFYHNQGCYELISGPMNRHAWGVAWFGFAILCWTFWVLLG

TMFYWSRIEY
```

By "UPK2 nucleic acid molecule" is meant a polynucleotide encoding a UPK2 polypeptide. An exemplary UPK2 nucleic acid molecule is provided at NCBI Accession No. NM_006760.3, and reproduced below:

>NM_006760.3
(SEQ ID NO: 15)
acttgcctcaggaacccagcctgccagcacctattccacctcccagccc agcatggcacccctgctgcccatccggaccttgcccttgatcctgattct gctggctctgctgtccccaggggctgcagacttcaacatctcaagcctct ctggtctgctgtccccggcgctaacggagagcctgctggttgccttgccc ccctgtcacctcacaggaggcaatgccacactgatggtccggagagccaa tgacagcaaagtggtgacgtccagctttgtggtgcctccgtgccgtgggc gcagggaactggtgagtgtggtggacagtggtgctggcttcacagtcact cggctcagtgcataccaggtgacaaacctcgtgccaggaaccaaattcta catttcctacctagtgaagaagggacagccactgagtccagcagagaga tcccaatgtccacactccctcgaaggaacatggaatccattgggctggt atggcccgcacaggggcatggtggtcatcacggtgctgctctctgtcgc catgttcctgctggtgctgggcttcatcattgccctggcactgggctcc gcaagtaaggaggtctgccggagcagcagcttctccaggaagcccaggg caccatccagctccccagcccacctgctcccaggcccaggcctgtggct cccttggtgccctcgcctcctcctcctgccctcctctcccctagagccct ctcctccctctgtccctctccttgccccagtgcctcaccttccaacact ccattattcctctcaccccactcctgtcagagttgactttcctcccattt taccactttaaacaccccataacaattcccccatccttcagtgaactaa gtccctataataaaggctgaggctgcatctgccaaaaaaaaaaaa By "UPK2 polypeptide" is meant a polypeptide or fragment thereof having at least about 85% amino acid identity to NCBI Accession No. NP_006751.1, as reproduced below:

>NP_006751.1
(SEQ ID NO: 16)
MAPLLPIRTLPLILILLALLSPGAADFNISSLSGLLSPALTESILVALPP

CHLTGGNATLMVRRANDSKVVTSSFVVPPCRGRRELVSVVDSGAGFTVTR

LSAYQVTNLVPGTKFYISYLVKKGTATESSREIPMSTLPRRNMESIGLGM

ARTGGMVVITVLLSVAMFLLVLGFIIALALGSRK

By "KRT20 nucleic acid molecule" is meant a polynucleotide encoding a KRT20 polypeptide. An exemplary KRT20 nucleic acid molecule is provided at NCBI Accession No. NM_019010.2, and reproduced below:

>NM_019010.2
(SEQ ID NO: 17)
gagacacactctgccccaaccatcctgaagctacaggtgctccctcctgg aatctccaatggatttcagtcgcagaagcttccacagaagcctgagctcc tccttgcaggccctgtagtcagtacagtgggcatgcagcgcctcgggac gacacccagcgtttatgggggtgctggaggccggggcatccgcatctcca actccagacacacggtgaactatgggagcgatctcacaggcggcgggac ctgtttgttggcaatgagaaaatggccatgcagaacctaaatgaccgtct agcgagctacctagaaaaggtgcggaccctggagcagtccaactccaaac ttgaagtgcaaatcaagcagtggtacgaaaccaacgccccgagggctggt cgcgactacagtgcatattacagacaaattgaagagctgcgaagtcagat taaggatgctcaactgcaaaatgctcggtgtgtcctgcaaattgataatg ctaaactggctgctgaggacttcagactgaagtatgagactgagagagga atacgtctaacagtggaagctgatctccaaggcctgaataaggtctttga tgacctaaccctacataaaacagatttggagattcaaattgaagaactga ataaagacctagctctcctcaaaaaggagcatcaggaggaagtcgatggc ctacacaagcatctgggcaacactgtcaatgtggaggttgatgctgctcc aggcctgaaccttggcgtcatcatgaatgaaatgaggcagaagtatgaag tcatggcccagaagaaccttcaagaggccaaagaacagtttgagagacag actgcagttctgcagcaacaggtcacagtgaatactgaagaattaaaagg aactgaggttcaactaacggagctgagacgcacctcccagagccttgaga tagaactccagtcccatctcagcatgaaagagtctttggagcacactcta gaggagaccaaggcccgttacagcagccagttagccaacctccagtcgct gttgagctctctggaggcccaactgatgcagattcggagtaacatggaac gccagaacaacgaataccatatccttcttgacataaagactcgacttgaa caggaaattgctacttaccgccgccttctggaaggagaagacgtaaaaac tacagaatatcagttaagcaccctggaagagagagatataaagaaaacca ggaagattaagacagtcgtgcaagaagtagtggatggcaaggtcgtgtca tctgaagtcaaagaggtggaagaaaatatctaaatagctaccagaaggag atgctgctgaggttttgaaagaaatttggctataatcttatctttgctcc ctgcaagaaatcagccataagaaagcactattaatactctgcagtgatta gaaggggtggggtggcgggaatcctatttatcagactctgtaattgaata taaatgttttactcagaggagctgcaaattgcctgcaaaaatgaaatcca gtgagcactagaatatttaaaacatcattactgccatctttatcatgaag cacatcaattacaagctgtagaccacctaatatcaatttgtaggtaatgt tcctgaaaattgcaatacatttcaattatactaaacctcacaaagtagag gaatccatgtaaattgcaaataaaccactttctaattttttcctgtttct gaattgtaaaacccctttgggagtccctggtttcttattgagccaattt ctggg By "KRT20 polypeptide" is meant a polypeptide or fragment thereof having at least about 85% amino acid identity to NCBI Accession No. NP_061883.1, as reproduced below:

>NP_061883.1
(SEQ ID NO: 18)
MDFSRRSFHRSLSSSLQAPVVSTVGMQRLGTTPSVYGGAGGRGIRISNSR

HTVNYGSDLTGGGDLFVGNEKMAMQNLNDRLASYLEKVRTLEQSNSKLEV

QIKQWYETNAPRAGRDYSAYYRQIEELRSQIKDAQLQNARCVLQIDNAKL

AAEDFRLKYETERGIRLTVEADLQGLNKVFDDLTLHKTDLEIQIEELNKD

LALLKKEHQEEVDGLHKHLGNTVNVEVDAAPGLNLGVIMNEMRQKYEVMA

QKNLQEAKEQFERQTAVLQQQVTVNTEELKGTEVQLTELRRTSQSLEIEL

QSHLSMKESLEHTLEETKARYSSQLANLQSLLSSLEAQLMQIRSNMERQN

NEYHILLDIKTRLEQEIATYRRLLEGEDVKTTEYQLSTLEERDIKKTRKI

KTVVQEVVDGKVVSSEVKEVEENI

By "GATA3 nucleic acid molecule" is meant a polynucleotide encoding a GATA3 polypeptide. An exemplary GATA3 nucleic acid molecule is provided at NCBI Accession No. NM_001002295.1, and reproduced below:

>NM_001002295.1
(SEQ ID NO: 19)
ggcgccgtcttgatactttcagaaagaatgcattccctgtaaaaaaaaa aaaaaatactgagagagggagagagagagagaagaagagagagagacgga gggagagcgagacagagcgagcaacgcaatctgaccgagcaggtcgtacg ccgccgcctcctcctctctgctcttcgctacccaggtgacccgagga gggactccgcctccgagcggctgaggaccccggtgcagaggagcctggct cgcagaattgcagagtcgtcgccccttttacaacctggtcccgttttat tctgccgtacccagttttggattttttgtcttccccttcttctctttgct aaacgacccctccaagataattttttaaaaaaccttctcctttgctcacct ttgcttcccagccttcccatcccccaccgaaagcaaatcattcaacgac ccccgaccctccgacggcaggagcccccgacctcccaggcggaccgccc tccctccccgcgcgcggttccgggccggcgagagggcgcgagcacagc cgaggccatggaggtgacggcggaccagccgcgctgggtgagccaccacc accccgccgtgctcaacgggcagcacccggacacgcaccacccgggcctc agccactcctacatggacgcggcgcagtaccgctgccggaggaggtgga tgtgcttttttaacatcgacggtcaaggcaaccacgtcccgccctactacg gaaactcggtcagggccacggtgcagaggtaccctccgacccaccacggg agccaggtgtgccgccgcctctgcttcatggatccctaccctggctgga cggcggcaaagccctgggcagccaccacaccgcctcccctggaatctca gccccttctccaagacgtccatccaccacggctcccggggcccctctcc gtctacccccggcctcgtcctcctccttgtcggggggccacgccagccc gcacctcttcaccttcccgcccaccccgccgaaggacgtctccccggacc catcgctgtccaccccaggctcggccggctcggccggcaggacgagaaa gagtgcctcaagtaccaggtgccctgcccgacagcatgaagctggagtc gtcccactcccgtggcagcatgaccgccctgggtggagcctcctcgtcga cccaccacccatcaccacctacccgccctacgtgcccgagtacagctcc ggactcttcccccccagcagcctgctgggcggctcccccaccggcttcgg atgcaagtccaggcccaaggcccggtccagcacagaaggcagggagtgtg tgaactgtgggggcaacctcgaccccactgtggcggcgagatggcacggga cactacctgtgcaacgcctgcgggctctatcacaaaatgaacggacgaa ccggcccctcattaagcccaagcgaaggctgtctgcagccaggagagcag ggacgtcctgtgcgaactgtcagaccaccacaaccacactctggaggagg aatgccaatggggaccctgtctgcaatgcctgtgggctctactacaagct tcacaatattaacagaccccctgactatgaagaaggaaggcatccagacca gaaaccgaaaaatgtctagcaaatccaaaaagtgcaaaaaagtgcatgac tcactggaggacttccccaagaacagctcgtttaacccggccgccctctc cagacacatgtcctccctgagccacatctcgcccttcagccactccagcc acatgctgaccacgcccacgccgatgcacccgccatccagcctgtcctttt ggaccacaccacccctccagcatggtcaccgccatgggttagagccctgc tcgatgctcacagggcccccagcgagagtccctgcagtcccttcgactt gcattttgcaggagcagtatcatgaagcctaaacgcgatggatatatgt ttttgaaggcagaaagcaaaattatgtttgccactttgcaaaggagctca ctgtggtgtctgtgttccaaccactgaatctggaccccatctgtgaataa gccattctgactcatatcccctatttaacagggtctctagtgctgtgaaa aaaaaaatgctgaacattgcatataacttatattgtaagaaatactgtac aatgactttattgcatctgggtagctgtaaggcatgaaggatgccaagaa gtttaaggaatatgggagaaatagtgtggaaattaagaagaaactaggtc tgatattcaaatggacaaactgccagttttgtttcctttcactggccaca gttgtttgatgcattaaaagaaatgaaaaaaagaaaaaagagaaaagaa aaaaaagaaaaaagttgtaggcgaatcatttgttcaaagctgttggcct ctgcaaaggaaataccagttctgggcaatcagtgttaccgttcaccagtt gccgttgagggtttcagagagcctttttctaggcctacatgctttgtgaa caagtccctgtaattgttgtttgtatgtataattcaaagcaccaaaataa gaaaagatgtagatttatttcatcatattatacagaccgaactgttgtat aaatttatttactgctagtcttaagaactgctttcttttcgtttgtttgtt tcaatattttccttctctctcaatttttggttgaataaactagattacat tcagttggcctaaggtggttgtgctcggagggtttcttgtttcttttcca ttttgttttggatgatatttattaaatagcttctaagagtccggcggca tctgtcttgtccctattcctgcagcctgtgctgagggtagcagtgtatga gctaccagcgtgcatgtcagcgacccctggcccgacaggccacgtcctgca atcggcccggctgcctcttcgccctgtcgtgttctgtgttagtgatcact gcctttaatacagtctgttggaataatattataagcataataataaagtg aaaatattttaaaactacaa By "GATA3 polypeptide" is meant a polypeptide or fragment thereof having at least about 85% amino acid identity to NCBI Accession No. NP_001002295.1, as reproduced below:

>NP_001002295.1
(SEQ ID NO: 20)
MEVTADQORWVSHHHPAVLNGQHPDTHHPGLSHSYMDAAQYPLPEEVDVL

FNIDGQGNHVPPYYGNSVRATVQRYPPTHHGSQVCRPPLLHGSLPWLDGG

KALGSHHTASPWNLSPFSKTSIHHGSPGPLSVYPPASSSSLSGGHASPHL

FTFPPTPPKDVSPDPSLSTPGSAGSARQDEKECLKYQVPLPDSMKLESSH

SRGSMTALGGASSSTHHPITTYPPYVPEYSSGLFPPSSLLGGSPTGFGCK

SRPKARSSTEGRECVNCGATSTPLWRRDGTGHYLCNACGLYHKMNGQNRP

LIKPKRRLSAARRAGTSCANCQTTTTTLWRRNANGDPVCNACGLYYKLHN

INRPLTMKKEGIQTRNRKMSSKSKKCKKVHDSLEDFPKNSSFNPAALSRH

MSSLSHISPFSHSSHMLTTPTPMHPPSSLSFGPHHPSSMVTAMG

By "FABP4 nucleic acid molecule" is meant a polynucleotide encoding a FABP4 polypeptide. An exemplary FABP4 nucleic acid molecule is provided at NCBI Accession No. NM_001442.2, and reproduced below:

```
>NM_001442.2
                                        (SEQ ID NO: 21)
gggtcacagcaccctcctgaaaactgcagcttccttctcaccttgaagaa taatcctagaaaactcacaaaatgtgtgatgcttttgtaggtacctggaa acttgtctccagtgaaaactttgatgattatatgaaagaagtaggagtgg gctttgccaccaggaaagtggctggcatggccaaacctaacatgatcatc agtgtgaatggggatgtgatcaccattaaatctgaaagtacctttaaaaa tactgagatttccttcatactgggccaggaatttgacgaagtcactgcag atgacaggaaagtcaagagcaccataaccttagatgggggtgtcctggta catgtgcagaaatgggatgaaaatcaaccaccataaagagaaaacgaga ggatgataaactggtggtggaatgcgtcatgaaaggcgtcacttccacga gagtttatgagagcataagccaagggacgttgacctggactgaagttc gcattgaactctacaacattctgtgggatatattgttcaaaaagatattg ttgttttccatgatttagcaagcaactaattttctcccaagctgatttta ttcaatatggttacgttggttaaataaacttttttttagatttagaaggtg atgtaatgatgtattcattgtgcttatgatgtattcttagtcataactga gtgaaggaaatgggaaatttgcattatttctttgttctgatatgaataat aacatatttcataataattcaaggtaaaaagggatatctatggatttccc taggtaggagataacaagtatgtaccattactgaatat
```

By "FABP4 polypeptide" is meant a polypeptide or fragment thereof having at least about 85% amino acid identity to NCBI Accession No. NP_001433.1, as reproduced below:

```
>NP_001433.1
                                        (SEQ ID NO: 22)
MCDAFVGTWKLVSSENFDDYMKEVGVGFATRKVAGMAKPNMIISVNGDVI

TIKSESTFKNTEISFILGQEFDEVTADDRKVKSTITLDGGVLVHVQKWDG

KSTTIKRKREDDKLVVECVMKGVTSTRVYERA
```

By "FOXA1 nucleic acid molecule" is meant a polynucleotide encoding a FOXA1 polypeptide. An exemplary FOXA1 nucleic acid molecule is provided at NCBI Accession No. NM_004496.3, and reproduced below:

```
>NM_004496.3
                                        (SEQ ID NO: 23)
gggcttcctcttcgcccgggtggcgttgggcccgcgcgggcgctcggg tgactgcagctgatcagctcccctcccccgccccgcgccgcgcggccg cccgtcgcttcgcacagggctggatggttgtattgggcagggtggctc caggatgttaggaactgtgaagatggaagggcatgaaaccagcgactg gaacagctactacgcagacacgcaggaggcctactcctccgtcccggt cagcaacatgaactcaggcctgggctccatgaactccatgaacaccta catgaccatgaacaccatgactacgagcggcaacatgaccccggcgtc cttcaacatgtcctatgccaacccgggcctaggggccggcctgagtcc cggcgcagtagccggcatgccggggggctcggcgggcgccatgaacag catgactgcggccggcgtgacggccatgggtacggcgctgagcccgag cggcatgggcgccatgggtgcgcagcaggcggcctccatgaatggcct gggcccctacgcggccgccatgaacccgtgcatgagccccatggcgta cgcgccgtccaacctgggccgcagccgcgcgggcggcggcggcgacgc caagacgttcaagcgcagctaccgcacgccaagccgccctactcgta catctcgctcatcaccatggccatccagcaggcgcccagcaagatgct cacgctgagcgagatctaccagtggatcatggaccttcttccctatta ccggcagaaccagcagcgctggcagaactccatccgccactcgctgtc cttcaatgactgcttcgtcaaggtggcacgctccccggacaagccggg caagggctcctactggacgctgcacccggactccggcaacatgttcga gaacggctgctacttgcgccgccagaagcgcttcaagtgcgagaagca gccgggggccggcggcgggggcgggagcggaagcgggggcagcggcgc caagggcggccctgagagccgcaaggaccctctggcgcctctaaccc cagcgccgactcgcccctccatcgggtgtgcacggaagaccggcca gctagagggcgcgccggccccgggcccgccgccagccccagactct ggaccacagtggggcgacggcgacaggggcgcctcggagttgaagac tccagcctcctcaactgcgcccccataagctccgggcccggggcgct ggcctctgtgcccgcctctcacccggcacacggcttggcaccccacga gtcccagctgcacctgaaaggggaccccactactccttcaaccaccc gttctccatcaacaacctcatgtcctcctcggagcagcagcataagct ggacttcaaggcatacgaacaggcactgcaatactcgccttacggctc tacgttgcccgccagcctgcctctaggcagcgcctcggtgaccaccag gagcccatcgagccctcagcctggagccggcgtactaccaaggtgt gtattccagacccgtcctaaacacttcctagctcccgggactgggggg tttgtctggcatagccatgctggtagcaagagagaaaaaatcaacagc aaacaaaaccacacaaaccaaaccgtcaacagcataataaaatcccaa caactattttatttcattttcatgcacaacctttcccccagtgcaa aagactgttacttattattgtattcaaaattcattgtgtatattact acaaagacaaccccaaaccaatttttttcctgcgaagtttaatgatcc acaagtgtatatgaaattctcctccttccttgcccccctctctttc ttccctctttccctccagacattctagtttgtggagggttatttaaa aaaacaaaaaggaagatggtcaagtttgtaaaatatttgtttgtgct ttttcccctccttacctgaccccctacgagtttacaggtctgtggca atactcttaaccataagaattgaaatggtgaagaaacaagtatacact agaggctcttaaaagtattgaaagacaatactgctgttatatagcaag acataaacagattataaacatcagagccatttgcttctcagtttacat
```

-continued

```
ttctgatacatgcagatagcagatgtctttaaatgaaatacatgtata ttgtgtatggacttaattatgcacatgctcagatgtgtagacatcctc cgtatatttacataacatatagaggtaatagataggtgatatacatga tacattctcaagagttgcttgaccgaaagttacaaggaccccaacccc tttgtcctctctacccacagatggccctgggaatcaattcctcaggaa ttgccctcaagaactctgcttcttgctttgcagagtgccatggtcatg tcattctgaggtcacataacacataaaattagtttctatgagtgtata ccatttaaagaattttttttttcagtaaaagggaatattacaatgttgg aggagagataagttatagggagctggatttcaaaacgtggtccaagat tcaaaaatcctattgatagtggccattttaatcattgccatcgtgtgc ttgtttcatccagtgttatgcactttccacagttggacatggtgttag tatagccagacgggtttcattattatttctctttgctttctcaatgtt aatttattgcatggtttattcttttttctttacagctgaaattgcttta aatgatggttaaaattacaaattaaattgttaattttttatcaatgtga ttgtaattaaaaatattttgatttaaataacaaaaataataccagatt ttaagccgtggaaaatgttcttgatcatttgcagttaaggacttttaaa taaatcaaatgttaacaaaagagcatttctgttattttttttcactta actaaatccgaagtgaatatttctgaatacgatatttttcaaattcta gaactgaatataaatgacaaaaatgaaaataaaattgttttgtctgtt gttataatgaatgtgtagctagtaaaaaggagtgaaagaaattcaagt aaagtgtataagttgatttaatattccaagagttgagattttttaagat tctttattcccagtgatgtttacttcattttttttttttttttgaca ccggcttaagccttctgtgtttcctttgagccttttcactacaaaatc aaatattaatttaactaccttttcctccttccccaatgtatcacttttc tttatctgagaattcttccaatgaaaataaaatatcagctgtggctga tagaattaagttgtgtccaaaaaaaaaaaaaaaaaaa
```

By "FOXA1 polypeptide" is meant a polypeptide or fragment thereof having at least about 85% amino acid identity to NCBI Accession No. NP_004487.2, as reproduced below:

>NP_004487.2
(SEQ ID NO: 24)
MLGTVKMEGHETSDWNSYYADTQEAYSSVPVSNMNSGLGSMNSMNTYM

TMNTMTTSGNMTPASFNMSYANPGLGAGLSPGAVAGMPGGSAGAMNSM

TAAGVTAMGTALSPSGMGAMGAQQAASMNGLGPYAAAMNPCMSPMAYA

PSNLGRSRAGGGGDAKTFKRSYPHAKPPYSYISLITMAIQQAPSKMLT

LSEIYQWIMDLFPYYFQNQQRWQNSIRHSLSFNDCFVKVARSPDKPGK

GSYWTLHPDSGNMFENGCYLRRQKRFKCEKQPGAGGGGGSGSGGSGAK

GGPESRKDPSGASNPSADSPLHRGVHGKTGQLEGAPAPGPAASPQTLD

HSGATATGGASELKTPASSTAPPISSGPGALASVPASHPAHGLAPHES

QLHLKGDPHYSFNHPFSINNLMSSSEQQHKLDFKAYEQALQYSPYGST

LPASLPLGSASVTTRSPIEPSALEPAYYQGVYSRPVLNTS

By "CD36 nucleic acid molecule" is meant a polynucleotide encoding a CD36 polypeptide. An exemplary CD36 nucleic acid molecule is provided at NCBI Accession No. NM_001001548.2, and reproduced below:

>NM_001001548.2
(SEQ ID NO: 25)
```
ctttcaattcctctggcaacaaaccacacactgggatctgacactgta gagtgctttctcttctcttttttggggggggagggggtgtggttgc atatttaaactctcacgcatttatgtactgaggactgcagtgtaggac tttcctgcagaataccatttgatcctattaagaattgtccaaatgttg gagcatttgattgaaaaatccttcttagccattttaaagatagctttc caatgattagacgaattgattctttctgtgactcatcagttcatttcc tgtaaaattcatgtcttgctgttgatttgtgaataagaaccagagctt gtagaaaccactttaatcatatccaggagtttgcaagaaacaggtgct taacactaattcacctcctgaacaagaaaaatgggctgtgaccggaac tgtgggctcatcgctggggctgtcattggtgctgtcctggctgtgttt ggaggtattctaatgccagttggagacctgcttatccagaagacaatt aaaaagcaagttgtcctcgaagaaggtacaattgcttttaaaaattgg gttaaaacaggcacagaagtttacagacagttttggatctttgatgtg caaaatccacaggaagtgatgatgaacagcagcaacattcaagttaag caaagaggtccttatacgtacagagttcgttttctagccaaggaaaat gtaacccaggacgctgaggacaacacagtctctttcctgcagcccaat ggtgccatcttcgaaccttcactatcagttggaacagaggctgacaac ttcacagttctcaatctggctgtggcagctgcatcccatatctatcaa aatcaatttgttcaaatgatcctcaattcacttattaacaagtcaaaa tcttctatgttccaagtcagaactttgagagaactgttatgggctat agggatccattttttgagtttggttccgtaccctgttactaccacagtt ggtctgttttatccttacaacaatactgcagatggagtttataaagtt ttcaatggaaaagataacataagtaaagttgccataatcgacacatat aaaggtaaaaggaatctgtcctattgggaaagtcactgcgacatgatt aatggtacagatgcagcctcatttccaccttttgttgagaaaagccag gtattgcagttcttttcttctgatatttgcaggtcaatctatgctgta tttgaatccgacattaatctgaaaggaatccctgtgtatagatttgtt cttccatccaaggcctttgcctctccagttgaaaacccagacaactat tgtttctgcacagaaaaaattatctcaaaaaattgtacatcatatggt gtgctagacatcagcaaatgcaaagaagggagacctgtgtacatttca cttcctcattttctgtatgcaagtcctgatgtttcagaacctattgat ggattaaacccaaatgaagaagaacataggacatacttggatattgaa cctataactggattcactttacaatttgcaaaacggctgcaggtcaac ctattggtcaagccatcagaaaaaattcaagtattaaagaatctgaag

```
aggaactatattgtgcctattctttggcttaatgagactgggaccatt
ggtgatgagaaggcaaacatgttcagaagtcaagtaactggaaaata
aacctccttggcctgatagaaatgatcttactcagtgttggtgtggtg
atgtttgttgcttttatgatttcatattgtgcatgcagatcgaaaaca
ataaaataaacctggctcaagcacaaaccaatttgtgttgttctgatt
caataattggtttctgggtggccaattcagaagaagagtgtacatgct
caacaaatcctaggccctgcattcctgtcatcctcatccggggaaac
accatcatcccagtagctgccctattcaactgcaacagtctccaggac
catcagtatactgcatttcatgtgcaccaaatattttgaaagacattt
ataaataattggcttatgactcatatttctctatgaataccttcatac
agcaggtataactcttttctttatgggcttaaatattttgtcactgat
cctgcaaatggacatcattttagcacactagcggtttatattttaagg
accttcattctctgttctgcacctcttctggaaattgagtaaattttg
cttttttttttttactcagttgcaattattgtatgaaatattacaaag
cgtagactatgcattgttattcattataatatttttgctgtcataat
cgcctcataaagacaggtttcaaccattaaaatatgttcttccttaaa
ttcctgtgcttttctagttcctcttgtgtcataaaatgtttatccta
attttctctctgaagtatattttatctgaatccacatttctttataaa
tccatagtccttgctgaaatatgctttctaaatttctaccactttgtt
ctaggctaatttttaagctaattggatgaagaacaaaaagacatttg
gtttcatccttacagcagtaggacaattgcaaggttttttccttttt
agcattagttctcctaaaaagctccagcatagaaagggaagataaacc
aaattctagcttgtgttttacccacagaaggatacaggacaaaggaat
agtaactggcctgtttggatactaaaatcgaaaataacttttagcctc
ctccttatgatagccgccagagtaaatgttgagcattactacagaaaa
gccacaaaccaagaatctacctgtttggaaagatcttttgcatctctg
aaggtgcttaaagcatacttagtgcctttccttttaactgggaagata
aaagaagtatctgtccaagatattaatatgtaagataacattgtagac
atgttcttctgataatacaaggtttattctatttgcattaggatattt
gtggacatgtccatctaatataaaggaaagttttttaatcattgaggc
atgtagggctgagttatataatgtagaaacttctaaagataattggat
gagaatatacatattgacctgtatattgactaatcatgactcagat
cttaatacagggatgatctcatagcatttagatatcagaaaaggtttt
gacctatgtctttaatattgtttgaatacatgtataatctttatca
ttcctcagtgtttcatttctcaaattctgtaaaaggaatataagagga
aagacaattcatatacaaagacaacgagattaaaaatatgcagtagga
aaaataattacttaaggggagattttttttacatgaaatctgggctttt
ggatgtgtgtgtgtgtgtgtgtgtgtgtgtgtgcacatatgcactg
tggtgggagtggggcaacttggggaatatgttacatgtgtgactttgt
tttgccctggcgaagttaatgttgttcagaaagggtaaatgtttggac
acttgcaattgctcatggatgaatttatatgtttagtcatagaaaaa
```

```
ttgtacccttgatagaagcacattttctttccaaagctggttattaa
ccacagaattatagcaggtattcataacttaagtttgaaaatcaatag
cgtctgcaaatggattaacagattagagaatcaacagcatcggaaaat
aggttaatgcatattgcttctaacaagtgcatgaagaaatagaagaag
ctatgtagctttcagttctgacagaaagggtgaaggagggtatcatt
tcaagaaaaaaatagctatcacgcaatggttatctctgaaaatattt
gtattaagatgtgtatacatggccaggcatggtggctcatgcctgtaa
tcccagcactttgggaggcaggtggatcacgaggtcaggagatcaaga
ccatcctggccaacatggtgaaacctcatctctactaaaaatacaaaa
atgagcggggtgtggtggcccatgcctgtagtcccagctgctcgggag
actgaatctcttgagcctgggaagcagaggttgcagtgaactgagatc
gcgtcactgcactccagcctggtgacagagcgagattccatctcaaaa
aaaaaaaacagtatgcacgtacaaatttcttaacctgttatcaatgtc
tgagctacataattatctttctagttggagtttgttctgtggctgctc
tcttcacctgccccttgtggcctgtctacaattctaaatggattttga
actcaatgtcgtcgcttctggtttcctgcatataccaatagcattacc
tatgactttttttttcctgagctattttcactgagctgagctaatgaa
ctaaaactgagttatgtttaatatttgtatcaaatacataaaaggaat
actgcttttccttttgtggctcaaaggtagctgcattttaaaatatt
tgtgaaaataaaaacttttgttattagaaaaatga
```

By "CD36 polypeptide" is meant a polypeptide or fragment thereof having at least about 85% amino acid identity to NCBI Accession No. NP_001001548.1, as reproduced below:

```
>NP_001001548.1
                                          (SEQ ID NO: 26)
MGCDRNCGLIAGAVIGAVLAVFGGILMPVGDLLIQKTIKKQVVLEEGT
IAFKNWVKTGTEVYRQFWIFDVQNPQEVMMNSSNIQVKQRGPYTYRVR
FLAKENVTQDAEDNTVSFLQPNGAIFEPSLSVGTEADNFTVLNLAVAA
ASHIYQNQFVQMILNSLINKSKSSMFQVRTLRELLWGYRDPFLSLVPY
PVTTTVGLFYPYNNTADGVYKVFNGKDNISKVAIIDTYKGKRNLSYWE
SHCDMINGTDAASFPPPFVEKSQVLQFFSSDICRSIYAVFESDVNLKGI
PVYRFVLPSKAFASPVENPDNYCFCTEKIISKNCTSYGVLDISKCKEG
RPVYISLPHFLYASPDVSEPIDGLNPNEEEHRTYLDIEPITGFTLQFA
KRLQVNLLVKPSEKIQVLKNLKRNYIVPILWLNETGTIGDEKANMFRS
QVTGKINLLGLIEMILLSVGVVMFVAFMISYCACRSKTIK
```

By "ACOX1 nucleic acid molecule" is meant a polynucleotide encoding a ACOX1 polypeptide. An exemplary ACOX1 nucleic acid molecule is provided at NCBI Accession No. NM_004035.6, and reproduced below:

>NM_004035.6

(SEQ ID NO: 27)

```
aaaaagtgctttattttcccactccccggacgcccagcagggcagttt
cttgaccttcggagccccttcccgaggatccgctcgggagcctcccc
tggccaggagcaggggattagtctgccccgcgaccggccccagccacg
acgcggacatcgcccctctgtctgggccgctgtcactcacgcgccaa
agggccacggagaagaaggggcgggccggggcgggccgggcgagcgg
aggcggggacttgcgccgtcctgaggctgcctcctagggtccggccgg
cgctggagctgcggatttagattgtcactgccacctcggtcggtgctt
acttcgctgccagctggtcgtcgccatgaacccggacctgcgcaggga
gcgggattccgccagcttcaacccggagctgcttacacacatcctgga
cggcagccccgagaaacccggcgccgccgagagatcgagaacatgat
cctgaacgacccagacttccagcatgaggacttgaacttcctcactcg
cagccagcgttatgaggtggctgtcaggaaaagtgccatcatggtgaa
gaagatgagggagtttggcatcgctgaccctgatgaaattatgtggtt
taaaaattttgtgcaccgagggcggcctgagcctctggatcttcactt
gggcatgttcctgcccaccttgcttcaccaggcaactgcggagcagca
ggagcgcttcttcatgcccgcctggaacttggagatcattggcactta
tgcccagacagagatgggtcatggaactccttcgaggcttggaaac
cacagccacgtatgaccctgaaacccaggagttcattctcaacagtcc
tactgtgacctccattaaatggtggcctggtgggcttggaaagacttc
aaatcatgcaatagttcttgcccagctcatcactaaggggaaatgcta
tggattacatgcctttatcgtacctattcgtgaaatcgggacccataa
gcctttgccaggaattaccgttggtgacatcggccccaaatttggtta
tgatgagatagacaatggctacctcaaaatggacaaccatcgtattcc
cagagaaaacatgctgatgaagtatgcccaggtgaagcctgatggcac
atacgtgaaaccgctgagtaacaagctgacttacgggaccatggtgtt
tgtcaggtccttccttgtgggagaagctgctcgggctctgtctaaggc
gtgcaccattgccatccgatacagcgctgtgaggcaccagtctgaaat
caagccaggtgaaccagaaccacagattttggattttcaaacccagca
gtataaactctttccactcctggccactgcctatgccttccagtttgt
gggcgcatacatgaaggagacctatcaccggattaacgaaggcattgg
tcaagggaccgagtgaactgcctgagcttcatgccctcaccgctgg
actgaaggctttcacctcctggactgcaaacactggcattgaagcatg
tcggatggcttgtggtgggcatggctattctcattgcagtggtcttcc
aaatatttatgtcaatttcaccccaagctgtacctttgagggagaaaa
cactgtcatgatgctccagacggctaggttcctgatgaaaagttatga
tcaggtgcactcaggaaagttggtgtgtggcatggtgtcctatttgaa
cgacctgcccagtcagcgcatccagccacagcaggtagcagtctggcc
aaccatggtggatatcaacagccccgaaagcctaaccgaagcatataa
actccgtgcagccagattagtagaaattgctgcaaaaaaccttcaaaa
agaagtgattcacagaaaaagcaaggaggtagcttggaacctaacttc
```

```
tgttgaccttgttcgagcaagtgaggcacattgccactatgtggtagt
taagctcttttcagaaaaactcctcaaaattcaagataaagccattca
agctgtcttaaggagtttatgtctgctgtattctctgtatgaatcag
tcagaacgcggggattccttcaggggagcatcatgacagagcctca
gattacacaagtaaaccagcgtgtaaaggagttactcactctgattcg
ctcagatgctgttgctttggttgatgcatttgattttcaggatgtgac
acttggctctgtgcttggccgctatgatgggaatgtgtatgaaaactt
gtttgagtgggctaagaactccccactgaacaaagcagaggtccacga
atcttacaagcacctgaagtcactgcagtccaagctctgaagtgtcac
aaggacaagtttaatctgcttcagaaagcgcctgtgtgcaactcaaat
tttgtggaatcttttcgaattcaaatagctatagagcaaatgataaa
ttgaccccttttataaatggagggaaaaatgaacagatttcagaga
ttaaatgaaaaaaagcagatgttttaagtgcaattaacactgaaagag
acctgttaaaccattcagaaaaagcttaagaaatgcgatatgacttcc
ttttgtaatgctgctgatcccagtagactatgacttttgataattagc
agaatttaactactgagtagttgattattttcacattttaattgctaa
tcactggctatataagtgttttaagcaaaggtattttgaagtggtg
tagaacccttccaagctttcctgctcagtgttctaccagacttaccct
ggggcctggcttaaaagcaggattgaagaaaagggactgggggaagga
aacttattggaaaacttgatgcgaatgagtttctgcttggcacagtct
ctgcctgcttgctctcctttgctgatggattgcatttatcaaactatt
catgctagcattttccaacgagggaacttattccgcacgggcctact
gtaggaccattgtctcgtgtaattaggaattttccatttgaaggattg
ctaaattgtcacagtagtaggaagtatagggaaacctctcagctgtgg
cactgttgtagctttggagtgcagagtgtaactctgggacaatcagat
ttcacatattctgtcatcttggcataagccattaaaagcttggagatt
actgtatttggcattaaaaaaaaatgtcacttaggtcagcactcccag
acgtagcacagaaaaacctttgacacaaaccatgtgttctgattttt
ggttcagaaatattgaaactgtgagttgttttttttttaacaactgg
gaaaaaacaaaaacaaaaaactatagttagaaaaatggaagttccata
ggttctatttcttactctatgtatggctttgttttcagtctatttcta
ggagctttctctgaatcgctaattgtcctttcagttgaaatctaattt
atacaatcattctatacttaaaggttaaatacatcttaattaattttt
tcttaaagtcaatgtaagtcactttgttttgttttttttaatctacg
ccatatgcctcatgaaaccagctgttctagaatcagtcctgagaatat
ggcttaattccatggaaacataactcctatcttgggacctgacataat
atctatctatcctggggaactggtaatatgagacttataggttacagc
agaaatgctacatgttgacaaaagccttaatcgttccactgggagaac
taattgataattgtgttaagattgaagattaaccctgtgttaatctca
cttgagtctatcctgacagtagttcagattctggaaaatgataaactg
acctgctagatgtgagaattgtttcaaaattagtgttgaaatacccttgt
```

```
tcacagatgaatatctgggcaggatctgagggtgtttggaatgacacc
ccccaatccagttgcatagatgggatgtctttgcaggtttgaggagat
catcgacctgcagagccccctttgacccagtacctcacgttttattta
aaatctaaatctggggccaggcgtggtggctcacgcctgtaatccaag
cactttgggaggccgaagcgggtggatcacctgaggtcaggagtttga
gaccatcctggccaacatggtgaaacccgtctctactgaaaaaaata
caaaaattagctgggcatggtggtagcacgcgcctgtagtcccagcta
ctcgggaggctgaggcaggataatcgcttgaacttggcgggtagaggt
tgcagtgagccaagatggtgccactacactgcagcctgggtggctgag
cgagactccgtctcaaaaaaaaaatctaaatctgacatttgatgctat
ttttattaatattggaatgttctgtcttgaactttattcaatataatc
aagaataaagatagagtaaacgtcactgatttgtactattaagagaga
aaaaatatgccacacaactaaacataggtttaaattggagtgatacct
gcctgagtggacagctgtaaatcagctgtaattactgcagttgtacca
atagttgtgagtggctccagtcactttaggagtccttggaagtacttg
gtacacatttgttggctgtaccttaaaggaagtggcaagtccagtttg
ttctctctaccacactagactgccactgacaagtttgggtctgttgga
ttcaaaattttgtaagccattttcacaagtacaaagatacattttaac
cttgtcttctccaaaattactgagtaggaattttattttttatcttttt
gagacagggtatcactgtcacccagactggagtgcagtggtgggatct
tggcttactgtgacctctgcctcccgggttcaaatggtcctccctcct
cagtctcctgagtagctgggacgacaggcacgtgccaccatgcccagc
taatttgttctattttttctgtagagacggggttttgccatgttgccc
aggctggtctcagactcctgggctcaagcgatcatttcgcctcagcct
cccaaagtgctgagattataggtgtgagccacagcatctggcccagag
tgaggagaattaatgagattttttgtgtgtgttagataatattgattt
aagcctttttttaaaaagtactctcaaccaaatacaaaattgaaaatg
tgaggtttaatagaaatgtgttggctatttgcaatggattttcttctt
gcccaagtgtttggagtctactttatgctctgtatttaaaaattagt
gacctcaaagcagagttgatgacacaggctttggggccctcatgttct
tgtctttagaacatatcactactaagtatcagcttatcttcagaacat
tacaacattcaccgtgttcatatgctttctgagaagtcaccacttgta
atttcagatcacatacacctgaaggcattttatagttcctaaagttaa
catgttagatctttttttttccaccccatgagggtctcactctcaccca
ggctggaatgcagtggtgtgattgtagcacacttttggccaccaactcc
tgggctcaagtgatcctcctgctttggcctcctctgagaagctgggat
tactggtgcacaccaccacacctggctaattttttatttttttttatt
tttggaaatagggtatggctatgttgccttgggcccgtcatgaactcc
tagcctcaggtgaccctcccacctcaggcctcccaaagggtttgggatt
acaggagtgagctactgcactgggccaacatgttaatttttttttttt
ttttttgagatggagtctcccaggcgggaatgcaatggtgcgatctc
gacttcactgcaatcttcacctcccgggttcgagcgattctcccacct
cagcctcctgagtagctgggattacaggcacctgccatcacgctcggc
taatttttgtattttgagcagagatggagtttcaccatgttggccagg
tgatctgcactcccactccccccacacttcccaaagtgctgggattac
aggcataagccacaagccacctcacccagccaacatgttacatcttaa
ttcttggattttcttcactgcagggctttgggtggagaaataaaactc
ttcaaatgcatgatcttggagatccctgtgaatcaataattctttaga
caactgcggctcaaaatccctcctttcccttttccgagttattccatc
catcttattagaaaggaagtgaattaggtgtaggtggtctgtaacacc
tgcacatcttttatacgtgtagagggtatgcctgggatatataggtt
gtcttcaagcagtagctgctactacagctagagagaggaggagtgcca
ggaaactgatgacctgagaccaagagtcttgttgatgttctgacttag
ataaaggttttgatcattttcatgaaataatgcagggaagtcatttct
gctgtttctttactactccattcttggaggattagaacaagtcacact
gtaattgactaaaacgacttttttatttttaaaatattgatggtgggtt
ttgctttttttttttttttttttttgagacgttgtcttgctctttca
cccagggtagagtgcagtggcgaaatcttggctcactgcaacctctgc
ctcccgggttcaagcaattctctgcctcagcctcctgagaagctggga
ttacagcgcctgccaccatgcctgtctagttttttgtatttttagta
gagacaggggtttcaccaagttggccaggctggtcttgaactcctgac
ctcgtgatccacccacctcggcctcccaaagtgctgggattacaggcg
tgagccaccgtgccggccagtgttttaactgtccacacttactaaa
ttttccagtacttcttcctatggttcatgatagtaaacacagaaacat
ataaggaacattattagagttaccagatgttagctgttgcatatgtgc
acattcctagattcaagggtgttttgccttaaatttaagtgggtcat
tggttgtcttgggaagatcatggaaaattcgggatttttagaattct
gaaccaaatatgttttgagtgtttcttagtaaatgtgtgatcttcca
ccttccacattcagactgcggactacacttcataaatgccttttatt
tccagttatggattcaactaaatgactgccttgggagcacataattac
tttgctacctttttccccctttgctgttgtggctcgagtttggttatc
acctgagaagatgcattgagcatatgttgttacccagccctggcttaa
tggtgtcctgtggggtaggggtgggaggacgaggggcacggggccaga
gcatgtgaatggatcatggttggacagctgtgacctgccagcactgcg
ggtaagcaaaactacaaaccgttcttcctctgtgacattgaataaac
cttaataaaattcataattagcacatactagaaaaaa
```

By "ACOX1 polypeptide" is meant a polypeptide or fragment thereof having at least about 85% amino acid identity to NCBI Accession No. NP_004026.2, as reproduced below:

>NP_004026.2

(SEQ ID NO: 28)

MNPDLRRERDSASFNPELLTHILDGSPEKTRRRREIENMILNDPDFQH

EDLNFLTRSQRYEVAVRKSAIMVKKMREFGIADPDEIMWFKNFVHRGR

PEPLDLHLGMFLPTLLHQATAEQQERFFMPAWNLEIIGTYAQTEMGHG

THLRGLETTATYDPETQEFILNSPTVTSIKWWPGGLGKTSNHAIVLAQ

LITKGKCYGLHAFIVPIREIGTHKPLPGITVGDIGPKFGYDEIDNGYL

KMDNHRIPRENMLMKYAQVKPDGTYVKPLSNKLTYGTMVFVRSFLVGE

AARALSKACTIAIRYSAVRGQSEIKPGEPEPQILDFQTQQYKLFPLLA

TAYAFQFVGAYMKETYHRINEGIGQGDLSELPELHALTAGLKAFTSWT

ANTGIEACRMACGGHGYSHCSGLPNIYVNFTPSCTFEGENTVMMLQTA

RFLMKSYDQVHSGKLVCGMVSYLNDLPSQRIQPQQVAVWPTMVDINSP

ESLTEAYKLRAARLVEIAAKNLQDEVIHRKSKEVAWNLTSVDLVRASE

AHCHYVVVKLFSEKLLKIQDKAIQAVLRSLCLLYSLYGISQNAGDFLQ

GSIMTEPQITQVNQRVKELLTLIRSDAVALVDAFDFQDVTLGSVLGRY

DGNVYENLFEWAKNSPLNKAEVHESYKHLKSLQSKL

By "HMGCS2 nucleic acid molecule" is meant a polynucleotide encoding a HMGCS2 polypeptide. An exemplary HMGCS2 nucleic acid molecule is provided at NCBI Accession No. NM_005518.3 NM_0055183, and reproduced below:

>NM_005518.3

(SEQ ID NO: 29)

ataaagtcctgccgggcaccactgggcatctctttcaaggtttctgct gggtttctgaactgctgggtttctgcttgctcctctggagatgcagcg tctgttgactccagtgaagcgcattctgcaactgacaagagcggtgca ggaaacctccctcacacctgctcgcctgctcccagtagcccaccaaag gttttctacagcctctgctgtcccctggccaaaacagatacttggcc aaggacgtgggcatcctggccctggaggtctacttcccagcccaata tgtgtgaccaaactgacctggagaagtataacaatgtggaagcaggaa gtatacagtgggcttgggccagacccgtatgggcttctgctcagtcca agaggacatcaactccctgtgcctgacggtggtgcaacggctgatgga gcgcatacagctcccatgggactctgtgggcaggctggaagtaggcac tgagaccatcattgacaagtccaaagctgtcaaaacagtgctcatgga actcttccaggattcaggcaatactgatattgagggcatagataccac caatgcctgctacggtggtactgcctccctcttcaatgctgccaactg gatggagtccagttcctgggatggtcgttatgccatggtggtctgtgg agacattgccgtctatcccagtggtaatgctcgtcccacaggtgggc cggagctgtggctatgctgattgggcccaaggcccctctggccctgga gcgagggctgaggggaacccatatggagaatgtgtatgacttctacaa accaaatttggcctcggagtacccaatagtggatgggaagctttccat ccagtgctacttgcgggccttggatcgatgttacacatcataccgtaa aaaaatccagaatcagtggaagcaagctggcagcgatcgacccttcac ccttgacgatttacagtacatgatctttcatacacccttttgcaagat ggtccagaagtctctggctcgcctgatgttcaatgacttcctgtcagc cagcagtgacacacaaaccagcttatataaggggctggaggctttcgg ggggctaaagctggaagacacctacaccaacaaggacctggataaagc acttctaaaggcctctcaggacatgttcgacaagaaaaccaaggcttc cctttacctctccactcacaatgggaacatgtacacctcatccctgta cgggtgcctggcctcgcttctgtcccaccactctgcccaagaactggc tggctccaggattggtgccttctcttatggctctggtttagcagcaag tttcttttcatttcgagtatcccaggatgctgctccaggctctcccct ggacaagttggtgtccagcacatcagacctgccaaaacgcctagcctc ccgaaagtgtgtgtctcctgaggagttcacagaaataatgaaccaaag agagcaattctaccataaggtgaatttctccccacctggtgacacaaa cagccttttcccaggtacttggtacctggagcgagtggacgagcagca tcgccgaaagtatgcccggcgtcccgtctaaaggtgttctgcagatcc atggaaagcttcctgggaaacgtatgctagcagagcttctccccgtga atcatattttaagatcccactcttagctggtaaatgaatttgaatcg acatagtagccccataagcatcagccctgtagagtgaggagccatctc tagcgggcccttcattcctctccatgctgcaatcactgtcctgggctt atggtgctatggactaggggtcctttgtgaaagagcaagatggagcaa tggagagaagacctcttcctgaatcactggactccagaaatgtgcatg cagatcagctgttgccttcaagatccagataaacttcctgtcatgtg ttagaactttattattattaatattgttaaacttctgtgctgttcctg tgaatctccaaattttgtaccttgttctaagctaatatatagcaatta aaaagagagaaagaggaaatgattcctgcgtttcttggaacccagaat acaaacccagcctaacatgcagcaagcctgctagaccttgtgggtcag agggctgggtccttgcctcacaggctgcctctgtcccttgcaattcc attctatttctgccacatgccaagtgctatgacaggtacaaggcaaat aagaacggtagaacacagcttccccagcccacttccctgttctaaag acaccacatagacagagagcagcagacaggggccagcaggagctgtag ttcagatcttcttggtcattccttgccgctgttatttgaacaaataaa cacagcgcaaaggttaacaagttttgccttctatagccaaaatataaa aaaataaataaattttgaaaaaaaaaaa By "HMGCS2 polypeptide" is meant a polypeptide or fragment thereof having at least about 85% amino acid identity to NCBI Accession No. NP_005509.1, as reproduced below:

>NP_005509.1

(SEQ ID NO: 30)

MQRLLTPVKRILQLTRAVQETSLTPARLLPVAHQRFSTASAVPLAKTD

TWPKDVGILALEVYFPAQYVDQTDLEKYNNVEAGKYTVGLGQTRMGFC

SVQEDINSLCLTVVQRLMERIQLPWDSVGRLEVGTETIIDKSKAVKTV

LMELFQDSGNTDIEGIDTTNACYGGTASLFNAANWMESSSWDGRYAMV

VCGDIAVYPSGNARPTGGAGAVAMLIGPKAPLALERGLRGTHMENVYD

FYKPNLASEYPIVDGKLSIQCYLRALDRCYTSYRKKIQNQWKQAGSDR

PFTLDDLQYMIFHTPFCKMVQKSLARLMFNDFLSASSDTQTSLYKGLE

AFGGLKLEDTYTNKDLDKALLKASQDMFDKKTKASLYLSTGNGNMYTS

SLYGCLASLLSHHSAQELAGSRIGAFSYGSGLAASFFSFRVSQDAAPG

SPLDKLVSSTSDLPKRLASRKCVSPEEFTEIMNQREQFYHKVNFSPPG

DTNSLFPGTWYLERVDEQHRRKYARRPV

By "ACSL5 nucleic acid molecule" is meant a polynucleotide encoding a ACSL5 polypeptide. An exemplary ACSL5 nucleic acid molecule is provided at NCBI Accession No. NM_016234.3, and reproduced below:

>NP_016234.3
(SEQ ID NO: 31)

```
taaaaccaggaagtgaagtccccgagcacgttagaaagcctgacatgg
cctgactcgggacagctcagagcagggcagaactggggacactctggg
ccggccttctgcctgcatggacgctctgaagccaccctgtctctggag
gaaccacgagcgagggaagaaggacagggactcgtgtggcaggaagaa
ctcagagccggaagcccccattcactagaagcactgagagatgcggc
ccctcgcagggtctgaatttcctgctgctgttcacaaagatgctttt
tatctttaacttttttgttttccccacttccgaccccggcgttgatctg
catcctgacatttggagctgccatcttcttgtggctgatcaccagacc
tcaacccgtcttacctcttcttgacctgaacaatcagtctgtgggaat
tgagggaggagcacggaaggggtttcccagaagaacaatgacctaac
aagttgctgcttctcagatgccaagactatgtatgaggttttccaaag
aggactagctgtgtctgacaatgggccctgcttgggatatagaaaacc
aaaccagccctacagatggctatcttacaaacaggtgtctgatagagc
agagtacctgggttcctgtctcttgcataaaggttatataatcatcacc
agaccagtttgtcggcatctttgctcagaataggccagagtggatcat
ctccgaattggcttgttacacgtactctatggtagctgtacctctgta
tgacaccttgggaccagaagccatcgtacatattgtcaacaaggctga
tatcgccatggtgatctgtgacacaccccaaaaggcattggtgctgat
agggaatgtagagaaaggcttcaccccgagcctgaaggtgatcatcct
tatgaccccctttgatgatgacctgaagcaaagagggagaagagtgg
aattgagatcttatccctatatgatgctgagaacctaggcaaagagca
cttcagaaaacctgtgcctcctagcccagaagacctgagcgtcatctg
cttcaccagtgggaccacaggtgaccccaaaggagccatgataaccca
tcaaaatatttgtttcaaatgctgctgcctttctcaaatgtgtggagca
tgcttatgagcccactcctgatgatgtggccatatcctacctccctct
ggctcatatgtttgagaggattgtacaggctgttgtgtacagctgtgg
agccagagttggattcttccaaggggatattcggttgctggctgacga
catgaagactttgaagcccacattgtttcccgcggtgcctcgactcct
taacaggatctacgataaggtacaaaatgaggccaagacaccccttgaa
``` gaagttcttgttgaagctggctgtttccagtaaaattcaaagagcttca aaagggtatcatcaggcatgatagttctgggacaagctcatctttgc aaagatccaggacagcctgggcggaagggttcgtgtaattgtcactgg agctgcccccatgtccacttcagtcatgacattcttccgggcagcaat gggatgtcaggtgtatgaagcttatggtcaaacagaatgcacaggtgg ctgtacatttacattacctggggactggacatcaggtcacgttgggt gccctggcttgcaattacgtgaagctggaagatgtggctgacatgaa ctactttacagtgaataatgaaggagaggtctgcatcaagggtacaaa cgtgttcaaaggatacctgaaggaccctgagaagacacaggaagccct ggacagtgatggctggcttcacacaggagacattggtcgctggctccc gaatggaactctgaagatcatcgaccgtaaaaagaacattttcaagct ggcccaaggagaatacattgcaccagagaagatagaaaatatctacaa caggagtcaaccagtgttacaaattttttgtacacggggagagcttacg gtcatccttagtaggagtggtggttcctgacacagatgtacttccctc atttgcagccaagcttggggtgaagggctcctttgaggaactgtgcca aaaccaagttgtaagggaagccattttagaagacttgcagaaaattgg gaaagaaagtggccttaaaacttttgaacaggtcaaagccatttttct tcatccagagccattttccattgaaaatgggctcttgacaccaacatt gaaagcaaagcgaggagagctttccaaatactttcggacccaaattga cagcctgtatgagcacatccaggattaggataaggtacttaagtacct gccggcccactgtgcactgcttgtgagaaaatggattaaaaactattc ttacatttgttttgcctttcctcctatttttttttaacctgttaaact ctaaagccatagcttttgttttatattgagacatataatgtgtaaact tagttcccaaataaatcaatcctgtctttcccatcttcgatgttgcta atattaaggcttcagggctactttttatcaacatgcctgtcttcaagat cccagtttatgttctgtgtccttcctcatgatttccaaccttaatact attagtaaccacaagttcaagggtcaaagggaccctctgtgccttctt cttttgttttgtgataaacataacttgccaacagtctctatgcttattt acatcttctactgttcaaactaagagattttaaattctgaaaaactg cttacaattcatgttttctagccactccacaaaccactaaaattttag ttttagcctatcactcatgtcaatcatatctatgagacaaatgtctcc gatgctcttctgcgtaaattaaattgtgtactgaagggaaaagtttga tcataccaaacatttcctaaactctctagttagatatctgacttggga gtattaaaaatttgggtctatgacatattgtccaaaaggaatgctgttc ttaaagcattatttacagtaggaactggggagtaaatctgttccctac agtttgctgctgagctggaagctgtggggaaggagttgacaggtggg cccagtgaacttttccagtaaatgaagcaagcactgaataaaaacctc ctgaactgggaacaaagatctacaggcaagcaagatgcccacacaaca ggcttattttctgtgaaggaaccaactgatctccccacccttggatt agagttcctgctctaccttacccacagataacacatgttgtttctact

```
tgtaaatgtaaagtctttaaaataaactattacagatacttaaaaaaa
aaaaaaaaaaaa
```

By "ACSL5 polypeptide" is meant a polypeptide or fragment thereof having at least about 85% amino acid identity to NCBI Accession No. NP_057318.2, as reproduced below:

>NP_057318.2
(SEQ ID NO: 32)
```
MDALKPPCLWRNHERGKKDRDSCGRKNSEPGSPHSLEALRDAAPSQGL
NFLLLFTKMLFIFNFLFSPLPTPALICILTFGAAIFLWLITRPQPVLP
LLDLNNQSVGIEGGARKGVSQKNNDLTSCCFSDAKTMYEVFQRGLAVS
DNGPCLGYRKPNQPYRWLSYKQVSKRAEYLGSCLLHKGYKSSPDQFVG
IFAQNRPEWIISELACYTYSMVAVPLYDTLGPEAIVHIVNKADIAMVI
CDTPQKALVLIGNVEKGFTPSLKVIILMDPFDDDLKQRGEKSGIEILS
LYDAENLGKEHFRKPVPPSPEDLSVICFTSGTTGDPKGAMITHQNIVS
NAAAFLKCVEHAYEPTPDDVAISYLPLAHMFERIVQAVVYSCGARVGF
FQGDIRLLADDMKTLKPTLFPAVPRLLNRIYDKVQNEAKTPLKKFLLK
LAVSSKFKELQKGIIRHDSFWDKLIFAKIQDSLGGRVRVIVTGAAPMS
TSVMTFFRAAMGCQVYEAYGQTECTGGCTFTLPGDWTSGHVGVPLACN
YVKLEDVADMNYFTVNNEGEVCIKGTNVFKGYLKDPEKTQEALDSDGW
LHTGDIGRWLPNGTLKIIDRKKNIFKLAQGEYIAPEKIENIYNRSQPV
LQIFVHGESLRSSLVGVVVPDTDVLPSFAAKLGVKGSFEELCQNQVVR
EAILEDLQKIGKESGLKTFEQVKAIFLHPEPFSIENGLLTPTLKAKRG
ELSKYFRTQIDSLYEHIQD
```

By "ALOX5 nucleic acid molecule" is meant a polynucleotide encoding a ALOX5 polypeptide. An exemplary ALOX5 nucleic acid molecule is provided at NCBI Accession No. NM_000698.4, and reproduced below:

>NM_000698.4
(SEQ ID NO: 33)
```
ggggccgggaccggggccagggaccagtggtggaggaggctgcggcg
ctagatgcggacacctggaccgccgcgccgaggctcccggcgctcgct
gctcccgcggcccgcgccatgccctcctacacggtcaccgtggccact
ggcagccagtggttcgccggcactgacgactacatctacctcagcctc
gtgggctcggcgggctgcagcgagaagcacctgctggacaagccttc
tacaacgacttcgagcgtggcgcggtggattcatacgacgtgactgtg
gacgaggaactgggcgagatccagctggtcagaatcgagaagcgcaag
tactggctgaatgacgactggtacctgaagtacatcacgctgaagacg
ccccacggggactacatcgagttcccctgctaccgctggatcaccggc
gatgtcgaggttgtcctgagggatggacgcgcaaagttggcccgagat
gaccaaattcacattctcaagcaacaccgacgtaaagaactggaaaca
cggcaaaaacaatatcgatggatggagtggaaccctggcttccccttg
agcatcgatgccaaatgccacaaggatttaccccgtgatatccagttt
gatagtgaaaaggagtggacttttgttctgaattactccaaagcgatg
gagaacctgttcatcaaccgcttcatgcacatgttccagtcttcttgg
aatgacttcgccgactttgagaaaatctttgtcaagatcagcaacact
atttctgagcgggtcatgaatcactggcaggaagacctgatgtttggc
taccagttcctgaatggctgcaaccctgtgttgatccggcgctgcaca
gagctgcccgagaagctcccggtgaccacggagatggtagagtgcagc
ctggagcggcagctcagcttggagcaggaggtccagcaagggaacatt
ttcatcgtggactttgagctgctggatggcatcgatgccaacaaaaca
gaccctgcacactccagttcctggccgctcccatctgcttgctgtat
aagaacctggccaacaagattgtccccattgccatccagctcaaccaa
atcccgggagatgagaaccctattttcctcccttcggatgcaaaatac
gactggcttttggccaaaatctgggtgcgttccagtgacttccacgtc
caccagaccatcacccaccttctgcgaacacatctggtgtctgaggtt
tttggcattgcaatgtaccgccagctgcctgctgtgcaccccattttc
aagctgctggtggcacacgtgagattcaccattgcaatcaacaccaag
gcccgtgagcagctcatctgcgagtgtggcctctttgacaaggccaac
gccacaggggcggtgggcacgtgcagatggtgcagagggccatgaag
gacctgacctatgcctcctgtgctttcccgaggccatcaaggcccgg
ggcatggagagcaaagaagacatcccctactacttctaccgggacgac
gggctcctggtgtgggaagccatcaggacgttcacggccgaggtggta
gacatctactacgagggcgaccaggtggtggaggaggacccggagctg
caggacttcgtgaacgatgtctacgtgtacggcatgcggggccgcaag
tcctcaggcttccccaagtcggtcaagagccgggagcagctgtcggag
tacctgaccgtggtgatcttcaccgcctccgcccagcacgccgcggtc
aacttcggccagtacgactggtgctcctggatccccaatgcgccccca
accatgcgagccccgccaccgactgccaagggcgtggtgaccattgag
cagatcgtggacacgctgcccgaccgcggccgctcctgctggcatctg
ggtgcagtgtgggcgctgagccagttccaggaaaacgagctgttcctg
ggcatgtacccagaagagcattttatcgagaagcctgtgaaggaagcc
atggccgattccgcaagaacctcgaggccattgtcagcgtgattgct
gagcgcaacaagaagaagcagctgccatattactacttgtcccagac
cggattccgaacagtgtggccatctgagcacactgccagtctcactgt
gggaaggccagctgccccagccagatggactccagcctgcctggcagg
ctgtctggccaggcctcttggcagtcacatctcttcctccgaggccag
tacctttccattttattctttgatcttcagggaactgcatagattgatc
aaagtgtaaacaccatagggacccattctacacagagcaggactgcac
agcgtcctgtccacacccagctcagcatttccacaccaagcagcaaca
gcaaatcacgaccactgatagatgtctattcttgttggagacatggga
tgattattttctgttctatttgtgcttagtccaattccttgcacatag
taggtacccaattcaattactattgaatgaattaagaattggttgcca
taaaataaatcagttcatttaaaatgaaaaaaaaaaaaaaaaaaaa
```

By "ALOX5 polypeptide" is meant a polypeptide or fragment thereof having at least about 85% amino acid identity to NCBI Accession No. NP_000689.1, as reproduced below:

```
>NP_000689.1
                                          (SEQ ID NO: 34)
MPSYTVTVATGSQWFAGTDDYIYLSLVGSAGCSEKHLLDKPFYNDFER

GAVDSYDVTVDEELGEIQLVRIEKRKYWLNDDWYLKYITLKTPHGDYI

EFPCYRWITGDVEVVLRDGRAKLARDDQIHILKQHRRKELETRQKQYR

WMEWNPGFPLSIDAKCHKDLPRDIQFDSEKGVDFVLNYSKAMENLFIN

RFMHMFQSSWNDFADFEKIFVKISNTISERVMNHWQEDLMFGYQFLNG

CNPVLIRRCTELPEKLPVTTEMVECSLERQLSLEQEVQQGNIFIVDFE

LLDGIDANKTDPCTLQFLAAPICLLYKNLANKIVPIAIQLNQIPGDEN

PIFLPSDAKYDWLLAKIWVRSSDFHVHQTITHLLRTHLVSEVFGIAMY

RQLPAVHPIFKLLVAHVRFTIAINTKAREQLICECGLFDKANATGGGG

HVQMVQRAMKDLTYASLCFPEAIKARGMESKEDIPYYFYRDDGLLVWE

AIRTFTAEVVDIYYEGDQVVEEDPELQDFVNDVYVYGMRGRKSSGFPK

SVKSREQLSEYLTVVIFTASAQHAAVNFGQYDWCSWIPNAPPTMRAPP

PTAKGVVTIEQIVDTLPDRGRSCWHLGAVWALSQFQENELFLGMYPEE

HFIEKPVKEAMARFRKNLEAIVSVIAERNKKKQLPYYYLSPDRIPNSV

AI
```

By "ACSL1 nucleic acid molecule" is meant a polynucleotide encoding a ACSL1 polypeptide. An exemplary ACSL1 nucleic acid molecule is provided at NCBI Accession No. NM_001995.3, and reproduced below:

```
>NM_001995.3
                                          (SEQ ID NO: 35)
gggcggggccgcgggagggcggggccggcgcggcgagcgcaccagcag catcctggctcagccgcggcggtggcggggcgcaaccagcgggccga ggcggcggcgccagcggcgccttaaatagcatccagagccggcgcggg gcagggagtgggctgcagtgacagccggcggcggagcggccggtccac ggaggagaattcagcttagagaactatcaacacaggacaatgcaagcc catgagctgttccggtattttcgaatgccagagctggttgacttccga cagtacgtgcgtactcttccgaccaacacgcttatgggcttcggagct tttgcagcactcaccaccttctggtacgccacgagacccaaacccctg aagccgccatgcgacctctccatgcagtcagtggaagtggcgggtagt ggtggtgcacgaagatccgcactacttgacagcgacgagcccttggtg tatttctatgatgatgtcacaacattatacgaaggtttccagaggggga atacaggtgtcaaataatggccttgtttaggctctcggaaaccagac caaccctatgaatggctttcatataaacaggttgcagaattgtcggag tgcataggctcagcactgatccagaagggcttcaagactgccccagat cagttcattggcatctttgctcaaaatagacctgagtgggtgattatt gaacaaggatgctttgcttattcgatggtgatcgttccactttatgat acccttggaaatgaagccatcacgtacatagtcaacaaagctgaactc
```

-continued
```
tctctggttttttgttgacaagccagagaaggccaaactcttattagag ggtgtagaaaataagttaataccaggcccttaaaatcatagttgtcatg gatgcctacggcagtgaactggtggaacgaggccagaggtgtgggggtg gaagtcaccagcatgaaggcgatggaggacctgggaagagccaacaga cggaagcccaagcctccagcacctgaagatcttgcagtaatttgtttc acaagtggaactacaggcaaccccaaaggagcaatggtcactcaccga aacatagtgagcgattgttcagcttttgtgaaagcaacagagaataca gtcaatccttgcccagatgatactttgatatcttcttgcctctcgcc catatgtttgagagagttgtagagtgtgtaatgctgtgtcatggagct aaaatcggattttttccaaggagatatcaggctgctcatggatgacctc aaggtgcttcaacccactgtcttccccgtggttccaagactgctgaac cggatgtttgaccgaattttcggacaagcaaacaccacgctgaagcga tggctcttggactttgcctccaagaggaaagaagcagagcttcgcagc ggcatcatcagaaacaacagcctgtgggaccggctgatcttccacaaa gtacagtcgagcctgggcggaagagtccggctgatggtgacaggagcc gccccggtgtctgccactgtgctgacgttcctcagagcagccctgggc tgtcagttttatgaaggatacggacagacagagtgcactgccgggtgc tgcctgaccatgcctggagactggaccgcaggccatgttggggccccg atgccgtgcaatttgataaaacttgttgatgtggaagaaatgaattac atggctgccgagggcgagggcgaggtgtgtgtgaaagggccaaatgta tttcagggctacttgaaggacccagcgaaaacagcagaagctttggac aaagacggctggttacacacaggggacattggaaaatggttaccaaat ggcaccttgaaaattatcgaccggaaaaagcacatatttaagctggca caaggagaatacatagccccctgaaaagattgaaaatatctacatgcga agtgagcctgttgctcaggtgtttgtccacggagaaagcctgcaggca tttctcattgcaattgtggtaccagatgttgagacattatgttcctgg gcccaaaagagaggatttgaagggtcgtttgaggaactgtgcagaaat aaggatgtcaaaaaagctatcctcgaagatatggtgagacttgggaag gattctggtctgaaaccatttgaacaggtcaaaggcatcacattgcac cctgaattattttctatcgacaatggccttctgactccaacaatgaag gcgaaaaggccagagctgcggaactatttcaggtcgcagatagatgac ctctattccactatcaaggtttagtgtgaagaagaaagctcagaggaa atggcacagttccacaatctcttctcctgctgatggccttcatgttgt taattttgaatacagcaagtgtagggaaggaagcgttcgtgtttgact tgtccattcggggttcttctcataggaatgctagaggaaacagaacac tgccttacagtcacctcatgttgcagaccatgtttatggtaatacaca cttttccaaaatgagccttaaaaattctaaggggatactataaatgtg ctaagttatttgagacttcctcagtttaaaaagtgggttttaaatctt ctgtctccctgttttttctaatcaaggggttaggactttgctatctctg agatgtctgctacttgctgcaaattctgcagctgtctgctgctctaaa gagtacagtgcactagagggaagtgttccctttaaaaataagaacaac
```

-continued

```
tgtcctggctggagaatctcacaagcggaccagagatcttttaaatc
cctgctactgtcccttctcacaggcattcacagaaccttctgattcg
taagggttacgaaactcatgttcttctccagtccctgtggtttctgt
tggagcataaggtttccagtaagcgggagggcagatccaactcagaac
catgcagataaggagcctctggcaaatgggtgctcatcagaacgcgtg
gattctctttcatggcagaatgctcttggactcggttctccaggcctg
attcccgactccatcctttttcagggggttatttaaaaatctgcctta
gattctatagtgaagacaagcatttcaagaaagagttacctggatcag
ccatgctcagctgtgacgcctgaataactgtctactttatcttcactg
aaccactcactctgtgtaaaggccaacagattttttaatgtggttttca
tatcaaaagatcatgttgggattaacttgccttttcccaaaaaata
aactctcaggcaagcatttctttaaagctattaagggagtatatactt
gagtacttattgaaatggacagtaataagcaaatgttcttataatgct
acctgatttctgtgaaatgtgtttgacaagccaaaattctaggatgta
gaaatctggaaagttcatttcctgggattcacttctccagggattttt
taaagttaatttgggaaattaacagcagttcactttattgtgagtctt
tgccacatttgactgaattgagctgtcatttgtacatttaaagcagct
gttttgggggtctgtgagagtacatgtattatatacaagcacaacaggg
cttgcactaaagaattgtcattgtaataacactacttggtagcctaac
ttcatatatgtattcttaattgcacaaaaagtcaataatttgtcacct
tggggttttgaatgtttgctttaagtgttggctatttctatgttttat
aaaccaaaacaaaatttccaaaaacaatgaaggaaaccaaaataaata
tttctgcatttcaggtgaaaaaaaaaaaaaaaaa
```

By "ACSL1 polypeptide" is meant a polypeptide or fragment thereof having at least about 85% amino acid identity to NCBI Accession No. NP_001986.2, as reproduced below:

>NP_001986.2

(SEQ ID NO: 36)
MQAHELFRYFRMPELVDFRQYVRTLPTNTLMGFGAFAALTTFWYATRP

KPLKPPCDLSMQSVEVAGSGGARRSALLDSDEPLVYFYDDVTTLYEGF

QRGIQVSNNGPCLGSRKPDQPYEWLSYKQVAELSECIGSALIQKGFKT

APDQFIGIFAQNRPEWVIIEQGCFAYSMVIVPLYDTLGNEAITYIVNK

AELSLVFVDKPEKAKLLLEGVENKLIPGLKIIVVMDAYGSELVERGQR

CGVEVTSMKAMEDLGRANRRKPKPPAPEDLAVICFTSGTTGNPKGAMV

THRNIVSDCSAFVKATENTVNPCPDDTLISFLPLAHMFERVVECVMLC

HGAKIGFFQGDIRLLMDDLKVLQPTVFPVVPRLLNRMFDRIFGQANTT

LKRWLLDFASKRKEAELRSGIIRNNSLWDRLIFHKVQSSLGGRVRLMV

TGAAPVSATVLTFLRAALGCQFYEGYGQTECTAGCCLTMPGDWTAGHV

GAPMPCNLIKLVDVEEMNYMAAEGEGEVCVKGPNVFQGYLKDPAKTAE

ALDKDGWLHTGDIGKWLPNGTLKIIDRKKHIFKLAQGEYIAPEKIENI

YMRSEPVAQVFVHGESLQAFLIAIVVPDVETLCSWAQKRGFEGSFEEL

CRNKDVKKAILEDMVRLGKDSGLKPFEQVKGITLHPELFSIDNGLLTP

TMKAKRPELRNYFRSQIDDLYSTIKV

Standard methods may be used to measure levels of a marker in any biological sample. Biological samples include tissue samples (e.g., cell samples, biopsy samples) and bodily fluids, including, but not limited to, blood, blood serum, plasma, saliva, urine, seminal fluids, and ejaculate. Methods for measuring levels of polypeptide include immunoassay, ELISA, western blotting and radioimmunoassay. Elevated levels of ACOX1, ALOX5, ACSL1, ACSL5, FABP4, HMGS2, and/or CD36 alone or in combination with one or more additional markers are considered a positive indicator of a PPARG activated cancer. The increase in ACOX1, ALOX5, ACSL1, ACSL5, FABP4, HMGS2, and/or CD36 levels may be by at least about 10%, 25%, 50%, 75% or more. Elevated levels of PPARG, UPK1A, UPK1B, UPK2, KRT20, FOXA1, and/or GATA3 luminal differentiation markers alone or in combination with one or more additional markers are considered a positive indicator of a PPARG activated cancer in the bladder. The increase in PPARG, UPK1A, UPK1B, UPK2, KRT20, FOXA1, and/or GATA3 levels may be by at least about 10%, 25%, 50%, 75% or more. In one embodiment, any increase in a marker of the disclosure is indicative of a PPARG activated cancer (e.g., bladder cancer).

Any suitable method can be used to detect one or more of the markers described herein. Successful practice of the disclosure can be achieved with one or a combination of methods that can detect and, preferably, quantify the markers. These methods include, without limitation, hybridization-based methods, including those employed in biochip arrays, mass spectrometry (e.g., laser desorption/ionization mass spectrometry), fluorescence (e.g. sandwich immunoassay), surface plasmon resonance, ellipsometry and atomic force microscopy. Expression levels of markers (e.g., polynucleotides or polypeptides) are compared by procedures well known in the art, such as RT-PCR, Northern blotting, Western blotting, flow cytometry, immunocytochemistry, binding to magnetic and/or antibody-coated beads, in situ hybridization, fluorescence in situ hybridization (FISH), flow chamber adhesion assay, ELISA, microarray analysis, or colorimetric assays. Methods may further include, one or more of electrospray ionization mass spectrometry (ESI-MS), ESI-MS/MS, ESI-MS/(MS)n, matrix-assisted laser desorption ionization time-of-flight mass spectrometry (MALDI-TOF-MS), surface-enhanced laser desorption/ionization time-of-flight mass spectrometry (SELDI-TOF-MS), desorption/ionization on silicon (DIOS), secondary ion mass spectrometry (SIMS), quadrupole time-of-flight (Q-TOF), atmospheric pressure chemical ionization mass spectrometry (APCI-MS), APCI-MS/MS, APCI-(MS)n, atmospheric pressure photoionization mass spectrometry (APPI-MS), APPI-MS/MS, and APPI-(MS)n, quadrupole mass spectrometry, Fourier transform mass spectrometry (FTMS), and ion trap mass spectrometry, where n is an integer greater than zero.

Detection methods may include use of a biochip array. Biochip arrays useful in the disclosure include protein and polynucleotide arrays. One or more markers are captured on the biochip array and subjected to analysis to detect the level of the markers in a sample.

Markers may be captured with capture reagents immobilized to a solid support, such as a biochip, a multiwell microtiter plate, a resin, or a nitrocellulose membrane that is subsequently probed for the presence or level of a marker. Capture can be on a chromatographic surface or a biospecific surface. For example, a sample containing the markers, such as serum, may be used to contact the active surface of a biochip for a sufficient time to allow binding. Unbound molecules are washed from the surface using a suitable eluant, such as phosphate buffered saline. In general, the more stringent the eluant, the more tightly the proteins are bound to be retained after the wash.

Upon capture on a biochip, analytes can be detected by a variety of detection methods selected from, for example, a gas phase ion spectrometry method, an optical method, an electrochemical method, atomic force microscopy and a radio frequency method. In one embodiment, mass spectrometry, and in particular, SELDI, is used. Optical methods include, for example, detection of fluorescence, luminescence, chemiluminescence, absorbance, reflectance, transmittance, birefringence or refractive index (e.g., surface plasmon resonance, ellipsometry, a resonant mirror method, a grating coupler waveguide method or interferometry). Optical methods include microscopy (both confocal and non-confocal), imaging methods and non-imaging methods. Immunoassays in various formats (e.g., ELISA) are popular methods for detection of analytes captured on a solid phase. Electrochemical methods include voltametry and amperometry methods. Radio frequency methods include multipolar resonance spectroscopy.

Mass spectrometry (MS) is a well-known tool for analyzing chemical compounds. Thus, in one embodiment, the methods of the present disclosure comprise performing quantitative MS to measure the serum peptide marker. The method may be performed in an automated (Villanueva, et al., *Nature Protocols* (2006) 1(2):880-891) or semi-automated format. This can be accomplished, for example with MS operably linked to a liquid chromatography device (LC-MS/MS or LC-MS) or gas chromatography device (GC-MS or GC-MS/MS). Methods for performing MS are known in the field and have been disclosed, for example, in US Patent Application Publication Nos: 20050023454; 20050035286; U.S. Pat. No. 5,800,979 and references disclosed therein.

The protein fragments, whether they are peptides derived from the main chain of the protein or are residues of a side-chain, are collected on the collection layer. They may then be analyzed by a spectroscopic method based on matrix-assisted laser desorption/ionization (MALDI) or electrospray ionization (ESI). The preferred procedure is MALDI with time of flight (TOF) analysis, known as MALDI-TOF MS. This involves forming a matrix on the membrane, e.g., as described in the literature, with an agent which absorbs the incident light strongly at the particular wavelength employed. The sample is excited by UV, or IR laser light into the vapor phase in the MALDI mass spectrometer. Ions are generated by the vaporization and form an ion plume. The ions are accelerated in an electric field and separated according to their time of travel along a given distance, giving a mass/charge (m/z) reading which is very accurate and sensitive. MALDI spectrometers are commercially available from PerSeptive Biosystems, Inc. (Framingham, Mass., USA) and are described in the literature, e.g., M. Kussmann and P. Roepstorff, cited above.

Magnetic-based serum processing can be combined with traditional MALDI-TOF. Through this approach, improved peptide capture is achieved prior to matrix mixture and deposition of the sample on MALDI target plates. Accordingly, methods of peptide capture are enhanced through the use of derivatized magnetic bead based sample processing.

MALDI-TOF MS allows scanning of the fragments of many proteins at once. Thus, many proteins can be run simultaneously on a polyacrylamide gel, subjected to a method of the disclosure to produce an array of spots on the collecting membrane, and the array may be analyzed. Subsequently, automated output of the results is provided by using the ExPASy server, as at present used for MIDI-TOF MS and to generate the data in a form suitable for computers.

Other techniques for improving the mass accuracy and sensitivity of the MALDI-TOF MS can be used to analyze the fragments of protein obtained on the collection membrane. These include the use of delayed ion extraction, energy reflectors and ion-trap modules. In addition, post source decay and MS--MS analysis are useful to provide further structural analysis. With ESI, the sample is in the liquid phase and the analysis can be by ion-trap, TOF, single quadrupole or multi-quadrupole mass spectrometers. The use of such devices (other than a single quadrupole) allows MS--MS or MSn analysis to be performed. Tandem mass spectrometry allows multiple reactions to be monitored at the same time.

Capillary infusion may be employed to introduce the marker to a desired MS implementation, for instance, because it can efficiently introduce small quantities of a sample into a mass spectrometer without destroying the vacuum. Capillary columns are routinely used to interface the ionization source of a MS with other separation techniques including gas chromatography (GC) and liquid chromatography (LC). GC and LC can serve to separate a solution into its different components prior to mass analysis. Such techniques are readily combined with MS, for instance. One variation of the technique is that high performance liquid chromatography (HPLC) can now be directly coupled to mass spectrometer for integrated sample separation/and mass spectrometer analysis.

Quadrupole mass analyzers may also be employed as needed to practice the disclosure. Fourier-transform ion cyclotron resonance (FTMS) can also be used for some disclosure embodiments. It offers high resolution and the ability of tandem MS experiments. FTMS is based on the principle of a charged particle orbiting in the presence of a magnetic field. Coupled to ESI and MALDI, FTMS offers high accuracy with errors as low as 0.001%.

In one embodiment, the marker qualification methods of the disclosure may further comprise identifying significant peaks from combined spectra. The methods may also further comprise searching for outlier spectra. In another embodiment, the method of the disclosure further comprises determining distant dependent K-nearest neighbors.

In another embodiment of the method of the disclosure, an ion mobility spectrometer can be used to detect and characterize serum peptide markers. The principle of ion mobility spectrometry is based on different mobility of ions. Specifically, ions of a sample produced by ionization move at different rates, due to their difference in, e.g., mass, charge, or shape, through a tube under the influence of an electric field. The ions (typically in the form of a current) are registered at the detector which can then be used to identify a marker or other substances in a sample. One advantage of ion mobility spectrometry is that it can operate at atmospheric pressure.

In an additional embodiment of the methods of the present disclosure, multiple markers are measured. The use of multiple markers increases the predictive value of the test and provides greater utility in diagnosis, toxicology, patient stratification and patient monitoring. The process called "Pattern recognition" detects the patterns formed by multiple markers greatly improves the sensitivity and specificity of clinical proteomics for predictive medicine. Subtle variations in data from clinical samples indicate that certain patterns of protein expression can predict phenotypes such as the presence or absence of a certain disease, a particular stage of cancer progression, or a positive or adverse response to drug treatments.

Expression levels of particular nucleic acids or polypeptides are correlated with a PPARG activated cancer, and thus are useful in diagnosis. Antibodies that bind a polypeptide described herein, oligonucleotides or longer fragments derived from a nucleic acid sequence described herein (e.g., an PPARG, UPK1A, UPK1B, UPK2, KRT20, FOXA1, and/or GATA3nucleic acid sequence), or any other method known in the art may be used to monitor expression of a polynucleotide or polypeptide of interest. Detection of an alteration relative to a normal, reference sample can be used as a diagnostic indicator of a PPARG activated cancer. In other embodiments, a 2, 3, 4, 5, or 6-fold change in the level of a marker of the disclosure is indicative of an activated PPARG cancer (e.g., bladder cancer). In yet another embodiment, an expression profile that characterizes alterations in the expression two or more markers is correlated with a particular disease state (e.g., bladder cancer). Such correlations are indicative of a PPARG activated cancer or the propensity to develop a PPARG activated cancer. In one embodiment, a PPARG activated cancer (e.g., bladder cancer) can be monitored using the methods and compositions of the disclosure.

In one embodiment, the level of one or more markers is measured on at least two different occasions and an alteration in the levels as compared to normal reference levels over time is used as an indicator of a PPARG activated cancer or the propensity to develop a PPARG activated cancer. The level of marker in the bodily fluids (e.g., blood, blood serum, plasma, saliva, urine, seminal fluids, and ejaculate) of a subject having a PPARG activated cancer or the propensity to develop such a condition may be altered by as little as 10%, 20%, 30%, or 40%, or by as much as 50%, 60%, 70%, 80%, or 90% or more relative to the level of such marker in a normal control. In general, levels of PPARG, UPK1A, UPK1B, UPK2, KRT20, FOXA1, and/or GATA3are present at low or undetectable levels in a healthy subject (i.e., those who do not have and/or who will not develop a PPARG activated cancer). In one embodiment, a subject sample of a bodily fluid (e.g., blood, blood serum, plasma, saliva, urine, seminal fluids, and ejaculate) is collected prior to the onset of symptoms of a PPARG activated cancer. In another example, the sample can be a tissue or cell collected prior to the onset of a PPARG activated cancer symptoms.

The diagnostic methods described herein can be used individually or in combination with any other diagnostic method described herein for a more accurate diagnosis of the presence or severity of a PPARG activated cancer (e.g., bladder cancer).

As indicated above, the disclosure provides methods for aiding a human cancer diagnosis using one or more markers, as specified herein. These markers can be used alone, in combination with other markers in any set, or with entirely different markers in aiding human cancer diagnosis. The markers are differentially present in samples of a human cancer patient and a normal subject in whom human cancer is undetectable. Therefore, detection of one or more of these markers in a person would provide useful information regarding the probability that the person may have a PPARG activated cancer or regarding the aggressiveness of the cancer.

The detection of the peptide marker is then correlated with a probable diagnosis of cancer and may be used to recommend a therapeutic modality that includes a modulator of PPARG signaling (e.g., and inverse-agonist of PPARG signaling). The measurement of markers may also involve quantifying the markers to correlate the detection of markers with a probable diagnosis of cancer. Thus, if the amount of the markers detected in a subject being tested is different compared to a control amount (i.e., higher than the control), then the subject being tested has a higher probability of having cancer.

The correlation may take into account the amount of the marker or markers in the sample compared to a control amount of the marker or markers (e.g., in normal subjects or in non-cancer subjects such as where cancer is undetectable). A control can be, e.g., the average or median amount of marker present in comparable samples of normal subjects in normal subjects or in non-cancer subjects such as where cancer is undetectable. The control amount is measured under the same or substantially similar experimental conditions as in measuring the test amount. As a result, the control can be employed as a reference standard, where the normal (non-cancer) phenotype is known, and each result can be compared to that standard, rather than re-running a control.

Accordingly, a marker profile may be obtained from a subject sample and compared to a reference marker profile obtained from a reference population, so that it is possible to classify the subject as belonging to or not belonging to the reference population. The correlation may take into account the presence or absence of the markers in a test sample and the frequency of detection of the same markers in a control. The correlation may take into account both of such factors to facilitate determination of cancer status.

In certain embodiments of the methods of qualifying cancer status, the methods further comprise managing subject treatment based on the status. The disclosure also provides for such methods where the markers (or specific combination of markers) are measured again after subject management. In these cases, the methods are used to monitor the status of the cancer, e.g., response to cancer treatment, remission of the disease or progression of the disease.

The markers of the present disclosure have a number of other uses. For example, they can be used to monitor responses to certain treatments of PPARG activated cancer. In yet another example, the markers can be used in heredity studies. For instance, certain markers may be genetically linked. This can be determined by, e.g., analyzing samples from a population of human cancer subjects whose families have a history of cancer. The results can then be compared with data obtained from, e.g., cancer subjects whose families do not have a history of cancer. The markers that are genetically linked may be used as a tool to determine if a subject whose family has a history of cancer is pre-disposed to having cancer.

Any marker, individually, is useful in aiding in the determination of cancer status. First, the selected marker is detected in a subject sample using the methods described herein. Then, the result is compared with a control that distinguishes cancer status from non-cancer status. As is well understood in the art, the techniques can be adjusted to increase sensitivity or specificity of the diagnostic assay depending on the preference of the diagnostician.

While individual markers are useful diagnostic markers, in some instances, a combination of markers provides greater predictive value than single markers alone. The detection of a plurality of markers (or absence thereof, as the case may be) in a sample can increase the percentage of true positive and true negative diagnoses and decrease the percentage of false positive or false negative diagnoses. Thus, preferred methods of the present disclosure comprise the measurement of more than one marker.

Microarrays

As reported herein, a number of markers (e.g., PPARG, UPK1A, UPK1B, UPK2, KRT20, FOXA1, and/or GATA3) have been identified that are associated with a PPARG activated cancer (e.g., bladder cancer). Methods for assaying the expression of these polypeptides are useful for characterizing a PPARG activated cancer. In particular, the disclosure provides diagnostic methods and compositions useful for identifying a polypeptide expression profile that identifies a subject as having or having a propensity to develop a PPARG activated cancer. Such assays can be used to measure an alteration in the level of a polypeptide.

The polypeptides and nucleic acid molecules of the disclosure are useful as hybridizable array elements in a microarray. The array elements are organized in an ordered fashion such that each element is present at a specified location on the substrate. Useful substrate materials include membranes, composed of paper, nylon or other materials, filters, chips, glass slides, and other solid supports. The ordered arrangement of the array elements allows hybridization patterns and intensities to be interpreted as expression levels of particular genes or proteins. Methods for making nucleic acid microarrays are known to the skilled artisan and are described, for example, in U.S. Pat. No. 5,837,832, Lockhart, et al. (*Nat. Biotech.* 14:1675-1680, 1996), and Schena, et al. (*Proc. Natl. Acad. Sci.* 93:10614-10619, 1996), herein incorporated by reference. Methods for making polypeptide microarrays are described, for example, by Ge (*Nucleic Acids Res.* 28: e3. i-e3. vii, 2000), MacBeath et al., (*Science* 289:1760-1763, 2000), Zhu et al.(*Nature Genet.* 26:283-289), and in U.S. Pat. No. 6,436,665, hereby incorporated by reference.

Protein Microarrays

Proteins (e.g., PPARG, UPK1A, UPK1B, UPK2, KRT20, FOXA1, and/or GATA3) may be analyzed using protein microarrays. Such arrays are useful in high-throughput low-cost screens to identify alterations in the expression or post-translation modification of a polypeptide of the disclosure, or a fragment thereof. In particular, such microarrays are useful to identify a protein whose expression is altered in a PPARG activated cancer (e.g., bladder cancer). In one embodiment, a protein microarray of the disclosure binds a marker present in a subject sample and detects an alteration in the level of the marker. Typically, a protein microarray features a protein, or fragment thereof, bound to a solid support. Suitable solid supports include membranes (e.g., membranes composed of nitrocellulose, paper, or other material), polymer-based films (e.g., polystyrene), beads, or glass slides. For some applications, proteins (e.g., antibodies that bind a marker of the disclosure) are spotted on a substrate using any convenient method known to the skilled artisan (e.g., by hand or by inkjet printer).

The protein microarray is hybridized with a detectable probe. Such probes can be polypeptide, nucleic acid molecules, antibodies, or small molecules. For some applications, polypeptide and nucleic acid molecule probes are derived from a biological sample taken from a patient, such as a bodily fluid (such as blood, blood serum, plasma, saliva, urine, seminal fluids, and ejaculate); a homogenized tissue sample (e.g. a tissue sample obtained by biopsy); or a cell isolated from a patient sample. Probes can also include antibodies, candidate peptides, nucleic acids, or small molecule compounds derived from a peptide, nucleic acid, or chemical library. Hybridization conditions (e.g., temperature, pH, protein concentration, and ionic strength) are optimized to promote specific interactions. Such conditions are known to the skilled artisan and are described, for example, in Harlow, E. and Lane, D., *Using Antibodies: A Laboratory Manual.* 1998, New York: Cold Spring Harbor Laboratories. After removal of non-specific probes, specifically bound probes are detected, for example, by fluorescence, enzyme activity (e.g., an enzyme-linked calorimetric assay), direct immunoassay, radiometric assay, or any other suitable detectable method known to the skilled artisan.

Nucleic Acid Microarrays

To produce a nucleic acid microarray, oligonucleotides may be synthesized or bound to the surface of a substrate using a chemical coupling procedure and an ink jet application apparatus, as described in PCT application WO95/251116 (Baldeschweiler et al.), incorporated herein by reference. Alternatively, a gridded array may be used to arrange and link cDNA fragments or oligonucleotides to the surface of a substrate using a vacuum system, thermal, UV, mechanical or chemical bonding procedure.

A nucleic acid molecule (e.g., RNA or DNA) derived from a biological sample may be used to produce a hybridization probe as described herein. The biological samples are generally derived from a patient, preferably as a bodily fluid (such as blood, blood serum, plasma, saliva, urine, seminal fluids, and ejaculate) or tissue sample (e.g., a tissue sample obtained by biopsy). For some applications, cultured cells or other tissue preparations may be used. The mRNA is isolated according to standard methods, and cDNA is produced and used as a template to make complementary RNA suitable for hybridization. Such methods are known in the art. The RNA is amplified in the presence of fluorescent nucleotides, and the labeled probes are then incubated with the microarray to allow the probe sequence to hybridize to complementary oligonucleotides bound to the microarray.

Incubation conditions are adjusted such that hybridization occurs with precise complementary matches or with various degrees of less complementarity depending on the degree of stringency employed. For example, stringent salt concentration will ordinarily be less than about 750 mM NaCl and 75 mM trisodium citrate, preferably less than about 500 mM NaCl and 50 mM trisodium citrate, and most preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and most preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

The removal of nonhybridized probes may be accomplished, for example, by washing. The washing steps that follow hybridization can also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and most preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a most preferred embodiment, wash steps will occur at 68° C. in 15 mM NaCl, 1.5 mM trisodium citrate, and 0.1% SDS. Additional variations on these conditions will be readily apparent to those skilled in the art.

A detection system may be used to measure the absence, presence, and amount of hybridization for all of the distinct nucleic acid sequences simultaneously (e.g., Heller et al., *Proc. Natl. Acad. Sci.* 94:2150-2155, 1997). Preferably, a scanner is used to determine the levels and patterns of fluorescence.

Diagnostic Kits

The disclosure provides kits for diagnosing or monitoring or for selecting a treatment for a PPARG activated cancer (e.g., bladder cancer). In one embodiment, the kit includes a composition containing at least one agent that binds a polypeptide or polynucleotide whose expression is increased in a PPARG activated cancer (e.g., bladder cancer). In another embodiment, the disclosure provides a kit that contains an agent that binds a nucleic acid molecule whose expression is altered in a PPARG activated cancer (e.g., bladder cancer). In some embodiments, the kit comprises a sterile container which contains the binding agent; such containers can be boxes, ampoules, bottles, vials, tubes, bags, pouches, blister-packs, or other suitable container forms known in the art. Such containers can be made of plastic, glass, laminated paper, metal foil, or other materials suitable for holding medicaments.

If desired the kit is provided together with instructions for using the kit to diagnose a PPARG activated cancer. The instructions will generally include information about the use of the composition for diagnosing a subject as having a PPARG activated cancer or having a propensity to develop a PPARG activated cancer. In other embodiments, the instructions include at least one of the following: description of the binding agent; warnings; indications; counter-indications; animal study data; clinical study data; and/or references. The instructions may be printed directly on the container (when present), or as a label applied to the container, or as a separate sheet, pamphlet, card, or folder supplied in or with the container.

Selection of a Treatment Method

After a subject is diagnosed as having a PPARG activated cancer (e.g., bladder cancer), a method of treatment is selected. In bladder cancer, for example, a number of standard treatment regimens are available. The marker profile of the neoplasia is used in selecting a treatment method.

Bladder cancers having increased levels of PPARG, UPK1A, UPK1B, UPK2, KRT20, FOXA1, and/or GATA3 have a marker profile that correlates with a cancer that may be associated with activation of PPARG signaling. According to the techniques herein, the presence of such biomarkers may signal a need to genotype the PPARG and/or the RX are a gene to determine the presence or absence of an activating mutation (e.g., T447M in PPARG or S427F in RXRA). In the event that either of these oncogenic driver mutations are present, and inverse-agonist therapeutic modality targeting PPARG signaling can be used such as, for example, T0070907 and/or SR10221. It is contemplated within the scope of the disclosure that any of the disclosed inverse-agonist can be used in combination with one or more alternate chemotherapeutic agents (e.g., alkylating agent, an anti-metabolite, an anti-microtubule agent, a topoisomerase inhibitor) and drugs currently approved for treatment of bladder cancer (e.g., Atezolizumab (anti-PD-L1 antibody; aka Tecentriq®), Avelumab (anti-PD-L1 antibody), a *Bacillus* Calmette-Guerin (BCG) therapy (optionally a *Bacillus* of Calmette and Guérin (BCG) strain of *Mycobacterium bovis* live, attenuated culture preparation, such as TheraCys® and/or TICE® BCG), Cisplatin, Doxorubicin Hydrochloride, Durvalumab (anti-PD-L1 antibody), Nivolumab (anti-PD-1 antibody; aka Opdivo©), Pembrolizumab (anti-PD-1 antibody), Platinol© (Cisplatin), Platinol©-AQ (Cisplatin), Thiotepa, anti-PD-1 antibodies, anti-PD-L1 antibodies, and the like). It is also contemplated within the scope of the disclosure that such agents can be used in combination with drugs (e.g., GEMCITABINE-CISPLATIN) or in combination with immunotherapies.

Therapeutic Agents

The present disclosure contemplates any therapeutic agent suitable for use in the methods described herein (e.g., inverse agonists, chemotherapeutic agents, and any type of anti-cancer agent to treat cancer). Suitable therapeutic agents include, but are not limited to, pharmaceutical drugs or compounds (e.g., inverse agonists), therapeutic antibodies, therapeutic proteins or biologics (e.g., hormone therapies), and nucleic acid molecules (e.g., siRNAs).

In embodiments, the therapeutic agent is an agent that has been shown to have inverse agonist properties against PPARG activated cancers (e.g., T0070907, SR10221, and the like). In related embodiments, the therapeutic agent is an existing market-approved pharmaceutical drug or other market-approved composition for treating cancer using a conventional approach.

The "chemotherapeutic agent" includes chemical reagents that inhibit the growth of proliferating cells or tissues wherein the growth of such cells or tissues is undesirable. Chemotherapeutic agents are well known in the art, and any such agent is suitable for use in the present disclosure. See, e.g., Anticancer Drugs: Design, Delivery and Pharmacology (Cancer Etiology, Diagnosis and Treatments) (eds. Spencer, P. & Holt, W.) (Nova Science Publishers, 2011); *Clinical Guide to Antineoplastic Therapy: A Chemotherapy Handbook* (ed. Gullatte) (Oncology Nursing Society, 2007); Chemotherapy and Biotherapy Guidelines and Recommendations for Practice (eds. Polovich, M. et al.) (Oncology Nursing Society, 2009); *Physicians' Cancer Chemotherapy Drug Manual* 2012 (eds. Chu, E. & DeVita, Jr., V. T.) (Jones & Bartlett Learning, 2011); *DeVita, Hellman, and Rosenberg's Cancer: Principles and Practice of Oncology* (eds. DeVita, Jr., V. T. et al.) (Lippincott Williams & Wilkins, 2011); and Clinical Radiation Oncology (eds. Gunderson, L. L. & Tepper, J. E.) (Saunders) (2011), the contents of which are hereby incorporated by references in their entirety.

In one embodiment, the pharmaceutical drug can be an alkylating agent. Alkylating agents directly damage DNA to prevent the cancer cell from reproducing. As a class of drugs, these agents are not phase-specific; in other words, they work in all phases of the cell cycle. Alkylating agents are used to treat many different cancers. Examples of alkylating agents include, for example, nitrogen mustards (e.g., mechlorethamine, chlorambucil, cyclophosphamide (Cytoxan®), ifosfamide, and melphalan), alkyl sulfonates (e.g., busulfan), triazines (e.g., dacarbazine (DTIC), temozolomide (Temodar®)), Nitrosoureas (including streptozocin, carmustine (BCNU), and lomustine), and ethylenimines (e.g., thiotepa and altretamine). In addition, platinum drugs (e.g., cisplatin, carboplatin, and oxalaplatin) are often considered alkylating agents because they kill cancer cells in a similar way. The disclosure contemplates all of these drugs, or combinations thereof.

In another embodiment, the disclosure contemplates any antimetabolite drug. Antimetabolites are a class of drugs that interfere with DNA and RNA growth by substituting for the normal building blocks of RNA and DNA. These agents damage cells during the S phase. They are commonly used to treat leukemias, cancers of the breast, ovary, and the intestinal tract, as well as other types of cancer. Exemplary antimetabolites include, but are not limited to, 5-fluorouracil (5-FU), 6-mercaptopurine (6-MP), Capecitabine (Xeloda®), Cladribine, Clofarabine, Cytarabine (Ara-C®), Floxuridine, Fludarabine, Gemcitabine (Gemzar®), Hydroxyurea, Methotrexate, Pemetrexed (Alimta®), Pentostatin, and Thioguanine.

Also contemplated are topoisomerase inhibitors. These drugs interfere with enzymes called topoisomerases, which help separate the strands of DNA so they can be copied. They are used to treat certain leukemias, as well as lung, ovarian, gastrointestinal, and other cancers. Examples of topoisomerase I inhibitors include topotecan and irinotecan (CPT-11). Examples of topoisomerase II inhibitors include etoposide (VP-16) and teniposide. Mitoxantrone also inhibits topoisomerase II.

The present disclosure also contemplates using therapeutic agents known as mitotic inhibitors. Mitotic inhibitors are often plant alkaloids and other compounds derived from natural products. They can stop mitosis or inhibit enzymes from making proteins needed for cell reproduction. These drugs work during the M phase of the cell cycle, but can damage cells in all phases. They are used to treat many different types of cancer including breast, lung, myelomas, lymphomas, and leukemias. These drugs are known for their potential to cause peripheral nerve damage, which can be a dose-limiting side effect. Examples of mitotic inhibitors include Taxanes (e.g., paclitaxel (Taxol®) and docetaxel (Taxotere®)), Epothilones (e.g., ixabepilone (Ixempra®)), Vinca alkaloids (e.g., vinblastine (Velban®), vincristine (Oncovin®), and vinorelbine (Navelbine®)), and Estramustine (Emcyt®).

The anti-cancer agents can also be corticosteroids. Steroids are natural hormones and hormone-like drugs that are useful in treating some types of cancer (lymphoma, leukemias, and multiple myeloma), as well as other illnesses. When these drugs are used to kill cancer cells or slow their growth, they are considered chemotherapy drugs. Corticosteroids are also commonly used as anti-emetics to help prevent nausea and vomiting caused by chemotherapy. They are used before chemotherapy to help prevent severe allergic reactions (hypersensitivity reactions), too. Examples include prednisone, methylprednisolone (e.g., Solumedrol®), and dexamethasone (e.g., Decadron®).

In certain embodiments, the pharmaceutical agent is selected from the group consisting of: Abiraterone Acetate, Afatinib, Aldesleukin, Alemtuzumab, Alitretinoin, Altretamine, Amifostine, Aminoglutethimide Anagrelide, Anastrozole, Arsenic Trioxide, Asparaginase, Azacitidine, Azathioprine, Bacillus Calmette-Guerin (BCG) therapies (e.g., TheraCys® BCG Live (Intravesical), which is a freeze-dried preparation made froin the Connaught strain of Bacillus Calmette and Guerin, which is an attenuated strain ofMlvcobacterium bovis, where a dose of TheraCys® BCG consists of one 81 mg vial of freeze-dried BCG reconstituted and diluted in 50 mL sterile, preservative-free saline; and TICE® BCG, which is a Bacillus of Calmette and Gurin (BCG) strain ofMycobacterium bovis live, attenuated culture preparation; 50 mg per vial; pwd for intravesical administration after reconstitution and dilution), Bendamustine, Bevacizumab, Bexarotine, Bicalutamide, Bleomycin, Bortezomib, Busulfan, Capecitabine, Carboplatin, Carmustine, Cetuximab, Chlorambucil, Cisplatin, Cladribine, Crizotinib, Cyclophosphamide, Cytarabine, Dacarbazine, Dactinomycin, Dasatinib, Daunorubicin, Denileukin diftitox, Decitabine, Docetaxel, Dexamethasone, Doxifluridine, Doxorubicin, Epirubicin, Epoetin Alpha, Epothilone, Erlotinib, Estramustine, Etinostat, Etoposide, Everolimus, Exemestane, Filgrastim, Floxuridine, Fludarabine, Fluorouracil, Fluoxymesterone, Flutamide, folate linked alkaloids, Gefitinib, Gemcitabine, Gemtuzumab ozogamicin, GM-CT-01, Goserelin, Hexamethylmelamine, Hydroxyureas, Ibritumomab, Idarubicin, Ifosfamide, Imatinib, Interferon alpha, Interferon beta, Irinotecan, Ixabepilone, Lapatinib, Leucovorin, Leuprolide, Lenalidomide, Letrozole, Lomustine, Mechlorethamine, Megestrol, Melphalan, Mercaptopurine, Methotrexate, Mitomycin, Mitoxantrone, Nelarabine, Nilotinib, Nilutamide, Octreotide, Ofatumumab, Oprelvekin, Oxaliplatin, Paclitaxel, Panitumumab, Pemetrexed, Pentostatin, polysaccharide galectin inhibitors, Procarbazine, Raloxifene, Retinoic acids, Rituximab, Romiplostim, Sargramostim, Sorafenib, Streptozocin, Sunitinib, Tamoxifen, Temsirolimus, Temozolamide, Teniposide, Thalidomide, Thioguanine, Thiotepa, Tioguanine, Topotecan, Toremifene, Tositumomab, Trametinib, Trastuzumab, Tretinoin, Valrubicin, VEGF inhibitors and traps, Vinblastine, Vincristine, Vindesine, Vinorelbine, Vintafolide (EC145), Vorinostat, and their functionally effective derivatives, pegylated forms, salts, polymorphisms, chiral forms and combinations thereof.

The disclosure also contemplates any derivative form of the aforementioned pharmaceutical agents and therapeutic agents. Common derivatizations may include, for example, adding a chemical moiety to improve solubility and/or stability, or a targeting moiety, which allows more specific targeting of the molecule to a specific cell or region of the body. The pharmaceutical agents can also be formulated in any suitable combinations, wherein the drugs can either mixed in individual form or coupled together in a manner that retains the functionality of each drug. The drugs can also be derivatized to include a radioisotope or other cell-killing moiety to make the molecule even more effective at killing the cell. In addition, the drugs, or a portion thereof, can be modified with fluorescence compound or other detectable labels which can allow tracking of the drug or agent in the body or within the tumor. The pharmaceutical drug or otherwise any of the aforementioned therapeutic agents can be provided in a precursor form such that they the drug only gains its activity or function after it has been processed in some manner, e.g., metabolized by a cell.

Therapeutic antibodies contemplated by the present disclosure can include any isotype (IgA, IgG, IgE, IgM, or IgD) of an anti-cancer antibody or immune-active fragment or derivative thereof. Such fragments can include, for example, single-chain variable fragments (scFv), antigen-binding fragment (Fab), crystallizable fragment (Fc) modified to contain an antigen or epitope binding region, and domain antibodies. Derivatized versions of therapeutic antibodies can include, for example, diabodies, nanobodies, and virtually any antibody-derived structure which contains or is engineered to contain an appropriate and effective antigen binding site.

Examples of antibody-based anticancer therapies that can be utilized by the disclosure can include, for example, Abagovomab, Alacizumab pegol, Alemtuzumab, Altumomab pentetate (Hybri-ceaker), Amatuximab, Anatumomab mafenatox, anti-PD-1 antibodies, Apolizumab, Arcitumomab (CEA-Scan), Belimumab, Bevacizumab, Bivatuzumab mertansine, Blinatumomab, Brentuximab vedotin, Cantuzumab mertansine, Cantuzumab ravtansine, Capromab pendetide (Prostascint), Catumaxomab (Removab), Cetuximab (Erbitux), Citatuzumab bogatox, Cixutumumab, Clivatuzumabtetraxetan (hPAM4-Cide), Conatumumab, Dalotuzumab, Denosumab, Drozitumab, Edrecolomab (Panorex), Enavatuzumab, Gemtuzumab, Ibritumomab tiuxetan, Ipilimumab (MDX-101), Ofatumumab, Panitumumab, Rituximab, Tositumomab, and Trastuzumab.

In some embodiment, therapeutic agents currently approved for treatment of bladder cancer can be used including, but not limited to, Atezolizumab, Cisplatin, Doxorubicin Hydrochloride, Nivolumab, Opdivo (Nivolumab), Platinol (Cisplatin), Platinol-AQ (Cisplatin), Tecentriq (Atezolizumab), and Thiotepa. In some embodiment, drug combinations such as Gemcitabine-Cisplatin can be used. In some embodiments, Atezolizumab, Cisplatin, Doxorubicin Hydrochloride, Nivolumab, Opdivo (Nivolumab), Platinol (Cisplatin), Platinol-AQ (Cisplatin), Tecentriq (Atezolizumab), and Thiotepa can be used in combination with immunotherapeutic agents.

The disclosure also contemplates that cancer treatment can be effectuated using a nucleic acid molecule that targets a specified "target gene" that has a role in cancer. The effect of the nucleic acid molecule on the target gene can include gene silencing, mRNA destruction, or inhibited transcription, or the like, such that the level of expression and/or conversion of the target gene to an operable encoded polypeptide are substantially affected (up or down) such that the cancer is inhibited and/or destroyed by the agent. The term "target gene" refers to nucleic acid sequences (e.g., genomic DNAs or mRNAs) encoding a target protein, peptide, or polypeptide, or that encode for or are regulatory nucleic acids (e.g., a "target gene" for purpose of the instant disclosure can also be a miRNA or miRNA-encoding gene sequence) which have a role in cancer. In certain embodiments, the term "target gene" is also meant to include isoforms, mutants, polymorphisms, and splice variants of target genes.

Any nucleic acid based agent well known in the art is suitable for use in the disclosure. Exemplary types of nucleic acid based agents include, but are not limited to, a CRISPR/Cas system, single stranded ribonucleic acid agents (e.g., microRNAs), antisense-type oligonucleotide agents, double-stranded ribonucleic acid agents, and the like.

Methods for constructing therapeutic nucleic acids are well known in the art. For example, interfering RNA can be assembled from two separate oligonucleotides, where one strand is the sense strand and the other is the antisense strand, wherein the antisense and sense strands are self-complementary (i.e., each strand comprises nucleotide sequence that is complementary to nucleotide sequence in the other strand; such as where the antisense strand and sense strand form a duplex or double stranded structure); the antisense strand comprises nucleotide sequence that is complementary to a nucleotide sequence in a target nucleic acid molecule or a portion thereof and the sense strand comprises nucleotide sequence corresponding to the target nucleic acid sequence or a portion thereof.

Alternatively, interfering RNA is assembled from a single oligonucleotide, where the self-complementary sense and antisense regions are linked by means of nucleic acid based or non-nucleic acid-based linker(s). The interfering RNA can be a polynucleotide with a duplex, asymmetric duplex, hairpin or asymmetric hairpin secondary structure, having self-complementary sense and antisense regions, wherein the antisense region comprises a nucleotide sequence that is complementary to nucleotide sequence in a separate target nucleic acid molecule or a portion thereof and the sense region having nucleotide sequence corresponding to the target nucleic acid sequence or a portion thereof. The interfering can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siRNA molecule capable of mediating RNA interference.

Methods for administering/delivering therapeutic nucleic acids are well known in the art. For example, therapeutic nucleic acid molecules may be delivered in a delivery vehicle, such as a lipid vesicle or other polymer carrier material known in the art. Non-limiting examples of additional lipid-based carrier systems (which may be prepared with at least one modified cationic lipid of the disclosure) suitable for use in the present disclosure include lipoplexes (see, e.g., U.S. Patent Publication No. 20030203865; and Zhang et al., *J. Control Release,* 100:165-180 (2004)), pH-sensitive lipoplexes (see, e.g., U.S. Patent Publication No. 2002/0192275), reversibly masked lipoplexes (see, e.g., U.S. Patent Publication Nos. 2003/0180950), cationic lipid-based compositions (see, e.g., U.S. Pat. No. 6,756,054; and U.S. Patent Publication No. 2005/0234232), cationic liposomes (see, e.g., U.S. Patent Publication Nos. 2003/0229040, 2002/0160038, and 2002/0012998; U.S. Pat. No. 5,908,635; and PCT Publication No. WO 01/72283), anionic liposomes (see, e.g., U.S. Patent Publication No. 2003/0026831), pH-sensitive liposomes (see, e.g., U.S. Patent Publication No. 2002/0192274; and AU 2003/210303), antibody-coated liposomes (see, e.g., U.S. Patent Publication No. 2003/0108597; and PCT Publication No. WO 00/50008), cell-type specific liposomes (see, e.g., U.S. Patent Publication No. 2003/0198664), liposomes containing nucleic acid and peptides (see, e.g., U.S. Pat. No. 6,207,456), liposomes containing lipids derivatized with releasable hydrophilic polymers (see, e.g., U.S. Patent Publication No. 2003/0031704), lipid-entrapped nucleic acid (see, e.g., PCT Publication Nos. WO 03/057190 and WO 03/059322), lipid-encapsulated nucleic acid (see, e.g., U.S. Patent Publication No. 2003/0129221; and U.S. Pat. No. 5,756,122), other liposomal compositions (see, e.g., U.S. Patent Publication Nos. 2003/0035829 and 2003/0072794; and U.S. Pat. No.

6,200,599), stabilized mixtures of liposomes and emulsions (see, e.g., EP1304160), emulsion compositions (see, e.g., U.S. Pat. No. 6,747,014), and nucleic acid micro-emulsions (see, e.g., U.S. Patent Publication No. 2005/0037086).

If suitable, any of the agents of the disclosure, including pharmaceutical drugs, biologics, and therapeutic antibodies, may also be delivered via the above described carrier systems. All carrier systems may further be modified with a targeting moiety or the like in order to facilitate delivery of the composition to a target tumor of interest.

In an embodiment, the present disclosure utilizes platinum compounds as the therapeutic agent. Platinum containing compound have been used for several years as an effective treatment of several types of cancers. Platinum based compounds (e.g., carboplatin, cisplatin, oxaliplatin) are anti-neoplastic agents administered by physicians intravenously (IV) to treat various cancers. Intravenous administration is generally used because the oral bioavailability of carboplatin alone is low (approximately 4%) and highly variable. Platinum based products potently kill fast dividing cells. However, administration of carboplatin by intravenous infusion results in drug throughout the body, killing healthy fast dividing cells including and especially bone marrow cells. Intravenous administration of carboplatin results in a dilute blood concentration of the drug reaching the tumor site. In addition, because of the dilute drug concentration there is poor penetration into the tumor cells.

Upon entering the cancer cells these compounds damage the DNA and cause cross links in the strands, thereby preventing future DNA production, which ultimately results in cancer cell death. This effect is apparently cell-cycle nonspecific. When given intravenously, platinum can cause severe blood disorders (e.g., anemia bone marrow suppression) resulting in infection or bleeding problems. The major route of elimination of the two main platinum compounds is renal excretion. Cisplatin and carboplatin are generic, platinum-based chemotherapeutic agents and widely available. The chemical name for carboplatin is platinum, diammine [1,1-cyclobutane-dicarboxylato(2-)-0,0']-(SP-4-2). Carboplatin is a crystalline powder with the molecular formula of $C_6H_{12}N_2O_4Pt$ and a molecular weight of 371.25. It is soluble in water at a rate of approximately 14 mg/mL, and the pH of a 1% solution is 5-7, whereas Cisplatin is soluble at approximately 1-2 mg/ML. These compounds are virtually insoluble in ethanol, acetone, and dimethylacetamide. They are currently administered only by intravenous infusion.

In another embodiment, the present disclosure employs thymidalate synthesis inhibitors. These agents include the agent 5-FU (fluorouracil), which has been in use against cancer for about 40 years. The compound acts in several ways, but principally as a thymidylate synthase inhibitor, interrupting the action of an enzyme which is a critical factor in the synthesis of the pyrimidine thymine-which is important in DNA replication. 5-FU is not orally absorbed. Currently the best treatment therapy for pancreatic cancer is a course of therapy using Gemcitabine (Gemzar).

As a pyrimidine analogue, these compounds are transformed inside the cell into different cytotoxic metabolites which are then incorporated into DNA and RNA, finally inducing cell cycle arrest and apoptosis by inhibiting the cell's ability to synthesize DNA. These compounds are typically S-phase specific drug and only active during certain cell cycles. In addition to being incorporated in DNA and RNA, these drugs have been shown to inhibit the activity of the exosome complex, an exoribonuclease complex of which the activity is essential for cell survival.

Therapeutic Uses

The present disclosure features methods for treating a PPARG activated cancer (e.g., bladder cancer), or the progression of a PPARG activated cancer, by administering one or more inverse-agonists that down-regulate PPARG signaling (e.g., as evidenced by reduced levels of expression of PPARG, UPK1A, UPK1B, UPK2, KRT20, FOXA1, and/or GATA3 nucleic acid molecules or polypeptides, or any other target gene whose expression is up-regulated by PPARG signaling). In other embodiments, the method involves administering an inhibitory nucleic acid molecule (e.g., an antisense oligonucleotide or RNAi agent as known in the art (e.g., a shRNA, a miRNA, a dsRNA, e.g., siRNA, DsiRNA, etc.), optionally a modified inhibitory nucleic acid, optionally the inhibitory nucleic acid molecule is formulated in a lipid nanoparticle for delivery, conjugated to a cholesterol moiety and/or a GalNAc moiety, etc.) or other agent that down-regulates PPARG signaling (e.g., by decreasing the expression or biological activity of PPARG, UPK1A, UPK1B, UPK2, KRT20, FOXA1, and/or GATA3 alone, or in combination with, any other marker described herein. Advantageously, such agents selectively target a PPARG activated cancer (e.g., bladder cancer). Compounds of the present disclosure can be administered by any appropriate route for the treatment or prevention of a PPARG activated cancer (e.g., bladder cancer). These can be administered to humans, domestic pets, livestock, or other animals with a pharmaceutically acceptable diluent, carrier, or excipient, in unit dosage form. Administration can be parenteral, intravenous, intra-arterial, subcutaneous, intramuscular, intracranial, intraorbital, ophthalmic, intraventricular, intracapsular, intraspinal, intracisternal, intraperitoneal, intranasal, aerosol, by suppositories, or oral administration.

Therapeutic formulations can be in the form of liquid solutions or suspensions; for oral administration, formulations can be in the form of tablets or capsules; and for intranasal formulations, in the form of powders, nasal drops, or aerosols.

Methods well known in the art for making formulations are found, for example, in *Remington: The Science and Practice of Pharmacy* (20th ed., ed. A. R. Gennaro, 2000, Lippincott Williams & Wilkins). Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers can be used to control the release of the compounds. Nanoparticulate formulations (e.g., biodegradable nanoparticles, solid lipid nanoparticles, liposomes) can be used to control the biodistribution of the compounds. Other potentially useful parenteral delivery systems include ethylene-vinyl acetate copolymer particles, osmotic pumps, implantable infusion systems, and liposomes. Formulations for inhalation can contain excipients, for example, lactose, or can be aqueous solutions containing, for example, polyoxyethylene-9-lauryl ether, glycholate and deoxycholate, or can be oily solutions for administration in the form of nasal drops, or as a gel. The concentration of the compound in the formulation will vary depending upon a number of factors, including the dosage of the drug to be administered, and the route of administration.

The compound can be optionally administered as a pharmaceutically acceptable salt, such as a non-toxic acid addition salts or metal complexes that are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acid such as hydrochloric acid, hydrobromic acid, sulfuric acid phosphoric acid, or the like. Metal complexes include zinc, iron, and the like.

Administration of compounds in controlled release formulations is useful where the compound of formula I has (i) a narrow therapeutic index (e.g., the difference between the plasma concentration leading to harmful side effects or toxic reactions and the plasma concentration leading to a therapeutic effect is small; generally, the therapeutic index, TI, is defined as the ratio of median lethal dose (LD50) to median effective dose (ED50)); (ii) a narrow absorption window in the gastro-intestinal tract; or (iii) a short biological half-life, so that frequent dosing during a day is required in order to sustain the plasma level at a therapeutic level.

Many strategies can be pursued to obtain controlled release in which the rate of release outweighs the rate of metabolism of the therapeutic compound. For example, controlled release can be obtained by the appropriate selection of formulation parameters and ingredients, including, e.g., appropriate controlled release compositions and coatings. Examples include single or multiple unit tablet or capsule compositions, oil solutions, suspensions, emulsions, microcapsules, microspheres, nanoparticles, patches, and liposomes.

Formulations for oral use include tablets containing the active ingredient(s) in a mixture with non-toxic pharmaceutically acceptable excipients. These excipients can be, for example, inert diluents or fillers (e.g., sucrose and sorbitol), lubricating agents, glidants, and antiadhesives (e.g., magnesium stearate, zinc stearate, stearic acid, silicas, hydrogenated vegetable oils, or talc).

Formulations for oral use can also be provided as chewable tablets, or as hard gelatin capsules wherein the active ingredient is mixed with an inert solid diluent, or as soft gelatin capsules wherein the active ingredient is mixed with water or an oil medium.

Pharmaceutical Compositions

Another aspect of the disclosure pertains to pharmaceutical compositions of the compounds of the disclosure. The pharmaceutical compositions of the disclosure typically comprise a compound of the disclosure and a pharmaceutically acceptable carrier. As used herein "pharmaceutically acceptable carrier" includes any and all solvents, dispersion media, coatings, antibacterial and antifungal agents, isotonic and absorption delaying agents, and the like that are physiologically compatible. The type of carrier can be selected based upon the intended route of administration. In various embodiments, the carrier is suitable for intravenous, intraperitoneal, subcutaneous, intramuscular, topical, transdermal or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the disclosure is contemplated. Supplementary active compounds can also be incorporated into the compositions.

Therapeutic compositions typically need to be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be advantageous to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. Moreover, the compounds can be administered in a time release formulation, for example in a composition which includes a slow release polymer, or in a fat pad described herein. The active compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are generally known to those skilled in the art.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, certain methods of preparation are vacuum drying and freeze-drying which yields a powder of the active ingredient plus any additional desired ingredient from a previously sterile-filtered solution thereof.

Depending on the route of administration, the compound can be coated in a material to protect it from the action of enzymes, acids and other natural conditions which can inactivate the agent. For example, the compound can be administered to a subject in an appropriate carrier or diluent co-administered with enzyme inhibitors or in an appropriate carrier such as liposomes. Pharmaceutically acceptable diluents include saline and aqueous buffer solutions. Enzyme inhibitors include pancreatic trypsin inhibitor, diisopropylfluoro-phosphate (DEP) and trasylol. Liposomes include water-in-oil-in-water emulsions as well as conventional liposomes (Strejan, et al., (1984) *J. Neuroimmunol* 7:27). Dispersions can also be prepared in glycerol, liquid polyethylene glycols, and mixtures thereof and in oils. Under ordinary conditions of storage and use, these preparations can contain a preservative to prevent the growth of microorganisms.

The active agent in the composition (e.g., inverse-agonists or modulators of PPAR signaling) optionally is formulated in the composition in a therapeutically effective amount. A "therapeutically effective amount" refers to an amount effective, at dosages and for periods of time necessary, to achieve the desired therapeutic result to thereby influence the therapeutic course of a particular disease state. A therapeutically effective amount of an active agent can vary according to factors such as the disease state, age, sex, and weight of the individual, and the ability of the agent to elicit a desired response in the individual. Dosage regimens can be adjusted to provide the optimum therapeutic response. A therapeutically effective amount is also one in which any toxic or detrimental effects of the agent are outweighed by the therapeutically beneficial effects. In another embodiment, the active agent is formulated in the composition in a prophylactically effective amount. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

The amount of active compound in the composition can vary according to factors such as the disease state, age, sex, and weight of the individual. Dosage regimens can be adjusted to provide the optimum therapeutic response. For example, a single bolus can be administered, several divided doses can be administered over time or the dose can be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the disclosure are dictated by and directly dependent on (a) the unique characteristics of the active compound and the particular therapeutic effect to be achieved, and (b) the limitations inherent in the art of compounding such an active compound for the treatment of sensitivity in individuals.

Exemplary dosages of compounds (e.g., inverse-agonists or modulators of PPAR signaling) of the disclosure include e.g., about 0.0001% to 5%, about 0.0001% to 1%, about 0.0001% to 0.1%, about 0.001% to 0.1%, about 0.005%-0.1%, about 0.01% to 0.1%, about 0.01% to 0.05% and about 0.05% to 0.1%.

The compound(s) of the disclosure can be administered in a manner that prolongs the duration of the bioavailability of the compound(s), increases the duration of action of the compound(s) and the release time frame of the compound by an amount selected from the group consisting of at least 3 hours, at least 6 hours, at least 12 hours, at least 24 hours, at least 48 hours, at least 72 hours, at least 4 days, at least 5 days, at least 6 days, at least 7 days, at least 2 weeks, at least 3 weeks, and at least a month, but at least some amount over that of the compound(s) in the absence of the fat pad delivery system. Optionally, the duration of any or all of the preceding effects is extended by at least 30 minutes, at least an hour, at least 2 hours, at least 3 hours, at least 6 hours, at least 12 hours, at least 24 hours, at least 48 hours, at least 72 hours, at least 4 days, at least 5 days, at least 6 days, at least 7 days, at least 2 weeks, at least 3 weeks or at least a month.

A compound of the disclosure can be formulated into a pharmaceutical composition wherein the compound is the only active agent therein. Alternatively, the pharmaceutical composition can contain additional active agents. For example, two or more compounds of the disclosure can be used in combination. Moreover, a compound of the disclosure can be combined with one or more other agents that have modulatory effects on cancer.

Screening Methods

The disclosure provides methods for identifying agents useful for the treatment or prevention of a PPARG activated cancer (e.g., bladder cancer) such as, for example, inverse-agonists of PPARG signaling. Screens for the identification of such modulators of PPARG signaling employ a PPARG reporter cell line engineered according to the methods herein. The use of such a PPARG reporter cell line, which expresses a fluorescently detectable FABP4 gene that serves as a visible readout of PPARG signaling, readily enables detection of modulators of PPARG signaling such as, for example, antagonists and inverse-agonists. As described in more detail below, an embodiment of a PPARG reporter cell line as described herein, includes a FABP4 gene having a NanoLuc™ reporter gene inserted into the 3' UTR that is expressed within a RT112 bladder cancer cell line. According to the techniques herein, increased levels of FABP4 expression are indicative of activated PPARG signaling. Agents identified as reducing the level of expression of the FABP4/NanoLuc™ reporter gene are particularly useful modulators of PPARG signaling, and can constitute particularly useful therapeutic modalities for treating PPARG activated cancers (e.g., bladder cancer).

Representative bladder cancer cell lines of the disclosure may include, but are not limited to, a RT112/84 cell, a UM-UC-9 cell (including a PPARG focal amplification), a RT112 cell, a 5637 cell (including a PPARG focal amplification), a HT-1197 cell (including RXRA p.S427F), a RT4 cell (including PPARG p.T447M), a KMBC2 cell, a CAL29 cell, a TCCSUP cell, a SW780 cell, and/or a UM-UC-1 cell.

Methods of observing changes in the level of expression of the FABP4/NanoLuc™ reporter gene are exploited in high throughput assays for the purpose of identifying compounds that modulate PPARG signaling, e.g., antagonists or inverse-agonists. Compounds that inhibit or modulate PPARG homo- or hetero-dimer binding (e.g., PPARG: RXRA binding), can be identified by such assays.

A number of methods are available for carrying out the disclosed PPARG reporter cell line screening assays to identify new candidate compounds that decrease the level of expression of the FABP4/NanoLuc™ reporter gene. In one example, candidate compounds are added at varying concentrations to the culture medium of cultured PPARG reporter cell line cells expressing one of the FABP4/NanoLuc™ reporter gene of the disclosure. Gene expression is then measured, for example, by microarray analysis, Northern blot analysis (Ausubel et al., supra), RT-PCR, using any appropriate fragment prepared from the nucleic acid molecule as a hybridization probe, or by any of a variety of fluorescent assays such as, for example, the NanoGlo Luciferase Assay (Promega, Madison, Wisconsin). The level of gene expression in the presence of the candidate compound is compared to the level measured in an un-induced control culture medium lacking the candidate molecule. A compound which reduces the expression of a FABP4/NanoLuc™ reporter gene, or a functional equivalent thereof, is considered useful in the disclosure; such a molecule can be used, for example, as a therapeutic agent to treat a PPARG activated cancer (e.g., bladder cancer).

In another example, the effect of candidate compounds may be measured at the level of polypeptide production using the same general approach and standard immunological techniques, such as fluorescent assay, Western blotting or immunoprecipitation with an antibody specific for a polypeptide encoded by the FABP4/NanoLuc™ reporter gene. For example, immunoassays may be used to detect or monitor the expression of at least one of the polypeptides of the disclosure in an organism. Polyclonal or monoclonal antibodies (produced as described above) that are capable of binding to such a polypeptide may be used in any standard immunoassay format (e.g., ELISA, Western blot, or RIA assay) to measure the level of the polypeptide. In some embodiments, a compound that promotes an increase in the expression or biological activity of the polypeptide is considered particularly useful. Again, such a molecule may be used, for example, as a therapeutic to delay, ameliorate, or treat a neoplasia in a human patient.

In yet another working example, candidate compounds can be screened for those that specifically bind to a polypeptide encoded by a PPARG or RXRA gene. The efficacy of such a candidate compound may be dependent upon its ability to interact with the ligand-binding domain of such a polypeptide or a functional equivalent thereof. Such an interaction can be readily assayed using any number of standard binding techniques and functional assays (e.g., a TR-FRET PPARG co-repressor assay, as described herein). In one embodiment, a candidate compound may be tested in vitro for its ability to specifically bind a polypeptide of the disclosure and induce an interaction between PPARG and a co-repressor (e.g., NCOR2 and/or NCOR2).

In another working example, a nucleic acid described herein (e.g., PPARG, UPK1A, UPK1B, UPK2, KRT20, FOXA1, and/or GATA3) is expressed as a transcriptional or translational fusion with a detectable reporter, and expressed in an isolated bladder cancer cell (e.g., RT112) under the control of an endogenous or heterologous promoter, such as an inducible promoter. The cell expressing the fusion protein is then contacted with a candidate compound, and the expression of the detectable reporter in that cell is compared to the expression of the detectable reporter in an untreated control cell. A candidate compound that alters the expression of the detectable reporter is a compound that is useful for the treatment of a neoplasia. Preferably, the compound decreases the expression of the reporter.

Potential antagonists or inverse-agonists include organic molecules, peptides, peptide mimetics, polypeptides, nucleic acids, and antibodies that bind to a nucleic acid sequence or polypeptide of the disclosure (e.g., a PPARG, RXRA, NCOR1, NCOR2, and the like). According to the techniques herein, inverse-agonists of the disclosure can include T0070907 (e.g., 2-Chloro-5-nitro-N-4-pyridinyl-benzamide) and/or SR10221 (see e.g., US Patent Publication No. 2017/0035730).

According to the techniques herein, T0070907 can have the following chemical structure:

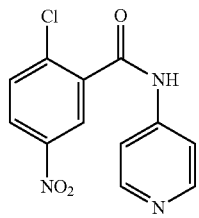 [SMILES: O=C(Nc1ccncc1)c1cc([N+](=O)[O-])ccc1Cl]

According to the techniques herein, SR10221 can have the following chemical structure:

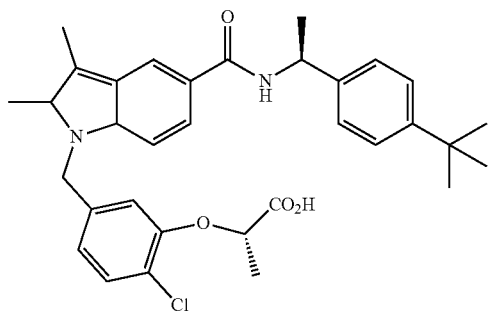 [SMILES: CC1=C2C=C(C(=O)N[C@@H](C)c3ccc(C(C)(C)C)cc3)C=CC2N(Cc2ccc(Cl)c(O[C@@H](C)C(=O)O)c2)C1C]

It is contemplated within the scope of the disclosure, that the inverse-agonists T0070907 and/or SR10221 can be derivatized by any of a variety of techniques known to one of skill in the art, and that these derivatized versions can be efficacious therapeutic agents for PPARG activated cancers. SR10221, derivatives and analogs thereof, and related compounds are described in detail in (see e.g., US Patent Publication No. 2017/0035730), which is hereby incorporated by reference in its entirety). The efficacy of such derivatized versions of these inverse-agonists can readily be tested by any of the screening procedures described herein. It is further contemplated within the scope of the disclosure that analogs of T0070907 and/or SR10221 can also be useful therapeutic agents against PPARG activated cancers.

Optionally, compounds identified in any of the above-described assays can be confirmed as useful in an assay for compounds that modulate the propensity of PPARG activated cancer cells to proliferate.

Small molecules of the disclosure preferably have a molecular weight below 2,000 daltons, more preferably between 300 and 1,000 daltons, and most preferably between 400 and 700 daltons. It is preferred that these small molecules are organic molecules.

CRISPR/Cas

It is contemplated within the scope of the disclosure, that the CRISPR/Cas system can be used to modify any of the nucleotides described herein, either for in vitro or in vivo manipulation of the nucleotides, or for therapeutic modulation of PPARG signaling within a PPARG activated cancer cell (e.g., bladder cancer). For example, the techniques herein provide that the CRISPR/Cas system can be used therapeutically to down regulate expression of a PPARG T447M variant and/or a RXRA S427F/Y variant, thereby down regulating PPARG signaling within a PPARG activated cancer cell. The CRISPR/Cas system is abundantly described in U.S. Pat. Nos. 8,795,965; 8,889,356; 8,771,945; 8,889,418; and 8,895,308, which are hereby incorporated by reference in their entirety.

Briefly, "CRISPR system" refers collectively to transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or other sequences and transcripts from a CRISPR locus. In some embodiments, one or more elements of a CRISPR system is derived from a type I, type II, or type III CRISPR system. In some embodiments, one or more elements of a CRISPR system is derived from a particular organism comprising an endogenous CRISPR system, such as *Streptococcus pyogenes*. In general, a CRISPR system is characterized by elements that promote the formation of a CRISPR complex at the site of a target sequence (also referred to as a protospacer in the context of an endogenous CRISPR system). In the context of formation of a CRISPR complex, "target sequence" refers to a sequence to which a guide sequence is designed to have complementarity, where hybridization between a target sequence and a guide sequence promotes the formation of a CRISPR complex. Full complementarity is not necessarily required, provided there is sufficient complementarity to cause hybridization and promote formation of a CRISPR complex. A target sequence may comprise any polynucleotide, such as DNA or RNA polynucleotides. In some embodiments, a target sequence is located in the nucleus or cytoplasm of a cell. In some embodiments, the target sequence may be within an organelle of a eukaryotic cell, for example, mitochondrion or chloroplast. A sequence or template that may be used for recombination into the targeted locus comprising the target sequences is referred to as an "editing template" or "editing polynucleotide" or "editing sequence". In aspects of the disclosure, an exogenous template polynucleotide may be referred to as an editing template. In an aspect of the disclosure the recombination is homologous recombination.

Typically, in the context of an endogenous CRISPR system, formation of a CRISPR complex (comprising a guide sequence hybridized to a target sequence and complexed with one or more Cas proteins) results in cleavage of one or both strands in or near (e.g., within 1, 2, 3, 4, 5, 6, 7, 8, 9, 10, 20, 50, or more base pairs from) the target sequence. Without wishing to be bound by theory, the tracr sequence, which may comprise or consist of all or a portion of a wild-type tracr sequence (e.g., about or more than about 20, 26, 32, 45, 48, 54, 63, 67, 85, or more nucleotides of a wild-type tracr sequence), may also form part of a CRISPR complex, such as by hybridization along at least a portion of the tracr sequence to all or a portion of a tracr mate sequence that is operably linked to the guide sequence. In some embodiments, the tracr sequence has sufficient complementarity to a tracr mate sequence to hybridize and participate in formation of a CRISPR complex. As with the target sequence, it is believed that complete complementarity is not needed, provided there is sufficient to be functional. In some embodiments, the tracr sequence has at least 50%, 60%, 70%, 80%, 90%, 95% or 99% of sequence complementarity along the length of the tracr mate sequence when optimally aligned. In some embodiments, one or more vectors driving expression of one or more elements of a CRISPR system are introduced into a host cell such that expression of the elements of the CRISPR system direct formation of a CRISPR complex at one or more target sites. For example, a Cas enzyme, a guide sequence linked to a tracr-mate sequence, and a tracr sequence could each be operably linked to separate regulatory elements on separate vectors. Alternatively, two or more of the elements expressed from the same or different regulatory elements, can be combined in a single vector, with one or more additional vectors providing any components of the CRISPR system not included in the first vector. CRISPR system elements that are combined in a single vector can be arranged in any suitable orientation, such as one element located 5' with respect to ("upstream" of) or 3' with respect to ("downstream" of) a second element. The coding sequence of one element can be located on the same or opposite strand of the coding sequence of a second element, and oriented in the same or opposite direction. In some embodiments, a single promoter drives expression of a transcript encoding a CRISPR enzyme and one or more of the guide sequence, tracr mate sequence (optionally operably linked to the guide sequence), and a tracr sequence embedded within one or more intron sequences (e.g., each in a different intron, two or more in at least one intron, or all in a single intron). In some embodiments, the CRISPR enzyme, guide sequence, tracr mate sequence, and tracr sequence are operably linked to and expressed from the same promoter.

In some embodiments, a vector comprises one or more insertion sites, such as a restriction endonuclease recognition sequence (also referred to as a "cloning site"). In some embodiments, one or more insertion sites (e.g., about or more than about 1, 2, 3, 4, 5, 6, 7, 8, 9, 10, or more insertion sites) are located upstream and/or downstream of one or more sequence elements of one or more vectors. In some embodiments, a vector comprises an insertion site upstream of a tracr mate sequence, and optionally downstream of a regulatory element operably linked to the tracr mate sequence, such that following insertion of a guide sequence into the insertion site and upon expression the guide sequence directs sequence-specific binding of a CRISPR complex to a target sequence in a eukaryotic cell. In some embodiments, a vector comprises two or more insertion sites, each insertion site being located between two tracr mate sequences so as to allow insertion of a guide sequence at each site. In such an arrangement, the two or more guide sequences can comprise two or more copies of a single guide sequence, two or more different guide sequences, or combinations of these. When multiple different guide sequences are used, a single expression construct can be used to target CRISPR activity to multiple different, corresponding target sequences within a cell. For example, a single vector may comprise about or more than about 1, 2, 3, 4, 5, 6, 7, 8, 9, 10, 15, 20, or more guide sequences. In some embodiments, about or more than about 1, 2, 3, 4, 5, 6, 7, 8, 9, 10, or more such guide-sequence-containing vectors may be provided, and optionally delivered to a cell.

In some embodiments, a vector comprises a regulatory element operably linked to an enzyme-coding sequence encoding a CRISPR enzyme, such as a Cas protein. Non-limiting examples of Cas proteins include Cas1, Cas1B, Cas2, Cas3, Cas4, Cas5, Cas6, Cas7, Cas8, Cas9 (also known as Csn1 and Csx12), Cas100, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologs thereof, or modified versions thereof. These enzymes are known; for example, the amino acid sequence of *S. pyogenes* Cas9 protein may be found in the SwissProt database under accession number Q99ZW2. In some embodiments, the unmodified CRISPR enzyme has DNA cleavage activity, such as Cas9. In some embodiments the CRISPR enzyme is Cas9, and may be Cas9 from *S. pyogenes* or *S. pneumoniae*. In some embodiments, the CRISPR enzyme directs cleavage of one or both strands at the location of a target sequence, such as within the target sequence and/or within the complement of the target sequence. In some embodiments, the CRISPR enzyme directs cleavage of one or both strands within about 1, 2, 3, 4, 5, 6, 7, 8, 9, 10, 15, 20, 25, 50, 100, 200, 500, or more base pairs from the first or last nucleotide of a target sequence. In some embodiments, a vector encodes a CRISPR enzyme that is mutated with respect to a corresponding wild-type enzyme such that the mutated CRISPR enzyme lacks the ability to cleave one or both strands of a target polynucleotide containing a target sequence. For example, an aspartate-to-alanine substitution (D10A) in the RuvC I catalytic domain of Cas9 from *S. pyogenes* converts Cas9 from a nuclease that cleaves both strands to a nickase (cleaves a single strand). Other examples of mutations that render Cas9 a nickase include, without limitation, H840A, N854A, and N863A. In some embodiments, a Cas9 nickase may be used in combination with guide sequence(s), e.g., two guide sequences, which target respectively sense and antisense strands of the DNA target. This combination allows both strands to be nicked and used to induce NHEJ. Applicants have demonstrated (data not shown) the efficacy of two nickase targets (i.e., sgRNAs targeted at the same location but to different strands of DNA) in inducing mutagenic NHEJ. A single nickase (Cas9-D10A with a single sgRNA) is unable to induce NHEJ and create indels but Applicants have shown that double nickase (Cas9-D10A and two sgRNAs targeted to different strands at the same location) can do so in human embryonic stem cells (hESCs). The efficiency is about 50% of nuclease (i.e., regular Cas9 without D10 mutation) in hESCs.

As a further example, two or more catalytic domains of Cas9 (RuvC I, RuvC II, and RuvC III) may be mutated to produce a mutated Cas9 substantially lacking all DNA cleavage activity. In some embodiments, a D10A mutation is combined with one or more of H840A, N854A, or N863A mutations to produce a Cas9 enzyme substantially lacking all DNA cleavage activity. In some embodiments, a CRISPR enzyme is considered to substantially lack all DNA cleavage activity when the DNA cleavage activity of the mutated enzyme is less than about 25%, 10%, 5%, 1%, 0.1%, 0.01%, or lower with respect to its non-mutated form. Other mutations may be useful; where the Cas9 or other CRISPR enzyme is from a species other than *S. pyogenes*, mutations in corresponding amino acids may be made to achieve similar effects.

In some embodiments, an enzyme coding sequence encoding a CRISPR enzyme is codon optimized for expression in particular cells, such as eukaryotic cells. The eukaryotic cells may be those of or derived from a particular organism, such as a mammal, including but not limited to human, mouse, rat, rabbit, dog, or non-human primate. In general, codon optimization refers to a process of modifying a nucleic acid sequence for enhanced expression in the host cells of interest by replacing at least one codon (e.g., about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database", and these tables can be adapted in a number of ways. See Nakamura, Y., et al. "Codon usage tabulated from the international DNA sequence databases: status for the year 2000" *Nucl. Acids Res.* 28:292 (2000). Computer algorithms for codon optimizing a particular sequence for expression in a particular host cell are also available, such as Gene Forge (Aptagen; Jacobus, Pa.), are also available. In some embodiments, one or more codons (e.g., 1, 2, 3, 4, 5, 10, 15, 20, 25, 50, or more, or all codons) in a sequence encoding a CRISPR enzyme correspond to the most frequently used codon for a particular amino acid.

In some embodiments, a vector encodes a CRISPR enzyme comprising one or more nuclear localization sequences (NLSs), such as about or more than about 1, 2, 3, 4, 5, 6, 7, 8, 9, 10, or more NLSs. In some embodiments, the CRISPR enzyme comprises about or more than about 1, 2, 3, 4, 5, 6, 7, 8, 9, 10, or more NLSs at or near the amino-terminus, about or more than about 1, 2, 3, 4, 5, 6, 7, 8, 9, 10, or more NLSs at or near the carboxy-terminus, or a combination of these (e.g., one or more NLS at the amino-terminus and one or more NLS at the carboxy terminus). When more than one NLS is present, each may be selected independently of the others, such that a single NLS may be present in more than one copy and/or in combination with one or more other NLSs present in one or more copies. In a preferred embodiment of the disclosure, the CRISPR enzyme comprises at most 6 NLSs. In some embodiments, an NLS is considered near the N- or C-terminus when the nearest amino acid of the NLS is within about 1, 2, 3, 4, 5, 10, 15, 20, 25, 30, 40, 50, or more amino acids along the polypeptide chain from the N-or C-terminus. Typically, an NLS consists of one or more short sequences of positively charged lysines or arginines exposed on the protein surface, but other types of NLS are known. Non-limiting examples of NLSs include an NLS sequence derived from: the NLS of the SV40 virus large T-antigen, having the amino acid sequence PKKKRKV (SEQ ID NO: 37); the NLS from nucleoplasmin (e.g., the nucleoplasmin bipartite NLS with the sequence KRPAATKKAGQAKKKK (SEQ ID NO: 38); the c-myc NLS having the amino acid sequence PAAKRVKLD (SEQ ID NO: 39) or RQRRNELKRSP (SEQ ID NO: 40); the hRNPA1 M9 NLS having the sequence NQSSNFGPMKGGNFGGRSSGPYGGGGQYFAKPRNQ-GGY (SEQ ID NO: 41); the sequence RMRIZFKNKGKD-TAELRRRRVEVSVELRKAKKDEQILKRRNV (SEQ ID NO: 42) of the IBB domain from importin-alpha; the sequences VSRKRPRP (SEQ ID NO: 43) and PPKKARED (SEQ ID NO: 44) of the myoma T protein; the sequence PQPKKKPL (SEQ ID NO: 45) of human p53; the sequence SALIKKKKKMAP (SEQ ID NO: 46) of mouse c-abl IV; the sequences DRLRR (SEQ ID NO: 47) and PKQKKRK (SEQ ID NO: 48) of the influenza virus NS1; the sequence RKLKKKIKKL (SEQ ID NO: 49) of the Hepatitis virus delta antigen; the sequence REKKKFLKRR (SEQ ID NO: 50) of the mouse Mx1 protein; the sequence KRKGD-EVDGVDEVAKKKSKK (SEQ ID NO: 51) of the human poly(ADP-ribose) polymerase; and the sequence RKCL-QAGMNLEARKTKK (SEQ ID NO: 52) of the steroid hormone receptors (human) glucocorticoid.

In general, the one or more NLSs are of sufficient strength to drive accumulation of the CRISPR enzyme in a detectable amount in the nucleus of a eukaryotic cell. In general, strength of nuclear localization activity may derive from the number of NLSs in the CRISPR enzyme, the particular NLS(s) used, or a combination of these factors. Detection of accumulation in the nucleus may be performed by any suitable technique. For example, a detectable marker may be fused to the CRISPR enzyme, such that location within a cell may be visualized, such as in combination with a means for detecting the location of the nucleus (e.g., a stain specific for the nucleus such as DAPI). Examples of detectable markers include fluorescent proteins (such as Green fluorescent proteins, or GFP; RFP; CFP), and epitope tags (HA tag, flag tag, SNAP tag). Cell nuclei may also be isolated from cells, the contents of which may then be analyzed by any suitable process for detecting protein, such as immunohistochemistry, Western blot, or enzyme activity assay. Accumulation in the nucleus may also be determined indirectly, such as by an assay for the effect of CRISPR complex formation (e.g., assay for DNA cleavage or mutation at the target sequence, or assay for altered gene expression activity affected by CRISPR complex formation and/or CRISPR enzyme activity), as compared to a control no exposed to the CRISPR enzyme or complex, or exposed to a CRISPR enzyme lacking the one or more NLSs.

In general, a guide sequence is any polynucleotide sequence having sufficient complementarity with a target polynucleotide sequence to hybridize with the target sequence and direct sequence-specific binding of a CRISPR complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g., the Burrows Wheeler Aligner), ClustalW, ClustalX, BLAT, Novoalign (Novocraft Technologies, ELAND (Illumina, San Diego, Calif), SOAP (available at soap.genomics.org.cn), and Maq (available at maq.sourceforge.net). In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. The ability of a guide sequence to direct sequence-specific binding of a CRISPR complex to a target sequence may be assessed by any suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence, such as by Surveyor assay as described herein. Similarly, cleavage of a target polynucleotide sequence may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions. Other assays are possible, and will occur to those skilled in the art.

A guide sequence may be selected to target any target sequence. In some embodiments, the target sequence is a sequence within a genome of a cell. Exemplary target sequences include those that are unique in the target genome. For example, for the *S. pyogenes* Cas9, a unique target sequence in a genome may include a Cas9 target site of the form MMMMMMMMNNNNNNNNNNNNNNNXGG where NNNNNNNNNNNNNXGG (N is A, G, T, or C; and X can be anything) has a single occurrence in the genome. A unique target sequence in a genome may include an *S. pyogenes* Cas9 target site of the form MMMMMMMM-MNNNNNNNNNNNNXGG where NNNNNNNNNNNNXGG (N is A, G, T, or C; X can be anything; and M may be A, G, T, or C, and need not be considered in identifying a sequence as unique) has a single occurrence in the genome. For the *S. thermophilus* CRISPR Cas9, a unique target sequence in a genome may include a Cas9 target site of the form MMM-MMMMMNNNNNNNNNNNNXXAGAAW (SEQ ID NO: 53) where NNNNNNNNNNNNXXAGAAW (SEQ ID NO: 54; N is A, G, T, or C; X can be anything; and W is A or T) has a single occurrence in the genome. A unique target sequence in a genome may include an *S. thermophilus* CRISPR1Cas9 target site of the form MMMMMM-MMMNNNNNNNNNNNXXAGAAW (SEQ ID NO: 55) where NNNNNNNNNNNXXAGAAW (SEQ ID NO: 56; N is A, G, T, or C; X can be anything; and W is A or T) has a single occurrence in the genome. For the *S. pyogenes* Cas9, a unique target sequence in a genome may include a Cas9 target site of the form MMMMMMMMMMNNNNN-NNNNNNNXGGXG where NNNNNNNNNNNNXGGXG (N is A, G, T, or C; and X can be anything) has a single occurrence in the genome. A unique target sequence in a genome may include an *S. pyogenes* Cas9 target site of the form MMMMMMMMMNNNNNNNNNNNNXGGXG where NNNNNNNNNNNXGGXG (N is A, G, T, or C; and X can be anything) has a single occurrence in the genome. In each of these sequences "M" may be A, G, T, or C, and need not be considered in identifying a sequence as unique.

In some embodiments, a guide sequence is selected to reduce the degree of secondary structure within the guide sequence. Secondary structure may be determined by any suitable polynucleotide folding algorithm. Some programs are based on calculating the minimal Gibbs free energy. An example of one such algorithm is mFold, as described by Zuker and Stiegler (*Nucleic Acids Res.* 9 (1981), 133-148). Another example folding algorithm is the online webserver RNAfold, developed at Institute for Theoretical Chemistry at the University of Vienna, using the centroid structure prediction algorithm (see e.g., A. R. Gruber et al., 2008, *Cell* 106(1): 23-24; and PA Carr and GM Church, 2009, *Nature Biotechnology* 27(12): 1151-62). Further algorithms may be found in U.S. application Ser. No. 61/836,080; incorporated herein by reference.

In general, a tracr mate sequence includes any sequence that has sufficient complementarity with a tracr sequence to promote one or more of: (1) excision of a guide sequence flanked by tracr mate sequences in a cell containing the corresponding tracr sequence; and (2) formation of a CRISPR complex at a target sequence, wherein the CRISPR complex comprises the tracr mate sequence hybridized to the tracr sequence. In general, degree of complementarity is with reference to the optimal alignment of the tracr mate sequence and tracr sequence, along the length of the shorter of the two sequences. Optimal alignment may be determined by any suitable alignment algorithm, and may further account for secondary structures, such as self-complementarity within either the tracr sequence or tracr mate sequence. In some embodiments, the degree of complementarity between the tracr sequence and tracr mate sequence along the length of the shorter of the two when optimally aligned is about or more than about 25%, 30%, 40%, 50%, 60%, 70%, 80%, 90%, 95%, 97.5%, 99%, or higher. In some embodiments, the tracr sequence is about or more than about 5, 6, 7, 8, 9, 10, 11, 12, 13, 14, 15, 16, 17, 18, 19, 20, 25, 30, 40, 50, or more nucleotides in length. In some embodiments, the tracr sequence and tracr mate sequence are contained within a single transcript, such that hybridization between the two produces a transcript having a secondary structure, such as a hairpin. Preferred loop forming sequences for use in hairpin structures are four nucleotides in length, and most preferably have the sequence GAAA. However, longer or shorter loop sequences may be used, as may alternative sequences. The sequences preferably include a nucleotide triplet (for example, AAA), and an additional nucleotide (for example C or G). Examples of loop forming sequences include CAAA and AAAG. In an embodiment of the disclosure, the transcript or transcribed polynucleotide sequence has at least two or more hairpins. In preferred embodiments, the transcript has two, three, four or five hairpins. In a further embodiment of the disclosure, the transcript has at most five hairpins. In some embodiments, the single transcript further includes a transcription termination sequence; preferably this is a polyT sequence, for example six T nucleotides. Further non-limiting examples of single polynucleotides comprising a guide sequence, a tracr mate sequence, and a tracr sequence are as follows (listed 5' to 3'), where "N" represents a base of a guide sequence, the first block of lower case letters represent the tracr mate sequence, and the second block of lower case letters represent the tracr sequence, and the final poly-T sequence represents the transcription terminator:

(1)
(SEQ ID NO: 57)
NNNNNNNNNNNNNNNNNNNNNgttttgtactctcaagatttaGAAAta aatcttgcagaagctacaaagataaggcttcatgccgaaatcaacacc ctgtcattttatggcagggtgttttcgttatttaaTTTTTT;

(2)
(SEQ ID NO: 58)
NNNNNNNNNNNNNNNNNNNNNgttttgtactctcaGAAAtgcagaagc tacaaagataaggcttcatgccgaaatcaacaccctgtcattttatgg cagggtgttttcgttatttaaTTTTTT;

(3)
(SEQ ID NO: 59)
NNNNNNNNNNNNNNNNNNNNNgttttgtactctcaGAAAtgcagaagc tacaaagataaggcttcatgccgaaatcaacaccctgtcattttatgg cagggtgtTTTTTT;

(4)
(SEQ ID NO: 60)
NNNNNNNNNNNNNNNNNNNNNgttttagagctaGAAAtagcaagttaaa ataaggctagtccgttatcaacttgaaaaagtggcaccgagtcggtgc

TTTTTT;

(5)
(SEQ ID NO: 61)
NNNNNNNNNNNNNNNNNNNNNgttttagagctaGAAATAGcaagttaaa ataaggctagtccgttatcaacttgaaaaagtgTTTTTT; and (6)
(SEQ ID NO: 62)
NNNNNNNNNNNNNNNNNNNNNgttttagagctagAAATAGcaagttaaa ataaggctagtccgttatcaTTTTTTT.

In some embodiments, sequences (1) to (3) are used in combination with Cas9 from *S. thermophilus* CRISPR1. In some embodiments, sequences (4) to (6) are used in combination with Cas9 from *S. pyogenes*. In some embodiments, the tracr sequence is a separate transcript from a transcript comprising the tracr mate sequence.

In some embodiments, a recombination template is also provided. A recombination template may be a component of another vector as described herein, contained in a separate vector, or provided as a separate polynucleotide. In some embodiments, a recombination template is designed to serve as a template in homologous recombination, such as within or near a target sequence (e.g., DNA encoding a PPARG T447M variant or a RXRA S427F/Y variant) nicked or cleaved by a CRISPR enzyme as a part of a CRISPR complex. A template polynucleotide may be of any suitable length, such as about or more than about 10, 15, 20, 25, 50, 75, 100, 150, 200, 500, 1000, or more nucleotides in length. In some embodiments, the template polynucleotide is complementary to a portion of a polynucleotide comprising the target sequence. When optimally aligned, a template polynucleotide might overlap with one or more nucleotides of a target sequences (e.g., about or more than about 1, 5, 10, 15, 20, 25, 30, 35, 40, 45, 50, 60, 70, 80, 90, 100 or more nucleotides). In some embodiments, when a template sequence and a polynucleotide comprising a target sequence are optimally aligned, the nearest nucleotide of the template polynucleotide is within about 1, 5, 10, 15, 20, 25, 50, 75, 100, 200, 300, 400, 500, 1000, 5000, 10000, or more nucleotides from the target sequence.

In some embodiments, the CRISPR enzyme is part of a fusion protein comprising one or more heterologous protein domains (e.g., about or more than about 1, 2, 3, 4, 5, 6, 7, 8, 9, 10, or more domains in addition to the CRISPR enzyme) such as, for example, a DNA encoding a PPARG T447M variant or a RXRA S427F/Y variant. A CRISPR enzyme fusion protein may comprise any additional protein sequence, and optionally a linker sequence between any two domains. Examples of protein domains that may be fused to a CRISPR enzyme include, without limitation, epitope tags, reporter gene sequences, and protein domains having one or more of the following activities: methylase activity, demethylase activity, transcription activation activity, transcription repression activity, transcription release factor activity, histone modification activity, RNA cleavage activity and nucleic acid binding activity. Non-limiting examples of epitope tags include histidine (His) tags, V5 tags, FLAG tags, influenza hemagglutinin (HA) tags, Myc tags, VSV-G tags, and thioredoxin (Trx) tags. Examples of reporter genes include, but are not limited to, glutathione-5-transferase (GST), horseradish peroxidase (HRP), chloramphenicol acetyltransferase (CAT) beta-galactosidase, beta-glucuronidase, luciferase, green fluorescent protein (GFP), HcRed, DsRed, cyan fluorescent protein (CFP), yellow fluorescent protein (YFP), and autofluorescent proteins including blue fluorescent protein (BFP). A CRISPR enzyme may be fused to a gene sequence encoding a protein or a fragment of a protein that bind DNA molecules or bind other cellular molecules, including but not limited to maltose binding protein (MBP), S-tag, Lex A DNA binding domain (DBD) fusions, GAL4 DNA binding domain fusions, and herpes simplex virus (HSV) BP16 protein fusions. Additional domains that may form part of a fusion protein comprising a CRISPR enzyme are described in US20110059502, incorporated herein by reference. In some embodiments, a tagged CRISPR enzyme is used to identify the location of a target sequence.

In some aspects, the disclosure provides methods comprising delivering one or more polynucleotides, such as or one or more vectors as described herein, one or more transcripts thereof, and/or one or proteins transcribed therefrom, to a host cell. In some aspects, the disclosure further provides cells produced by such methods, and organisms (such as animals, plants, or fungi) comprising or produced from such cells. In some embodiments, a CRISPR enzyme in combination with (and optionally complexed with) a guide sequence is delivered to a cell. Conventional viral and non-viral based gene transfer methods can be used to introduce nucleic acids in mammalian cells or target tissues. Such methods can be used to administer nucleic acids encoding components of a CRISPR system to cells in culture, or in a host organism. Non-viral vector delivery systems include DNA plasmids, RNA (e.g., a transcript of a vector described herein), naked nucleic acid, and nucleic acid complexed with a delivery vehicle, such as a liposome. Viral vector delivery systems include DNA and RNA viruses, which have either episomal or integrated genomes after delivery to the cell. For a review of gene therapy procedures, see Anderson, *Science* 256:808-813 (1992); Nabel & Felgner, *TIBTECH* 11:211-217 (1993); Mitani & Caskey, *TIBTECH* 11:162-166 (1993); Dillon, *TIBTECH* 11:167-175 (1993); Miller, *Nature* 357:455-460 (1992); Van Brunt, *Biotechnology* 6(10):1149-1154 (1988); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology*, Doerfler and Bohm (eds) (1995); and Yu et al., *Gene Therapy* 1:13-26 (1994).

This disclosure is further illustrated by the following examples which should not be construed as limiting. The contents of all references, patents, and published patent applications cited throughout this application, as well as the figures, are incorporated herein by reference.

EXAMPLES

Example 1: RXRA p.S427F/Y Hotspot Mutations and Focal Amplification of PPARG Activated PPARG and PPARA Signaling in Bladder Cancer Newly available sequence information from an expanded TCGA bladder cancer cohort (14) showed further enrichment of RXRA p.S427F/Y hotspot missense mutations (FIG. 1A). Such mutations in RXRA may elicit changes in gene expression and cell function by impacting the association of RXRA with its heterodimer partners and affect transactivation through altered recruitment of transcriptional regulators. FIG. 1B shows gene expression data from the expanded TCGA cohort of bladder cancer tumors with RXRA p.S427F/Y mutations. Similar results to the original publication (2) were obtained, indicating an enrichment of "PPAR signaling pathway" genes as shown in FIG. 1B. Note that the KEGG "PPAR signaling pathway" gene set also includes target genes of PPARG, PPARA, and PPARD. However, up-regulated genes in tumor specimens bearing the RXRA p.S427 hotspot mutation include classic PPARG and PPARA target genes such as ELOVL6, ACOX1, ACSL5, and HMGCS2 (FIG. 1), with no involvement of PPARD target genes.

Analysis of this larger TCGA cohort did not reveal any novel recurrent mutations in PPARG or PPARA. However, it should be noted that there is a PPARG p.T447M mutation found in the RT4 bladder cancer cell line (15). This missense mutation is enriched across all cancers relative to other PPARG somatic mutations (16, 17), although the sample size is currently too small to nominate this event as a hotspot mutation and it does not appear to be enriched in bladder cancer (data not shown). Interestingly, the PPARG p.T447 residue is directly juxtaposed to the RXRA p.S427 residue in the ligand-activated conformation in the structure of the RXRA/PPARG co-crystal (PDB ID: 1FM6) (18), suggesting that these can be complementary mutations, in which PPARG p.T447M is able to phenocopy the effects of RXRA p.S427F/Y on activating the PPARG signaling pathway.

As shown in FIG. 1C, the presence of focal amplifications of PPARG in ~15% of bladder tumors was confirmed. This alteration is strongly correlated with expression of PPARG (see e.g., FIG. 1D), as well as with expression of luminal bladder cancer markers such as GATA3, UPK2, UPK1A, UPK1B and KRT20 (see e.g., FIG. 1E). Furthermore, it should also be noted that there are significant recurrent alterations in members of the established RXRA-PPARG interactome, including NCOR1, EP300, and NCOA3. Taken as a whole, these observations strongly support the hypothesis that activation of the PPARG signaling pathway is associated with urothelial differentiation and activation of lipid metabolism, and that these are key oncogenic drivers in pathogenesis of bladder cancer.

Figure 1F:
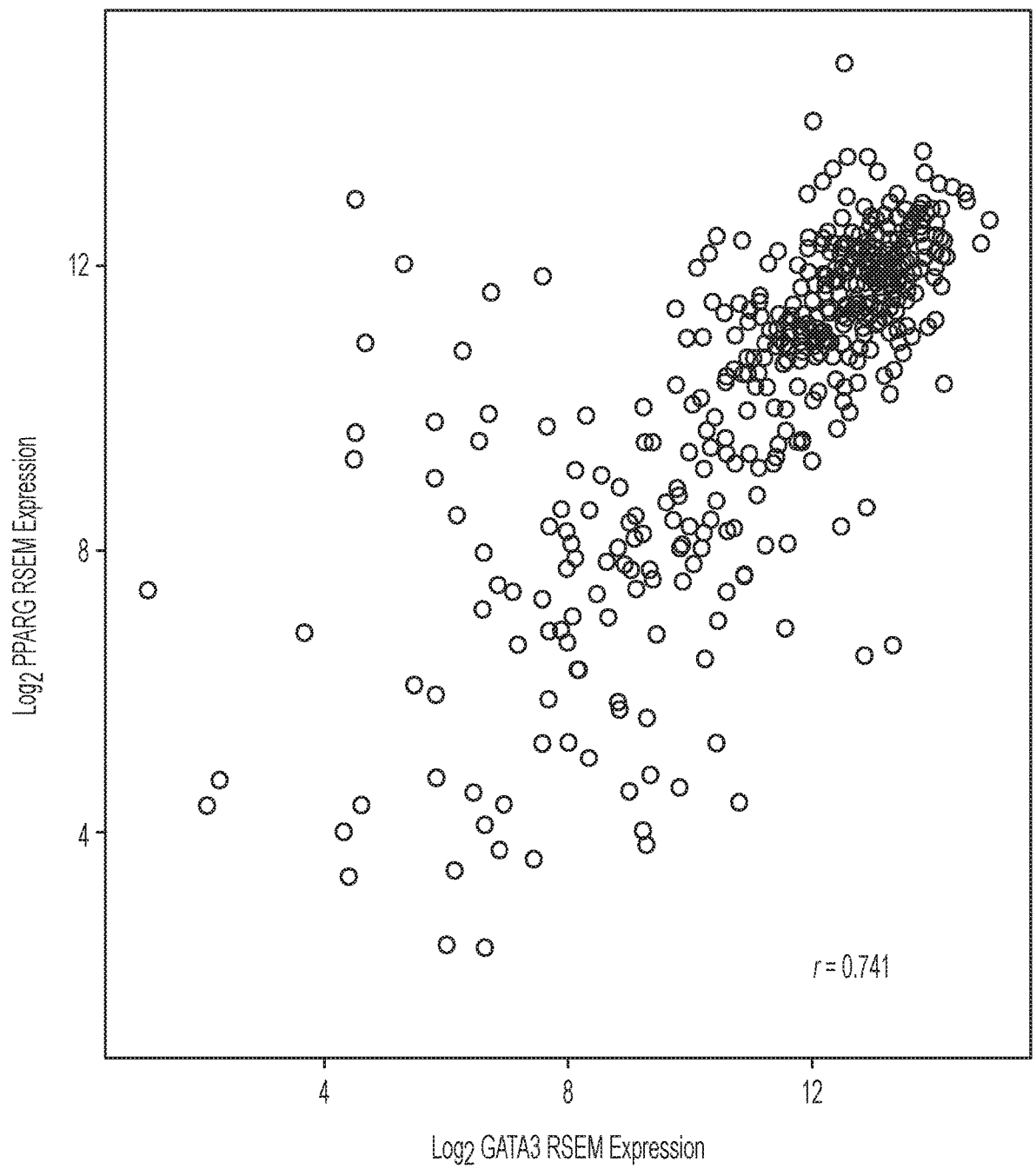
Figure 1G:
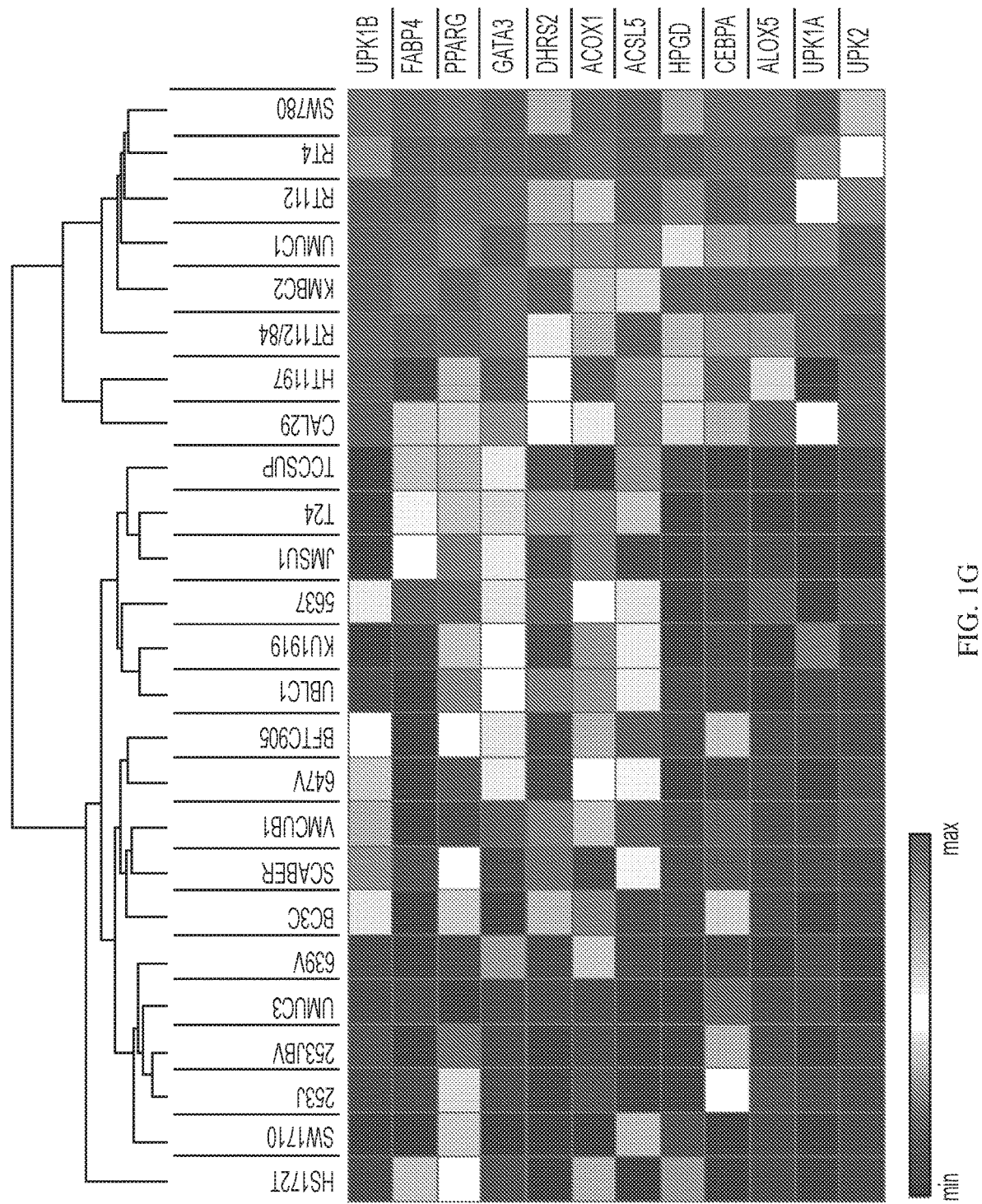
Figure 1H:
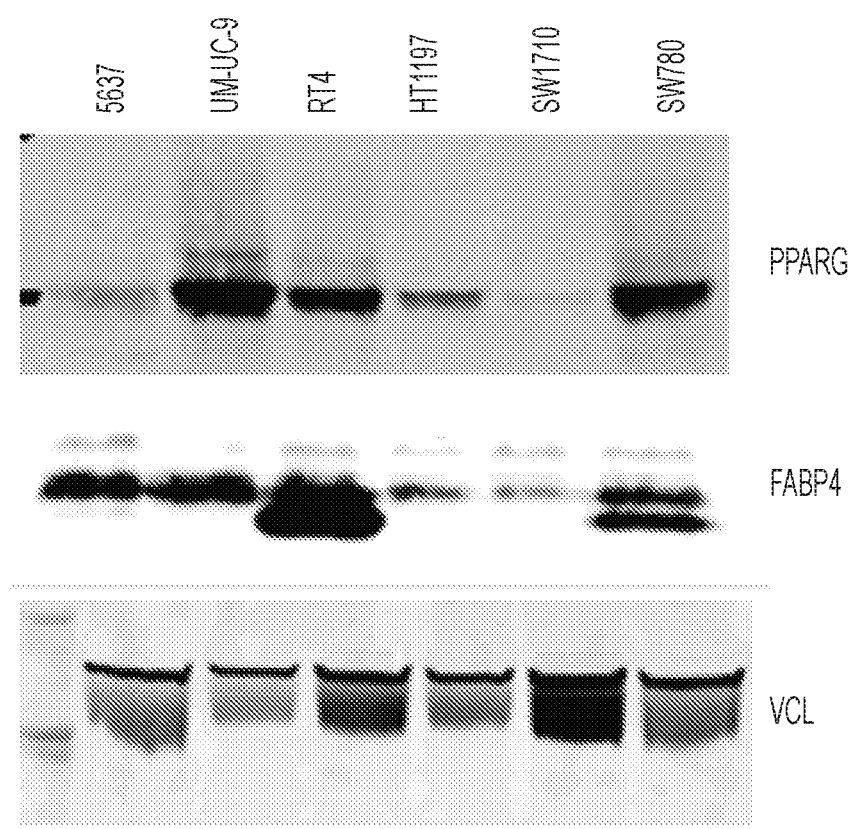
Figure 1I:
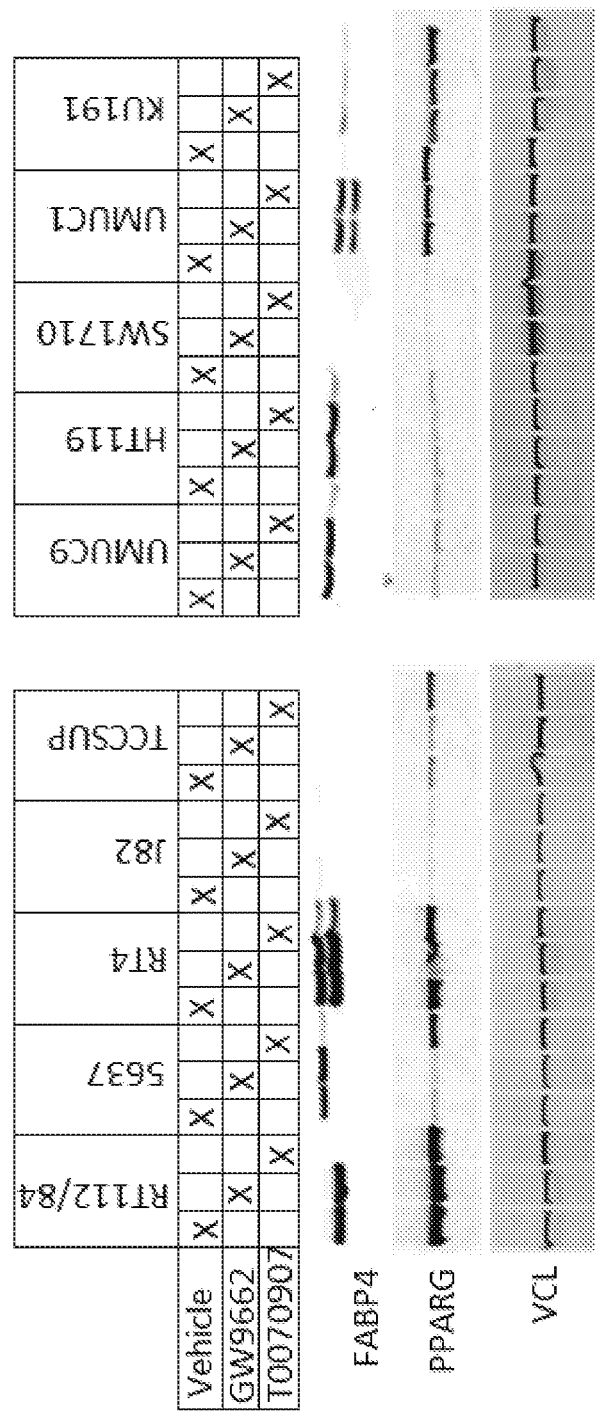

As shown in FIG. 1F, PPARG and GATA3 gene expression is correlated across the TCGA bladder cancer cohort (REF) in RSEM (log 2) normalized. FIG. 1G shows a heatmap of gene expression (RSEM) across bladder cancer cell lines in CCLE indicating luminal differentiation markers and PPARG target genes from using data (Entrez_20120929) grouped by Euclidean distance. FIG. 1H shows Western blots of PPARG, FABP4, and VCL in several urinary tract cell lines. FIG. 1I shows immunoblot analysis of lysates from bladder cancer cell lines treated for 7 days with vehicle (DMSO), antagonist (GW9662 @ 100 nM), and inverse-agonist (T0070907 @ 100 nM).

Example 2: PPARG Signaling was Activated by Overexpression of RXRA p.S427F/Y and PPARG p.T447M Mutant Alleles To determine the biological effects of mutations in RXRA and PPARG, cDNAs encoding wild-type and mutant alleles were ectopically expressed in the SW780 bladder cancer cell line by lentiviral vectors and stable pools were used for analysis. SW780 cells are wild-type for PPARG and RXRA, but have high levels of PPARG, and elevated expression of PPARG target genes (see e.g., FIGS. 1G and 1H).

Figure 2A:
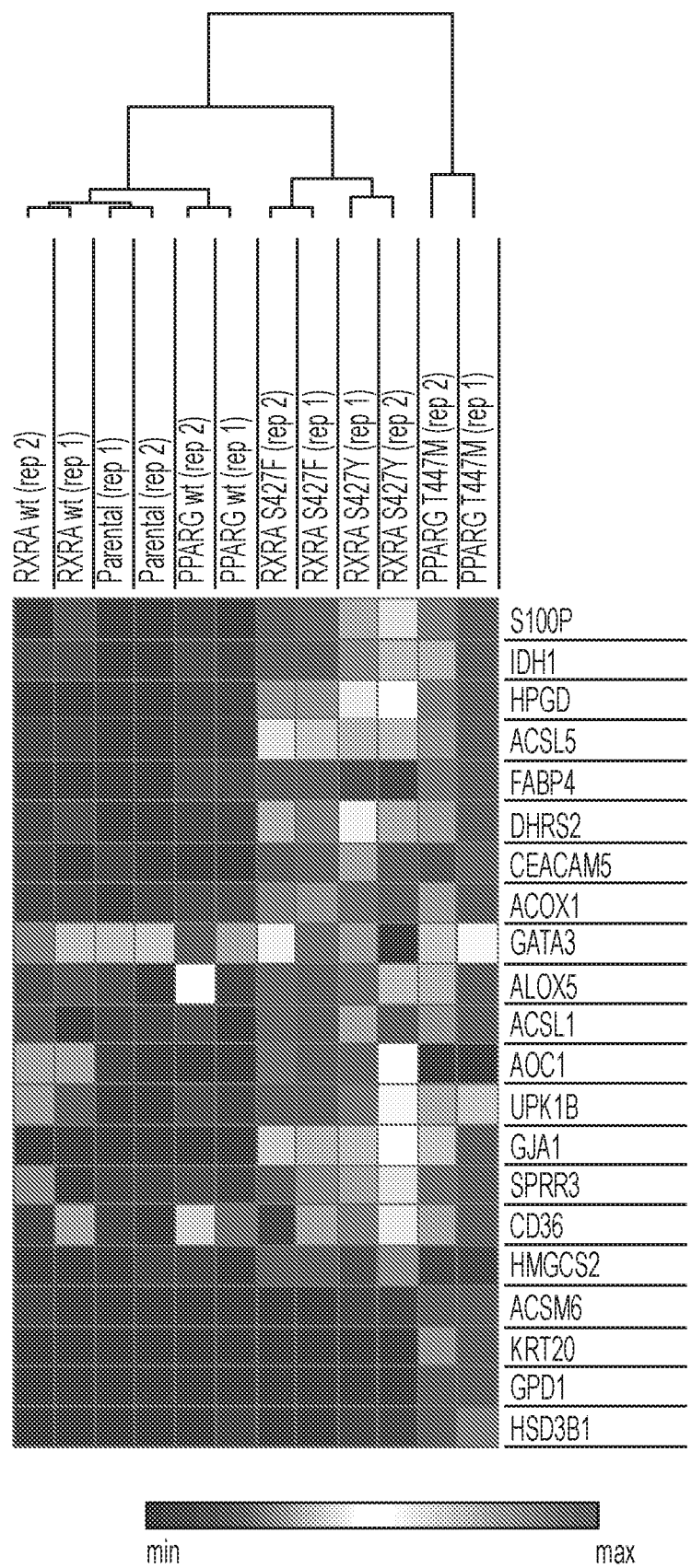
FIGS. 2A-F show that a PPARG pathway was likely activated by overexpression of RXRA S427F/S427Y mutant alleles in bladder cancer cells.
Figure 2B:
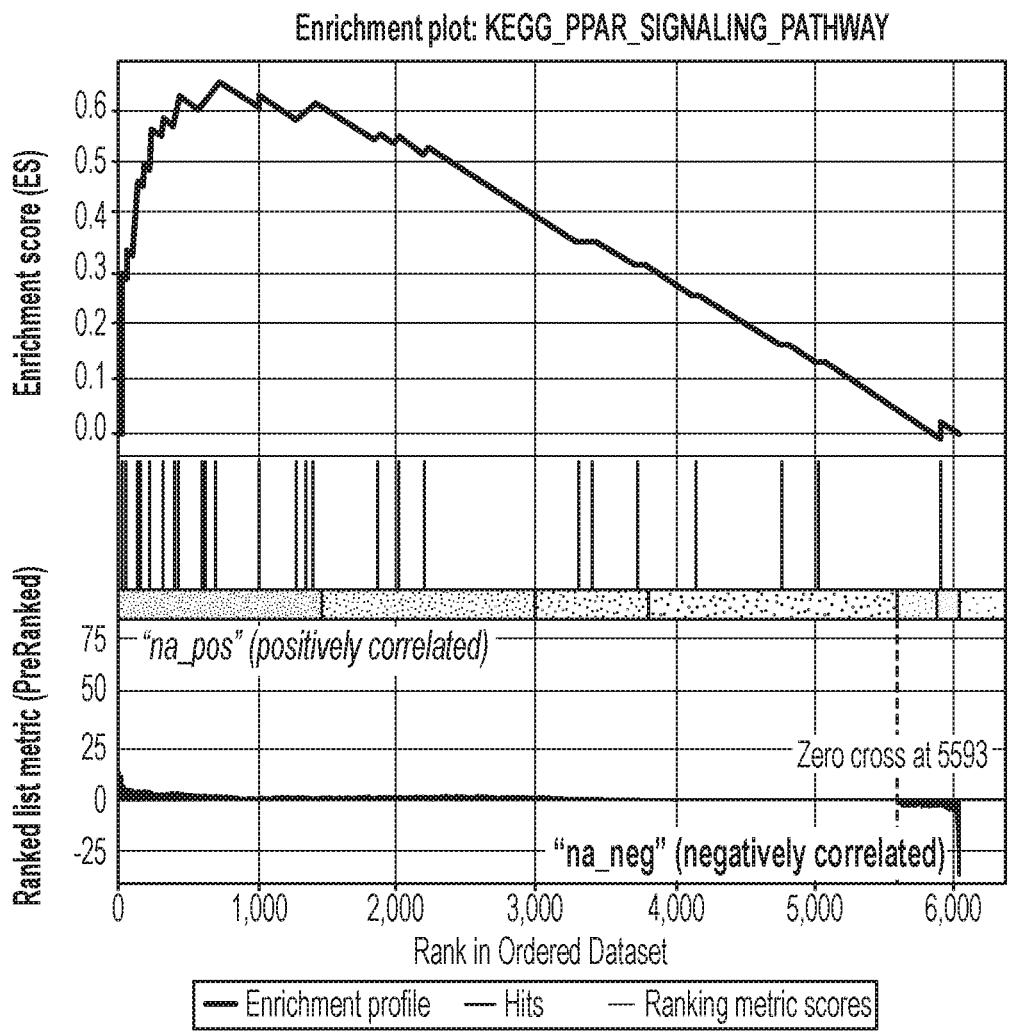
Figure 2C:
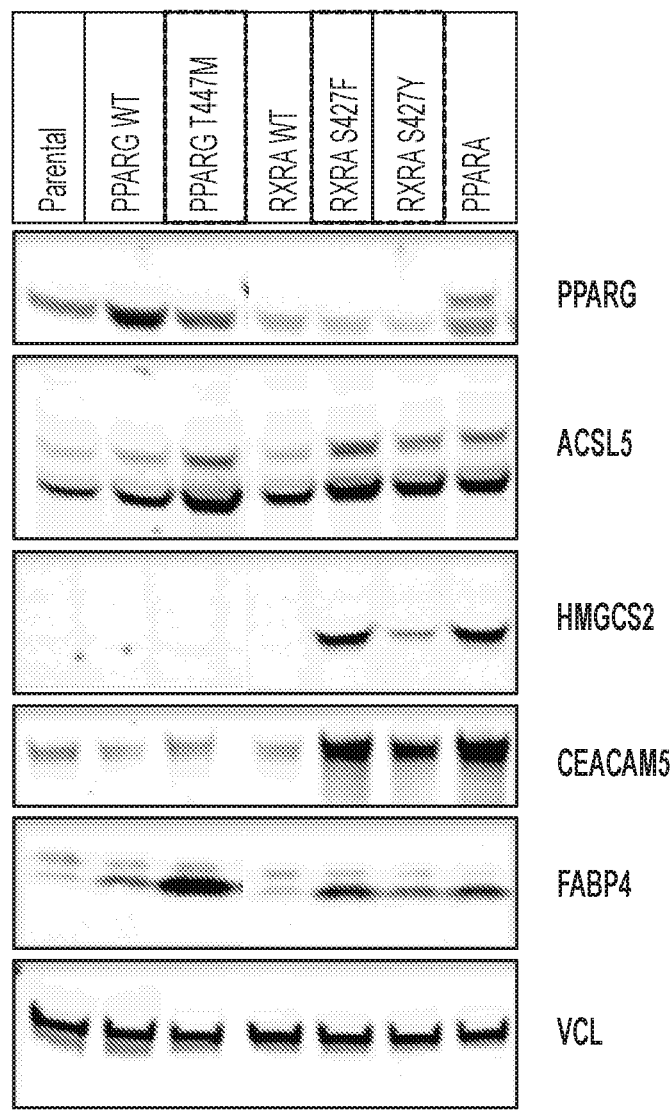
Figure 2D:
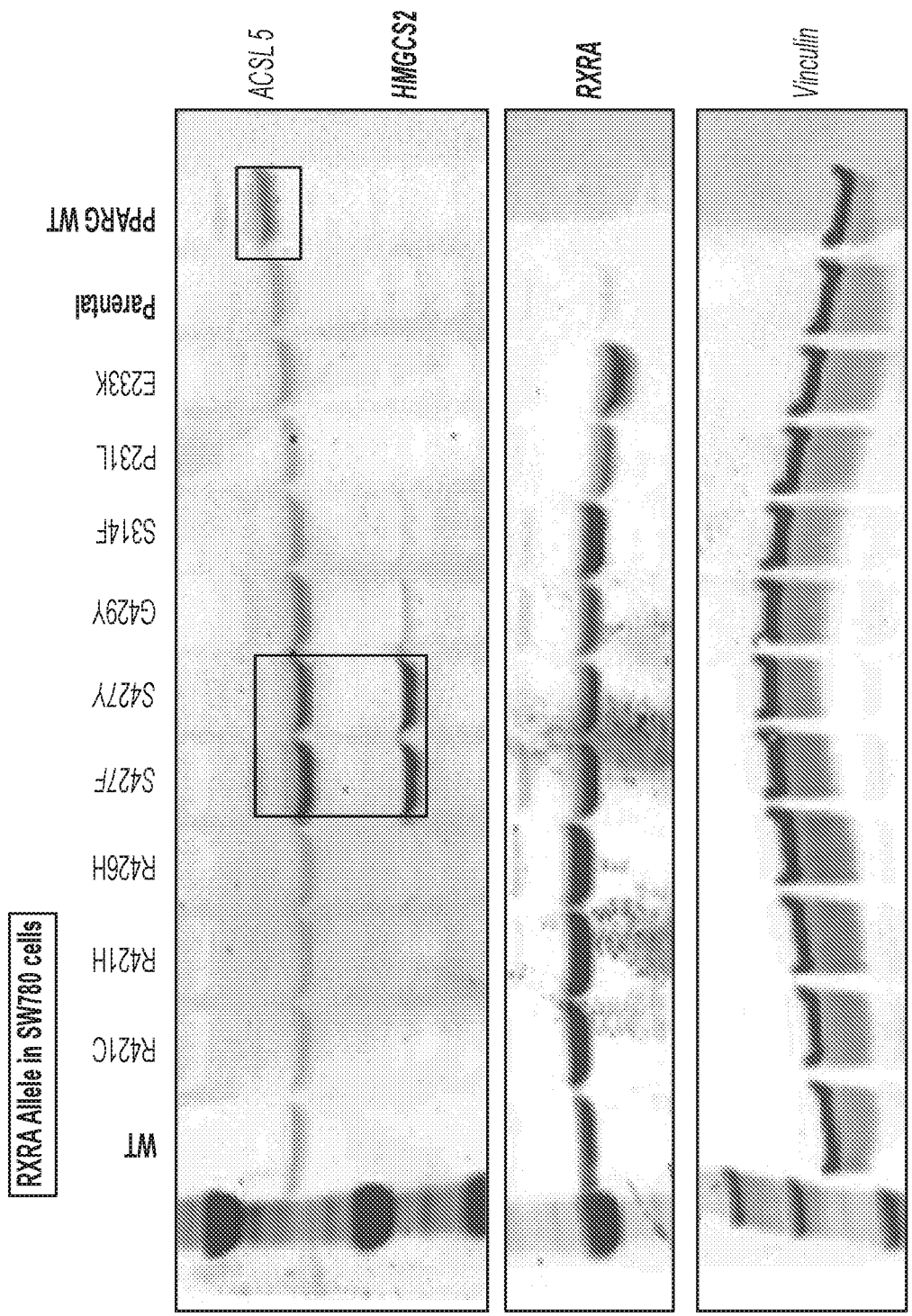
Figure 2E:
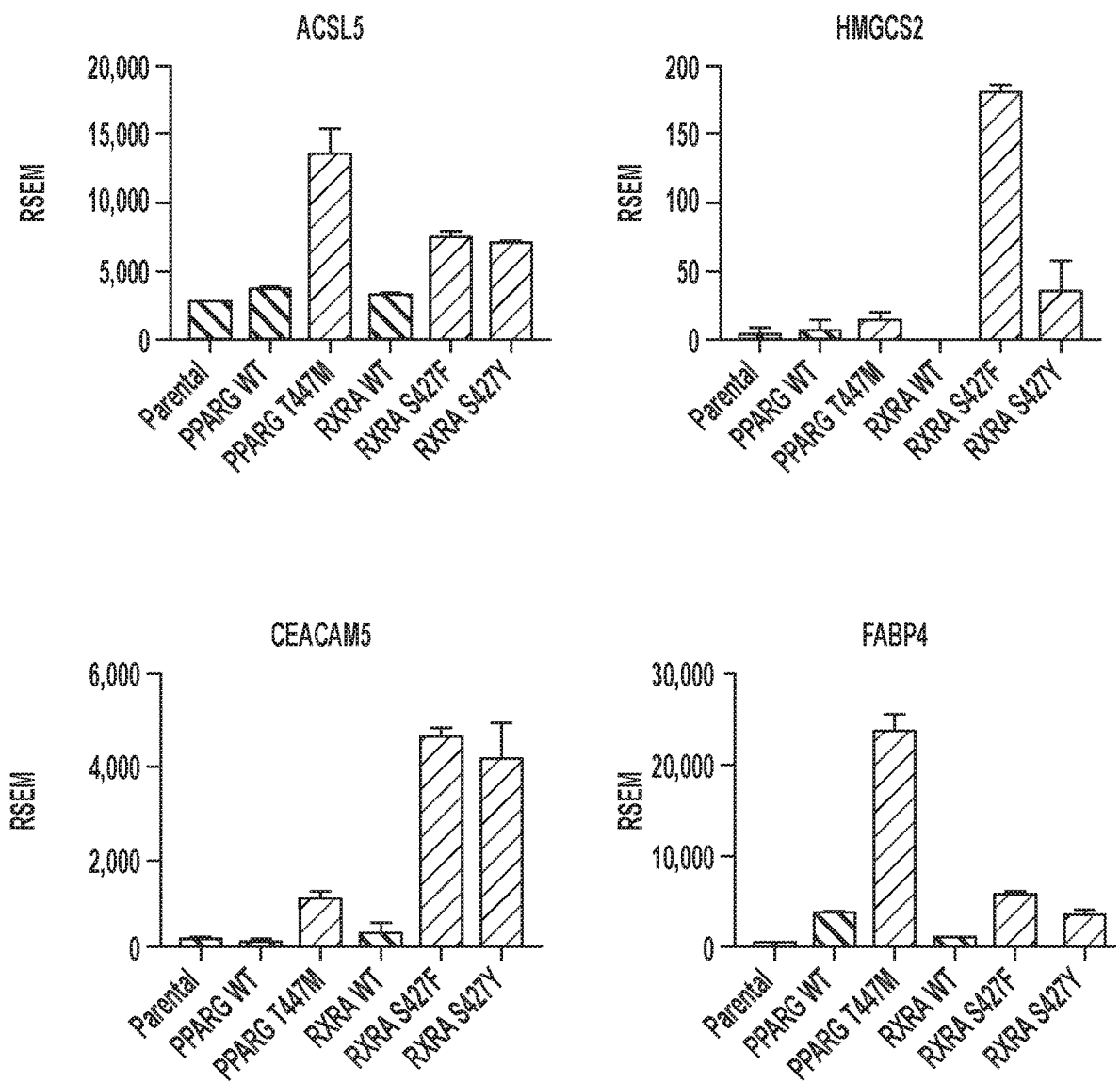
Figure 2F:
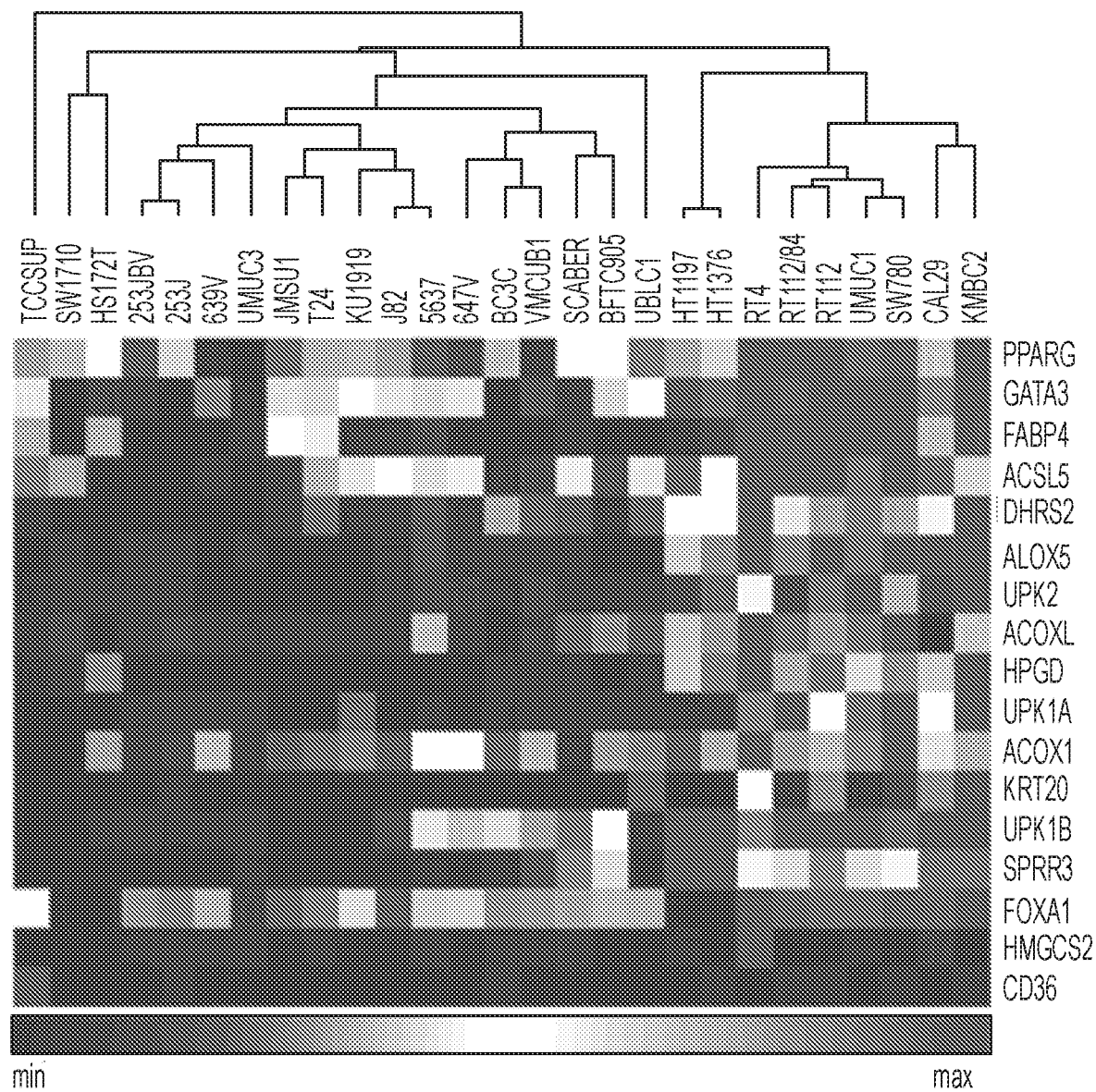

Samples were first evaluated using RNA sequencing to compare gene expression profiles between mutant allele samples versus wild-type or versus parental cells (FIG. 2A). As predicted by the previous TCGA dataset, Gene Set Enrichment Analysis (GSEA) (19, 20) confirmed that the "PPAR signaling pathway" was the most significantly up-regulated KEGG pathway gene set in cells overexpressing the RXRA and PPARG mutant alleles (FIG. 2B). RXRA hotspot mutant alleles p.S427F and p.S427Y, as well as a PPARG-mutant allele found in RT4 cells, p.T447M in PPARG isoform 1, NP_005028, also commonly referred to as PPARG p.T475M in isoform 2, NP_056953.2, were selected for initial testing. RNA sequencing was performed on parental SW780 cells in comparison with cells expressing wild-type or mutant PPARG or RXRA alleles. SW780 cells with ectopic expression of RXRA p.S427F/Y and PPARG p.T447M-mutant alleles demonstrated upregulation of canonical PPARA and PPARG target genes such as ACSL5, HMGCS2, and FABP4 (FIG. 2E). Immunoblot assays confirmed significant upregulation of several of the corresponding proteins in SW780 cells expressing mutant RXRA and PPARG alleles (FIG. 2C) even though parental SW780 cells appear to have elevated expression of PPARG and PPARG target genes when compared with other bladder cancer cell lines (FIG. 2F). These data are consistent with the observations of increased expression of these PPAR targets in patient bladder tumors bearing RXRA hotspot mutations (2). These data also mirrored the observations from patients having RXRA hotspot mutations (2) and for the first time established a direct role for both PPARG p.T447M and RXRA p.S427F/Y in up-regulating PPARG target genes.

It was also noted that a discrete set of genes was upregulated by RXRA p. S427F/Y, such as HMGSC2 and CEACAM5, which were minimally regulated by any of the PPARG alleles. In follow-up immunoblot studies, wild-type PPARA was included and it was observed that both HMGCS2 and CEACAM5 were selectively upregulated upon ectopic expression of PPARA, but not PPARG (FIG. 2C), indicating that these are likely PPARA targets. It was also observed that there were more pronounced effects of RXRA p.S427F compared with the p. S427Y allele on gene expression of HMGCS2, FABP4, and others by RNA sequencing (FIG. 2E), which was confirmed on the protein level by immunoblot assays (FIG. 2C). This may indicate a stronger phenotype for RXRA p.S427F, which is consistent with the higher frequency of this allele in bladder cancer patients (2). Ectopic expression of other RXRA-mutant alleles, selected on the basis of apparent clusters (e.g., p.P231L, p.E233K), and sequence proximity to S427 (p.R421C, p.R421H, p.R426H, p.G429Y) from pancancer genomics analysis (17), had no activity in these assays (FIG. 2D).

The testing also included a panel of additional RXRA mutant alleles that have been reported in publicly available cancer genomics databases (17) and which are proximal to the RXRA p.S427 mutations, namely R421C/H, R426H, and G429Y, or present in mutation clusters, namely P231L, E233K, and S314F. Ectopic expression of these RXRA mutant alleles did not up-regulate PPARG target genes in SW780 bladder cancer cells (FIG. 2D), suggesting that these alterations were alternatively passenger mutations, inactivating or silent alterations, having tissue/lineage-selective effects, or acted through interactions with other heterodimer partners of RXRA that are distinct from PPARG. In the context of bladder lineage, therefore, only the RXRA p.S427F/Y mutant alleles activated PPARG signaling.

Example 3: PPARG-Activated Cell Lines were Genetically Dependent on PPARG

A number of bladder cancer cell lines exhibited a gene expression signature indicative of PPARG activation and also showed enhanced expression of luminal differentiation markers (FIGS. 1G-I); some of these lines harbored somatic alterations in RXRA or PPARG, including HT-1197 (RXRA p.S427F), RT4 (PPARG p.T447M), 5637 (PPARG focal amplification) (15, 21), and UM-UC-9 (PPARG focal amplification) ((22) and data not shown), while others possessed no obvious PPARG activating somatic alterations (RT112/84, Cal29, SW780, and UM-UC-1) (FIGS. 1G-I). Cell lines exhibiting limited expression of PPARG or PPARG target genes (SW1710, KU19.19, and UM-UC-3) were also identified. This panel of cell lines enabled in vitro study of both the biology, and essentiality of PPARG in bladder cancer.

To test for dependency of PPARG in these cell lines, CRSIPR/Cas9 knockout studies using a high-precision competition dependency assay were performed. Briefly, the relative effect of knockout of PPARG on cell proliferation vs knockout of an essential gene (KIF11 or PSMA1) vs knockout of a non-essential gene (PPIB or HPRT) or PPARG intron control was compared. The sgRNAs targeting these genes were cloned into lentiviral vectors that co-expressed one of three different fluorescent proteins, which allowed for unambiguous identification of transduced cells in complex pools: PPARG knockout cells were labelled with YFP, essential control knockout cells were labelled with RFP, and non-essential (or PPARG intron) control knockout cells were labelled with CFP. In the competition format, replicate pools of cells are generated at the beginning of the experiment in which each gene knockout/color are at equivalent abundance. Changes in relative abundance of each are monitored during progressive serial passage by counting fluorescent nuclei using high-content imaging.

Figure 3A:
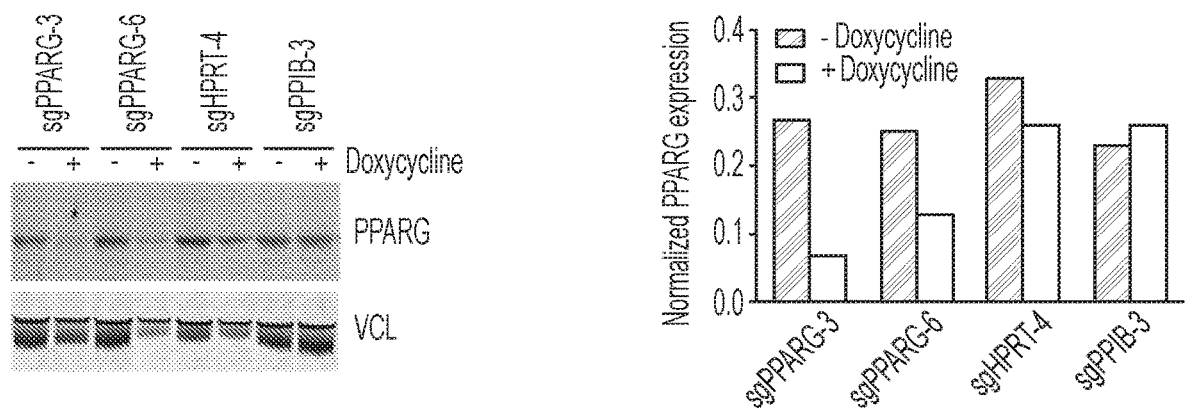
FIGS. 3A-D show cell lines with PPARG pathway activation were dependent on PPARG.
Figure 3B:
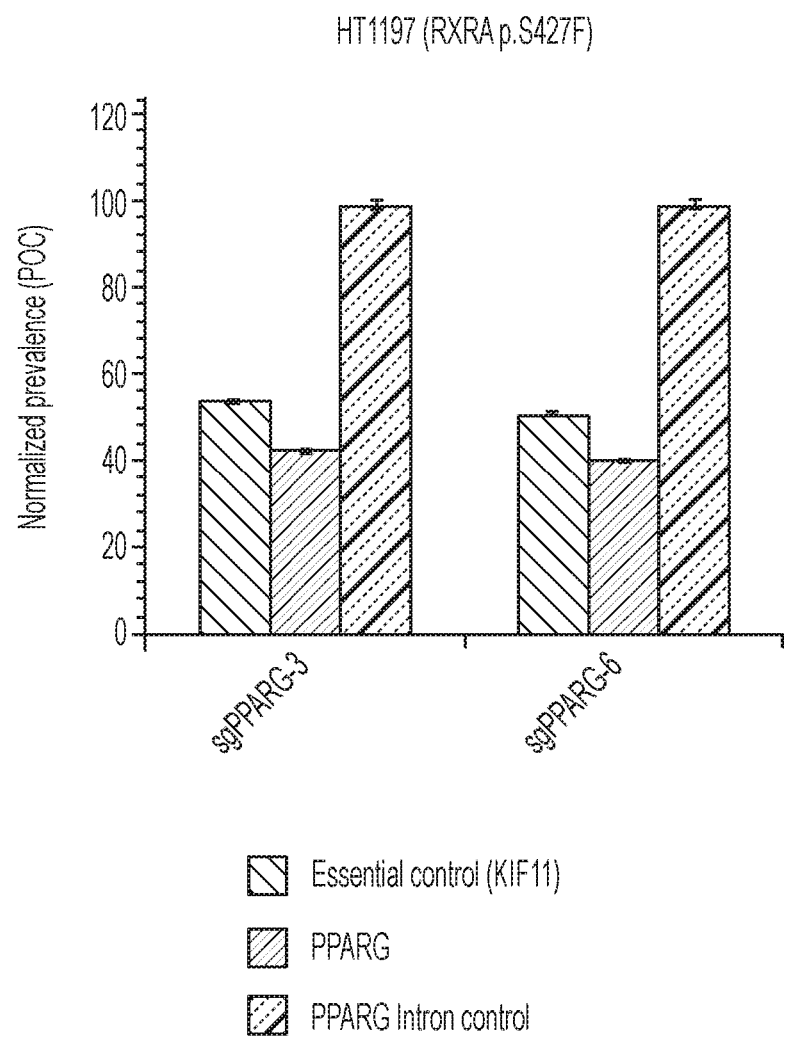
Figure 3C:
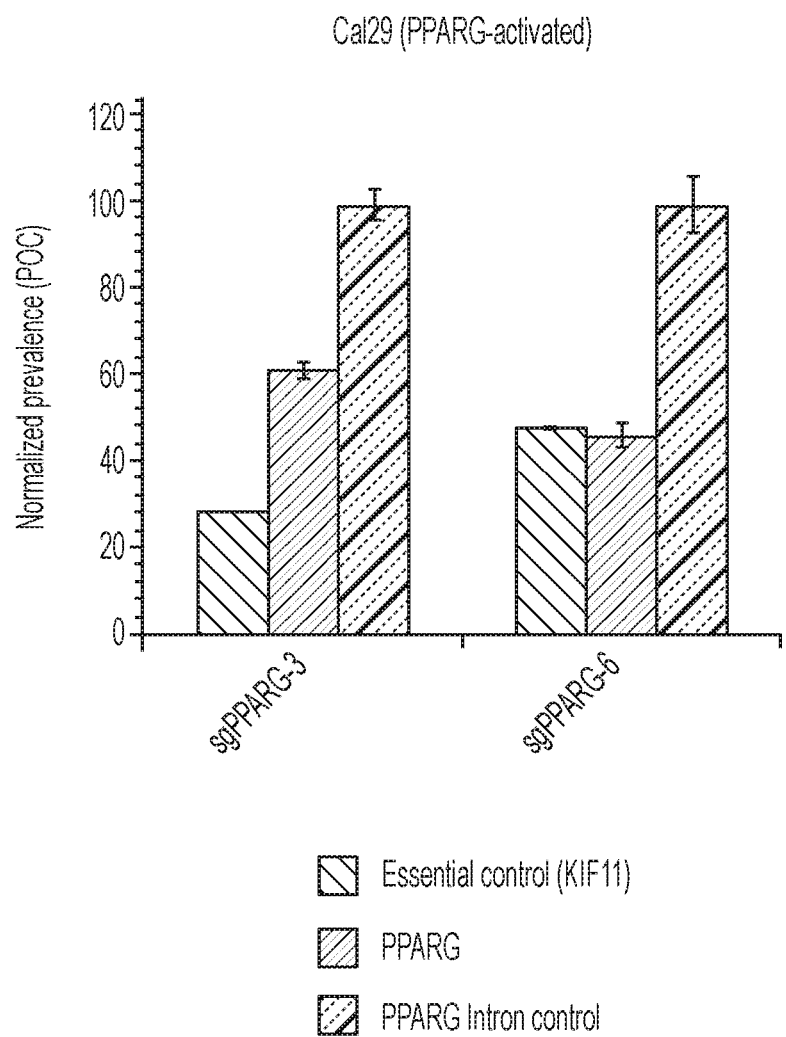
Figure 3D:
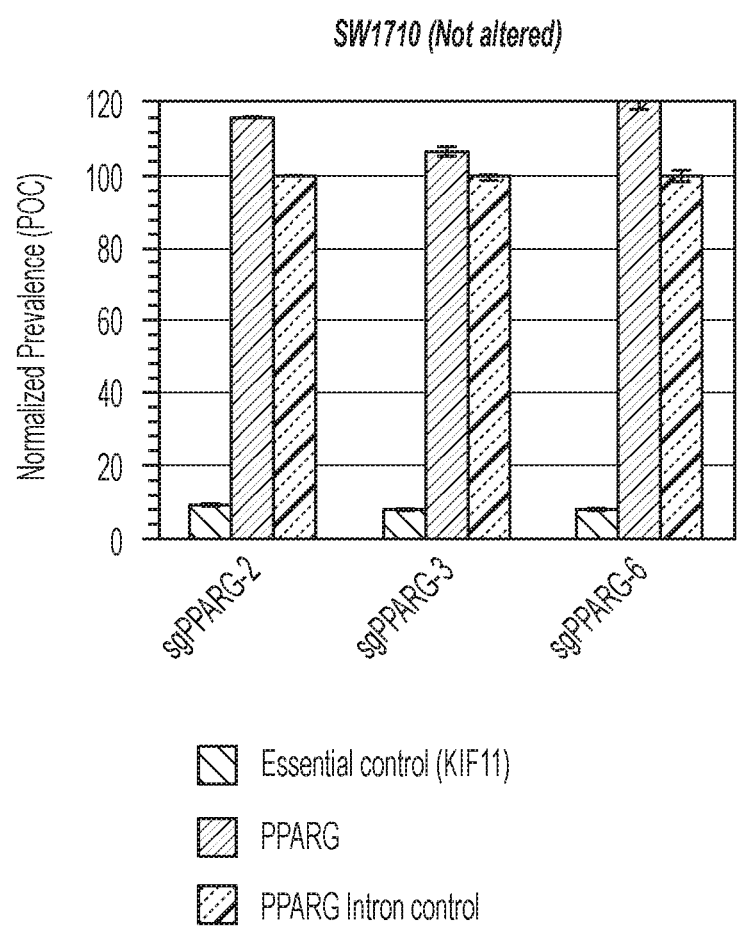

FIGS. 3A-D show cell lines with PPARG pathway activation were dependent on PPARG. The competition assay was run over five cell lines. FIG. 3A shows that PPARG sgRNA's 2, 3, and 6 knocked out PPARG protein in 5637 cells. FIGS. 3B-D depict a CRISPR/Cas9 competition screen performed to measure relative proliferation of cells harboring sgRNA targeting PPARG (yellow), non-essential control of PPARG intron (cyan), and essential control gene KIF11 (red). Cells lines were infected with lentivirus encoding both fluorescent marker and sgRNA prior to pooling cells for assay. As shown in FIG. 3B, HT-11197 is the only cell line available with an RXRA p.S427F mutation, and it exhibits a strong PPARG-dependency in this assay. The Cal29 and RT-112 cell lines that have a similarly activated PPARG signaling pathway also exhibit this dependency, as shown in FIGS. 3C and 3D, respectively. However, the SW1710 and UM-UC-3 cell lines with low PPARG/FABP4 expression are insensitive to PPARG knockout (FIG. 3). Cell lines included HT-1997 (FIG. 3B; RXRA p.S427F), Cal 29 (FIG. 3C; PPARG-activated) and SW1710 (FIG. 3D; not altered, neutral control). These results indicate that PPARG-activated bladder cancer cell lines are dependent upon a functional PPARG.

It should be noted that cell lines containing PPARG focal amplifications were not included in the analysis in order to avoid the well-known copy number sensitivity artifact inherent to the CRISPR/Cas9 platform. In preliminary experiments it was determined that RT4 had inadequate hCas9 expression to support gene knockout studies, which is unfortunate since it is the only cell line available with a PPARG pT447M mutation.

Figure 4A:
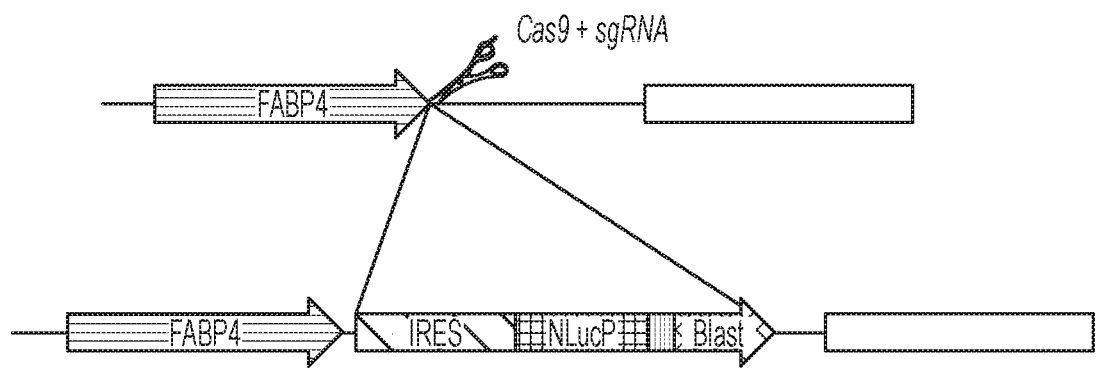
FIGS. 4A-D show that PPARG inverse-agonists, but not antagonists, decreased basal activity by inducing active repression.
Figure 4B:
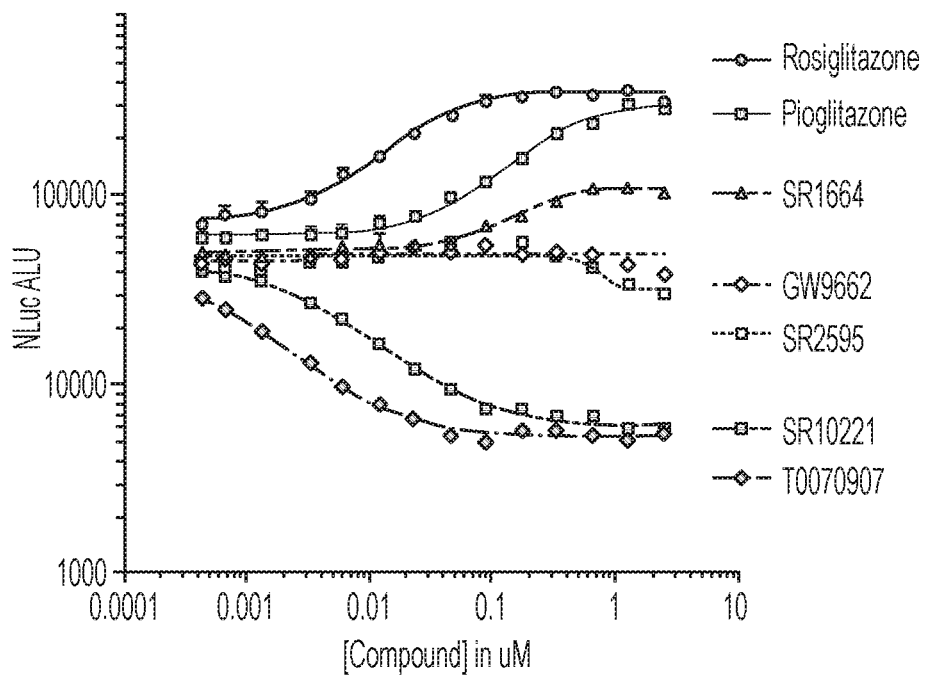
Figure 4C:
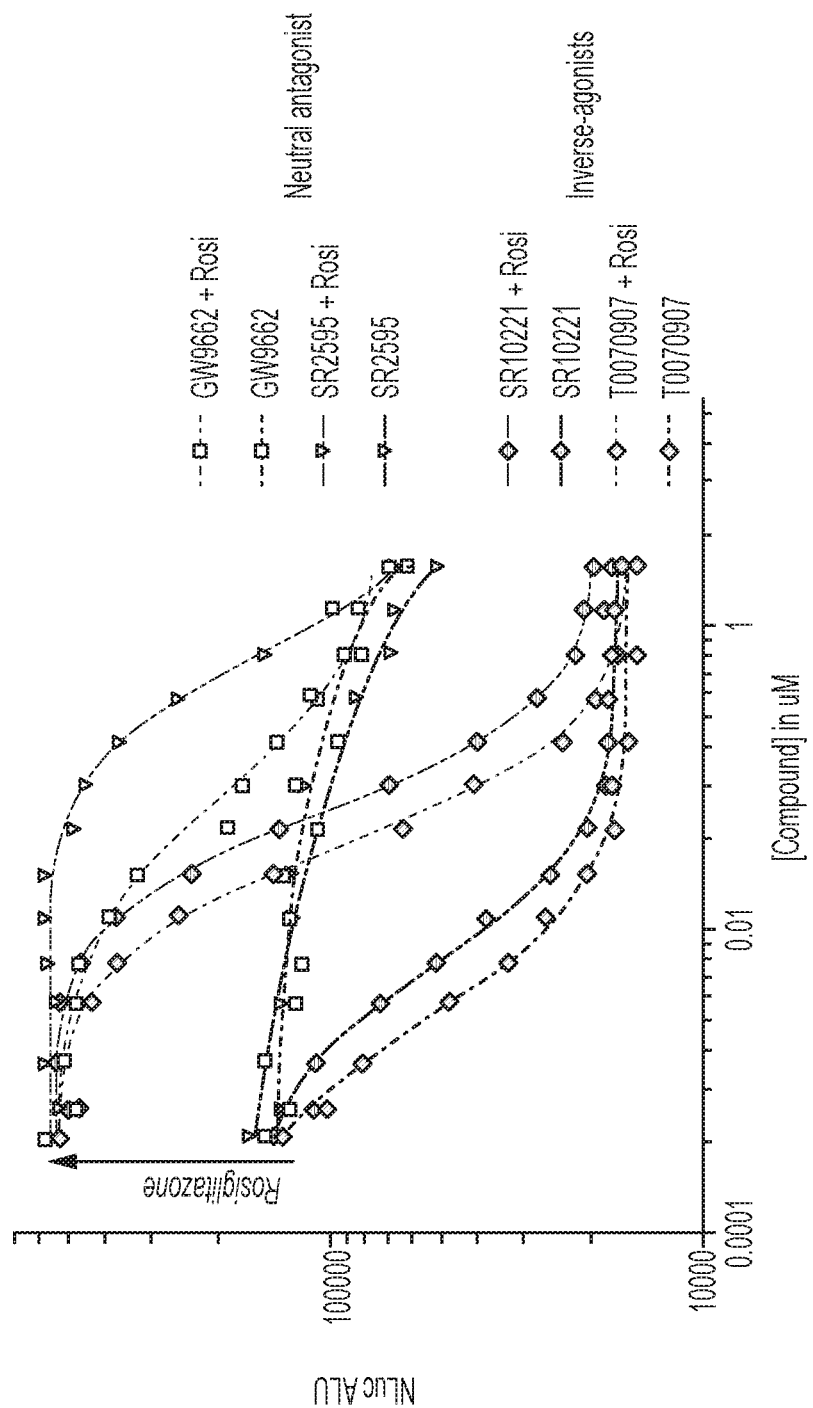
Figure 4D:
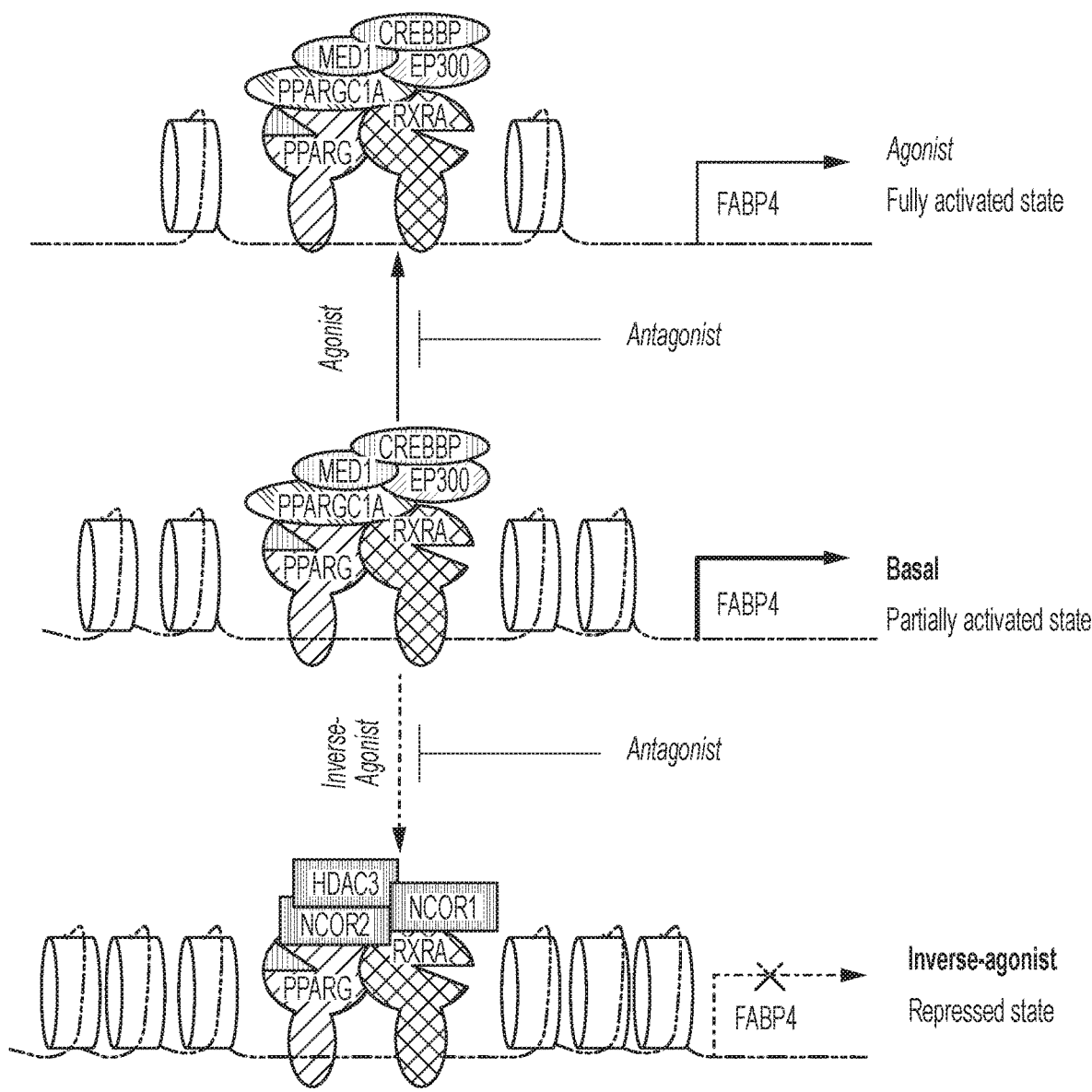

Example 4: PPARG Inverse-Agonists Decreased Target Gene Expression in PPARG-Activated Cell Lines The study of the phenotype of PPARG-activating genome alterations is facilitated by a wide variety of compounds that modulate PPARG activity, including agonists, antagonists, and inverse agonists. PPARG agonists increase recruitment of coactivators such as CREBBP, PGC1a (PPARGC1A), and MED1 to the RXRA-PPARG complex, leading to increased expression of target genes (FIG. 4D, top; 51). PPARG inverse agonists recruit co-repressors such as NCOR1, NCOR2, and HDAC3, leading to a decrease in basal expression of target genes (FIG. 4D, bottom; 51). In contrast, PPARG antagonists have minimal effects on basal receptor function but are able to prevent both agonists and inverse-agonists from binding the receptor, thereby blocking their effects (FIG. 4D; 51).

To evaluate the effects of PPARG modulators on target gene expression and further characterize their biological activity in the context of PPARG-activated bladder cancer, the cellular response to two closely related PPARG modulators, T0070907 and GW9662, was first tested. Although these compounds have similar potency and selectivity profiles and share a remarkably similar structure, they behave quite differently in cellular assays, with T0070907 functioning as an inverse-agonist and GW9662 functioning as an antagonist. In preliminary experiments across the panel of bladder cancer cell lines, it was found that dosing with T0070907, but not GW9662, was able to reduce expression of FABP4 (FIG. 1I).

Figure 8A:
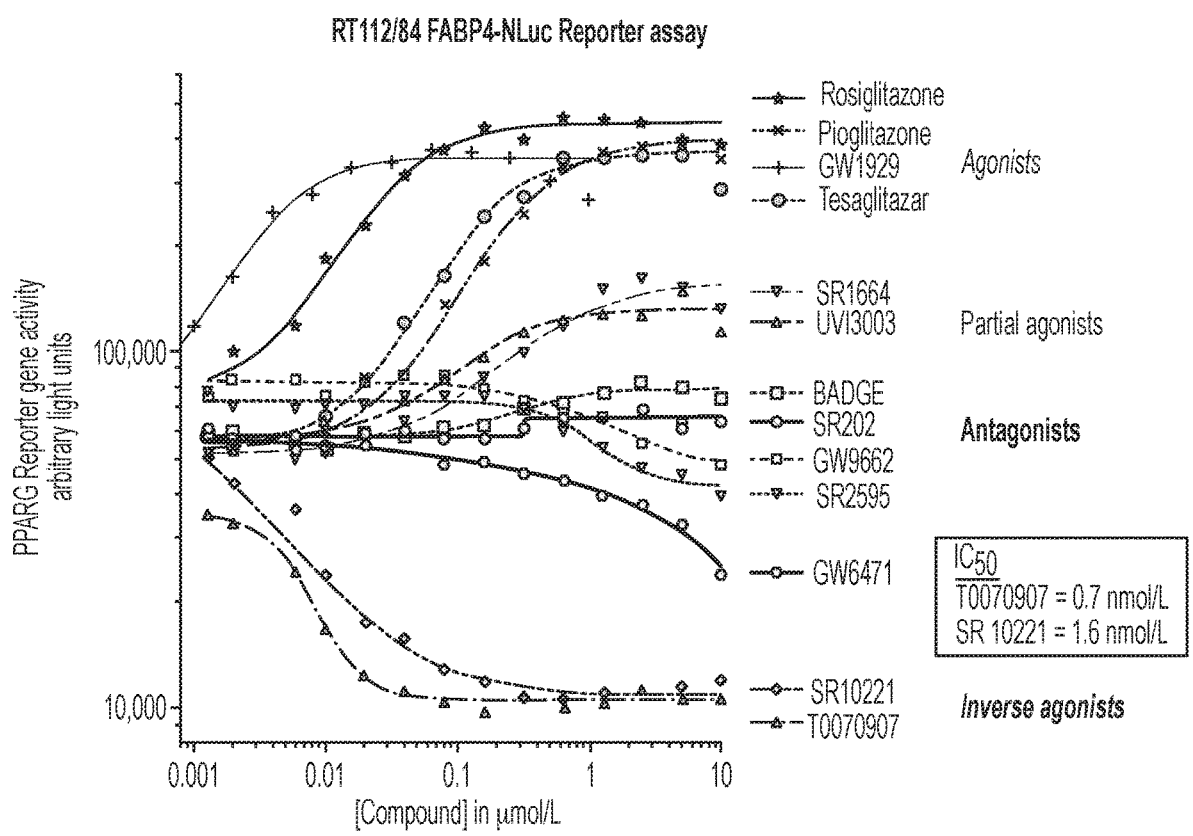
FIGS. 8A-E show data depicting the cellular and biochemical characterization of PPARG modulators. PPARG inverse-agonists decrease basal activity by inducing active repression. PPARG-activated RT112/84 bladder cancer cell line engineered to contain the NanoLuc gene in the 30 UTR of a canonical PPARG target gene, FABP4, was used to profile the effect of compounds on PPARG-dependent gene transactivation.
Figure 8B:
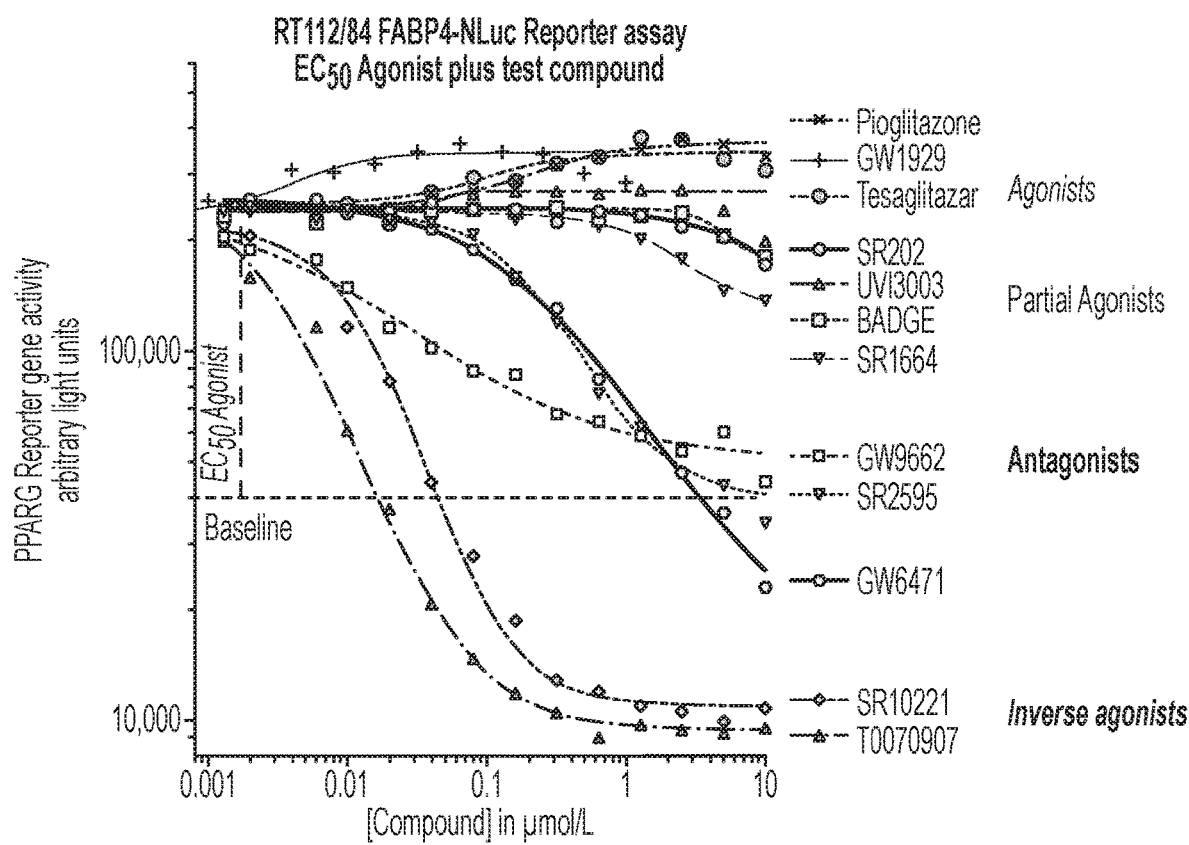
Figure 8C:
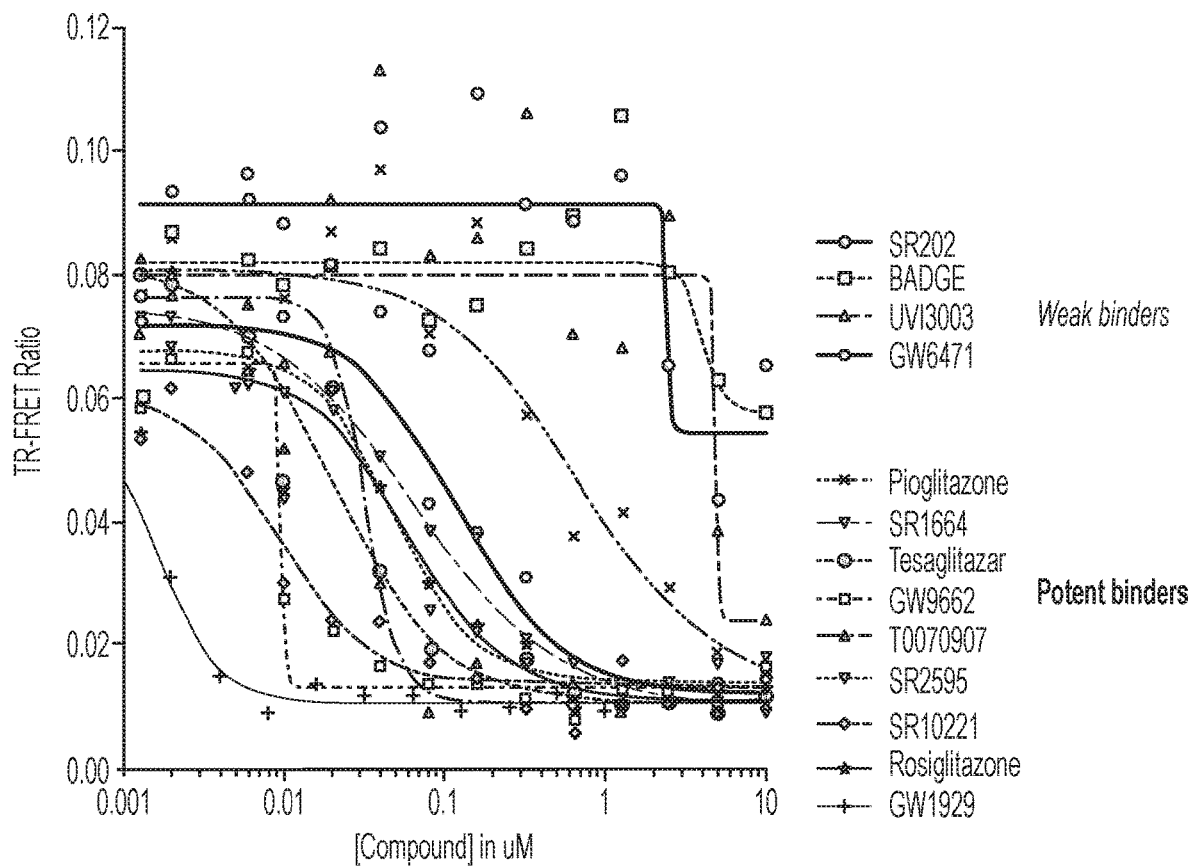
Figure 9A:
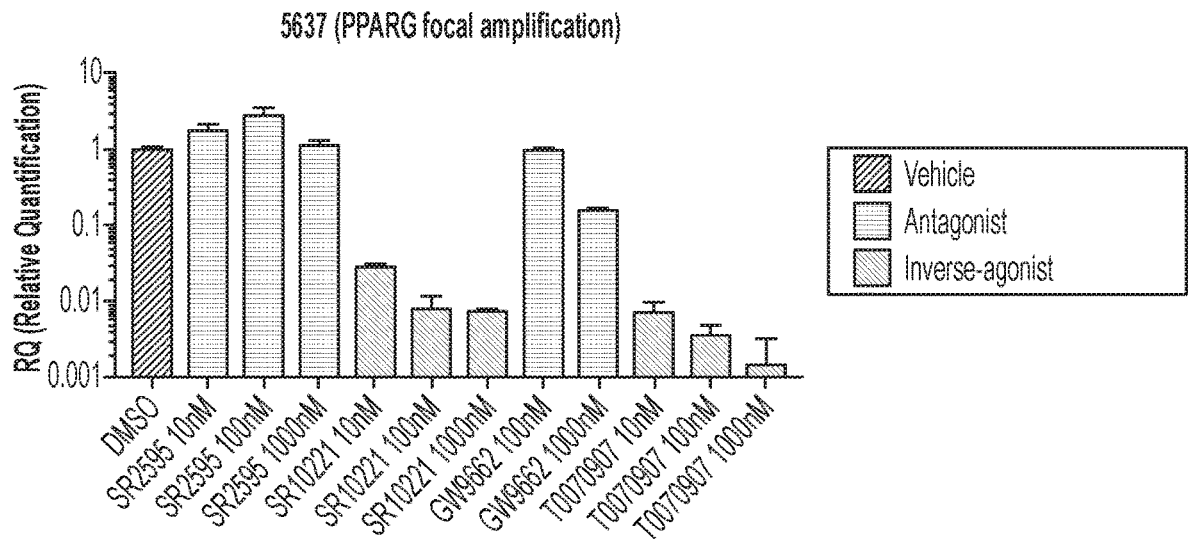
FIGS. 9A-C show three bar graphs depicting quantitative TaqMan qRT-PCR analysis of FABP4 gene expression after overnight treatment with indicated modulators showing that the basal expression of FABP4 was reduced by PPARG inverse-agonists, but not antagonists, in 5637 cells (FIG. 9A), UM-UC-9 cells (FIG. 9B), as compared to primary human adipocyte cells (FIG. 9C), respectively. Data are reported as relative quantification (RQ) for FABP4 compared to GAPDH for test sample after normalization to DMSO control (mean+/−SD, n=3).
Figure 9B:
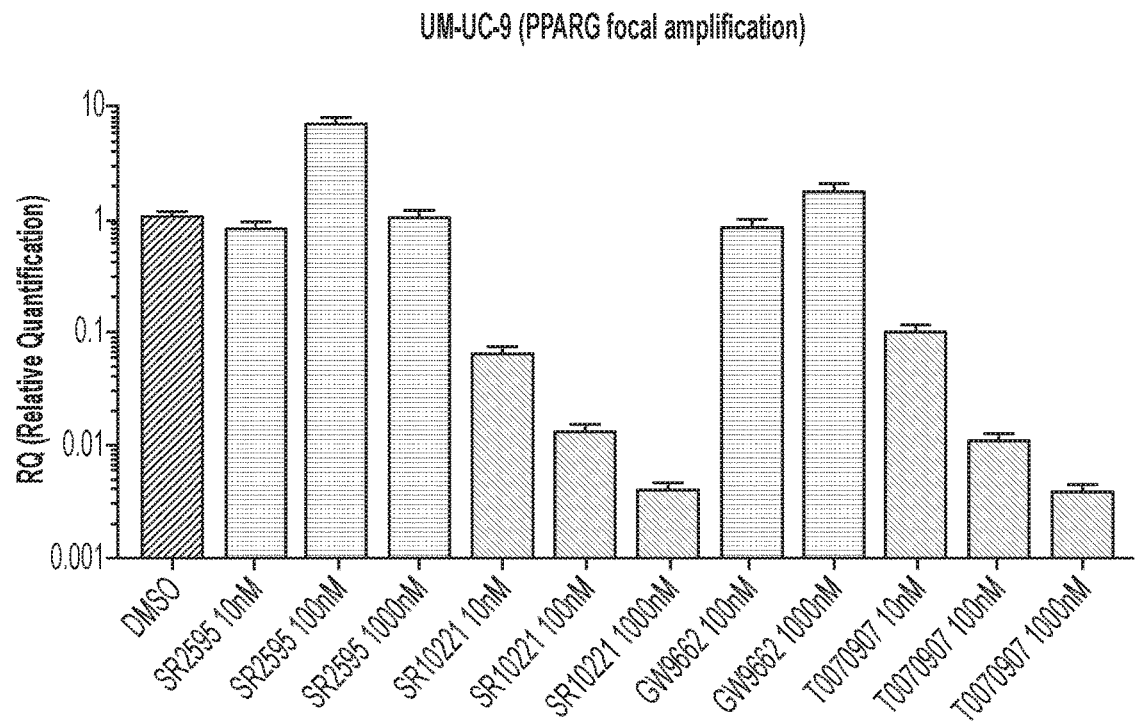
Figure 9C:
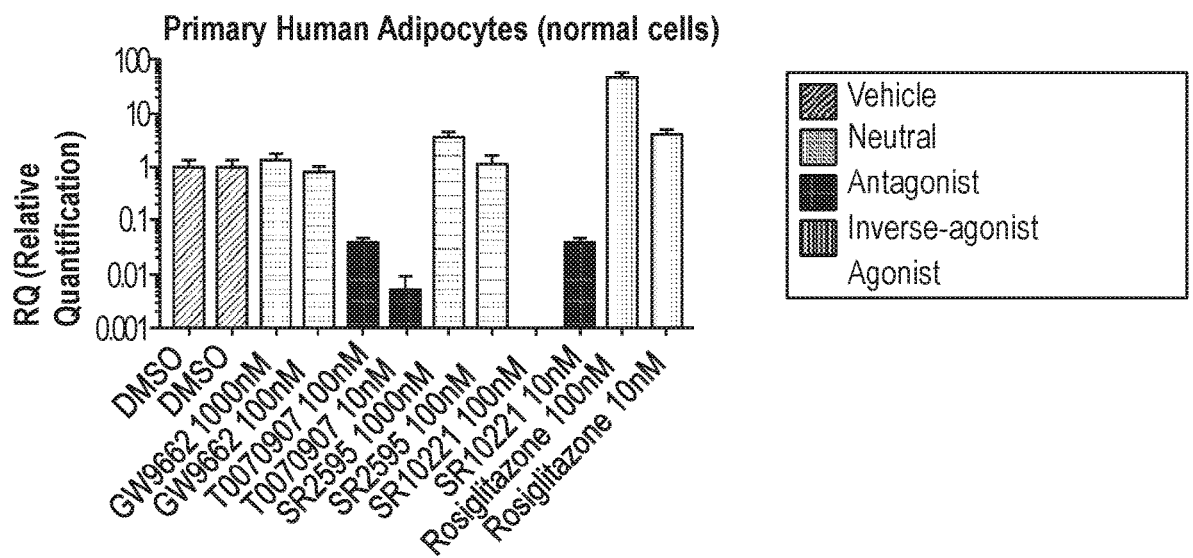
Figure 14:
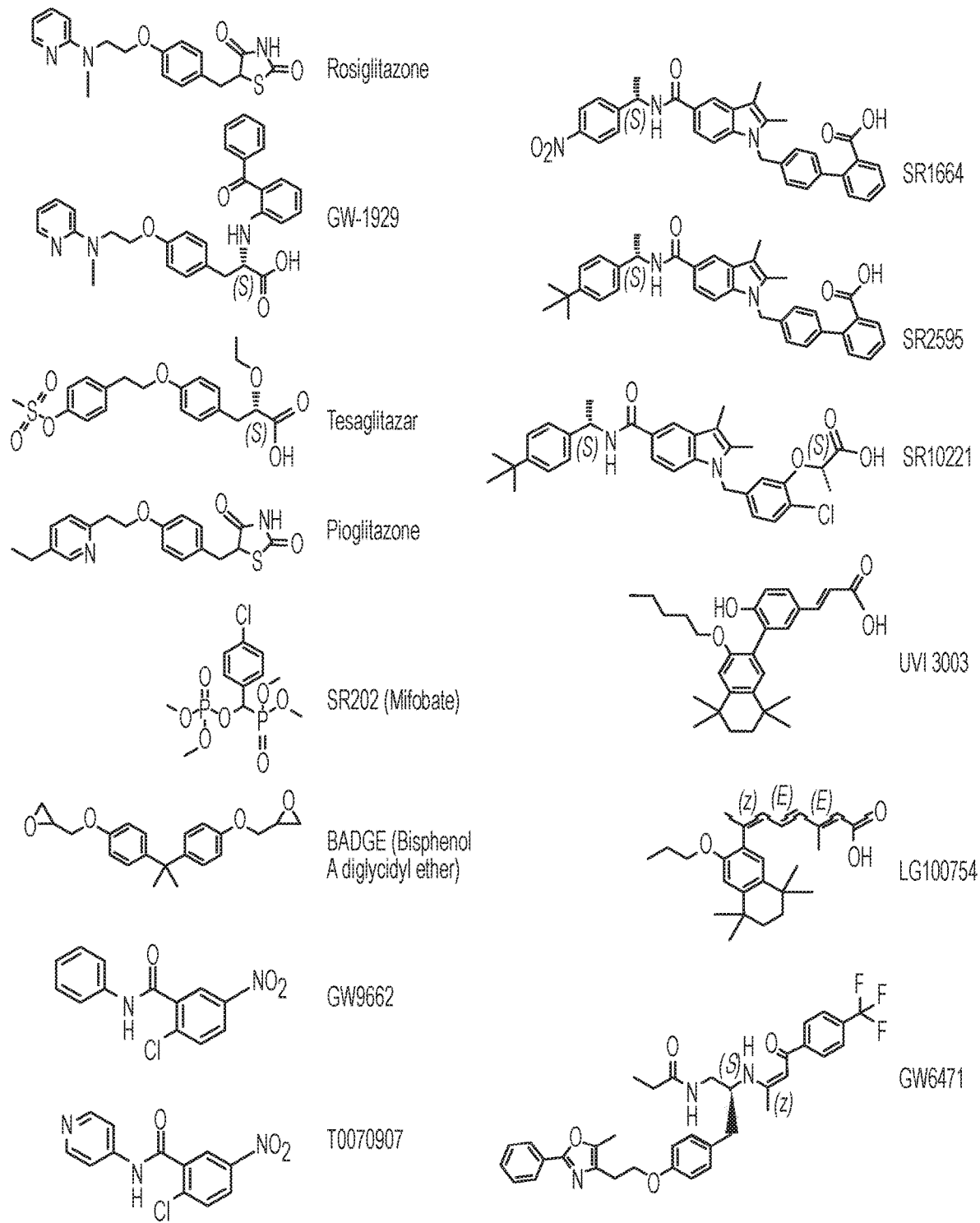
FIG. 14 depicts the chemical structures of Rosiglitazone, GW-1929, Tesaglitazar, Pioglitazone, SR202 (Mifobate), BADGE (Bisphenol A diglycidyl ether), GW9662, T0070907, SR1664, SR2595, SR10221, UVI3003, L100754, and GW6471.

Next, a PPARG reporter cell line was engineered to enable higher throughput assays to evaluate PPARG transactivation. Briefly, a destabilized NanoLuc luciferase reporter gene was inserted into the 3'-UTR of the FABP4 gene in the RT112/84 bladder cancer cell line using CRISPR/Cas9 mediated homology-directed repair (FIG. 4A). This reporter cell line was used to characterize the cellular response to a wide variety of commercially available PPARG agonists, antagonists, and inverse-agonists to determine if any resulted in decrease of basal activity in the reporter cell line, thus indicating inverse-agonism in the context of bladder cancer (FIGS. 8A-C). Because many compounds that target nuclear receptors are selective modulators, which have context-dependent activity profiles (51), this reporter cell line was used to characterize the activity of 13 previously characterized PPARG agonists, antagonists, and inverse-agonists (46, 49, 23-59). The full PPARG agonists, including rosiglitazone, pioglitazone, tesaglitazar, and GW1929, were able to increase the basal activity of the PPARG reporter from 5.5- to 7.4-fold in this assay (FIG. 8A, indicated in red). The partial agonists, including UVI3003 and SR1664, increased the basal activity of the reporter from 1.4- to 3.1-fold (FIG. 8A, indicated in black). The antagonists, including BADGE, SR202, GW9662, and SR2595, had minimal detectable effect on this unstimulated reporter (FIG. 8A, indicated in light blue). The PPARA-selective inverse agonist GW6471 exerted a modest inhibitory effect. Finally, the two inverse-agonists tested, T0070907 and SR10221, reduced basal PPARG reporter activity by 85% to 88% (FIG. 8A, indicated in dark blue and green). Interestingly, the closely related structural analogs (FIG. 14) of these compounds, GW9662 and SR2595, respectively, were essentially neutral antagonists in this assay. The only compounds that were potent and efficacious in reducing reporter activity were T0070907 and SR10221 (FIG. 4A). Interestingly, closely related analogs of these compounds, GW9662 and SR2595, respectively, did not show this effect in the absence of ligand, but did act as antagonists, reducing agonist induced activity (FIG. 4B). These data are in alignment with quantitative PCR analysis of FABP4 gene expression in 5637 and UM-UC-9 cells. FIG. 4C shows representative data from dose-response testing of select tool compounds in RT112/84 FABP4-NLucP assayed after overnight treatment in the presence of an agonist, Rosiglitazone, at the EC50. FIG. 4D shows a representation of PPARG transactivation complex in agonist activated state (top) and inverse-agonist induced repressed state (bottom). In particular, FIGS. 9A-C show three bar graphs depicting quantitative PCR analysis of FABP4 gene expression showing that the basal expression of FABP4 was reduced by PPARG inverse-agonists, but not antagonists, in 5637 cells (FIG. 9A), UM-UC-9 cells (FIG. 9B), as compared to primary human adipocyte cells (FIG. 9C), respectively. These data clearly indicated that all of the compounds tested, only T0070907 and SR10221 were acting as fully efficacious PPARG inverse-agonists in the context of PPARG-activated bladder cancer cell lines, but did not exclude that these and others can be selective modulators with potential for lineage dependent functions, such as inverse-agonism in other contexts.

Figure 5:
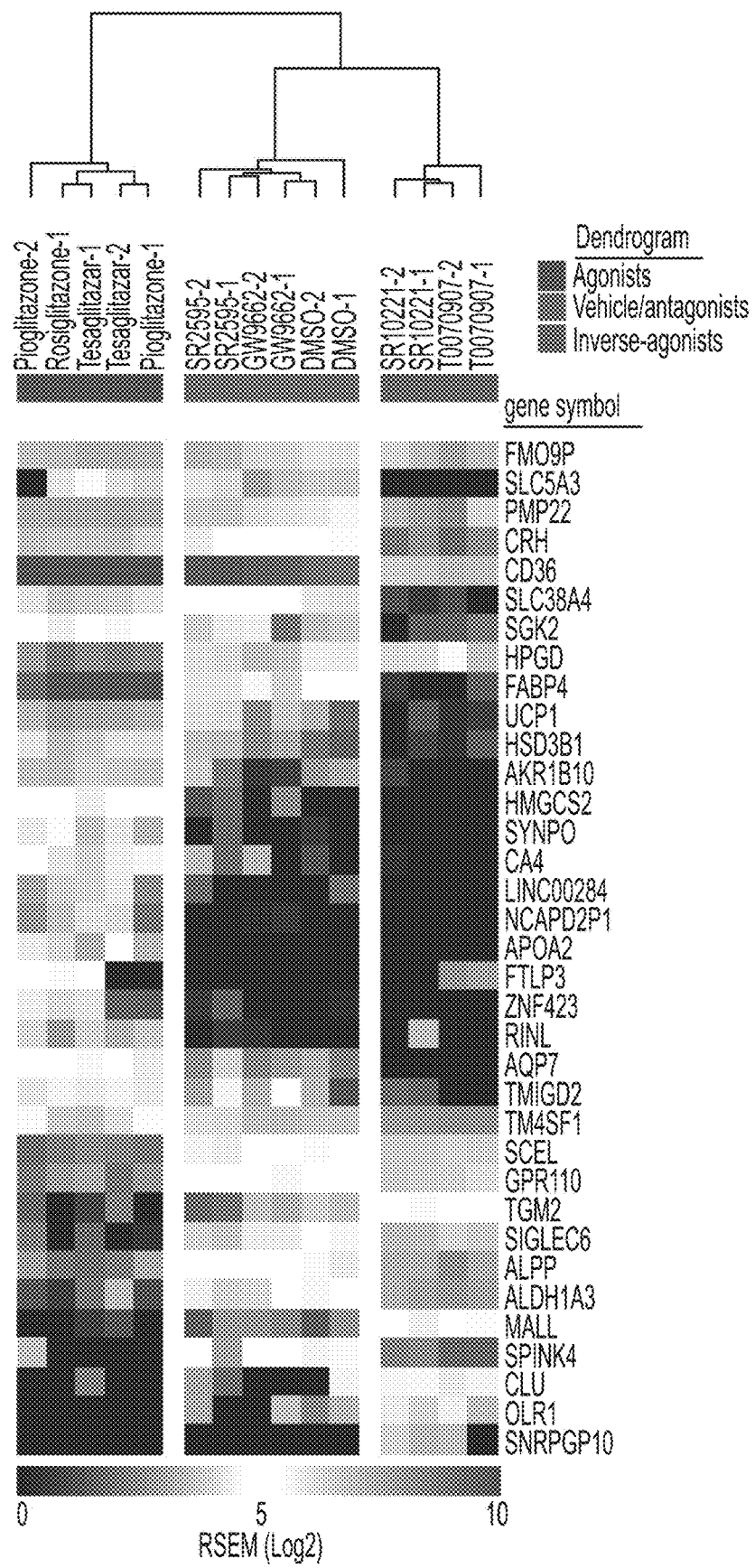
FIG. 5 shows that lipid metabolism genes are inhibited by PPARG inverse-agonists. A heat map of the top differentially regulated genes in UM-UC-9 cells treated with PPARG modulators for 7 days at 500 nM; inverse-agonists (T0070907, SR10221), vehicle, antagonists (GW9662, SR2595), and agonists (Rosiglitazone, Pioglitazone, Tesaglitatzar) and indicates that lipid metabolism genes were inhibited by PPARG inverse-agonists. RNA sequencing data is reported as transcripts per million (TPM) (log 2) with heat map generation and hierarchical clustering of columns performed using Morpheus software package on the World Wide Web at (www)software.broadinstitute.org/morpheus/).

To gain a mechanistic understanding of the effects of PPARG inverse agonists, the effects of long-term dosing of PPARG modulators on the transcriptional profile of the PPARG amplified cell line, UM-UC-9, were evaluated. Briefly, UM-UC-9 cells were treated for 7 days with indicated PPARG modulators dosed at 500 nM and analyzed gene expression using RNAseq. Many canonical PPARG target genes were amongst the top differentially expressed genes that were upregulated with PPARG agonists and downregulated with inverse-agonists (e.g., FABP4, UCP1, etc.)(FIG. 5). In the other direction, genes that are more abundantly expressed upon treatment with inverse agonists include ALPP, SPINK4, and ALDH1A3 (FIG. 5). Without being bound by theory, it is believed that PPARG activation leads to upregulated expression of metabolic genes and these alterations can provide a growth advantage for these cell lines, and that PPARG inverse-agonists are able to counteract this effect and reduce the metabolic rate, resulting in reduced growth rate (FIG. 6A-I).

To evaluate antagonist and inverse-agonist activity in more detail, compounds were tested in the presence of a PPARG agonist, rosiglitazone, for their impact on ligand-activated PPARG reporter activity. Here, the agonists gave little additional stimulation (FIG. 8B, indicated in black). The antagonists GW9662 and SR2595 decreased the agonist-induced signal back to the original baseline (FIG. 8B, indicated in light blue), whereas the inverse agonists T0070907 and SR10221 further reduced the agonist induced signal 80%-90% below baseline (FIG. 8B, indicated in dark blue and green). These data align with quantitative PCR analysis of FABP4 gene expression in 5637 and UM-UC-9 cells treated with PPARG antagonists and inverse-agonists (FIGS. 9A-9B) and establish that the reporter assay accurately represents the effects of PPARG modulators on target gene expression in bladder cancer cell lines.

Next, the effects of long-term dosing on the transcriptional profile of the PPARG-amplified cell line, UMUC-9, were evaluated. Briefly, UM-UC-9 cells were treated for 7 days with various PPARG modulators dosed at 500 nmol/L and gene expression was analyzed using RNA sequencing. Many canonical PPARG target genes were amongst the top differentially expressed genes that were upregulated with PPARG agonists and downregulated with inverse-agonists, for example FABP4 and UCP1 (FIG. 5). Genes that were more abundantly expressed upon treatment with inverse-agonists included ALPP, SPINK4, and ALDH1A3 (FIG. 5). Hierarchical clustering of the gene expression signatures indicated that GW9662 and SR2595 cluster with vehicle-treated controls. Therefore, the PPARG inverse-agonists, T0070907 and SR10221, are clearly biologically distinct from the antagonists, GW9662 and SR2595, in bladder cancer cells. While both SR2595 and SR10221 were described as PPARG inverse-agonists when tested in mouse 3T3-L1 cells (49), the studies described herein using human bladder cancer cells suggest that SR10221, but not SR2595, behaves as an inverse-agonist in these cells (FIGS. 5, 8A; 8B, 9A, and 9B). In summary, the in vitro pharmacological properties of known PPARG modulators have been characterized and two distinct chemotypes with bona-fide inverse-agonist activity in PPARG-activated bladder cancer cells were identified.

Example 5: PPARG-Activated Cell Lines were Sensitive to PPARG Inverse-Agonists

To determine if treatment of PPARG-activated bladder cancer cell lines with PPARG modulators impacted viability, a variety of compounds were tested in proliferation assays. Initial studies with compounds tested in a range up to 10 μM indicated that many of the compounds exhibited non-selective toxicity at the higher concentrations (data not shown). However, a modest but reproducible effect of T0070907 and SR10221 was noticed, with IC50 values in the range of −20-30 nM when tested in PPARG-amplified 5637 cells (data not shown). The IC50 values are within range of the IC50/EC50 values observed in the biochemical and cellular reporter gene assays. Furthermore, it is well below the reported biochemical IC50s of T0070907 in the context of PPARA and PPARD (23).

A panel of bladder cancer cell lines with PPARG modulators in colony formation assays was then tested (FIG. 10), kinetic proliferation assays (IncuCyte Zoom; Essen Bioscience) using cell lines treated with a single concentration of compound (100 nM-500 nM), and end-point dose-response assays (CellTiter Glo or CyQuant). The PPARG-activated cell lines tested were preferentially sensitive to the T0070907 and SR10221 PPARG inverse-agonists, but not sensitive to the GW9662 or SR2595 neutral antagonists (FIG. 6). These data indicate that proliferation of the PPARG-activated subset of bladder cancer cell line is dependent on PPARG activity, and inhibition of this activity with T0070907 or SR10221 results in decreased proliferative potential. FIG. 12 shows a table summarizing the results of cell proliferation assays showing that PPARG inverse-agonists inhibited proliferation of PPARG activated bladder cancer cell lines.

Example 6: PPARG Inverse-Agonists Induced a Repressive Complex Through Inducing Interactions with Co-Repressor NCOR2

A selection of PPARG modulators were evaluated in a variety of biochemical assays to gain an understanding of their activities. To evaluate binding affinity, a PPARG competition binding assay that measures displacement of a fluorescent PPARG ligand from the PPARG ligand-binding domain was used. All PPARG modulators evaluated were able to bind PPARG LBD (FIG. 8A) and compete with a low affinity pan-PPAR fluorescent ligand (Fluormone, ThermoFisher). However, maximal activity of SR202 and BADGE was limited at the maximal concentrations tested (10 uM), and suggests weak activity which is consistent with literature reports.

To evaluate inverse-agonism, a TR-FRET PPARG co-repressor assay (ThermoFisher) that measures recruitment of a fluorescent NCOR1 or NCOR2 corepressor peptide to the PPARG ligand-binding domain was used (ThermoFisher). Both T0070907 and SR10221 induce interaction between PPARG and NCOR2 and this activity is distinguished from the remaining PPARG antagonists (FIG. 8B). However, only T0070907 induced this interaction with NCOR1 (data not shown). Combined with the reporter assay data, this suggests that NCOR2 may be the critical co-repressor required for PPARG inverse-agonism in bladder cancer.

Figure 8D:
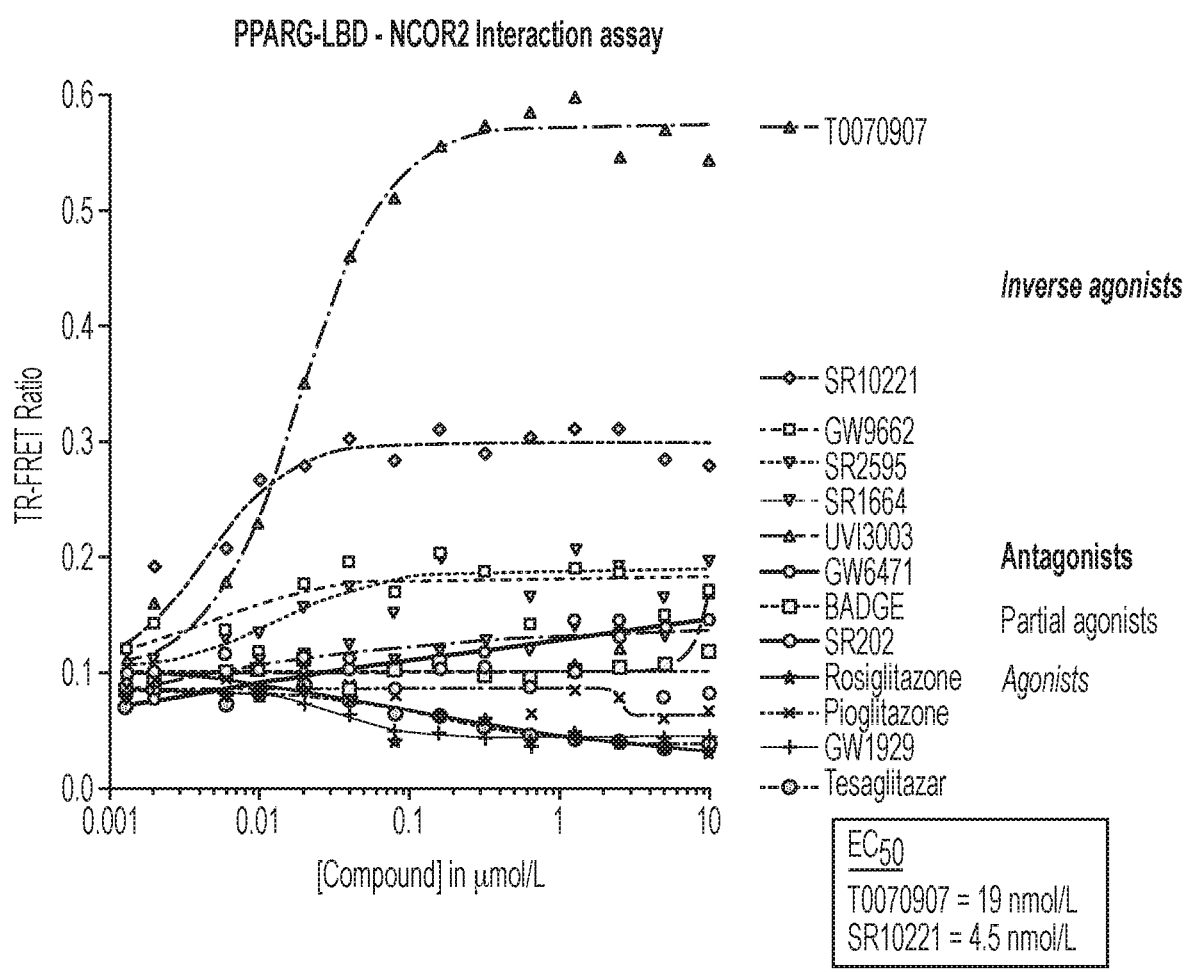
Figure 8E:
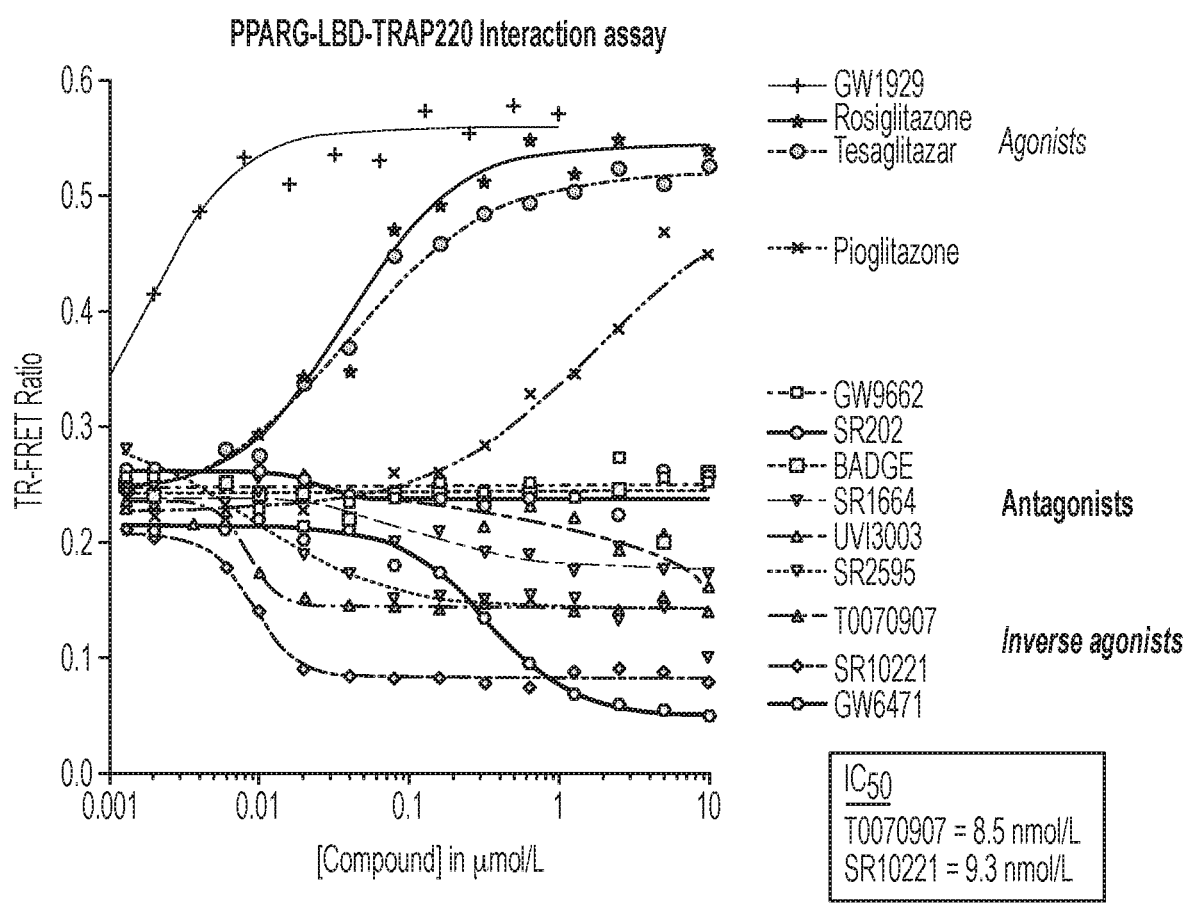

FIGS. 8C-E show the results of dose-response testing of a panel of PPARG modulators in competitive ligand-binding TR-FRET biochemical assay (FIG. 8C), in PPARG ligand binding domain—co-activator peptide interaction assay using TRAP220 (MED1) peptide (FIG. 8D), and in PPARG ligand binding domain—co-repressor peptide interaction assay using SMRT (NCOR2) peptide (FIG. 8E).

To determine effects on interactions between PPARG and coregulators, PPARG modulators were tested in two TR-FRET biochemical interaction assays for agonism and inverse-agonism. Agonism was quantitated using a coactivator assay, which measured the interaction between the PPARG ligand-binding domain and a fluorescently-labeled peptide from TRAP220/MED1. Full agonists, such as rosiglitazone, tesaglitazar, GW1929, and pioglitazone, enhanced interaction between PPARG and MED1 coactivator peptide, resulting in an increase in fluorescent signal from 2.2- to 3.0-fold (FIG. 8E, indicated in red). The antagonists and partial agonists, BADGE, SR202, GW9662, UVI3003, and SR1664 had minimal effect in this assay (FIG. 8E, indicated in gray and light blue). The PPARA-selective inverse-agonist GW6471, PPARG antagonist SR2595, and PPARG inverse-agonists, T0070907, and SR10221, exerted a modest inhibitory effect of 40% to 60% (FIG. 8E, indicated in dark blue and gray). To evaluate inverse-agonism biochemically, ligand-dependent interactions were measured between PPARG ligand-binding domain and corepressor peptides from NCoR/NCOR1 and SMRT/NCOR2. The majority of PPARG partial agonists and antagonists had minimal effect on the NCOR2 assay signal (FIG. 8D). PPARG inverse-agonists, T0070907 and SR10221 (FIG. 8D, indicated in dark blue), increased signal 3- to 6-fold, whereas antagonists GW9662 and SR2595 (FIG. 8D, indicated in light blue), induced only a small increase in signal of 1.7-fold. A decrease in signal of 50%-60% was observed with the rosiglitazone, tesaglitazar, and GW1929 agonists (FIG. 8D, indicated in red).

In addition to the PPARG-NCOR2 interaction assay described above, interactions between PPARG and a peptide from the corepressor NCOR1 were measured. In the PPARG-NCOR1 interaction assay, T0070907 induced signal 6- to 8-fold, whereas the antagonist GW9662 induced signal 2.5-fold and inverse agonist, SR10221, induced signal less than 2-fold, and antagonist, SR2595, had no effect (data not shown). The potent inverse agonist activity of SR10221 in cellular assays (FIGS. 5, 8A-8B; and 9A-9B) and biochemical PPARG-LBD-NCOR2assay (FIG. 8D), but not PPARG-LBD-NCOR1 interaction assay (FIG. 8D), suggests that NCOR2 may be the functional corepressor mediating PPARG inverse-agonist activity in bladder cancer cells.

Example 7: PPARG/GATA3 Network in Bladder Cancer

The top gene in the bladder cancer TCGA dataset whose expression is correlated with PPARG is GATA3 (FIG. 1F). This is an unexpected parallel to ESR1 positive luminal breast cancer, where estrogen receptor (ESR1) and GATA3 expression are tightly correlated (along with FOXA1). In luminal breast cancer, GATA3 and ESR1 are known to co-regulate expression of each other and form a positive feedback loop for their expression (24). Without being bound by theory, it is believed that a parallel regulatory network may exist for PPARG and GATA3 in luminal bladder cancer.

Example 8: PPARG as Driver of Urothelial Differentiation

PPARG is a master regulator of adipocyte differentiation. Studies of rat urothelial cells have shown that luminal differentiation markers (UPK1A, UPK1B, and KRT20) are up-regulated in primary rat urinary cells by PPARG agonists (25). It was also observed that increased expression of urothelial differentiation markers (UPK1A, UPK1B, UPK2, KRT20 and GATA3) in the above-described RNAseq studies. These genes were similarly reported to be upregulated in previous studies linking them to the luminal subtype of bladder cancer (22, 26). PPARG activation may be a defining lineage event for luminal bladder cancer, but if, and how this may lead to oncogenic activation will need further investigation.

Rosiglitazone induces the expression of urothelial differentiation markers (UPK1A, UPK1B, and KRT20) in primary culture of rat urothelial cells (25). In human bladder cancer samples, expression of the PPARG and GATA3 transcription factors has been correlated with expression of a number of differentiation markers (UPK1A, UPK1B, UPK2, KRT20), which are key biomarkers for the luminal subset of bladder cancer (22, 26). However, a direct link between PPARG expression and expression of these genes has not been established in bladder cancer.

Example 9: PPARA/PPARG Dual Agonist and Bladder Cancer

In addition to the genomic evidence for a potential oncogenic driver role of PPARG (PPARA) in bladder cancer, there is also rodent and human pharmacological evidence. The potential risk for promotion of bladder cancer by PPARG modulators was first illuminated in rodent toxicity studies published by the FDA in 2004 (5, 6). However, in the context of the PPARG-selective modulators, this effect appeared specific to Pioglitazone, but was not observed with more selective PPARG modulator, Rosiglitazone (8). The data surrounding risk for bladder cancer associated with the use of PPARG agonist, Pioglitazone, has become more clear with a recent retrospective study showing a clear increase in hazard ratio with long term treatment of Pioglitazone (8). Notably, Pioglitazone is reportedly less selective towards PPARA compared to Rosiglitazone, and has been hypothesized that some of the observed oncogenic effect, in rodents, may be due, in part, to PPARA activation. In the studies by El Hage, 5 of the 6 tested PPARA/PPARG dual agonists (Glitazars) caused bladder cancer in rodent toxicity studies (5), thus providing further evidence for a link between PPAR signaling and bladder cancer. Since highly selective PPARG (or PPARA) agonists do not appear to promote bladder cancer, there may be an interplay between these two receptors that is required for oncogenic activation in the bladder, and that in humans, it may require a pre-existing lesion to be susceptible to these effects.

Example 10: RXRA p.S427F/Y Model

Figure 7A:
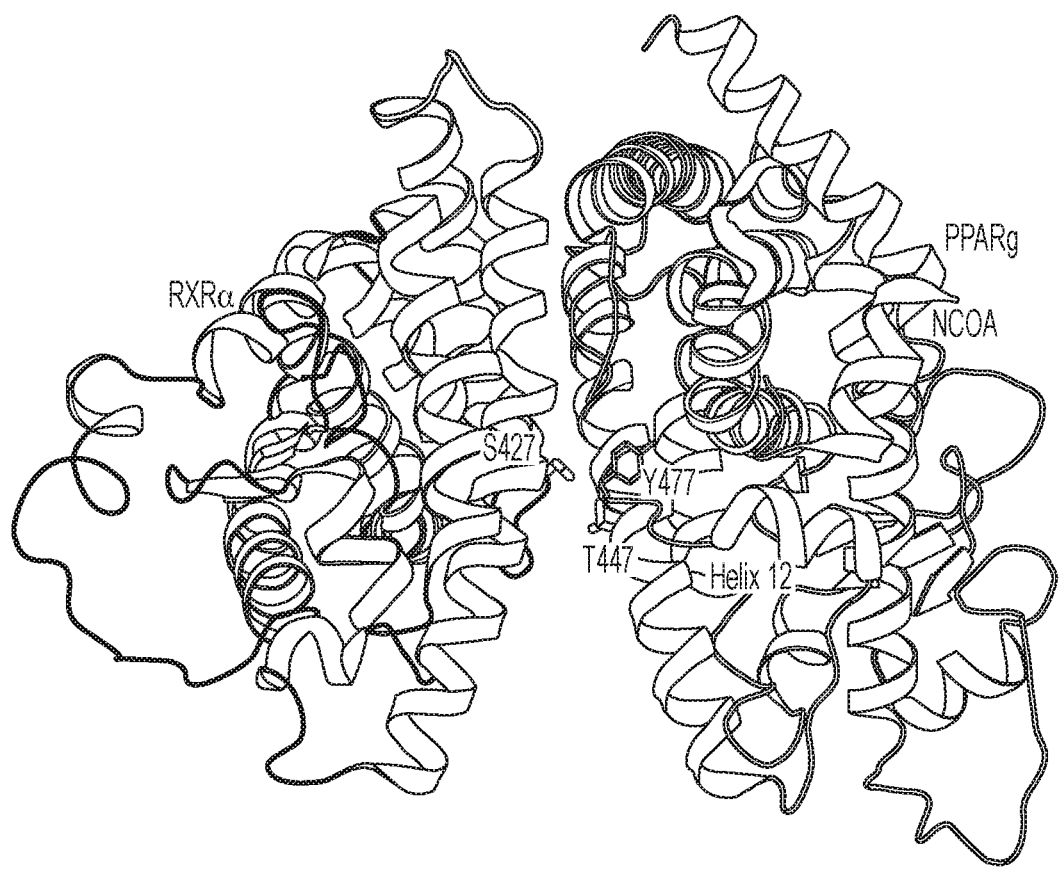
FIGS. 7A-C show structural models for RXRA p.S427F-mediated activation of PPARG showing proximity of RXRA S427 and the C-terminal amino acids of PPARG, Y477, in the ligand-activated state in ribbon mode (FIG. 7A) and space-filling (FIG. 7B).
Figure 7B:
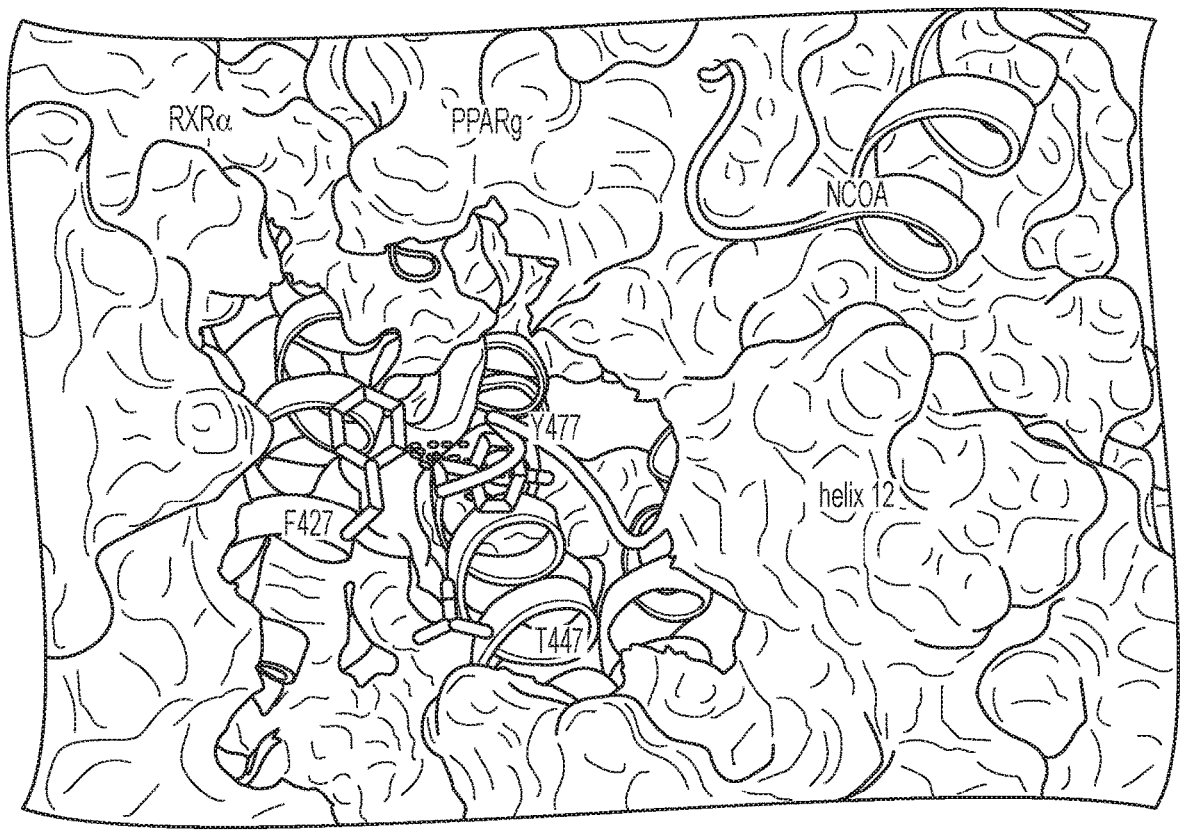
Figure 7C:

The co-crystal structure of RXRA/PPARG (PDB ID: 1FM6) (18) shows that the S427 position of RXRA is located in the dimerization interface with PPARG in the ligand-activated state, and this positioning is similarly observed in the molecular model with RXRA/PPARA (27). In the activated state, helix 12 of PPARG is closed, thereby creating a binding cleft for co-activator proteins. The c-terminal amino acid of PPARG (and PPARA), is a tyrosine, directly adjacent to the RXRA S427 position in the active conformation. Without being bound by theory, it is believed that RXRA p.S427F/Y mutations may induce a ligand-independent interaction between the RXRA 427 position and the c-terminal tyrosine of PPARG (and possibly PPARA/PPARD) through pi-stacking or other forces (FIG. 7), leading to ligand-independent activation of RXRA/PPARG (and possibly RXRA/PPARA and/or RXRA PPARD). It is also possible that the S427 hotspot mutations may result in disruption of the interactions between RXRA and its other heterodimer partners (e.g., RARA, VDR, TR), possibly shifting equilibrium of RXRA towards PPARG (Bruce Spiegelman, personal communication). This model provides a mechanistic hypothesis for RXRA p.S427F/Y mutations driving ligand-independent, selective activation of the PPARs, but not other RXRA heterodimer partners.

Example 11: PPARG as a Driver of Cancer Metabolism

Figure 11:
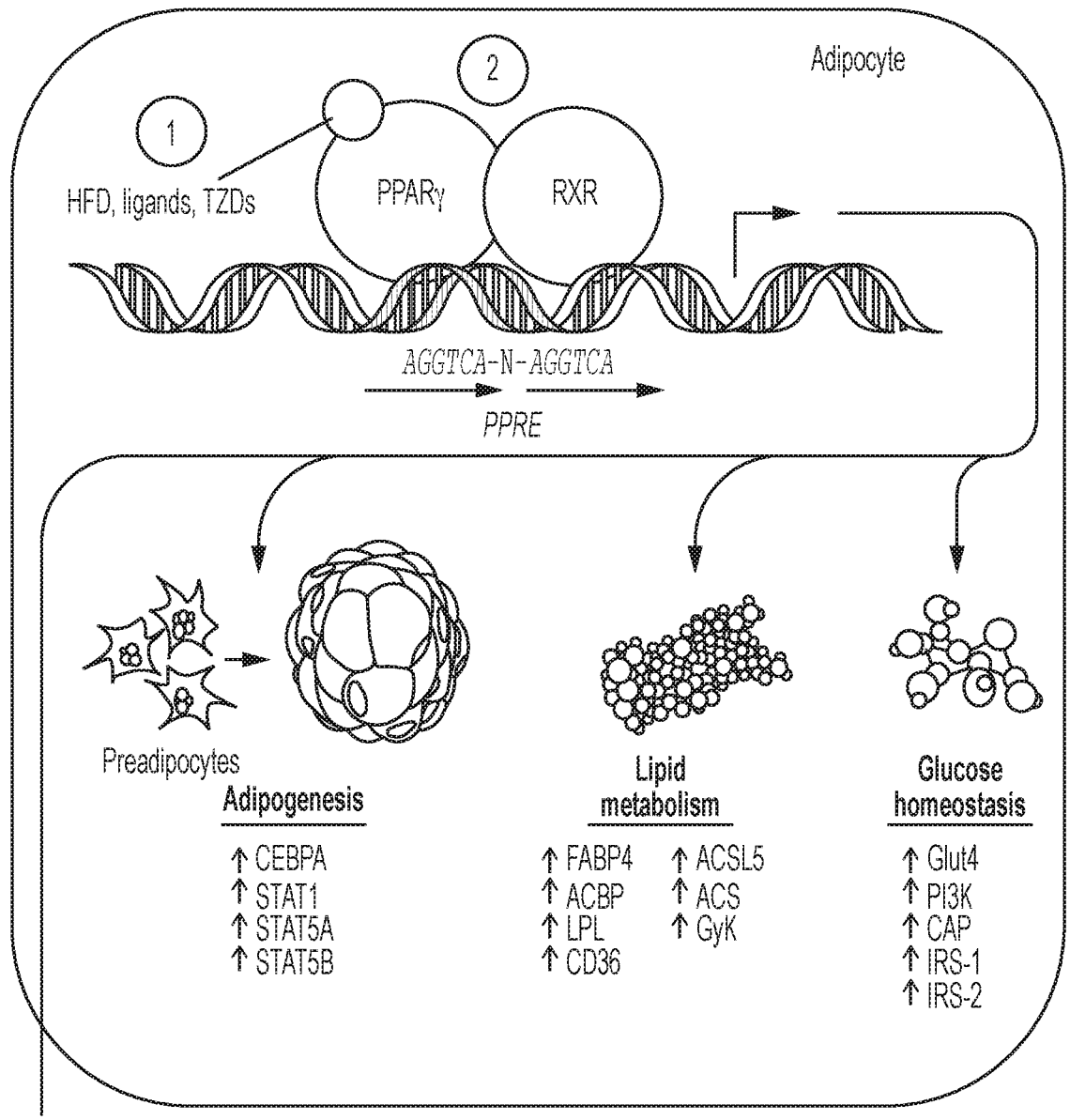
FIG. 11 depicts a schematic summary of PPAR signaling roles in adipose tissues. Figure discloses SEQ ID NO: 1.
Figure 13A:
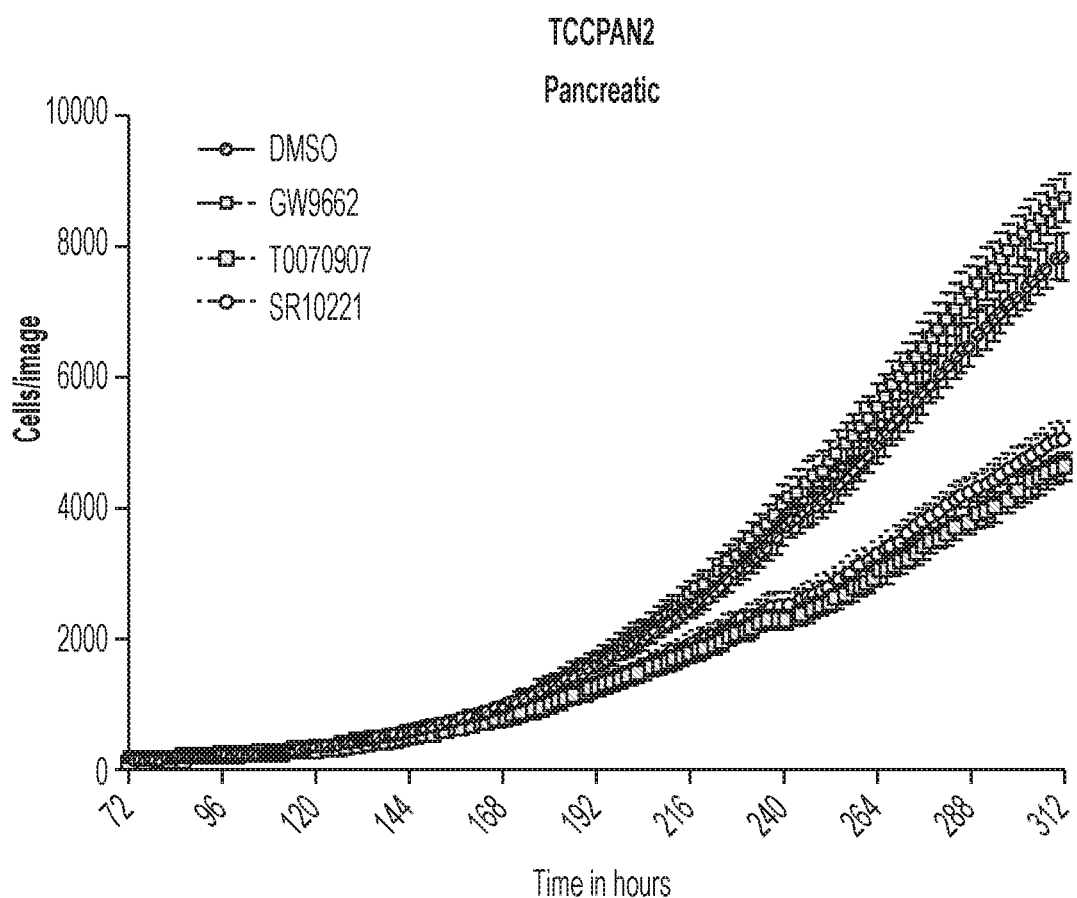
FIGS. 13A-D show that additional PPARG activated cell lines were sensitive to inverse-agonists, but not antagonists.
Figure 13B:
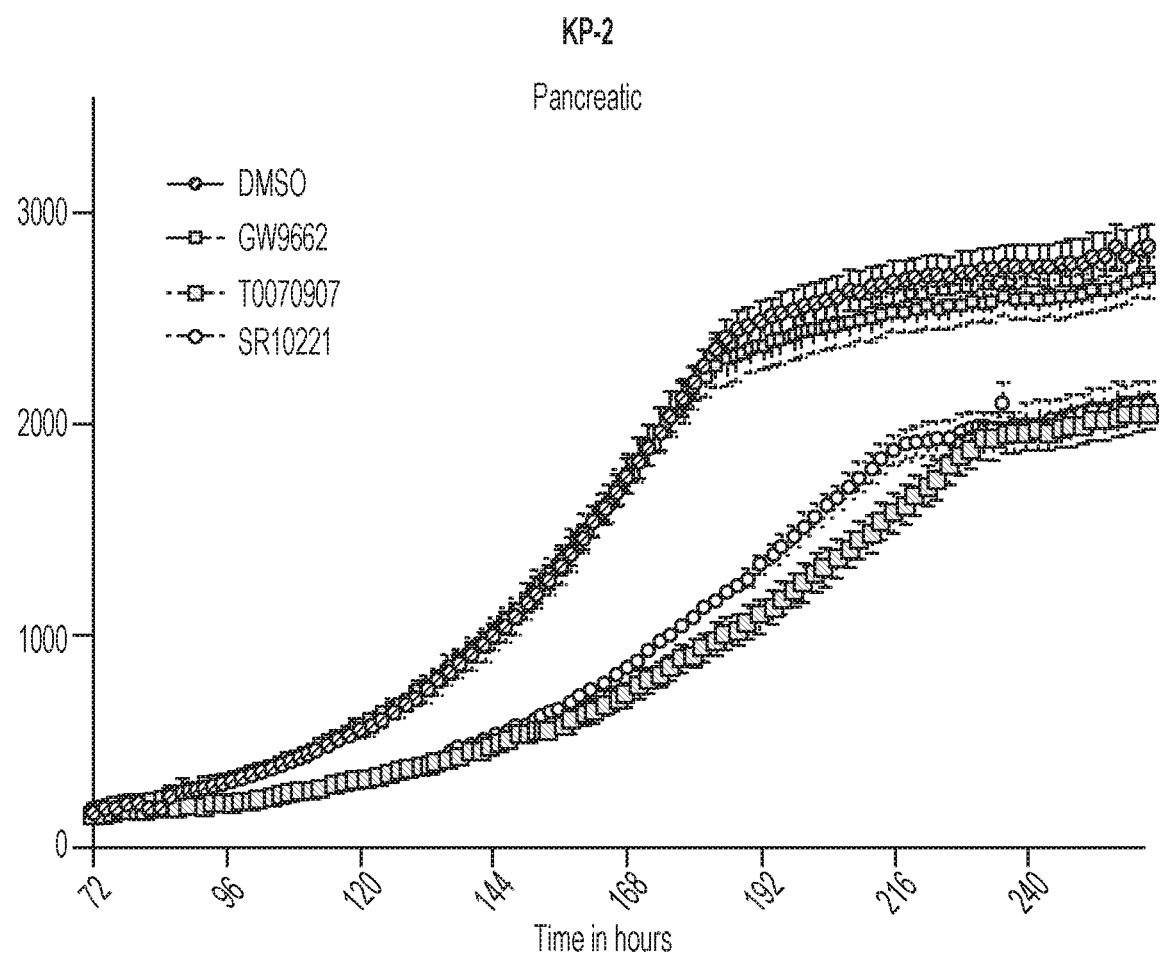
Figure 13C:
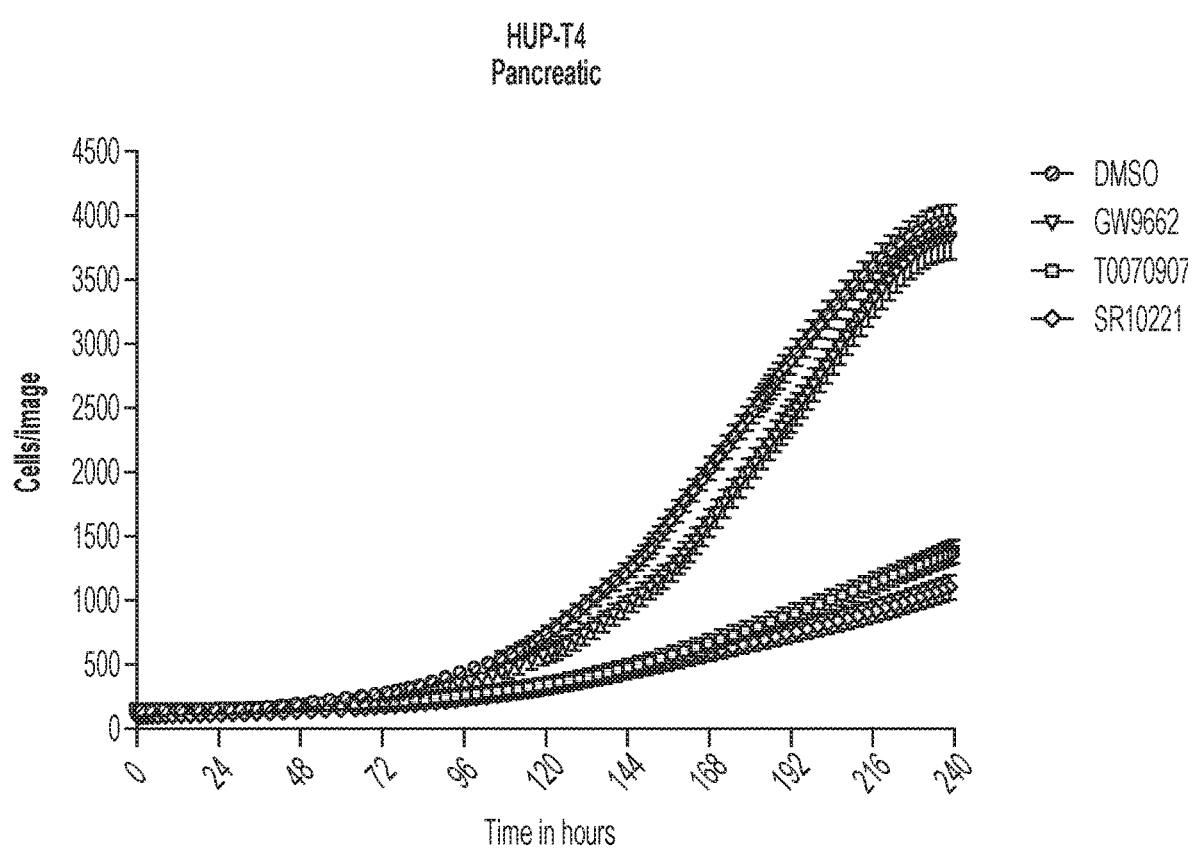
Figure 13D:
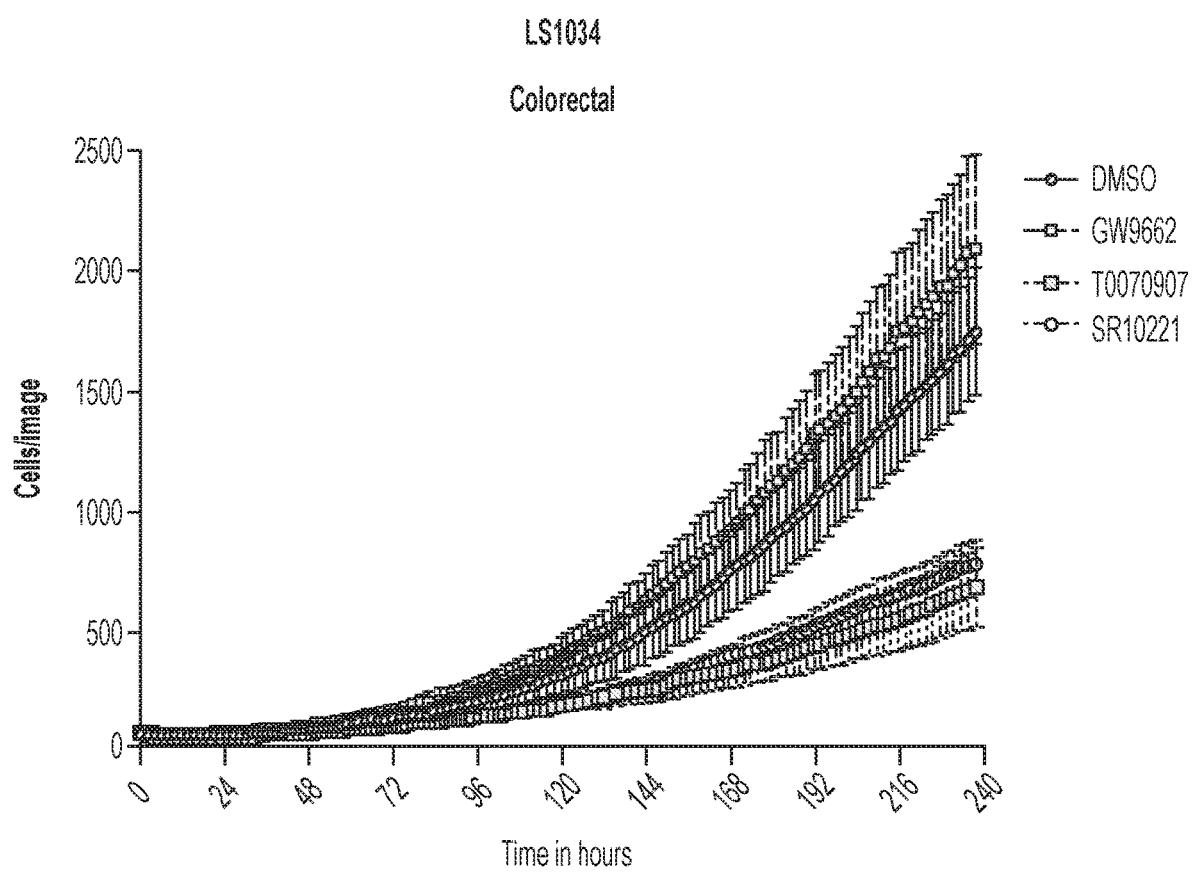

FIG. 11 provides an overview of PPARG signaling. An oncogenic role in breast cancer for activated PPARG, driven by PML and PPARGC1A (PGC1α) by enhancing fatty acid oxidation was postulated by Carracedo (28, 29). Work from Pilar Caro et al (30) focused on a subset of diffuse large-cell B-cell lymphoma (DLBCL) cell lines exhibiting enrichment of genes involved in oxidative phosphorylation and the TCA cycle, and hypothesized that PPARG activation was involved. They further found T0070907 was able to attenuate growth of this subset of DLBCL cells by decreasing oxidative phosphorylation. However, their study used much higher concentrations of T0070907 (1-15 uM) than the present studies (100 nM-500 nM) which does not preclude possible effects on PPARA (apparent Ki~850 nM) in addition to PPARG (apparent Ki~1 nM) (23) in the Caro et al study.

An interesting potential link to bladder cancer and lipid metabolism can be speculated by analysis of the metabolomics study from the urine of bladder cancer patients by Hoque et al, whereby they found that metabolites related to lipid metabolism were the best predictive biomarkers of disease (31). Further work is needed to investigate the link to PPARG modulation by inverse-agonists and if there is a direct and measurable link to luminal bladder cancer and urinary metabolites, this may provide a non-invasive sample for biomarker analysis to stratify patients or follow activity of PPARG-targeted therapeutics.

According to the techniques herein, a genetic and pharmacologic dependence on PPARG in the luminal subset of bladder cancer cell lines has been identified. While shutting down activity of PPARG in the whole animal was initially a major concern of this approach due to predicted on-mechanism complications, such as lipodystrophy and insulin resistance, recent reports suggest that PPARG biology (32, 33) and pharmacology (34) may be more convoluted than this simple view. The present disclosure provides a well-defined patient population and clear therapeutic approach for further application and/or development (including, e.g., testing for on-mechanism toxicity).

Example 12: Growth Rate Inhibition of Pancreatic and Colorectal Cancer Cells In Vitro with PPARG Inverse-Agonists—Kinetic Proliferation Using IncuCyte To determine if treatment of other types of PPARG-activated cancer cell lines with PPARG modulators impacted viability, a variety of compounds were tested in proliferation assays with both pancreatic and colorectal cell lines.

To enable cell-counting, cell lines were transduced with a lentiviral vector encoding nuclear-targeted GFP (TagGFP2-H2B), and stable pools generated following selection for puromycin-resistance. Cell lines were maintained for at least 7 days following selection prior to expansion and seeding into 96-well plates for further analysis. For kinetic proliferation assays, 96-well plates were imaged in phase-contrast and green fluorescence mode every two hours using IncuCyte Zoom (Essen BioScience, Ann Arbor MI). Using IncuCyte software, the number of fluorescent nuclei were counted to monitor quantitative changes in cell number over time. Media and compounds were replaced approximately every 3-4 days.

As shown in FIGS. 13A-D, a panel of pancreatic and colorectal cancer cell lines were tested in kinetic proliferation assays with several PPARG modulators, including GW9662, T0070907, and SR10221, all of which were dosed at 500 nM. DMSO treatment was also included as a vehicle control. The PPARG-activated cell lines tested were preferentially sensitive to the T0070907 and SR10221 PPARG inverse-agonists, but not sensitive to the GW9662 or SR2595 neutral antagonists (FIGS. 13A-D). These data indicate that proliferation of the PPARG-activated subset of pancreatic and colorectal cancer cell line is dependent on PPARG activity, and inhibition of this activity with T0070907 or SR10221 results in decreased proliferative potential.

Figure 6A:
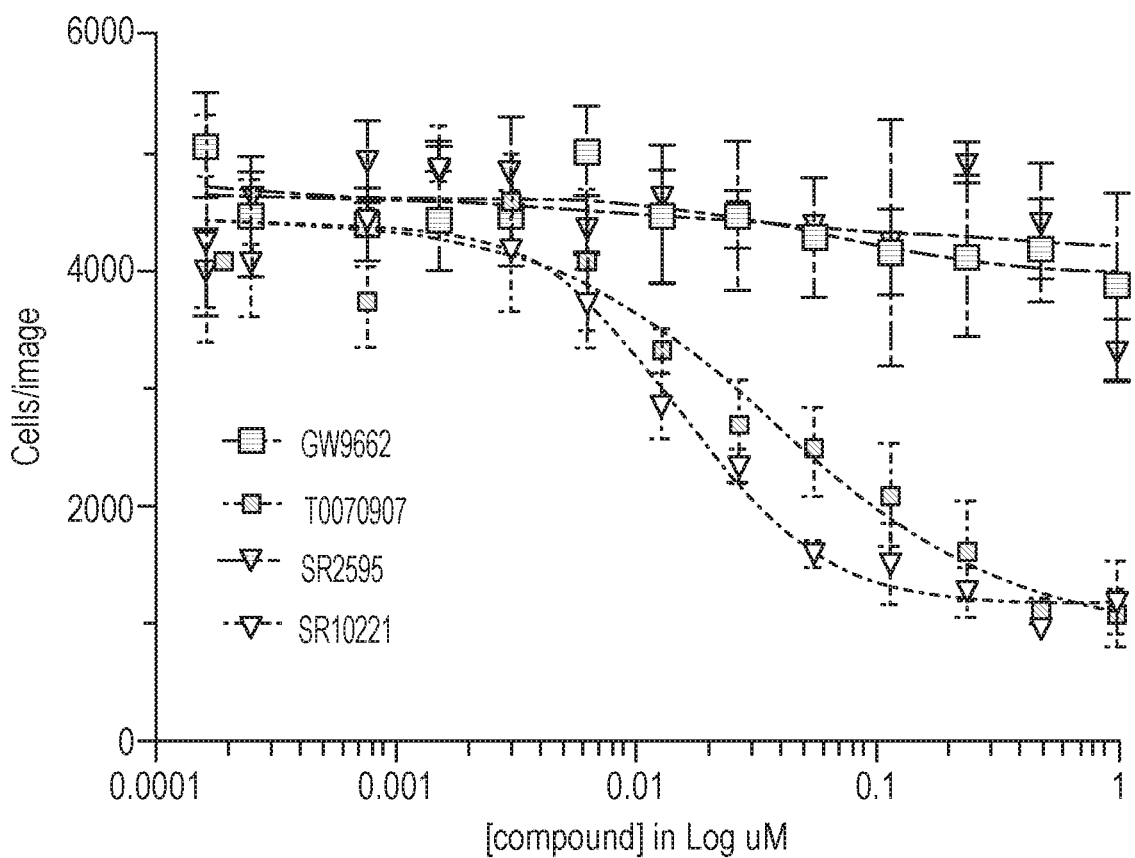
FIGS. 6A-I show that PPARG activated cell lines were sensitive to inverse-agonists, but not antagonists.

Example 13: PPARG Inverse-Agonists Inhibit the Proliferation of PPARG Activated Cell Lines To determine whether PPARG modulators affect the proliferation and/or viability of PPARG-activated bladder cancer cell lines, a direct cell counting-based assay was performed. This assay likely avoids potential artifacts associated with the use of an ATP content-based assay, given that PPAR modulators are known to regulate cellular metabolic activity. Both inverse-agonists, T0070907 and SR10221, significantly reduced proliferation of UM-UC-9 cells, compared with DMSO control (P<0.001; FIG. 6A, indicated in green), with calculated IC50 values of 39 and 16 nmol/L. In contrast, both antagonists tested, GW9662 and SR2595, had no significant effects on cell proliferation (FIG. 6A, indicated in gray). These IC50 values align well with the calculated IC50s from both the cell-based reporter gene assay (FIG. 8A) and the biochemical corepressor assay (FIG. 8D). They are also close to the respective reported biochemical IC50s against PPARG, and two orders of magnitude below that reported for activity against PPARA and PPARD (23), suggesting that the observed anti-proliferative effects in UM-UC-9 cells are due to downregulation of PPARG target genes.

Figure 6B:
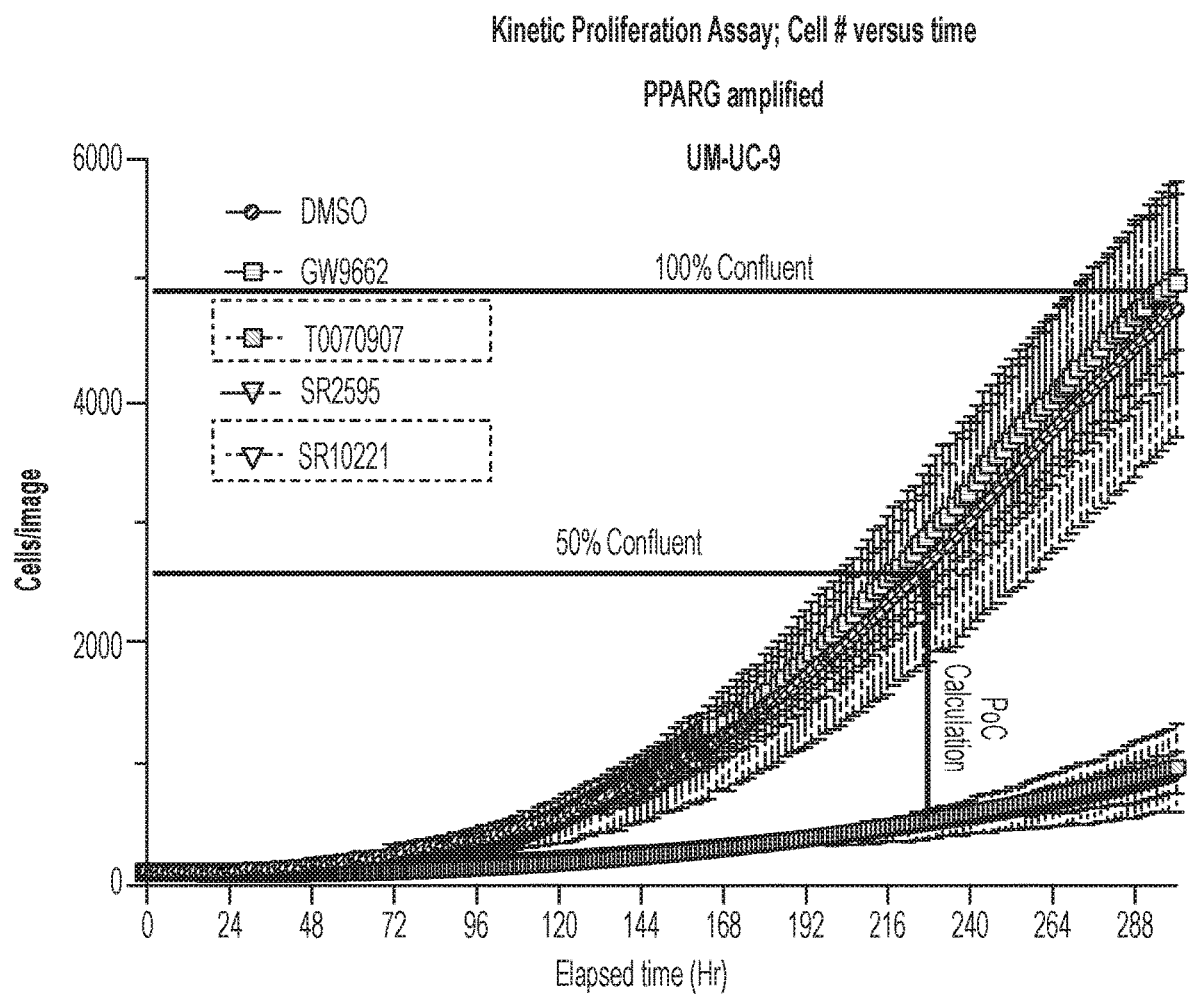
Figure 6C:
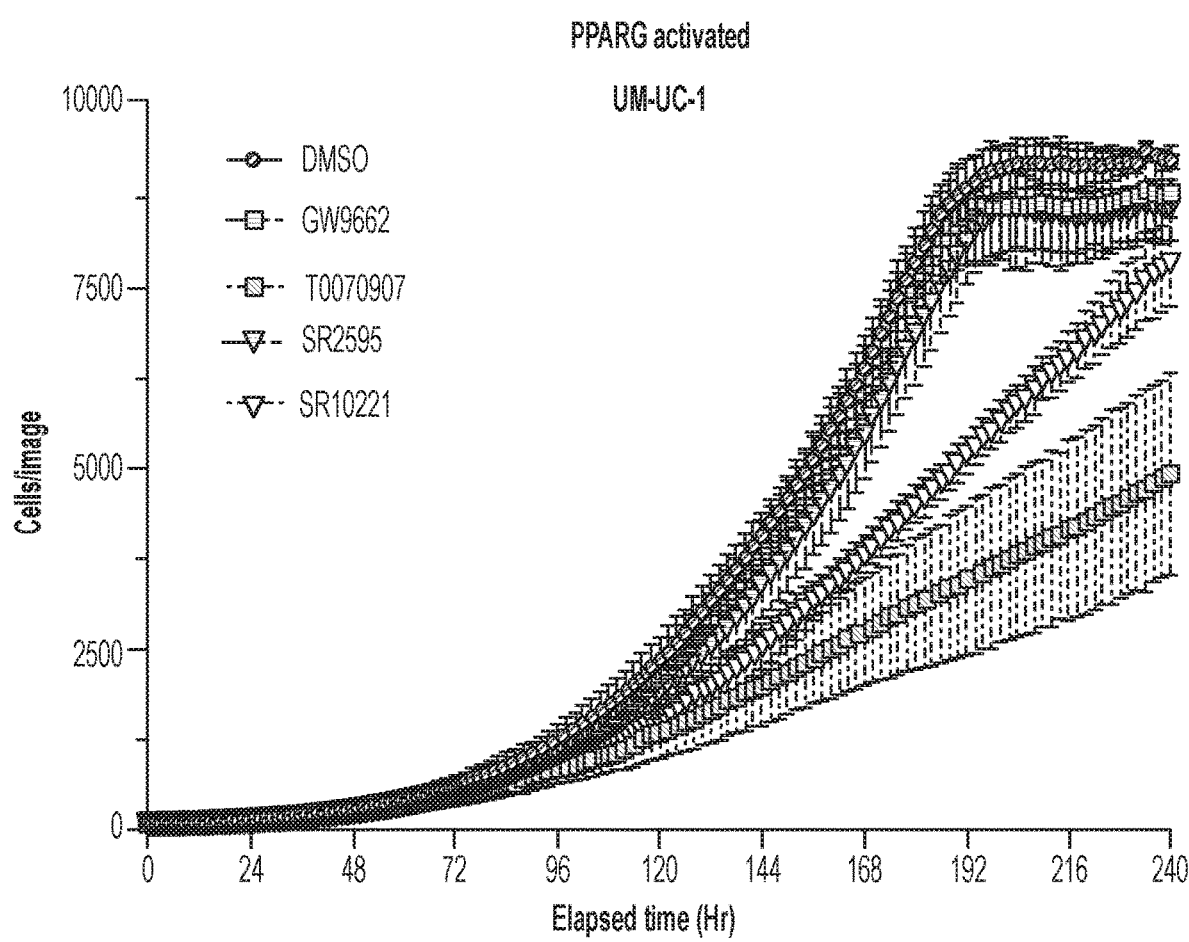
Figure 6D:
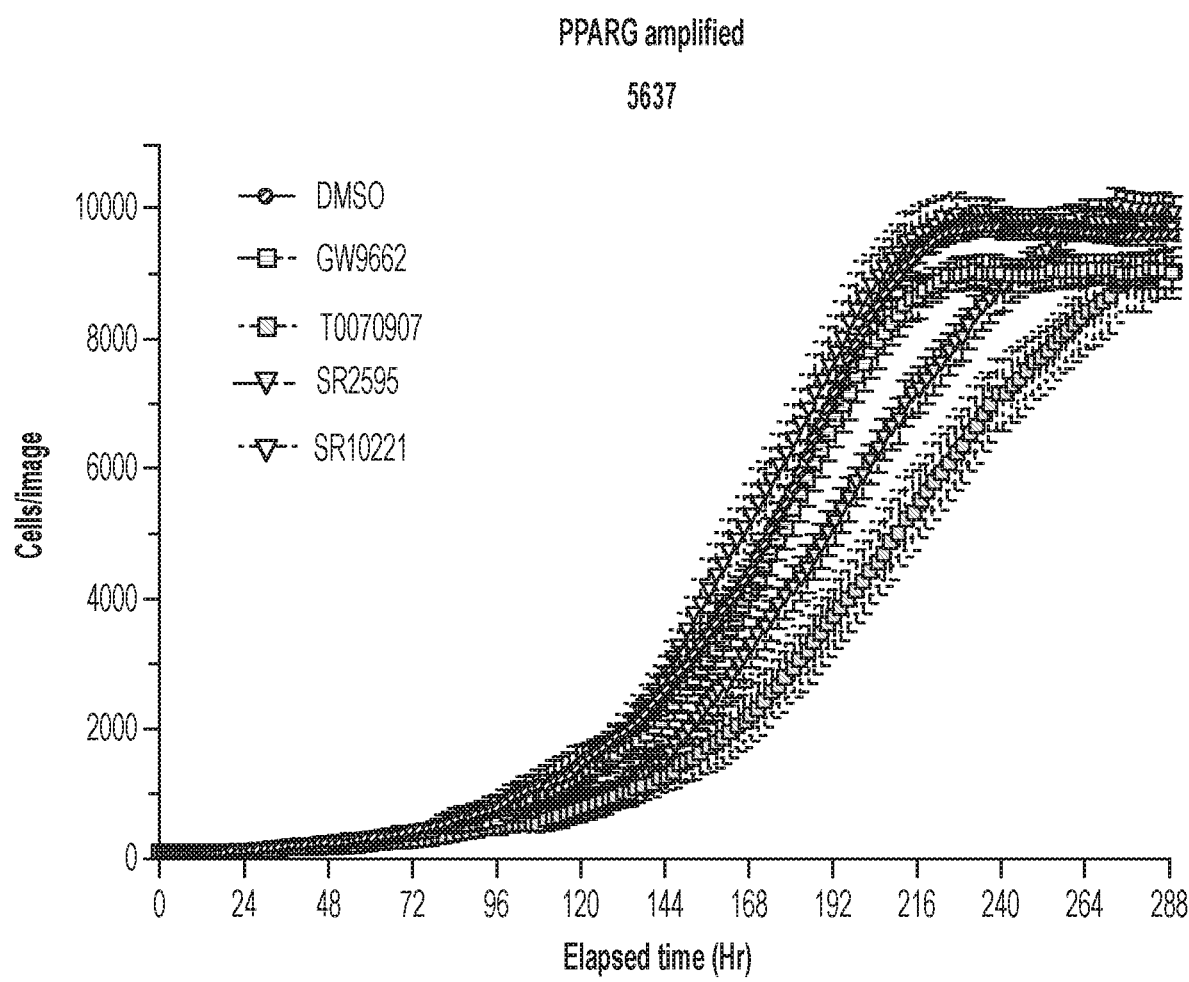
Figure 6E:
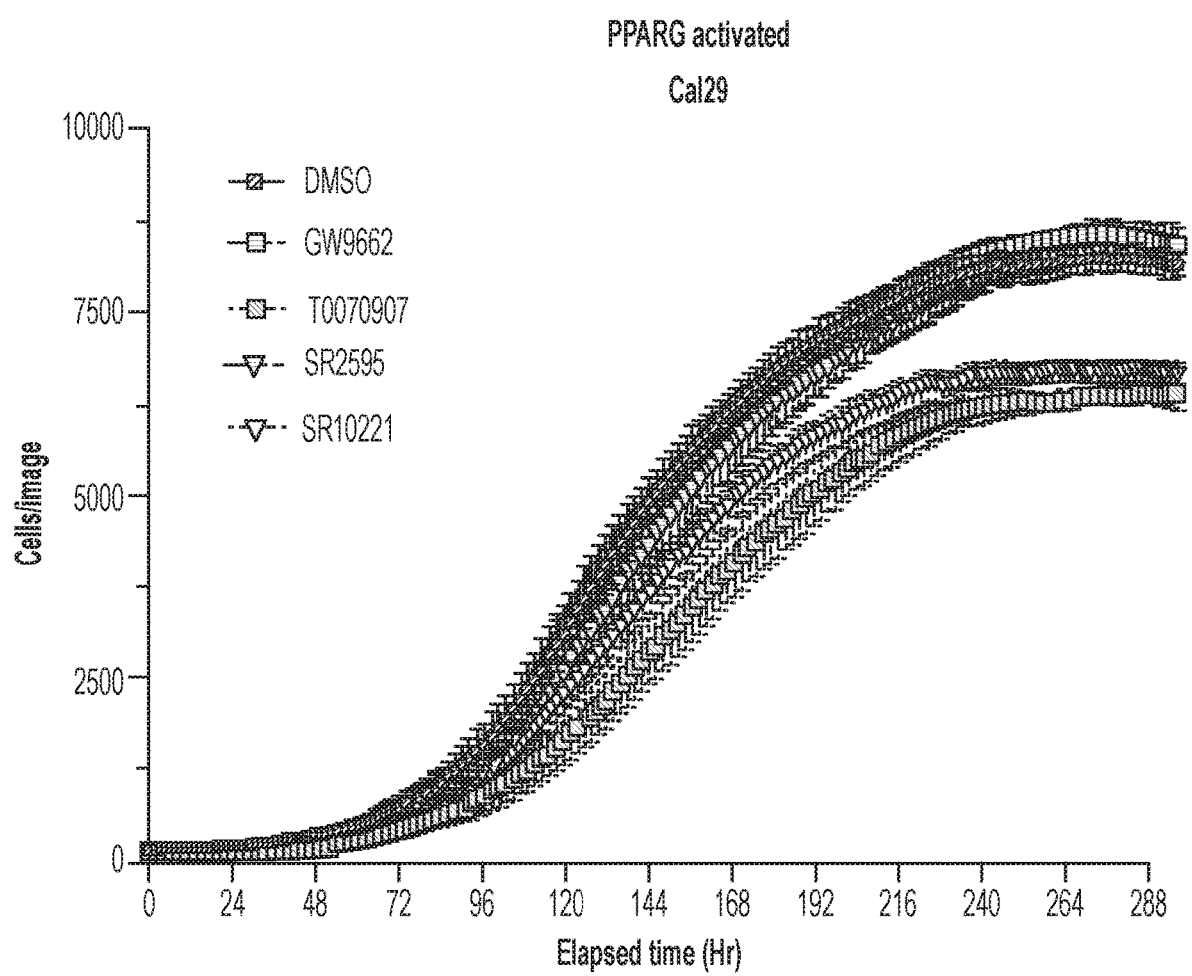
Figure 6F:
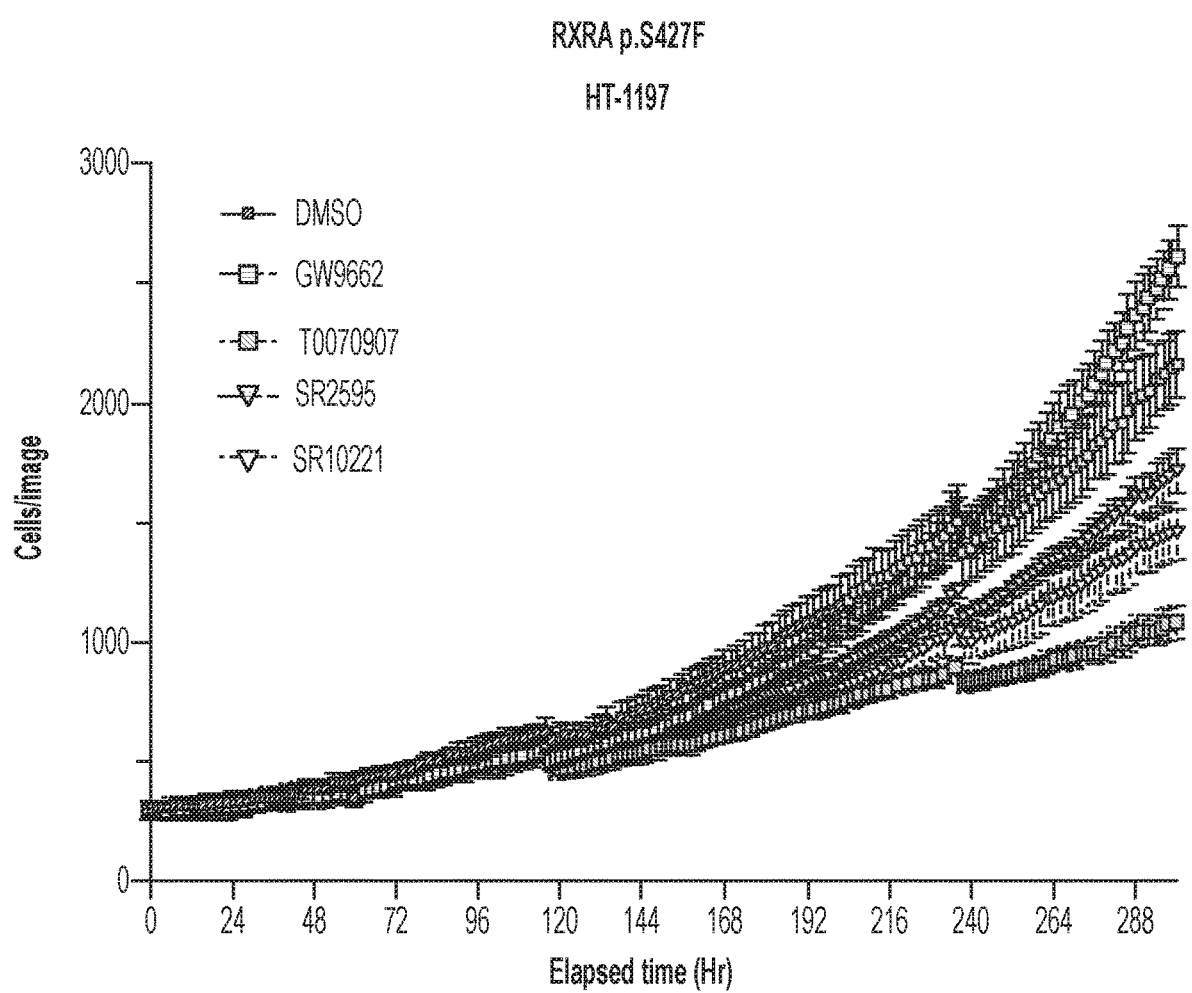
Figure 6G:
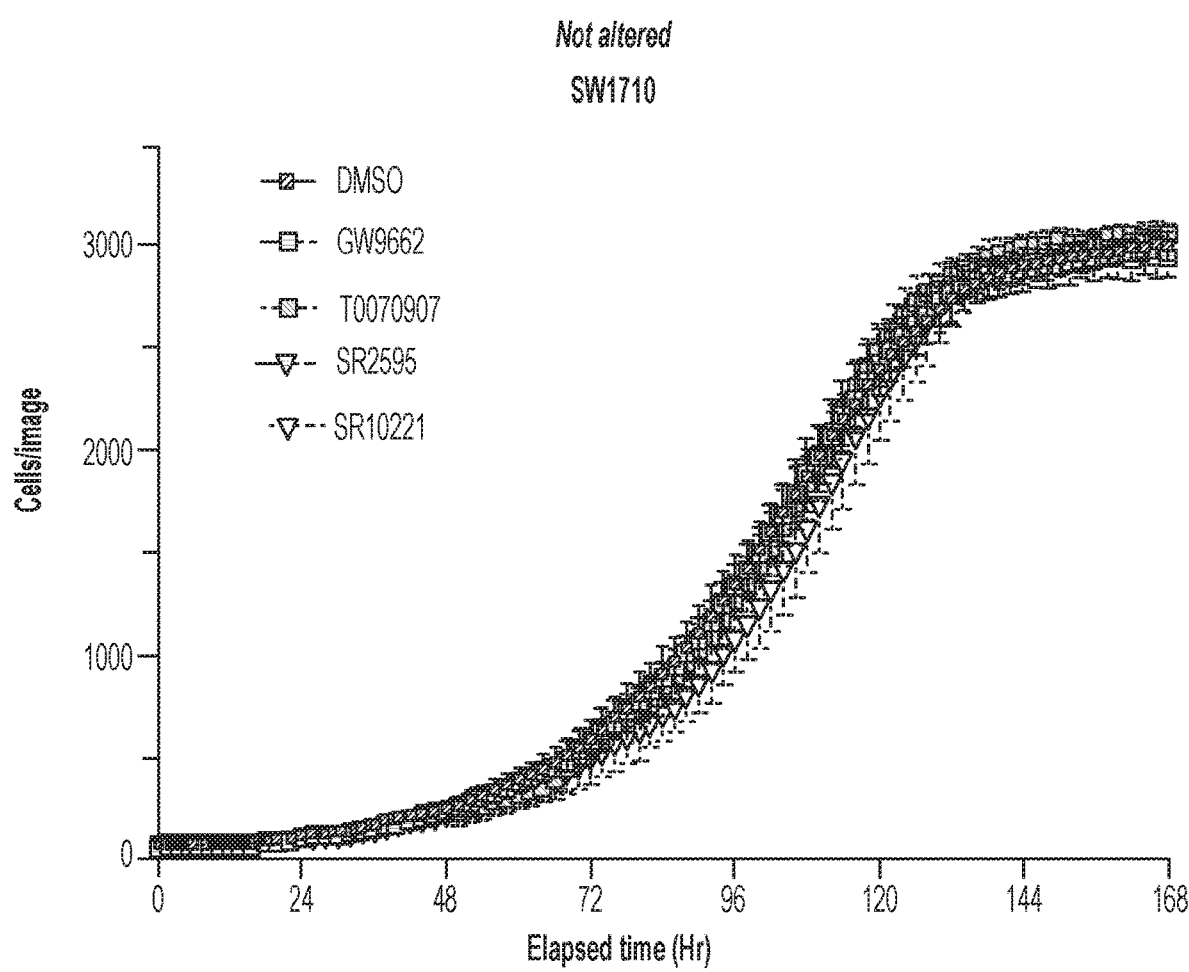
Figure 6H:
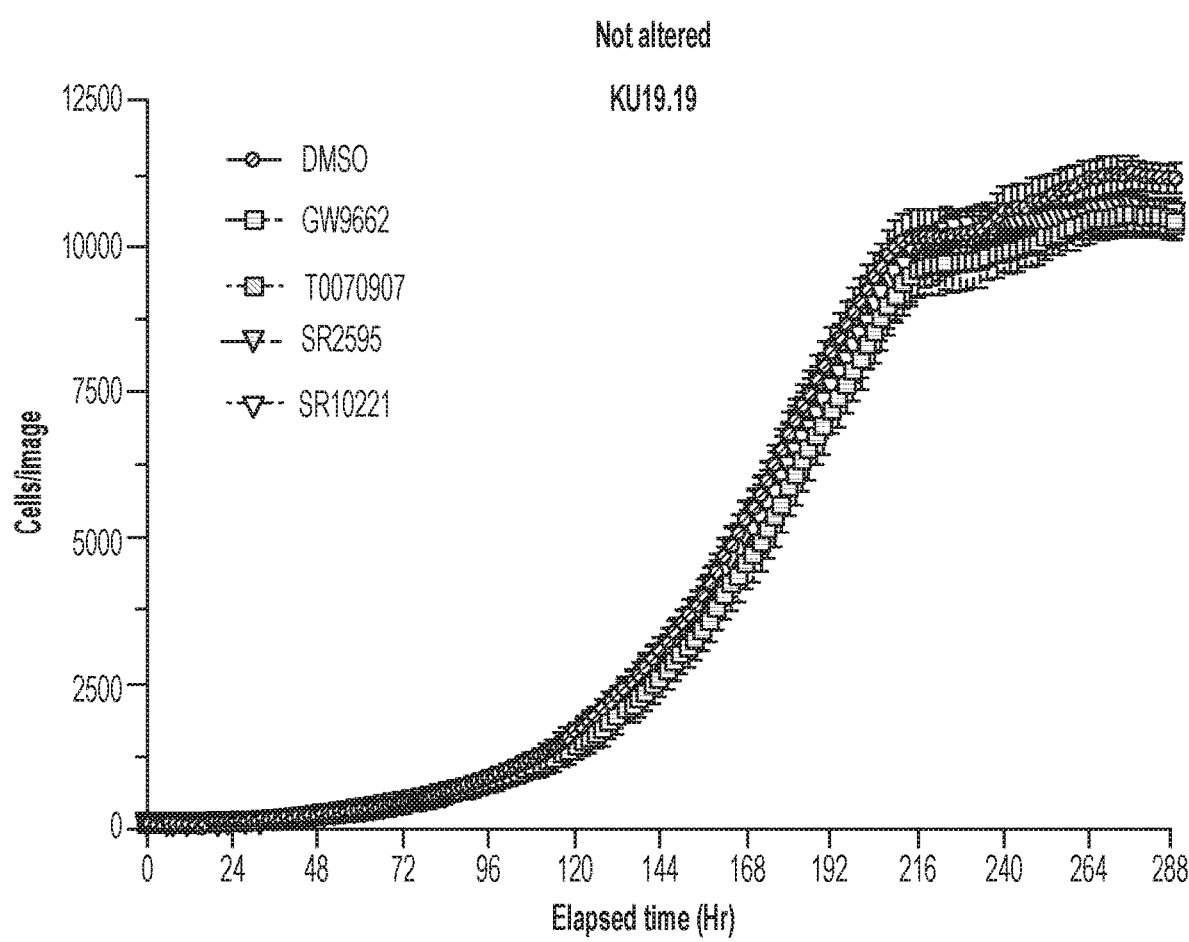
Figure 6I:
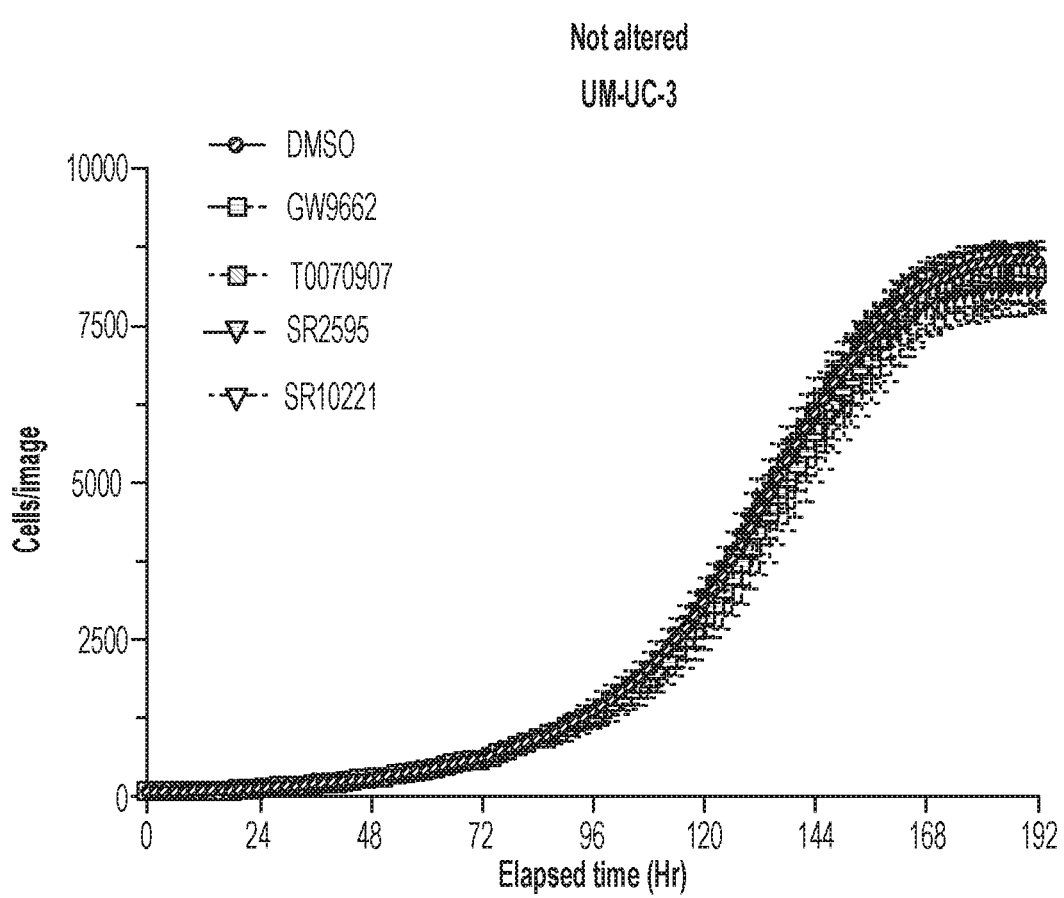
Figure 10:
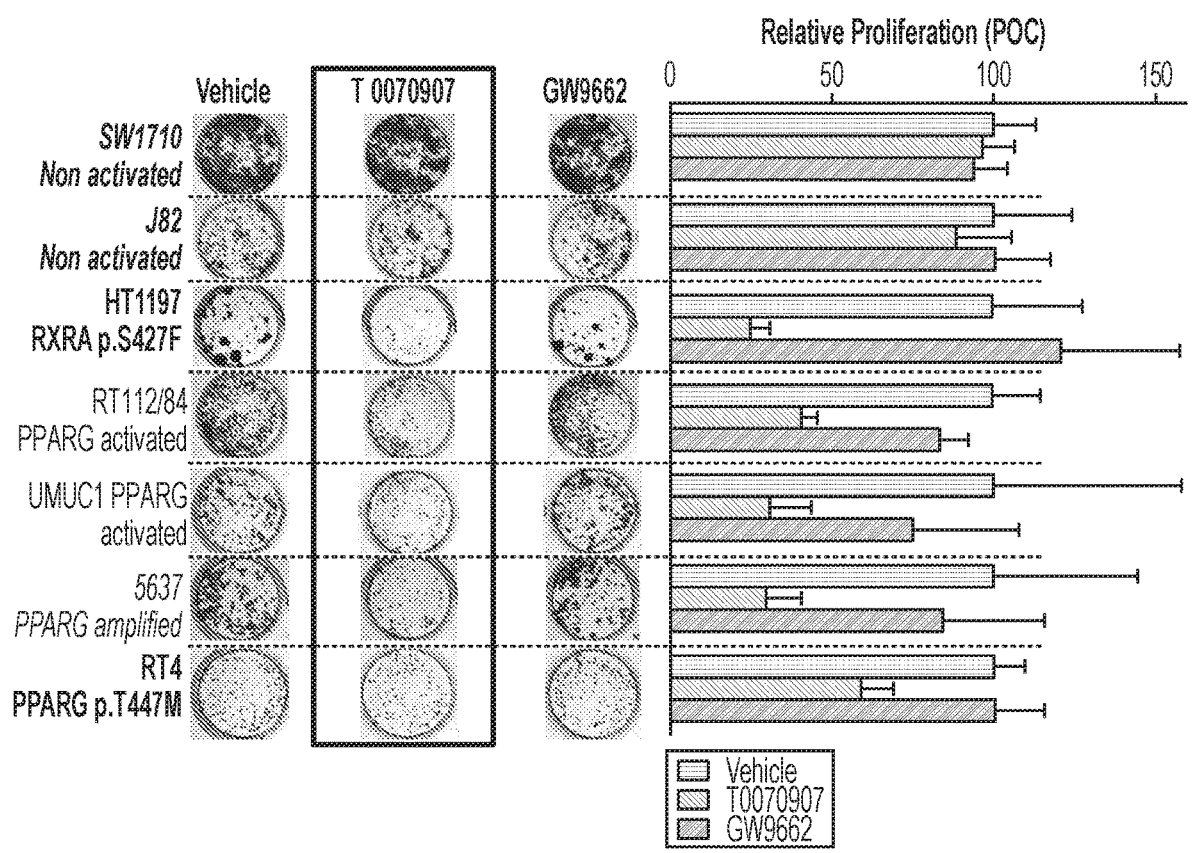
FIG. 10 shows that PPARG inverse-agonists inhibit proliferation of PPARG activated bladder cancer cell lines in clonogenic assays. Clonogenic growth assays of bladder cancer cell lines after treatment for 7-19 days with PPARG modulators (100 nM), as indicated, and DMSO as vehicle control. Clonogenic proliferation at the end of the experiment was evaluated by visualization of colonies by crystal violet staining (left), and quantitatively by UV absorption of crystal violet extracted from samples (right). Data are relative proliferation of test samples compared to vehicle as percent of control. Graph represents mean POC+/−SEM (n=3).

This assay was expanded to include an additional 8 representative bladder cancer cell lines, including cell lines with PPARG amplification, RXRA p.S427F mutation, activated gene signature, and control cell lines with low level expression of PPARG and target genes. As it was not always possible to accurately calculate an IC50 value, an alternative quantitative endpoint assay was used, which measures the relative number of cells in the DMSO vehicle control compared with treatment with 100 nmol/L of each compound with analysis performed at the time required for the cells to reach 50% confluency in the DMSO control. Representative data for the UM-UC-9 cell line are shown in FIG. 6B, and is tabulated for the tested bladder cancer cell lines in Table 1. Similar to the full dose-response assay (FIG. 6A), the T0070907 and SR10221 inverse-agonists reduce proliferation by 81% and 80% relative to control, whereas the GW9662 and SR2595 antagonists have no effect. This significant (P<0.01) preferential sensitivity to PPARG inverse-agonists, but not antagonists, is maintained across all of the PPARG-activated cell lines in the panel, including the RXRA p.S427F cell line, HT-1197 (41), the PPARG-amplified cell lines, 5637 and UM-UC-9, and the PPARG activation gene signature cell lines Cal29, UM-UC-1, and RT112/84 (FIG. 12). The SW1710, UM-UC-3, and KU19.19 cells lines that did not exhibit high expression of PPARG or target genes (FIG. 2F) were insensitive to PPARG inverse-agonists and antagonists (FIG. 12). Similar results were obtained with these cell lines in parallel studies using clonogenic assays to quantify colony-forming ability (FIG. 10). These data reveal that proliferation of the PPARG-activated subset of bladder cancer cell lines, but not control bladder cancer cell lines, is dependent on PPARG activity, and inhibition of this activity with the inverse-agonists, T0070907 or SR10221, results in decreased proliferative potential.

Example 14: PPARG-Activated Cell Lines are Genetically Dependent on PPARG

To test for PPARG dependency in PPARG-activated cell lines with an orthogonal approach, CRISPR/Cas9 knockout studies were performed using a high-precision multicolor competition dependency assay (Strathdee and colleagues, manuscript in preparation). Briefly, it was first validated that guide RNAs against PPARG were able to significantly diminish PPARG expression by Western immunoblot after normalization to loading control vinculin, VCL (FIG. 3A). Next, the relative effect of knockout of PPARG on cell proliferation was compared to knockout of an essential gene (KIF11) and to knockout of a nonessential gene (HPRT or PPIB) or PPARG intron control. The sgRNAs targeting these genes were cloned into lentiviral vectors that coexpress one of three different fluorescent proteins, YFP, RFP, or CFP, and which allowed for unambiguous identification of transduced cells in complex pools: PPARG knockout cells were labeled with YFP, essential control knockout cells were labeled with RFP, and nonessential (or PPARG intron) control knockout cells were labeled with CFP. In the competition format, replicate pools of cells are generated at the beginning of the experiment in which each gene knockout/color are at equivalent abundance. Changes in relative abundance of each population are monitored during progressive serial passage by counting fluorescent nuclei using high-content imaging. Relative changes are plotted as percent of control of the normalized prevalence of on-test sgRNAs as a percent of nonessential sgRNA control targeting an intron of PPARG.

Analysis of three bladder cancer cell lines showed a clear PPARG dependency in PPARG-activated cells. The growth of the SW1710 cell line, which shows low PPARG/FABP4 expression (FIG. 2F), is insensitive to PPARG knockout (FIG. 3D). In contrast, HT-1197 the only known cell line with an RXRA p.S427F mutation (15), exhibited a strong PPARG dependency in this CRISPR competition assay (FIG. 3B). The Cal29 cell line, with a highly activated PPARG signaling pathway (FIG. 2), also exhibits clear PPARG dependency (FIG. 3C). In preliminary experiments it was determined that the RT4 cell line supported inadequate hCas9 expression for use in gene knockout experiments, which is unfortunate since it is the only cell line available with a PPARG p.T447M mutation. Note that cell lines containing PPARG focal amplifications were not included to avoid the well-known copy number sensitivity artifact inherent to the CRISPR/Cas9 platform (60, 61). Based on the foregoing, it was concluded that PPARG-activated bladder cancer cell lines are dependent upon a functional PPARG.

Figure 15:
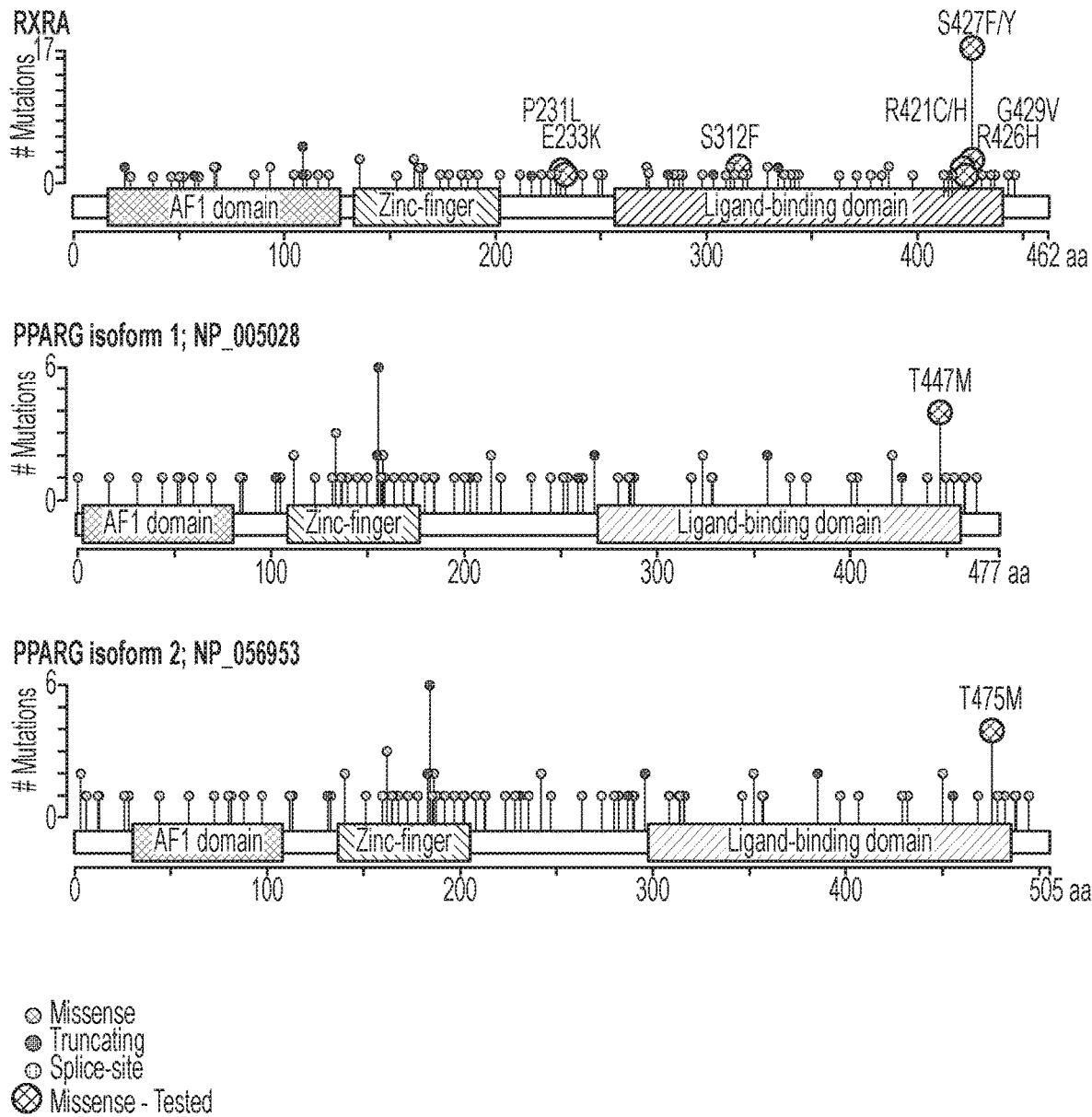
FIG. 15 is a diagram showing somatic alterations in RXRA and PPARG. Pan-cancer genomics analysis of all non-provisional studies in cBioportal accessed on Jul. 19, 2017, displaying mutations in lollipop plot format to indicate the number of samples with each indicated alteration. Multiple isoforms of PPARG result from different translational start sites. PPARG isoform 2, NP_056953, is the more common reference sequence used, however this isoform is preferentially expressed in adipocytes. PPARG isoform 1, NP_005028, is the dominant isoform in other tissues, including bladder. Numbering for both PPARG isoforms is shown. RXRA and PPARG mutant alleles tested herein are indicated by an enlarged green circle with outline.

Recently, genomic analysis of bladder cancer revealed that the PPARG signaling pathway is significantly activated in tumors, and that this can be driven by either RXRA p.S427F/Y mutations or PPARG focal amplifications (2, 44). As disclosed herein, it has been confirmed that these alterations, in addition to PPARG p.T447M mutation, which may be emerging as a new hotspot (FIG. 15), activate the PPARG signaling pathway, and that cell lines with the corresponding mutations are genetically dependent on PPARG and are also sensitive to pharmacologic inactivation using PPARG inverse-agonists.

One model to explain this data is that these alterations confer ligand-independent activation of PPARG. In the case of RXRA p.S427F/Y and PPARG p.T447M mutations this could be achieved by the gain of hydrophobic interactions that lock PPARG helix 12 into the active conformation, phenocopying the agonist induced state in the absence of ligand. Cocrystal structures of RXRA/PPARG (e.g., PDB ID: 1FM6 and PDB ID: 5JI0; refs. 44, 18) show that the S427 position of RXRA is located in the dimerization interface with PPARG in the ligand-activated state, directly adjacent to both the T447 residue and c-terminus Y477 residue of PPARG. This positioning is also conserved in homology models of RXRA/PPARA (27). RXRA p.S427F/Y mutations may also disrupt interactions between RXRA and its other heterodimer partners (e.g., RARA, VDR, and TR), further shifting equilibrium of RXRA further toward PPARs (15).

It has been established that other mechanisms can lead to ligand independent activation of PPARG. For example, signaling by insulin through the actions of MAP kinases leads to phosphorylation of PPARG in the AF-1 domain, which can lead to ligand independent activation (62). Insulin-dependent PPARG activation is not sensitive to inhibition by the PPARG antagonist GW9662, whereas ligand-driven activation by PPARG agonist, cigitazone, is sensitive to GW9662 (63). As disclosed herein, PPARG-activated bladder cancer cells, through PPARG amplification, RXRA p. S427F mutation, or other unknown mechanisms, are similarly not responsive to antagonists, including GW9662 and SR2595, but are sensitive to inverse-agonists. Because PPARG inverse-agonists induce a conformational change in the ligand-binding domain to actively recruit corepressors to the complex, these could overcome ligand-independent signaling, as shown herein.

The impact of PPARG on bladder cancer signaling is supported by the evidence that PPARA/PPARG dual agonists cause bladder cancer in rodents, although there are conflicting epidemiological data that PPARA/PPARG agonists are associated with increased rates of disease in humans (8, 9, 11, 12, 47).

PPARG as a therapeutic target in bladder cancer can be seen as analogous to targeting androgen receptor in prostate cancer or estrogen receptor in breast cancer. One of the hallmarks of luminal cancers is the expression of a ligand-activated nuclear receptor. Therapeutic targeting of the nuclear receptors in patients with these cancers can be a very effective therapeutic approach as in the example of targeting ESR1-positive luminal breast cancer with anti-estrogens and AR-positive prostate cancer with androgen deprivation therapy. PPARG agonists upregulate expression of luminal differentiation markers UPK1A, UPK1B, and KRT20 in primary rat urothelial cells (25). These same genes, plus GATA3, and FOXA1 are the key luminal markers of bladder cancer from human patients (22, 26) and bladder cancer cell lines (45). The lineage-defining role of GATA3, FOXA1, and PPARG in luminal bladder cancer is reminiscent of luminal breast cancer, in which coordinated expression of GATA3, FOXA1, and ESR1 enable chromatin remodeling and regulate luminal gene expression programs (24, 64); whereas in prostate cancer, FOXA1 and GATA2 (65) coordinately regulate the activity AR (53) and distribution and selectivity for AR response elements.

The steroid hormone receptors ESR1 and AR are also in the nuclear receptor superfamily; however, distinct from PPARG, they utilize high-affinity ligands for signaling. Endogenous production of estrogen in breast tissue, and testosterone/dihyrotestosterone in the testes, are required for receptor activation. Therefore, in the context of ligand-activation, antagonists of ESR1 and AR are effective therapies for primary cancers. Another effective strategy in breast and prostate cancer are therapies leading to inhibition of ligand production, such as the use of aromatase inhibitors for treatment of breast cancer and androgen deprivation therapy for prostate cancer. In contrast, PPARG does not have a high-affinity endogenous ligand and is considered a lipid sensor, with low affinity for its ligands (54). Therefore, mechanisms leading to ligand-independent activation of PPARG, and not ligand-dependent signaling, appear to be the primary driver of PPARG activity and will require different pharmacologic properties than in the case of targeting ligand-activated ESR1 or AR with a pure antagonist.

Patients treated with anti-estrogen and anti-androgen therapy commonly develop resistance, with common mechanisms being somatic alterations that lead to either ligand hypersensitivity or ligand-independent signaling. In the case of ESR1, recurrent mutations at Y537 lead to ligand-independent signaling (Robinson and colleagues, 2013) and due to being in the ligand-binding domain, also confer resistance to ESR1 antagonists. In the case of AR, gene amplification leads to ligand hypersensitivity, whereas point mutations and alternative splicing can lead to ligand-independent activation (68). To attenuate ligand-independent activation of ESR1, a new class of compounds was developed that lead to receptor degradation. Selective estrogen receptor degraders have had promising clinical outcomes, with fulvestrant reaching clinical approval and providing a new hope for ERP breast cancer patients refractory to selective estrogen receptor modulators and aromatase inhibitors. On the basis of the fact that there appears to be high level of ligand-independent PPARG signaling in bladder cancer, the efforts disclosed herein focused on validating inverse-agonists as a candidate therapeutic strategy. However, a selective PPARG destabilizer could be another promising therapeutic approach worth exploring.

The present studies have demonstrated a genetic and pharmacologic dependence on PPARG in PPARG-activated, luminal bladder cancer cell lines, and provide a well-defined patient population and clear therapeutic hypothesis. Because PPARG agonists rosiglitazone and pioglitazone are used for the treatment of diabetes by a mechanism of sensitizing cells to insulin, lowering blood glucose, and lowering lipid levels (69), one can predict that a PPARG inverse-agonist can have an opposing effect, eliciting symptoms of diabetes. Furthermore, patients with deleterious PPARG mutations have an increased risk for diabetes and can exhibit lipodystrophy and insulin resistance (70). Although there are concerns for on-mechanism complications for PPARG inverse-agonists as a potential therapy for bladder cancer, there is renewed hope that rigorous testing and a deep understanding of emerging PPARG biology and pharmacology (49) can overcome these hurdles through selective receptor modulation. Recent advances have highlighted a potential role for oncogenic activation of PPARG in bladder cancer to regulate inflammatory cytokines, thereby regulating immune cell infiltration and immunosurveillance (44). Further studies of PPARG in bladder cancer will help to evaluate whether PPARG inverse agonists can complement conventional and emerging therapies including other genomically defined therapeutic targets such as FGFR inhibitors, in addition to immune checkpoint blockade.

Methods and Materials:

Rosiglitazone, Pioglitazone, Tesaglitazar, GW9662, T0070907, and SR1664 were purchased from Tocris Bioscience (Minneapolis, MN). SR2595 and SR10221 were synthesized according to published methods (17). The UM-UC-9 cell line was purchased from Sigma-Aldrich (St. Louis, MO). The chemical structures of various molecules described herein are presented in FIG. 14. All other cell lines were obtained from the Cancer Cell Line Encyclopedia (Broad Institute, Cambridge MA). The PPARG C26H12, PPARG 81B8, and FABP4 D25B3 antibodies were obtained from Cell Signaling Technology (Beverly, MA). The ACSL5 ab57210 and HMCGS2 EPR8642 antibodies were obtained from Abcam (Cambridge, MA). The vinculin V9264 antibody was obtained from Sigma-Aldrich (St. Louis MO). All secondary antibodies were obtained from Li-Cor Biosciences (Lincoln, NE).

Cell lines: The UM-UC-9 cell line was purchased from Sigma-Aldrich. All other cell lines were obtained from the Cancer Cell Line Encyclopedia (Broad Institute, Cambridge, MA), which obtained them from the original source and performed cell line authentication (21). To reduce bias from cell culture medium, all cell lines were maintained in MEM-a medium supplemented with 10% Tetsystem approved FBS (Clontech).

Biochemical Assays: The LanthaScreen TR-FRET PPAR gamma Competitive Binding Assay and LanthaScreen TR-FRET PPAR gamma Coactivator Assay were obtained from ThermoFisher Scientific. Assays were performed according to the manufacturer's protocol. In order to assay inverse-agonism, the Coactivator assay was modified by the use of fluorescently labeled co-repressor peptides (NCoR1 ID2 peptide, SMRT ID2 peptide) to convert from agonist mode (coactivator recruitment) into inverse-agonist mode (corepressor recruitment).

Ectopic cDNA expression: Wild type ORFs for RXRA and PPARGv1 were obtained from the Genomics Perturbation Platform (Broad Institute, Cambridge MA) in pDONR Gateway cloning vectors. Various mutant alleles were generated using QuikChange Site-Directed Mutagenesis (Agilent, Santa Clara CA). ORFs were then subcloned into lentiviral expression vectors using Gateway LR Clonase and infectious lentiviral particles were generated using standard procedures.

SW780 bladder cancer cell lines was transduced with a lentiviral vector encoding the specified RXRA or PPARG ORFs under control of constitutive CMV or EF1α promoter, and stable pools were generated following selection for blasticidin-resistance. Cell lines were maintained for at least 7 days following selection prior to expansion for further analysis.

RNAseq analysis: RNA was isolated using RNEasy (Qiagen) and an RNAseq library was prepared using NEBNext Ultra Directional RNA Library Prep Kit for Illumina and NEBNext Multiplex Oligos for Illumina (New England BioLabs). RNAseq sequencing was performed using an Illumina MiSeq instrument according to the manufacturers protocol. Sequence data was analyzed using Firehose (Broad Institute, Cambridge MA) to map transcripts and calculate RPKM (SW780 cDNA expression) or TPM (UM-UC-9).

For UM-UC-9 RNAseq experiment, the resulting reads were used to calculate transcript abundance in units of TPM (transcripts per million) (18), which were then adjusted using TMM normalization (19) for comparison. Log fold-change and Mann-Whitney test significance was used to identify differentially expressed genes between the agonist and inverse-agonist-treated samples.

Proliferation Assays: To enable cell-counting experiments, cell lines were transduced with a lentiviral vector encoding nuclear-targeted GFP, TagGFP2-H2B (Evrogen), and stable pools generated following selection for puromycin resistance. Cell lines were maintained for at least 7 days following selection prior to expansion and seeding into 96- or 384-well plates for further analysis. For kinetic proliferation assays, 96-well plates (n 1% 4 per condition) were imaged and counted every two hours using IncuCyte Zoom (Essen BioScience). Media and compounds were replaced approximately every 3-4 days. For endpoint assays to measure dose-response, cells were plated in 384-well plates, dosed with compound, and upon reaching approximately 70% to 90% confluence in control wells, cells were either counted using fluorescence imaging (Incu-Cyte Zoom) or incubated with CyQuant (Thermo Fisher) at the indicated time and plates were read with a fluorescent plate reader.

CRISPR/Cas9 Genetic Dependency studies: Cell lines were first transduced with a lentiviral vector encoding hSpCas9 under control of a tetracycline-inducible CMV promoter (CMV-TO; Thermo Fisher Scientific) and stable pools generated following selection for blasticidin resistance. Following confirmation of regulated Cas9 expression by Western blot analysis, the cells were transduced with a lentiviral vector encoding a sgRNA under control of a tetracycline-inducible H1 promoter (H1-TO, Thermo Fisher Scientific) and double-stable pools were generated following selection for puromycin resistance. In addition to providing for regulated sgRNA expression, these lentiviral vectors also constitutively express one of three nuclear-targeted fluorescent proteins to enable unambiguous identification of transduced cells in subsequent cell counting experiments: YFP-expressing vectors were used for sgRNAs targeting PPARG; CFP-expressing vectors were used for sgRNAs targeting non-essential control genes, and RFP-expressing vectors were used for sgRNAs targeting essential control genes.

6-8 different sgRNAs per gene of interest were evaluated using Western blot analysis to identify 2-3 highly active, doxycycline inducible guides targeting PPARG (sgPPARG-3: GTCTTCTCAGAATAATAAGG (SEQ ID NO: 63), sgPPARG-6: GTTTCAGAAATGCCTTGCAG (SEQ ID NO: 64)) for use in these experiments. KIF 11 (sgKIF11-3: GGTGGTGGTGAGATGCAGGT (SEQ ID NO: 65)) was used as an essential control gene, and a sgRNA targeting PPARG intronic sequence (sgPPARG-21: GATACTGCTG-CATTAGACCAG (SEQ ID NO: 66)) was used as a nonessential controls.

Following generation of stable pools of for each sgRNA were combined in equivalent numbers within replicate wells of 6-well plate and doxycycline was added to one of the replicates to induce Cas9 and sgRNA. Cells were passaged every 3-5 days and one replicate maintained under doxycycline induction, with second replicate maintained in the absence of doxycycline. During each passage, four replicate wells were passaged into 96-well plates for fluorescent imaging and fixed with methanol for imaging 1-3 days after passage into 96-well plates. Changes in relative abundance of cells containing the on-test sgRNA, nonessential sgRNA, and essential sgRNA were thus followed by comparing relative abundance of cells based on fluorescent label (yellow, cyan, red) through serial passages for a period of 28 days. Cells with stably transduced TREx-inducible vectors were all maintained continuously in MEMa medium containing 10% Tet-system approved FBS (Clontech).

Western Blot Analysis: Western blots were performed using standard protocols with semi-dry transfer Trans-Blot® SD (Bio-Rad Hercules, CA), Li-Cor Odyssey Blocking buffer, and imaging with LiCor Odyssey Imaging System (LI-COR Lincoln, NE). Briefly, cells were grown in 6-well plates and harvested using Complete Lysis-M with protease and phosphatase inhibitors (Roche *Applied Science*). Western blot analyses were performed using standard protocols with semi-dry transfer Trans-Blot SD (Bio-Rad), LI-COR Odyssey Blocking buffer, and imaging with LI-COR Odyssey Imaging System (LI-COR). The anti-PPARG C26H12, anti-PPARG 81B8, anti-FABP4 D25B3, and anti-CEACAM5 CB30 antibodies were obtained from Cell Signaling Technology. The anti-ACSL5 ab57210 and anti-HMCGS2 EPR8642 antibodies were obtained from Abcam. The anti-VCL (vinculin) V9264 antibody was obtained from Sigma-Aldrich. All primary antibodies were tested at 1:1, 000 dilutions, with the exception of anti-VCL, which was tested at a 1:5,000 dilution. Secondary goat anti-mouse 926-68020, and goat-anti-rabbit 926-32211 antibodies were obtained from LI-COR Biosciences and used at 1:15,000 dilutions.

RT112-FABP4-NLucP Reporter Gene Assay: Reporter cell line was generated by engineering NanoLuc gene into the 3' UTR of FABP4 in RT112/84 cells using CRISPR/Cas9 guided genome engineering. Single cell clones were generated and the clone with the widest dynamic range selected for use. Assays were performed by seeding 384-well plates with ~10,000 cells per well in MEMalpha containing 10% FBS and dosing compounds at indicated concentration using HP D300 digital dispenser (HP/Tecan). 18-24 hours after dosing with compound, cells were assayed using NanoGlo Luciferase Assay Reagent (Promega Madison, WI) and plates were read using EnVision Multilabel Reader (PerkinElmer Waltham, MA).

Data availability: Bladder cancer incidence and survival data were obtained from Howlader and colleagues (2015) *SEER data submission, posted to the SEER web site, April 2016. SEER Cancer Statistics Review*, 1975 to 2013. National Cancer Institute on the World Wide Web at (www) seer.cancer.gov/csr/1975_2013/. The provisional TCGA muscle-invasive urothelial carcinoma data are available from the Broad Institute TCGA Genome Data Analysis Center. Analysis-ready standardized TCGA data from Broad GDAC Firehose 2016_01_28 run. on the World Wide Web at (www)doi.org/10.7908/C1 1GOKM9. CCLE Affymetrix U133b2 arrays mRNA expression data is available on the World Wide Web at (www)portals.broadinstitute.org/ccle/ (21). RNA sequencing data are available through the National Center for Biotechnology Information BioProject accession no. PRJNA396067.

REFERENCES

1. Howlader N N A, Krapcho M, Miller D, Bishop K, Altekruse S F, Kosary C L, Yu M, Ruhl J, Tatalovich Z, Mariotto A, Lewis D R, Chen H S, Feuer E J, Cronin K A (eds). (*SEER Cancer Statistics Review*, 1975-2013. (National Cancer Institute, Bethesda, MD).
2. Cancer Genome Atlas Research N (2014) Comprehensive molecular characterization of urothelial bladder carcinoma. *Nature* 507(7492):315-322.
3. Guo G, et al. (2013) *Whole-genome and whole-exome sequencing of bladder cancer identifies frequent alterations in genes involved in sister chromatid cohesion and segregation*. Nature Genetics 45(12):1459-1463.
4. Evans Ronald M & Mangelsdorf David J (2014) Nuclear Receptors, *RXR, and the Big Bang. Cell* 157(1):255-266.
5. El Hage J (2005) Toxicity Profiles of Peroxisome Proliferator-Activated Receptor (PPAR) Agonists and Preclinical Safety Profile for Muraglitazar. FDA Report CDER.
6. Tannehill-Gregg S H, et al. (2007) Rodent Carcinogenicity Profile of the Antidiabetic Dual PPAR and Agonist Muraglitazar. *Toxicological Sciences* 98(1):258-270.
7. Waites C R, Dominick M A, Sanderson T P, & Schilling BE (2007) Nonclinical Safety Evaluation of Muraglitazar, a Novel PPAR/Agonist. *Toxicological Sciences* 100(1): 248-258.
8. Tuccori M, et al. (2016) Pioglitazone use and risk of bladder cancer: population based cohort study. Bmj i1541.
9. Lewis JD, et al. (2015) Pioglitazone Use and Risk of Bladder Cancer and Other Common Cancers in Persons With Diabetes. *Jama* 314(3):265.
10. Mamtani R, et al. (2012) *Association Between Longer Therapy With Thiazolidinediones and Risk of Bladder Cancer: A Cohort Study. JNCIJournal of the National Cancer Institute* 104(18):1411-1421.
11. Tseng C-H (2012) *Pioglitazone and bladder cancer in human studies: Is it diabetes itself, diabetes drugs, flawed analyses or different ethnicities? Journal of the Formosan Medical Association* 111(3):123-131.
12. Turner R M, et al. (2014) Thiazolidinediones and associated risk of bladder cancer: a systematic review and meta-analysis. *British Journal of Clinical Pharmacology* 78(2):258-273.
13. Aoki T (2007) Current Status of Carcinogenicity Assessment of Peroxisome Proliferator-Activated Receptor Agonists by the US FDA and a Mode-of-Action Approach to the Carcinogenic Potential. Journal of Toxicologic Pathology 20(4):197-202.
14. Commons G D (2016) Genomic Data Commons Data Portal.
15. Forbes S A, et al. (2015) COSMIC: exploring the world's knowledge of somatic mutations in human cancer. *Nucleic Acids Res* 43(Database issue):D805-811.
16. Bray N L, Pimentel H, Melsted P, & Pachter L (2016) Near-optimal probabilistic RNA-seq quantification. *Nature Biotechnology* 34(5):525-527.
17. Lawrence M S, et al. (2014) Discovery and saturation analysis of cancer genes across 21 tumour types. *Nature* 505(7484):495-501.
18. Gampe R T, Jr., et al. (2000) Asymmetry in the PPAR-gamma/RXRalpha crystal structure reveals the molecular basis of heterodimerization among nuclear receptors. *Mol Cell* 5(3):545-555.
19. Mootha V K, et al. (2003) PGC-1α-responsive genes involved in oxidative phosphorylation are coordinately downregulated in human diabetes. *Nature Genetics* 34(3): 267-273.
20. Subramanian A, et al. (2005) Gene set enrichment analysis: A knowledge-based approach for interpreting genome-wide expression profiles. *Proceedings of the National Academy of Sciences, USA* 102(43):15545-15550.
21. Barretina J, et al. (2012) The Cancer Cell Line Encyclopedia enables predictive modelling of anticancer drug sensitivity. *Nature* 483(7391):603-607.
22. Biton A, et al. (2014) Independent component analysis uncovers the landscape of the bladder tumor transcriptome and reveals insights into luminal and basal subtypes. *CellRep* 9(4):1235-1245.

23. Lee G, Elwood F, McNally J, Weiszmann J, Lindstrom M, Amaral K, Nakamura M, Miao S, Cao P, Learned R M, Chen J L, Li Y (2002) T0070907, a Selective Ligand for Peroxisome Proliferator-activated Receptor gamma, Functions as an Antagonist of Biochemical and Cellular Activities. *Journal of Biological Chemistry* 277(22): 19649-19657.

24. Eeckhoute J, et al. (2007) Positive Cross-Regulatory Loop Ties GATA-3 to Estrogen Receptor Expression in Breast Cancer. *Cancer Research* 67(13):6477-6483.

25. Varley C L & Southgate J (2008) Effects of PPAR agonists on proliferation and differentiation in human urothelium. *Experimental and Toxicologic Pathology* 60(6):435-441.

26. Choi W, et al. (2014) Identification of Distinct Basal and Luminal Subtypes of Muscle-Invasive Bladder Cancer with Different Sensitivities to Frontline Chemotherapy. *Cancer Cell* 25(2):152-165.

27. Venalainen T, Molnir F, Oostenbrink C, Carlberg C, & Perakyla M (2010) Molecular mechanism of allosteric communication in the human PPARα-RXRα heterodimer. Proteins: Structure, *Function, and Bioinformatics* 78(4):873-887.

28. Carracedo A, Cantley L C, & Pandolfi P P (2013) Cancer metabolism: fatty acid oxidation in the limelight. *Nature Reviews Cancer* 13(4):227-232.

29. Carracedo A, et al. (2012) A metabolic prosurvival role for PML in breast cancer. *Journal of Clinical Investigation* 122(9):3088-3100.

30. Caro P, et al. (2012) Metabolic Signatures Uncover Distinct Targets in Molecular Subsets of Diffuse Large B Cell Lymphoma. *Cancer Cell* 22(4):547-560.

31. Hoque MO, et al. (2014) Bladder Cancer Biomarker Discovery Using Global Metabolomic Profiling of Urine. *PLoS ONE* 9(12):e115870.

32. Banks AS, et al. (2014) *An ERK/Cdk5 axis controls the diabetogenic actions of PPARγ.* *Nature* 517(7534):391-395.

33. Choi JH, et al. (2010) Anti-diabetic drugs inhibit obesity-linked phosphorylation of PPARγ by Cdk5. *Nature* 466 (7305):451-456.

34. Marciano DP, et al. (2015) Pharmacological repression of PPARγ promotes osteogenesis. *Nature Communications* 6:7443.

35. Rosenberg JE, Hoffman-Censits J, Powles T, van der Heijden M S, Balar A V, Necchi A, et al. Atezolizumab in patients with locally advanced and metastatic urothelial carcinoma who have progressed following treatment with platinum-based chemotherapy: a single-arm, multicentre, phase 2 trial. *Lancet* 2016; 387:1909-20.

36. Sharma P, Retz M, Siefker-Radtke A, Baron A, Necchi A, Bedke J, et al. Nivolumab in metastatic urothelial carcinoma after platinum therapy (CheckMate 275): a multicentre, single-arm, phase 2 trial. *Lancet Oncol* 2017; 18:312-22.

37. Apolo A B, Infante J R, Balmanoukian A, Patel M R, Wang D, Kelly K, et al. Avelumab, an anti-programmed death-ligand 1 antibody, in patients with refractory metastatic urothelial carcinoma: results from a multicenter, phase Ib study. *J Clin Oncol* 2017;35: 2117-24.

38. Massard C, Gordon M S, Sharma S, Rafii S, Wainberg Z A, Luke J, et al. Safety and efficacy of durvalumab (MEDI4736), an anti-programmed cell death ligand-1 immune checkpoint inhibitor, in patients with advanced urothelial bladder cancer. *J Clin Oncol* 2016; 34:3119-25.

39. Iyer G, Hanrahan A J, Milowsky M I, Al-Ahmadie H, Scott S N, Janakiraman M, et al. Genome sequencing identifies a basis for everolimus sensitivity. *Science* 2012; 338:221.

40. Liu D, Plimack E R, Hoffman-Censits J, Garraway L A, Bellmunt J, Van Allen E, et al. Clinical validation of chemotherapy response biomarker ERCC2 in muscle-invasive urothelial bladder carcinoma. *JAMA* Oncol 2016; 2:1094.

41. Van Allen E M, Mouw K W, Kim P, Iyer G, Wagle N, Al-Ahmadie H, et al. *Somatic ERCC2 mutations correlate with cisplatin sensitivity in muscle invasive urothelial carcinoma.* Cancer Discov 2014; 4:1140-53.

42. Wagle N, Grabiner B C, Van Allen E M, Hodis E, Jacobus S, Supko J G, et al. Activating mTOR mutations in a patient with an extraordinary response on a phase I trial of everolimus and pazopanib. *Cancer Discov* 2014; 4:546-53.

43. Ahmadian M, Suh J M, Hah N, Liddle C, Atkins A R, Downes M, et al. PPARgamma signaling and metabolism: the good, the bad and the future. *Nat Med* 2013; 19:557-66.

44. KorpalM, Puyang X, Jeremy Wu Z, Seiler R, Furman C, OoHZ, et al. Evasion of immunosurveillance by genomic alterations of PPARg/RXRa in bladder cancer. *Nat Commun* 2017; 8:103. doi: 10.1038/s41467-017-00147-w.

45. Warrick JI, Walter V, Yamashita H, Chung E, Shuman L, Amponsa VO, et al. FOXA1, GATA3 and PPAR cooperate to drive luminal subtype in bladder cancer: a molecular analysis of established human cell lines. *Sci Rep* 2016; 6:38531.

46. Sakamoto J, Kimura H, Moriyama S, Odaka H, Momose Y, Sugiyama Y, et al. Activation of human peroxisome proliferator-activated receptor (PPAR) subtypes by pioglitazone. *Biochem Biophys Res Commun* 2000; 278:704-11.

47. Lubet R A, Fischer S M, Steele V E, Juliana M M, Desmond R, Grubbs C J. Rosiglitazone, a PPAR gamma agonist: potent promoter of hydroxybutyl(butyl)nitrosamine-induced urinary bladder cancers. *Int J Cancer* 2008; 123:2254-9.

48. Dominick M A, White M R, Sanderson T P, Van Vleet T, Cohen SM, Arnold LE, et al. Urothelial carcinogenesis in the urinary bladder of male rats treated with muraglitazar, a PPAR alpha/gamma agonist: Evidence for urolithiasis as the inciting event in the mode of action. *Toxicol Pathol* 2006; 34:903-20.

49. Marciano D P, Kuruvilla D S, Boregowda S V, Asteian A, Hughes T S, Garcia-Ordonez R, et al. Pharmacological repression of PPARgamma promotes osteogenesis. *Nat Commun* 2015; 6:7443.

50. Robinson MD, Oshlack A. A scaling normalization method for differential expression analysis of RNA-seq data. *Genome Biol* 2010;11:R25.

51. Gronemeyer H, Gustafsson J A, Laudet V. Principles for modulation of the nuclear receptor superfamily. *Nat Rev Drug Discov* 2004; 3:950-64.

52. Leesnitzer L M, Parks D J, Bledsoe R K, Cobb J E, Collins J L, Consler T G, et al. Functional consequences of cysteine modification in the ligand binding sites of peroxisome proliferator activated receptors by GW9662. Biochemistry 2002; 41:6640-50.

53. Brown K K, Henke BR, Blanchard S G, Cobb J E, Mook R, Kaldor I, et al. A novel N-aryl tyrosine activator of peroxisome proliferator-activated receptor-gamma reverses the diabetic phenotype of the Zucker diabetic fatty rat. *Diabetes* 1999; 48:1415-24.
54. Cesario R M, Klausing K, Razzaghi H, Crombie D, Rungta D, Heyman R A, et al. The rexinoid LG100754 is a novel RXR:PPARgamma agonist and decreases glucose levels in vivo. *Mol Endocrinol* 2001; 15:1360-9.
55. Cronet P, Petersen J F, Folmer R, Blomberg N, Sjoblom K, Karlsson U, et al. Structure of the PPARalpha and -gamma ligand binding domain in complex with AZ 242; ligand selectivity and agonist activation in the PPAR family. *Structure* 2001; 9:699-706.
56. Lehmann J M, Moore L B, Smith-Oliver T A, Wilkison W O, Willson T M, Kliewer S A. An antidiabetic thiazolidinedione is a high affinity ligand for peroxisome proliferator-activated receptor gamma (PPAR gamma). *J Biol Chem* 1995; 270:12953-6.
57. Rieusset J, Touri F, Michalik L, Escher P, Desvergne B, Niesor E, et al. A new selective peroxisome proliferator-activated receptor gamma antagonist with anti obesity and antidiabetic activity. *Mol Endocrinol* 2002; 16:2628-44.
58. Wright H M, Clish C B, Mikami T, Hauser S, Yanagi K, Hiramatsu R, et al. A synthetic antagonist for the peroxisome proliferator-activated receptor gamma inhibits adipocyte differentiation. *J Biol Chem* 2000; 275:1873-7.
59. Xu H E, Stanley T B, Montana V G, Lambert M H, Shearer B G, Cobb J E, et al. Structural basis for antagonist-mediated recruitment of nuclear co-repressors by PPARalpha. *Nature* 2002; 415:813-7.
60. Aguirre A J, Meyers R M, Weir B A, Vazquez F, Zhang C Z, Ben-David U, et al. Genomic copy number dictates a gene-independent cell response to CRISPR/Cas9 targeting. *Cancer Discov* 2016; 6:914-29.
61. Munoz D M, Cassiani P J, Li L, Billy E, Korn J M, Jones M D, et al. CRISPR screens provide a comprehensive assessment of cancer vulnerabilities but generate false-positive hits for highly amplified genomic regions. *Cancer Discov* 2016; 6:900-13.
62. Zhang B, Berger J, Zhou G, Elbrecht A, Biswas S, White-Carrington S, et al. Insulin- and mitogen-activated protein kinase-mediated phosphorylation and activation of peroxisome proliferator-activated receptor gamma. *J Biol Chem* 1996; 271:31771-4.
63. Al-Rasheed N M, Chana R S, Baines R J, Willars G B, Brunskill N J. Ligand independent activation of peroxisome proliferator-activated receptor-gamma by insulin and C-peptide in kidney proximal tubular cells: dependent on phosphatidylinositol 3-kinase activity. *J Biol Chem* 2004; 279:49747-54.
64. Theodorou V, Stark R, Menon S, Carroll J S. GATA3 acts upstream of FOXA1 in mediating ESR1 binding by shaping enhancer accessibility. *Genome Res* 2013; 23:12-22.
65. Zhao J C, Fong K W, Jin H J, Yang Y A, Kim J, Yu J. FOXA1 acts upstream of GATA2 and AR in hormonal regulation of gene expression. *Oncogene* 2016; 35:4335-44.
66. Jin H J, Zhao J C, Wu L, Kim J, Yu J. Cooperativity and equilibrium with FOXA1 define the androgen receptor transcriptional program. *Nat Commun* 2014; 5:3972.
67. Poulsen L, Siersbaek M, Mandrup S. PPARs: fatty acid sensors controlling metabolism. *Semin Cell Dev Biol* 2012; 23:631-9.
68. Chandrasekar T, Yang J C, Gao A C, Evans C P. Mechanisms of resistance in castration-resistant prostate cancer (CRPC). *Transl Androl Urol* 2015; 4:365-80.
69. Saltiel A R, Olefsky J M. Thiazolidinediones in the treatment of insulin resistance and type II diabetes. *Diabetes* 1996; 45:1661-9.
70. Semple R K, Chatterjee V K, O'Rahilly S. PPAR gamma and human metabolic disease. *J Clin Invest* 2006; 116: 581-9.

EQUIVALENTS

Those skilled in the art will recognize, or be able to ascertain using no more than routine experimentation, many equivalents to the specific embodiments of the disclosure described herein. Such equivalents are intended to be encompassed by the following claims.

SEQUENCE LISTING

```
<160> NUMBER OF SEQ ID NOS: 66

<210> SEQ ID NO 1
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: a, c, t, g, unknown or other

<400> SEQUENCE: 1
aggtcanagg tca                                                        13

<210> SEQ ID NO 2
<211> LENGTH: 1892
<212> TYPE: DNA
<213> ORGANISM: Homo sapiens

<400> SEQUENCE: 2
ggcgcccgcg cccgccccg cgccgggccc ggctcggccc gacccggctc cgccgcgggc     60
```

| | |
|---|---|
| aggcggggcc cagcgcactc ggagcccgag cccgagccgc agccgccgcc tggggcgctt | 120 |
| gggtcggcct cgaggacacc ggagaggggc gccacgccgc cgtggccgca gatttgaaag | 180 |
| aagccaacac taaaccacaa atatacaaca aggccatttt ctcaaacgag agtcagcctt | 240 |
| taacgaaatg accatggttg acacagagat gccattctgg cccaccaact ttgggatcag | 300 |
| ctccgtggat ctctccgtaa tggaagacca ctcccactcc tttgatatca agcccttcac | 360 |
| tactgttgac ttctccagca tttctactcc acattacgaa gacattccat tcacaagaac | 420 |
| agatccagtg gttgcagatt acaagtatga cctgaaactt caagagtacc aaagtgcaat | 480 |
| caaagtggag cctgcatctc caccttatta ttctgagaag actcagctct acaataagcc | 540 |
| tcatgaagag ccttccaact ccctcatggc aattgaatgt cgtgtctgtg agataaagc | 600 |
| ttctggattt cactatggag ttcatgcttg tgaaggatgc aagggtttct tccggagaac | 660 |
| aatcagattg aagcttatct atgacagatg tgatcttaac tgtcggatcc acaaaaaaag | 720 |
| tagaaataaa tgtcagtact gtcggtttca gaaatgcctt gcagtgggga tgtctcataa | 780 |
| tgccatcagg tttgggcgga tgccacaggc cgagaaggag aagctgttgg cggagatctc | 840 |
| cagtgatatc gaccagctga atccagagtc cgctgacctc cgggccctgg caaaacattt | 900 |
| gtatgactca tacataaagt ccttcccgct gaccaaagca aaggcgaggg cgatcttgac | 960 |
| aggaaagaca acagacaaat caccattcgt tatctatgac atgaattcct taatgatggg | 1020 |
| agaagataaa atcaagttca aacacatcac ccccctgcag gagcagagca agaggtggc | 1080 |
| catccgcatc tttcagggct gccagtttcg ctccgtggag gctgtgcagg agatcacaga | 1140 |
| gtatgccaaa agcattcctg gttttgtaaa tcttgacttg aacgaccaag taactctcct | 1200 |
| caaatatgga gtccacgaga tcatttacac aatgctggcc tccttgatga ataaagatgg | 1260 |
| ggttctcata tccgagggcc aaggcttcat gacaagggga tttctaaaga gcctgcgaaa | 1320 |
| gccttttggt gactttatgg agcccaagtt tgagtttgct gtgaagttca atgcactgga | 1380 |
| attagatgac agcgacttgg caatatttat tgctgtcatt attctcagtg agaccgccc | 1440 |
| aggtttgctg aatgtgaagc ccattgaaga cattcaagac aacctgctac aagccctgga | 1500 |
| gctccagctg aagctgaacc accctgagtc ctcacagctg tttgccaagc tgctccagaa | 1560 |
| aatgacagac ctcagacaga ttgtcacgga acacgtgcag ctactgcagg tgatcaagaa | 1620 |
| gacggagaca gacatgagtc ttcacccgct cctgcaggag atctacaagg acttgtacta | 1680 |
| gcagagagtc ctgagccact gccaacattt cccttcttcc agttgcacta ttctgaggga | 1740 |
| aaatctgaca cctaagaaat ttactgtgaa aaagcatttt aaaagaaaa gttttagaa | 1800 |
| tatgatctat tttatgcata ttgtttataa agacacattt acaatttact tttaatatta | 1860 |
| aaaattacca tattatgaaa ttgctgatag ta | 1892 |

<210> SEQ ID NO 3
<211> LENGTH: 477
<212> TYPE: PRT
<213> ORGANISM: Homo sapiens

<400> SEQUENCE: 3

Met Thr Met Val Asp Thr Glu Met Pro Phe Trp Pro Thr Asn Phe Gly
1               5                   10                  15

Ile Ser Ser Val Asp Leu Ser Val Met Glu Asp His Ser His Ser Phe
            20                  25                  30

Asp Ile Lys Pro Phe Thr Thr Val Asp Phe Ser Ser Ile Ser Thr Pro
        35                  40                  45

```
His Tyr Glu Asp Ile Pro Phe Thr Arg Thr Asp Pro Val Val Ala Asp
 50                  55                  60

Tyr Lys Tyr Asp Leu Lys Leu Gln Glu Tyr Gln Ser Ala Ile Lys Val
 65                  70                  75                  80

Glu Pro Ala Ser Pro Pro Tyr Tyr Ser Glu Lys Thr Gln Leu Tyr Asn
                 85                  90                  95

Lys Pro His Glu Glu Pro Ser Asn Ser Leu Met Ala Ile Glu Cys Arg
             100                 105                 110

Val Cys Gly Asp Lys Ala Ser Gly Phe His Tyr Gly Val His Ala Cys
         115                 120                 125

Glu Gly Cys Lys Gly Phe Phe Arg Arg Thr Ile Arg Leu Lys Leu Ile
 130                 135                 140

Tyr Asp Arg Cys Asp Leu Asn Cys Arg Ile His Lys Lys Ser Arg Asn
145                 150                 155                 160

Lys Cys Gln Tyr Cys Arg Phe Gln Lys Cys Leu Ala Val Gly Met Ser
                165                 170                 175

His Asn Ala Ile Arg Phe Gly Arg Met Pro Gln Ala Glu Lys Glu Lys
            180                 185                 190

Leu Leu Ala Glu Ile Ser Ser Asp Ile Asp Gln Leu Asn Pro Glu Ser
        195                 200                 205

Ala Asp Leu Arg Ala Leu Ala Lys His Leu Tyr Asp Ser Tyr Ile Lys
210                 215                 220

Ser Phe Pro Leu Thr Lys Ala Lys Ala Arg Ala Ile Leu Thr Gly Lys
225                 230                 235                 240

Thr Thr Asp Lys Ser Pro Phe Val Ile Tyr Asp Met Asn Ser Leu Met
                245                 250                 255

Met Gly Glu Asp Lys Ile Lys Phe Lys His Ile Thr Pro Leu Gln Glu
            260                 265                 270

Gln Ser Lys Glu Val Ala Ile Arg Ile Phe Gln Gly Cys Gln Phe Arg
        275                 280                 285

Ser Val Glu Ala Val Gln Glu Ile Thr Glu Tyr Ala Lys Ser Ile Pro
290                 295                 300

Gly Phe Val Asn Leu Asp Leu Asn Asp Gln Val Thr Leu Leu Lys Tyr
305                 310                 315                 320

Gly Val His Glu Ile Ile Tyr Thr Met Leu Ala Ser Leu Met Asn Lys
                325                 330                 335

Asp Gly Val Leu Ile Ser Glu Gly Gln Gly Phe Met Thr Arg Glu Phe
            340                 345                 350

Leu Lys Ser Leu Arg Lys Pro Phe Gly Asp Phe Met Glu Pro Lys Phe
        355                 360                 365

Glu Phe Ala Val Lys Phe Asn Ala Leu Glu Leu Asp Asp Ser Asp Leu
370                 375                 380

Ala Ile Phe Ile Ala Val Ile Ile Leu Ser Gly Asp Arg Pro Gly Leu
385                 390                 395                 400

Leu Asn Val Lys Pro Ile Glu Asp Ile Gln Asp Asn Leu Leu Gln Ala
                405                 410                 415

Leu Glu Leu Gln Leu Lys Leu Asn His Pro Glu Ser Ser Gln Leu Phe
            420                 425                 430

Ala Lys Leu Leu Gln Lys Met Thr Asp Leu Arg Gln Ile Val Thr Glu
        435                 440                 445

His Val Gln Leu Leu Gln Val Ile Lys Lys Thr Glu Thr Asp Met Ser
450                 455                 460

Leu His Pro Leu Leu Gln Glu Ile Tyr Lys Asp Leu Tyr
```

465    470    475

<210> SEQ ID NO 4
<211> LENGTH: 9809
<212> TYPE: DNA
<213> ORGANISM: Homo sapiens

<400> SEQUENCE: 4

| | | | | | |
|---|---|---|---|---|---|
| gcgggctggg | gggagggaga | ggggttgagt | caagatggcg | gccaaggtgg | cgaagcagca | 60 |
| gccgcggcgg | cggcggcggc | tggagtgagc | gtccgactcg | ccgcgccgaa | cgaggtcccg | 120 |
| gtgtagggcc | gcgcgccgtg | gccgcgtccc | actcctcagg | ccggggcgca | cgtcggctcc | 180 |
| cacgcttagc | cagctcccgg | tggtttccta | gaaacatgat | tgtttattgg | cattgatctc | 240 |
| acagtctggt | gaggacttct | ttactgataa | tgtcaagttc | aggttatcct | cccaaccaag | 300 |
| gagcattcag | cacagaacaa | agtcgttatc | ctcctcactc | tgtccagtat | acatttccca | 360 |
| acaccgccca | ccagcaggag | ttcgcagtcc | ctgattatcg | ttcctctcat | cttgaagtga | 420 |
| gtcaggcatc | acagcttttg | cagcaacagc | agcagcaaca | gcttcgaagg | cgaccttcct | 480 |
| tgctttcaga | atttcaccca | ggttctgaca | ggcctcaaga | aaggagaact | agttatgaac | 540 |
| cgtttcatcc | aggcccatcc | ccagtggatc | atgattcact | ggaatcgaag | cgaccacgtc | 600 |
| tggaacaggt | ttctgattct | cattttcagc | gtgtcagtgc | tgcggttttg | cctttagtgc | 660 |
| acccgctgcc | agaagggctg | agggcttctg | cagatgctaa | gaaggatcca | gcattcggag | 720 |
| gcaaacatga | agctccatcc | tctccaattt | cggggcaacc | atgtggagat | gatcaaaatg | 780 |
| cttcaccttc | aaaactctca | aaggaagagt | taatacagag | tatggatcgt | gtagatcgag | 840 |
| aaattgcaaa | agtagaacag | cagatcctta | aactgaaaaa | gaaacaacaa | cagcttgaag | 900 |
| aagaggcagc | taaacctcct | gagcctgaga | agcccgtgtc | ccctcctcct | gtggagcaga | 960 |
| aacaccgcag | tattgtccaa | attatttatg | atgagaatcg | gaaaaagca | gaagaagctc | 1020 |
| ataaaatttt | tgaaggtctt | ggcccaaaag | ttgaactgcc | actgtataac | cagccatcag | 1080 |
| ataccaaggt | gtaccatgag | aacatcaaga | caaaccaggt | gatgaggaaa | aaactcattt | 1140 |
| tatttttaa | aagaagaaat | catgcaagaa | aacaaaggga | acaaaaaatc | tgccagcgtt | 1200 |
| atgatcagct | catggaggca | tgggagaaaa | aagtggacag | aatagaaaat | aatcctcgga | 1260 |
| ggaaagctaa | agaaagcaaa | acaagggaat | actatgaaaa | gcagtttcca | gaaattcgaa | 1320 |
| aacaaagaga | acagcaagaa | agatttcagc | gagttgggca | gaggggagct | ggtctttcag | 1380 |
| ccaccattgc | taggagtgag | catgagattt | ctgaaattat | tgatgggctc | tctgagcagg | 1440 |
| agaataatga | gaaacaaatg | cggcagctct | ctgtgattcc | acctatgatg | tttgatgcag | 1500 |
| aacaaagacg | agtcaagttc | attaacatga | atgggcttat | ggaggaccct | atgaaagtgt | 1560 |
| ataaagatag | gcagtttatg | aatgtttgga | ctgaccatga | aaaggagatc | tttaaggaca | 1620 |
| agtttatcca | gcatccaaaa | aactttggac | taattgcatc | atacttggag | aggaagagtg | 1680 |
| ttcctgattg | tgttttgtat | tactatttaa | ccaagaaaaa | tgagaattat | aaagccctcg | 1740 |
| tcagaaggaa | ttatgggaaa | cgcagaggca | gaaaccagca | aattgctcga | ccctcgcaag | 1800 |
| aagaaaaagt | agaagaaaaa | gaagaggata | agcagaaaaa | acagaaaaaa | aagaagaag | 1860 |
| aaagaaaga | tgagaggaa | aaagatgaaa | aagaagactc | caagaaaat | accaaggaaa | 1920 |
| aggacaagat | agatggtaca | gcagaagaaa | ctgaggaaag | agagcaagcc | acaccccggg | 1980 |
| ggcgaaagac | tgccaacagt | cagggccgcc | gtaagggccg | gatcaccagg | tccatgacaa | 2040 |
| acgaagctgc | agctgccagt | gctgcagccg | cagcggctac | tgaagagccc | ccaccacctc | 2100 |

```
tgccaccgcc accagaaccc atttctacag agcctgtgga gacctctcga tggacagaag    2160
aagaaatgga agttgctaaa aaaggtctag tagaacatgg tcgtaactgg gcagcaattg    2220
ctaaaatggt gggaacgaaa agtgaagctc aatgtaaaaa cttctatttt aactataaaa    2280
ggcgacacaa tcttgacaac ctcttacagc agcataaaca gaaaacttca cgaaaacctc    2340
gtgaagagcg agatgtgtct caatgtgaaa gtgtcgcttc cactgtttct gctcaggagg    2400
atgaagatat tgaagcctcc aatgaagaag aaaatccaga agacagcgaa gttgaagctg    2460
tcaagcccag cgaggacagt cctgaaaatg ctacttctcg aggaaacaca gaacctgcgg    2520
ttgagcttga gcccaccacg gaaactgcac ccagtacatc tccctcctta gcagttccaa    2580
gtacaaaacc agctgaagat gaaagtgtgg agacccaggt gaatgacagc atcagtgctg    2640
agacagcaga gcagatggat gtagatcagc aggagcacag tgctgaagag ggttctgttt    2700
gtgatccccc acccgctacc aaagctgact ctgtggacgt tgaagtgagg gtgccagaaa    2760
accatgcatc taaagttgaa ggtgataata ccaaagaaag agacttggat agagccagtg    2820
agaaggtgga acctagagat gaagatttgg tggtagctca gcaaataaat gcccaaaggc    2880
ccgagcccca gtcagacaat gattccagtg ccacgtgcag cgctgatgag gatgtggatg    2940
gagagccaga gaggcagaga atgtttccta tggactcaaa gccttcactg ttaaacccca    3000
ctggatctat actcgtctca tctccgttaa aaccaaatcc actggatctg ccacagcttc    3060
agcatcgagc tgctgttatc ccaccaatgg tatcctgcac cccatgtaac ataccaattg    3120 gaacccagt gagcggctat gctctctacc agcgacacat taaagcaatg catgagtcag    3180
cactcctgga ggagcagcgg cagagacaag aacagataga tttggaatgt agaagttcta    3240
caagtccatg tggcacatcc aagagtccaa acagagagtg ggaagtcctt cagcctgctc    3300
cacatcaagt gataactaat ctccctgaag gcgttcggct tccgacaact cgaccaacca    3360
ggccaccgcc ccctctcatc ccgtcatcca aaaccacagt ggcttcagaa aaaccatctt    3420
ttataatggg aggctccatc tcacagggaa caccaggcac ttatttgact tctcataatc    3480
aggcttccta cactcaagaa acacccaagc cgtcagtggg atctatctct cttggactgc    3540
cacggcaaca ggaatctgcc aaatcagcta ctttgcccta catcaagcag gaagaatttt    3600
ctccccgaag ccaaaactca caacctgagg gtctgttggt cagggcccaa catgaaggtg    3660
tagtcagagg taccgcagga gccatacaag aaggaagtat aactcgggga actccaacca    3720
gcaaaatttc agtggagagc attccatccc tacggggctc tatcactcag ggcaccccgg    3780 ctctgccccca gactggcata ccaacagagg cttggtgaa ggggtccatt tcgagaatgc    3840
ccattgaaga cagcagtcct gagaaaggca gagaggaagc tgcatccaaa ggccatgtta    3900
tttatgaagg caaaagtgga catatcttgt catatgataa tattaagaat gcccgagaag    3960
ggactaggag tccaagaaca gctcatgaaa tcagtttaaa gagaagctat gaatcagtgg    4020
aaggaaatat aaagcaaggg atgtcaatga gggagtctcc tgtatcagca ccgttagagg    4080
ggctgatatg ccgagcatta cccaggggga gtcctcattc tgacctcaaa gaaaggactg    4140
tattgtctgg ctccataatg caggggacac caagagcaac aactgaaagc tttgaagatg    4200
gccttaaata tcccaaacaa attaaaaggg aaagtcctcc catacgagca tttgaaggtg    4260
ccattaccaa aggaaaacca tatgatggca tcaccaccat caaagaaatg gggcgttcca    4320
ttcatgagat tccaaggcaa gatattttaa ctcaggaaag tcggaaaact ccagaagtgg    4380
tccagagcac acggccgata attgagggtt ccatttccca gggcacacca ataaagtttg    4440
```

```
acaacaactc aggtcaatct gccatcaaac acaatgtcaa atccttaatc acggggccta    4500
gcaaactatc ccgtggaatg cctccgctgg aaattgtgcc agagaacata aaagtggtag    4560 aacgggaaa atatgaggat gtgaaagcag gcgagaccgt gcgttcccgg cacacgtcag    4620
tggtaagctc tggcccctcc gttcttaggt ccacactgca tgaagctccc aaagcacaac    4680
tgagccctgg gatttatgat gacaccagtg cacggaggac ccctgtgagt tatcaaaaca    4740
ccatgtccag aggctcaccc atgatgaaca gaacttctga tgttacaatt tcttctaaca    4800
agtctaccaa tcatgaaagg aaatcgacac tgacccctac ccagagggaa agtatcccag    4860
cgaagtctcc agtgcctggg gtggaccctg tcgtgagcca cagtccgttt gatccccatc    4920
acagaggcag cactgcaggc gaggtttatc ggagccacct gcccacgcac ttggatccag    4980
ccatgccttt tcacagggct ttggatcctg cagcggctgc ttacctgttt cagagacagc    5040
tttcaccaac tccaggttac ccaagtcagt atcagcttta cgcaatggag aacacaagac    5100
agacaatctt aaatgattac attacctcac aacagatgca agtgaacttg cgtccagatg    5160
tggccagagg actctcccca agagagcagc cactgggtct cccatacccca gcaacgagag    5220 gaatcattga cctgaccaat atgcctccaa caattttagt gcctcatcca ggggaacaa    5280 gcactcctcc catggacaga atcacttata ttcctggtac acagattact ttccctccca    5340
ggccgtacaa ctctgcttcc atgtctccag gacacccaac acaccttgca gctgctgcaa    5400
gtgctgagag ggaacgggaa cgggagcggg agaaggagcg ggagcgggaa cggattgctg    5460
cagcttcctc cgacctctac ctgcggccag gctcagaaca gcctggccga cctggcagtc    5520
atggatatgt tcgctcccct tcccttcag taagaactca ggagaccatg ttgcaacaga    5580
gacccagtgt tttccaagga accaatggaa ccagtgtaat cacacctttg gatccaactg    5640
ctcagctacg aatcatgcca ctgctgctg ggggcccttc aataagccaa ggcctgccag    5700
cctcccgtta caacactgct gcggatgccc tggctgctct tgtggatgct gcagcttctg    5760 cacccccagat ggatgtgtcc aaaacaaaag agagtaagca tgaagctgcc aggttagaag    5820
aaaatttgag aagcaggtca gcagcagtta gtgaacagca gcagctagag cagaaaaccc    5880
tggaggtgga aagagatct gttcagtgtt tatacacttc ttcagccttt ccaagtggca    5940
agccccagcc tcattcttca gtagtttatt ctgaggctgg aaagataaa gggcctcctc    6000 caaaatccag atatgaggaa gagctaagga ccagagggaa gactaccatt actgcagcta    6060
acttcataga cgtgatcatc acccggcaaa ttgcctcgga caaggatgcg agggaacgtg    6120
gctctcaaag ttcagactct tctagtagct tatcttctca caggtatgaa acacctagcg    6180
atgctattga ggtgataagt cctgccagct cacctgcgcc accccaggag aaactgcaga    6240
cctatcagcc agaggttgtt aaggcaaatc aagcggaaaa tgatcctacc agacaatatg    6300
aaggaccatt acatcactat cgaccacagc aggaatcacc atctccccaa caacagctgc    6360 cccttcttc acaggcagag ggaatggggc aagtgcccag gacccatcgg ctgatcacac    6420
ttgctgatca catctgtcaa attatcacac aagattttgc tagaaatcaa gtttcctcgc    6480
agactcccca gcagcctcct acttctacat tccagaactc accttctgct tggtatctat    6540
cacctgtgag gactaaaaca tcaaaccgtt acagcccaga atcccaggct cagtctgtcc    6600
atcatcaaag accaggttca agggtctctc cagaaaatct tgtggacaaa tccaggggaa    6660
gtaggcctgg aaaatcccca gagaggagtc acgtctcttc ggagccctac gagcccatct    6720
ccccacccca ggttccggtt gtgcatgaga acaggacga cttgctgctc ttgtctcaga    6780
ggggcgcaga gcctgcagag cagaggaatg atgcccgctc accagggagt ataagctact    6840
```

-continued

| | |
|---|---|
| tgccttcatt cttcaccaag cttgaaaata catcacccat ggttaaatca aagaagcagg | 6900 |
| agattttcg taagttgaac tcctctggtg gaggtgactc tgatatggca gctgctcagc | 6960 |
| caggaactga gatctttaat ctgccagcag ttactacgtc aggctcagtt agctctagag | 7020 |
| gccattcttt tgctgatcct gccagtaatc ttgggctgga agacattatc aggaaggctc | 7080 |
| tcatgggaag ctttgatgac aaagttgagg atcatggagt tgtcatgtcc cagcctatgg | 7140 |
| gagtagtgcc tggtactgcc aacacctcag ttgtgaccag tggtgagaca cgaagagagg | 7200 |
| aaggggaccc atcacctcat tcaggaggag tttgcaaacc aaagctgatc agcaagtcaa | 7260 |
| acagcaggaa atctaagtct cctatacctg ggcaaggcta cttaggaacg gaacggccct | 7320 |
| cttcagtctc ctctgtacat tcagaagggg attaccatag gcagacgcca gggtgggcct | 7380 |
| gggaagacag gccctcttca acaggctcaa ctcagtttcc ttataaccct ctgactatgc | 7440 |
| ggatgctcag cagtactcca ccaacaccga ttgcatgtgc tccctctgcg gtgaaccaag | 7500 |
| cagctcctca ccaacagaac aggatctggg agcgagagcc tgccccactg ctctcagcac | 7560 |
| agtacgagac cctgtcggat agtgatgact gaactgcaca aagtgagggg aacagggtgc | 7620 |
| aggagaggga tctctagttt ttgtggttta attttagta gcaggtcaaa aacctgccct | 7680 |
| cctgtgactt attccctgag acttttcagg agagccagcc cacagatgat gaagaaatga | 7740 |
| tggaagttca tttggagagt caaatgggaa aaaacaaac aaaaaactgc ctttgataca | 7800 |
| ggcaattcag tggactataa taatagtgga gggttgagat gtagagtttt taaaaagtga | 7860 |
| acagttgctg ttcttacatc tgtaaagaaa accataatgt cttttaaatca ctcttctgta | 7920 |
| aatagatgac cttttttgcag tgtatatccc cttgctgtag tatctggtgt acttatgttc | 7980 |
| aaatcagcgc atcaactttg ggggtgattt taaaaatct ttttgtctat ctatcttttt | 8040 |
| aaccctagcc ttctaaacaa cctcatacag cccagttaca taatgttggc tgtcacgggc | 8100 |
| attgtacttt tatctgatat tgtttcctct aaattcagct ttccagtgat gtttaaaatc | 8160 |
| ttgtgaaaat gtttagattt ttaacacaga ccctgtcata aatctgtac attagggtca | 8220 |
| aaaggtaaaa gtaacaaatt ctgccatatt gtaaatttcc agtgcaggct ttaattttt | 8280 |
| tttttcatta gtagcactga aaaaatatta ctgcatgggt atgttctagt tcagtttata | 8340 |
| aagtttaaaa ggcttatttg aggcatacct cactgttacg cacactggta atttaaccat | 8400 |
| gcccctaagt attccttttc tcctgcattt gatgcagccc aacaaagctt ttgttttgaa | 8460 |
| ataaatttga ctaccctgtc catagctaca gtagattatt tgtggtttaa ggctcctggt | 8520 |
| gtctcaggtt ccaaaggaaa agcttacata ttttcccctt agtttgaata tatgattggt | 8580 |
| tgggttaaaa gataatgatc tgtgtagtat ttagataagc tttatgctgc atcctgaaaa | 8640 |
| actcatggta aacacagtcc tttttcccca tcactatgga ccagcattta ctctcacttt | 8700 |
| gctcccttgg gacaagagtt tactgttaaa tgttttcatt tcacagagtc tcaaggtgca | 8760 |
| aataatttaa aagactgaat tctaaactaa ttatggtact agagggccag ttttatcttt | 8820 |
| cattaagaat tgcttgctga atttttaaagt ttttttcata caatttatca tagcatttaa | 8880 |
| gtatctttct ataacataga tactaacagt tttgggagaa tgccactggt aactggaaag | 8940 |
| gggagaaaca gatctctcag gatgataaaa attagcactt tacagacttt caagtagacc | 9000 |
| taaactttta aacaaagta ctcaaggctt ttaaggaagc agctctgtga ttagctactg | 9060 |
| accaagaccc tcctatcact ggtgtctaat ccctatgtta cagatgaaga cacaggttta | 9120 |
| gtactttgcc catatagtta aattagtgac agagataggc cataagccca catttgtctt | 9180 |

-continued

| | |
|---|---|
| cagtcaaagc tttcactcct gtccctgttc cactcctgta tacctgaggt ccccaacata | 9240 |
| aactttagat caggcttagt ggtcagcatt cctagtactt ggaaagttgg tattttttac | 9300 |
| aacagatata tgtaaacata taaaaatttc aaaatgaatg aaaaacagtg actaaatgtt | 9360 |
| ccacttcaca gttttctgct gaattttttt ttttcaggta ctggtaatat tttagagttt | 9420 |
| gttaataatt tatattgcca acctaccata aaagagatta tgatggtatt tttctatgac | 9480 |
| cctgagggtc ttaagctatt ctgagtcaga atacagttga cccttgaaca acacgggttt | 9540 |
| gaactgtgtg ggtccactta tacatggatt tcttccacc tctgccaccc aagatagcaa | 9600 |
| gaccaacccc ttctcatcct cagcctattc aacatgaaga tgacaaggat gaagaccttc | 9660 |
| atgatgatcc acttccactt aatgaatagt aaatatattt tctcttcctt ataatcttaa | 9720 |
| caaacatttt ctcttctcta gcttacttta ttgtaagaat acagtatata atacatatac | 9780 |
| aaaatatgtg tcaaaaaaaa aaaaaaaaa | 9809 |

<210> SEQ ID NO 5
<211> LENGTH: 2440
<212> TYPE: PRT
<213> ORGANISM: Homo sapiens

<400> SEQUENCE: 5

Met Ser Ser Ser Gly Tyr Pro Pro Asn Gln Gly Ala Phe Ser Thr Glu
1               5                   10                  15

Gln Ser Arg Tyr Pro Pro His Ser Val Gln Tyr Thr Phe Pro Asn Thr
            20                  25                  30

Arg His Gln Gln Glu Phe Ala Val Pro Asp Tyr Arg Ser Ser His Leu
        35                  40                  45

Glu Val Ser Gln Ala Ser Gln Leu Leu Gln Gln Gln Gln Gln Gln Gln
    50                  55                  60

Leu Arg Arg Arg Pro Ser Leu Leu Ser Glu Phe His Pro Gly Ser Asp
65                  70                  75                  80

Arg Pro Gln Glu Arg Arg Thr Ser Tyr Glu Pro Phe His Pro Gly Pro
                85                  90                  95

Ser Pro Val Asp His Asp Ser Leu Glu Ser Lys Arg Pro Arg Leu Glu
            100                 105                 110

Gln Val Ser Asp Ser His Phe Gln Arg Val Ser Ala Ala Val Leu Pro
        115                 120                 125

Leu Val His Pro Leu Pro Glu Gly Leu Arg Ala Ser Ala Asp Ala Lys
    130                 135                 140

Lys Asp Pro Ala Phe Gly Gly Lys His Glu Ala Pro Ser Ser Pro Ile
145                 150                 155                 160

Ser Gly Gln Pro Cys Gly Asp Asp Gln Asn Ala Ser Pro Ser Lys Leu
                165                 170                 175

Ser Lys Glu Glu Leu Ile Gln Ser Met Asp Arg Val Asp Arg Glu Ile
            180                 185                 190

Ala Lys Val Glu Gln Gln Ile Leu Lys Leu Lys Lys Lys Gln Gln Gln
        195                 200                 205

Leu Glu Glu Glu Ala Ala Lys Pro Pro Glu Pro Glu Lys Pro Val Ser
    210                 215                 220

Pro Pro Pro Val Glu Gln Lys His Arg Ser Ile Val Gln Ile Ile Tyr
225                 230                 235                 240

Asp Glu Asn Arg Lys Lys Ala Glu Glu Ala His Lys Ile Phe Glu Gly
                245                 250                 255

Leu Gly Pro Lys Val Glu Leu Pro Leu Tyr Asn Gln Pro Ser Asp Thr

```
                260                 265                 270
Lys Val Tyr His Glu Asn Ile Lys Thr Asn Gln Val Met Arg Lys Lys
                275                 280                 285
Leu Ile Leu Phe Phe Lys Arg Arg Asn His Ala Arg Lys Gln Arg Glu
                290                 295                 300
Gln Lys Ile Cys Gln Arg Tyr Asp Gln Leu Met Glu Ala Trp Glu Lys
305                 310                 315                 320
Lys Val Asp Arg Ile Glu Asn Asn Pro Arg Arg Lys Ala Lys Glu Ser
                325                 330                 335
Lys Thr Arg Glu Tyr Tyr Glu Lys Gln Phe Pro Glu Ile Arg Lys Gln
                340                 345                 350
Arg Glu Gln Gln Glu Arg Phe Gln Arg Val Gly Gln Arg Gly Ala Gly
                355                 360                 365
Leu Ser Ala Thr Ile Ala Arg Ser Glu His Glu Ile Ser Glu Ile Ile
                370                 375                 380
Asp Gly Leu Ser Glu Gln Glu Asn Asn Glu Lys Gln Met Arg Gln Leu
385                 390                 395                 400
Ser Val Ile Pro Pro Met Met Phe Asp Ala Glu Gln Arg Arg Val Lys
                405                 410                 415
Phe Ile Asn Met Asn Gly Leu Met Glu Asp Pro Met Lys Val Tyr Lys
                420                 425                 430
Asp Arg Gln Phe Met Asn Val Trp Thr Asp His Glu Lys Glu Ile Phe
                435                 440                 445
Lys Asp Lys Phe Ile Gln His Pro Lys Asn Phe Gly Leu Ile Ala Ser
                450                 455                 460
Tyr Leu Glu Arg Lys Ser Val Pro Asp Cys Val Leu Tyr Tyr Tyr Leu
465                 470                 475                 480
Thr Lys Lys Asn Glu Asn Tyr Lys Ala Leu Val Arg Arg Asn Tyr Gly
                485                 490                 495
Lys Arg Arg Gly Arg Asn Gln Gln Ile Ala Arg Pro Ser Gln Glu Glu
                500                 505                 510
Lys Val Glu Glu Lys Glu Glu Asp Lys Ala Glu Lys Thr Glu Lys Lys
                515                 520                 525
Glu Glu Glu Lys Lys Asp Glu Glu Lys Asp Glu Lys Glu Asp Ser
                530                 535                 540
Lys Glu Asn Thr Lys Glu Lys Asp Lys Ile Asp Gly Thr Ala Glu Glu
545                 550                 555                 560
Thr Glu Glu Arg Glu Gln Ala Thr Pro Arg Gly Arg Lys Thr Ala Asn
                565                 570                 575
Ser Gln Gly Arg Arg Lys Gly Arg Ile Thr Arg Ser Met Thr Asn Glu
                580                 585                 590
Ala Ala Ala Ser Ala Ala Ala Ala Thr Glu Glu Pro Pro
                595                 600                 605
Pro Pro Leu Pro Pro Pro Glu Pro Ile Ser Thr Glu Pro Val Glu
                610                 615                 620
Thr Ser Arg Trp Thr Glu Glu Met Glu Val Ala Lys Lys Gly Leu
625                 630                 635                 640
Val Glu His Gly Arg Asn Trp Ala Ala Ile Ala Lys Met Val Gly Thr
                645                 650                 655
Lys Ser Glu Ala Gln Cys Lys Asn Phe Tyr Phe Asn Tyr Lys Arg Arg
                660                 665                 670
His Asn Leu Asp Asn Leu Leu Gln Gln His Lys Gln Lys Thr Ser Arg
                675                 680                 685
```

```
Lys Pro Arg Glu Glu Arg Asp Val Ser Gln Cys Glu Ser Val Ala Ser
690                 695                 700

Thr Val Ser Ala Gln Glu Asp Glu Ile Glu Ala Ser Asn Glu Glu
705                 710                 715                 720

Glu Asn Pro Glu Asp Ser Glu Val Glu Ala Val Lys Pro Ser Glu Asp
                    725                 730                 735

Ser Pro Glu Asn Ala Thr Ser Arg Gly Asn Thr Glu Pro Ala Val Glu
                740                 745                 750

Leu Glu Pro Thr Thr Glu Thr Ala Pro Ser Thr Ser Pro Ser Leu Ala
            755                 760                 765

Val Pro Ser Thr Lys Pro Ala Glu Asp Glu Ser Val Glu Thr Gln Val
770                 775                 780

Asn Asp Ser Ile Ser Ala Glu Thr Ala Glu Gln Met Asp Val Asp Gln
785                 790                 795                 800

Gln Glu His Ser Ala Glu Glu Gly Ser Val Cys Asp Pro Pro Ala
                805                 810                 815

Thr Lys Ala Asp Ser Val Asp Val Glu Val Arg Val Pro Glu Asn His
                820                 825                 830

Ala Ser Lys Val Glu Gly Asp Asn Thr Lys Glu Arg Asp Leu Asp Arg
            835                 840                 845

Ala Ser Glu Lys Val Glu Pro Arg Asp Glu Asp Leu Val Val Ala Gln
850                 855                 860

Gln Ile Asn Ala Gln Arg Pro Glu Pro Gln Ser Asp Asn Asp Ser Ser
865                 870                 875                 880

Ala Thr Cys Ser Ala Asp Glu Asp Val Asp Gly Glu Pro Glu Arg Gln
                885                 890                 895

Arg Met Phe Pro Met Asp Ser Lys Pro Ser Leu Leu Asn Pro Thr Gly
                900                 905                 910

Ser Ile Leu Val Ser Ser Pro Leu Lys Pro Asn Pro Leu Asp Leu Pro
            915                 920                 925

Gln Leu Gln His Arg Ala Ala Val Ile Pro Pro Met Val Ser Cys Thr
930                 935                 940

Pro Cys Asn Ile Pro Ile Gly Thr Pro Val Ser Gly Tyr Ala Leu Tyr
945                 950                 955                 960

Gln Arg His Ile Lys Ala Met His Glu Ser Ala Leu Leu Glu Glu Gln
                965                 970                 975

Arg Gln Arg Gln Glu Gln Ile Asp Leu Glu Cys Arg Ser Ser Thr Ser
                980                 985                 990

Pro Cys Gly Thr Ser Lys Ser Pro Asn Arg Glu Trp Glu Val Leu Gln
            995                 1000                1005

Pro Ala Pro His Gln Val Ile Thr Asn Leu Pro Glu Gly Val Arg
    1010                1015                1020

Leu Pro Thr Thr Arg Pro Thr Arg Pro Pro Pro Leu Ile Pro
    1025                1030                1035

Ser Ser Lys Thr Thr Val Ala Ser Glu Lys Pro Ser Phe Ile Met
    1040                1045                1050

Gly Gly Ser Ile Ser Gln Gly Thr Pro Gly Thr Tyr Leu Thr Ser
    1055                1060                1065

His Asn Gln Ala Ser Tyr Thr Gln Glu Thr Pro Lys Pro Ser Val
    1070                1075                1080

Gly Ser Ile Ser Leu Gly Leu Pro Arg Gln Gln Glu Ser Ala Lys
    1085                1090                1095
```

```
Ser Ala Thr Leu Pro Tyr Ile Lys Gln Glu Glu Phe Ser Pro Arg
1100                1105                1110

Ser Gln Asn Ser Gln Pro Glu Gly Leu Leu Val Arg Ala Gln His
1115                1120                1125

Glu Gly Val Val Arg Gly Thr Ala Gly Ala Ile Gln Glu Gly Ser
1130                1135                1140

Ile Thr Arg Gly Thr Pro Thr Ser Lys Ile Ser Val Glu Ser Ile
1145                1150                1155

Pro Ser Leu Arg Gly Ser Ile Thr Gln Gly Thr Pro Ala Leu Pro
1160                1165                1170

Gln Thr Gly Ile Pro Thr Glu Ala Leu Val Lys Gly Ser Ile Ser
1175                1180                1185

Arg Met Pro Ile Glu Asp Ser Ser Pro Glu Lys Gly Arg Glu Glu
1190                1195                1200

Ala Ala Ser Lys Gly His Val Ile Tyr Glu Gly Lys Ser Gly His
1205                1210                1215

Ile Leu Ser Tyr Asp Asn Ile Lys Asn Ala Arg Glu Gly Thr Arg
1220                1225                1230

Ser Pro Arg Thr Ala His Glu Ile Ser Leu Lys Arg Ser Tyr Glu
1235                1240                1245

Ser Val Glu Gly Asn Ile Lys Gln Gly Met Ser Met Arg Glu Ser
1250                1255                1260

Pro Val Ser Ala Pro Leu Glu Gly Leu Ile Cys Arg Ala Leu Pro
1265                1270                1275

Arg Gly Ser Pro His Ser Asp Leu Lys Glu Arg Thr Val Leu Ser
1280                1285                1290

Gly Ser Ile Met Gln Gly Thr Pro Arg Ala Thr Thr Glu Ser Phe
1295                1300                1305

Glu Asp Gly Leu Lys Tyr Pro Lys Gln Ile Lys Arg Glu Ser Pro
1310                1315                1320

Pro Ile Arg Ala Phe Glu Gly Ala Ile Thr Lys Gly Lys Pro Tyr
1325                1330                1335

Asp Gly Ile Thr Thr Ile Lys Glu Met Gly Arg Ser Ile His Glu
1340                1345                1350

Ile Pro Arg Gln Asp Ile Leu Thr Gln Glu Ser Arg Lys Thr Pro
1355                1360                1365

Glu Val Val Gln Ser Thr Arg Pro Ile Ile Glu Gly Ser Ile Ser
1370                1375                1380

Gln Gly Thr Pro Ile Lys Phe Asp Asn Asn Ser Gly Gln Ser Ala
1385                1390                1395

Ile Lys His Asn Val Lys Ser Leu Ile Thr Gly Pro Ser Lys Leu
1400                1405                1410

Ser Arg Gly Met Pro Pro Leu Glu Ile Val Pro Glu Asn Ile Lys
1415                1420                1425

Val Val Glu Arg Gly Lys Tyr Glu Asp Val Lys Ala Gly Glu Thr
1430                1435                1440

Val Arg Ser Arg His Thr Ser Val Val Ser Ser Gly Pro Ser Val
1445                1450                1455

Leu Arg Ser Thr Leu His Glu Ala Pro Lys Ala Gln Leu Ser Pro
1460                1465                1470

Gly Ile Tyr Asp Asp Thr Ser Ala Arg Arg Thr Pro Val Ser Tyr
1475                1480                1485

Gln Asn Thr Met Ser Arg Gly Ser Pro Met Met Asn Arg Thr Ser
```

```
                1490                1495                1500
Asp Val Thr Ile Ser Ser Asn Lys Ser Thr Asn His Glu Arg Lys
    1505                1510                1515

Ser Thr Leu Thr Pro Thr Gln Arg Glu Ser Ile Pro Ala Lys Ser
    1520                1525                1530

Pro Val Pro Gly Val Asp Pro Val Val Ser His Ser Pro Phe Asp
    1535                1540                1545

Pro His His Arg Gly Ser Thr Ala Gly Glu Val Tyr Arg Ser His
    1550                1555                1560

Leu Pro Thr His Leu Asp Pro Ala Met Pro Phe His Arg Ala Leu
    1565                1570                1575

Asp Pro Ala Ala Ala Ala Tyr Leu Phe Gln Arg Gln Leu Ser Pro
    1580                1585                1590

Thr Pro Gly Tyr Pro Ser Gln Tyr Gln Leu Tyr Ala Met Glu Asn
    1595                1600                1605

Thr Arg Gln Thr Ile Leu Asn Asp Tyr Ile Thr Ser Gln Gln Met
    1610                1615                1620

Gln Val Asn Leu Arg Pro Asp Val Ala Arg Gly Leu Ser Pro Arg
    1625                1630                1635

Glu Gln Pro Leu Gly Leu Pro Tyr Pro Ala Thr Arg Gly Ile Ile
    1640                1645                1650

Asp Leu Thr Asn Met Pro Pro Thr Ile Leu Val Pro His Pro Gly
    1655                1660                1665

Gly Thr Ser Thr Pro Pro Met Asp Arg Ile Thr Tyr Ile Pro Gly
    1670                1675                1680

Thr Gln Ile Thr Phe Pro Pro Arg Pro Tyr Asn Ser Ala Ser Met
    1685                1690                1695

Ser Pro Gly His Pro Thr His Leu Ala Ala Ala Ala Ser Ala Glu
    1700                1705                1710

Arg Glu Arg Glu Arg Glu Arg Glu Lys Glu Arg Glu Arg Glu Arg
    1715                1720                1725

Ile Ala Ala Ala Ser Ser Asp Leu Tyr Leu Arg Pro Gly Ser Glu
    1730                1735                1740

Gln Pro Gly Arg Pro Gly Ser His Gly Tyr Val Arg Ser Pro Ser
    1745                1750                1755

Pro Ser Val Arg Thr Gln Glu Thr Met Leu Gln Gln Arg Pro Ser
    1760                1765                1770

Val Phe Gln Gly Thr Asn Gly Thr Ser Val Ile Thr Pro Leu Asp
    1775                1780                1785

Pro Thr Ala Gln Leu Arg Ile Met Pro Leu Pro Ala Gly Gly Pro
    1790                1795                1800

Ser Ile Ser Gln Gly Leu Pro Ala Ser Arg Tyr Asn Thr Ala Ala
    1805                1810                1815

Asp Ala Leu Ala Ala Leu Val Asp Ala Ala Ala Ser Ala Pro Gln
    1820                1825                1830

Met Asp Val Ser Lys Thr Lys Glu Ser Lys His Glu Ala Ala Arg
    1835                1840                1845

Leu Glu Glu Asn Leu Arg Ser Arg Ser Ala Ala Val Ser Glu Gln
    1850                1855                1860

Gln Gln Leu Glu Gln Lys Thr Leu Glu Val Glu Lys Arg Ser Val
    1865                1870                1875

Gln Cys Leu Tyr Thr Ser Ser Ala Phe Pro Ser Gly Lys Pro Gln
    1880                1885                1890
```

-continued

```
Pro His Ser Ser Val Val Tyr Ser Glu Ala Gly Lys Asp Lys Gly
    1895                1900                1905

Pro Pro Pro Lys Ser Arg Tyr Glu Glu Glu Leu Arg Thr Arg Gly
    1910                1915                1920

Lys Thr Thr Ile Thr Ala Ala Asn Phe Ile Asp Val Ile Ile Thr
    1925                1930                1935

Arg Gln Ile Ala Ser Asp Lys Asp Ala Arg Glu Arg Gly Ser Gln
    1940                1945                1950

Ser Ser Asp Ser Ser Ser Ser Leu Ser Ser His Arg Tyr Glu Thr
    1955                1960                1965

Pro Ser Asp Ala Ile Glu Val Ile Ser Pro Ala Ser Ser Pro Ala
    1970                1975                1980

Pro Pro Gln Glu Lys Leu Gln Thr Tyr Gln Pro Glu Val Val Lys
    1985                1990                1995

Ala Asn Gln Ala Glu Asn Asp Pro Thr Arg Gln Tyr Glu Gly Pro
    2000                2005                2010

Leu His His Tyr Arg Pro Gln Gln Glu Ser Pro Ser Pro Gln Gln
    2015                2020                2025

Gln Leu Pro Pro Ser Ser Gln Ala Glu Gly Met Gly Gln Val Pro
    2030                2035                2040

Arg Thr His Arg Leu Ile Thr Leu Ala Asp His Ile Cys Gln Ile
    2045                2050                2055

Ile Thr Gln Asp Phe Ala Arg Asn Gln Val Ser Ser Gln Thr Pro
    2060                2065                2070

Gln Gln Pro Pro Thr Ser Thr Phe Gln Asn Ser Pro Ser Ala Leu
    2075                2080                2085

Val Ser Thr Pro Val Arg Thr Lys Thr Ser Asn Arg Tyr Ser Pro
    2090                2095                2100

Glu Ser Gln Ala Gln Ser Val His His Gln Arg Pro Gly Ser Arg
    2105                2110                2115

Val Ser Pro Glu Asn Leu Val Asp Lys Ser Arg Gly Ser Arg Pro
    2120                2125                2130

Gly Lys Ser Pro Glu Arg Ser His Val Ser Ser Glu Pro Tyr Glu
    2135                2140                2145

Pro Ile Ser Pro Pro Gln Val Pro Val Val His Glu Lys Gln Asp
    2150                2155                2160

Ser Leu Leu Leu Leu Ser Gln Arg Gly Ala Glu Pro Ala Glu Gln
    2165                2170                2175

Arg Asn Asp Ala Arg Ser Pro Gly Ser Ile Ser Tyr Leu Pro Ser
    2180                2185                2190

Phe Phe Thr Lys Leu Glu Asn Thr Ser Pro Met Val Lys Ser Lys
    2195                2200                2205

Lys Gln Glu Ile Phe Arg Lys Leu Asn Ser Ser Gly Gly Gly Asp
    2210                2215                2220

Ser Asp Met Ala Ala Ala Gln Pro Gly Thr Glu Ile Phe Asn Leu
    2225                2230                2235

Pro Ala Val Thr Thr Ser Gly Ser Val Ser Ser Arg Gly His Ser
    2240                2245                2250

Phe Ala Asp Pro Ala Ser Asn Leu Gly Leu Glu Asp Ile Ile Arg
    2255                2260                2265

Lys Ala Leu Met Gly Ser Phe Asp Asp Lys Val Glu Asp His Gly
    2270                2275                2280
```

| | | | | | | | | | | |
|---|---|---|---|---|---|---|---|---|---|---|
| Val | Val | Met | Ser | Gln | Pro | Met | Gly | Val | Pro | Gly | Thr Ala Asn |
| 2285 | | | | 2290 | | | | 2295 | | |
| Thr | Ser | Val | Val | Thr | Ser | Gly | Glu | Thr | Arg | Arg | Glu Glu Gly Asp |
| 2300 | | | | | 2305 | | | | 2310 | | |
| Pro | Ser | Pro | His | Ser | Gly | Gly | Val | Cys | Lys | Pro | Lys Leu Ile Ser |
| 2315 | | | | | 2320 | | | | 2325 | | |
| Lys | Ser | Asn | Ser | Arg | Lys | Ser | Lys | Ser | Pro | Ile | Pro Gly Gln Gly |
| 2330 | | | | | 2335 | | | | 2340 | | |
| Tyr | Leu | Gly | Thr | Glu | Arg | Pro | Ser | Ser | Val | Ser | Ser Val His Ser |
| 2345 | | | | | 2350 | | | | 2355 | | |
| Glu | Gly | Asp | Tyr | His | Arg | Gln | Thr | Pro | Gly | Trp | Ala Trp Glu Asp |
| 2360 | | | | | 2365 | | | | 2370 | | |
| Arg | Pro | Ser | Ser | Thr | Gly | Ser | Thr | Gln | Phe | Pro | Tyr Asn Pro Leu |
| 2375 | | | | | 2380 | | | | 2385 | | |
| Thr | Met | Arg | Met | Leu | Ser | Ser | Thr | Pro | Pro | Thr | Pro Ile Ala Cys |
| 2390 | | | | | 2395 | | | | 2400 | | |
| Ala | Pro | Ser | Ala | Val | Asn | Gln | Ala | Ala | Pro | His | Gln Gln Asn Arg |
| 2405 | | | | | 2410 | | | | 2415 | | |
| Ile | Trp | Glu | Arg | Glu | Pro | Ala | Pro | Leu | Leu | Ser | Ala Gln Tyr Glu |
| 2420 | | | | | 2425 | | | | 2430 | | |
| Thr | Leu | Ser | Asp | Ser | Asp | Asp | | | | | |
| 2435 | | | | | 2440 | | | | | | |

<210> SEQ ID NO 6
<211> LENGTH: 8857
<212> TYPE: DNA
<213> ORGANISM: Homo sapiens

<400> SEQUENCE: 6

```
gccggcgccc taggaggcgg cggcgggagg atcgcgtccc gacccgaggc cgggcctgct      60
gcgcgccccc agcccgatcg gcaccgccac ttgcctgagc gccccggcgg cccgagcgcg     120
ccccaagccc gggcgccacc gctgccacct ccgcgaggtc tccctgagtc tttgaggaca     180
cagcctcgct ggaggcagtt tctggtgcca gtgacggggt ggcccgtgag ctgatgacga     240
ggactggctt ttaatccttg gtggtgatta agagaaagct tattgggcc tgggagcagc      300
tccccgccga cccccaccac catgtcggga tccacacagc ctgtggcaca gacgtggagg     360
gccactgagc cccgctaccc gccccacagc ctttcctacc cagtgcagat cgcccggacg     420
cacacggacg tcgggctcct ggagtaccag caccactccc gcgactatgc ctcccacctg     480
tcgcccggct ccatcatcca gccccagcgg cggaggccct ccctgctgtc tgagttccag     540
cccgggaatg aacggtccca ggagctccac ctgcggccag agtcccactc ataccctgccc    600
gagctgggga agtcagagat ggagttcatt gaaagcaagc gccctcggct agagctgctg     660
cctgaccccc tgctgcgacc gtcaccctg ctggccacgg gccagcctgc gggatctgaa      720
gacctcacca aggaccgtag cctgacgggc aagctggaac cggtgtctcc ccccagcccc     780
ccgcacactg accctgagct ggagctggtg ccgccacggc tgtccaagga ggagctgatc     840
cagaacatgg accgcgtgga ccagagagatc accatggtag agcagcagat ctctaagctg     900
aagaagaagc agcaacagct ggaggaggag gctgccaagc gcccgagcc tgagaagccc       960
gtgtcaccgc cgcccatcga gtcgaagcac cgcagcctgg tgcagatcat ctacgacgag    1020
aaccggaaga aggctgaagc tgcacatcgg attctggaag gctgggggcc ccaggtggag    1080
ctgccgctgt acaaccagcc ctccgacacc cggcagtatc atgagaacat caaaataaac    1140
```

```
caggcgatgc ggaagaagct aatcttgtac ttcaagagga ggaatcacgc tcggaaacaa      1200
tgggagcaga agttctgcca gcgctatgac cagctcatgg aggcctggga gaagaaggtg      1260
gagcgcatcg agaacaaccc ccggcggcgg gccaaggaga gcaaggtgcg cgagtactac      1320
gagaagcagt tccctgagat ccgcaagcag cgcgagctgc aggagcgcat gcagagcagg      1380
gtgggccagc ggggcagtgg gctgtccatg tcggccgccc gcagcgagca cgaggtgtca      1440
gagatcatcg atggcctctc agagcaggag aacctggaga agcagatgcg ccagctggcc      1500
gtgatcccgc ccatgctgta cgacgctgac cagcagcgca tcaagttcat caacatgaac      1560
gggcttatgg ccgaccccat gaaggtgtac aaagaccgcc aggtcatgaa catgtggagt      1620
gagcaggaga aggagacctt ccgggagaag ttcatgcagc atcccaagaa ctttggcctg      1680
atcgcatcat tcctggagag gaagacagtg gctgagtgcg tcctctatta ctacctgact      1740
aagaagaatg agaactataa gagcctggtg agacggagct atcggcgccg cggcaagagc      1800
cagcagcagc aacaacagca gcagcagcag cagcagcagc agcagcagca gcccatgccc      1860
cgcagcagcc aggaggagaa agatgagaag gagaaggaaa aggaggcgga gaaggaggag      1920
gagaagccgg aggtggagaa cgacaaggaa gacctcctca aggagaagac agacgacacc      1980
tcaggggagg acaacgacga aaggaggct gtggcctcca aaggccgcaa aactgccaac       2040
agccagggaa gacgcaaagg ccgcatcacc cgctcaatgg ctaatgaggc caacagcgag      2100
gaggccatca ccccccagca gagcgccgag ctggcctcca tggagctgaa tgagagttct      2160
cgctggacag aagaagaaat ggaaacagcc aagaaggtc tcctggaaca cggccgcaac       2220
tggtcggcca tcgcccggat ggtgggctcc aagactgtgt cgcagtgtaa gaacttctac      2280
ttcaactaca agaagaggca gaacctcgat gagatcttgc agcagcacaa gctgaagatg      2340
gagaaggaga ggaacgcgcg gaggaagaag aagaaagcgc cggcggcggc cagcgaggag      2400
gctgcattcc cgcccgtggt ggaggatgag gagatggagg cgtcgggcgt gagcggaaat      2460
gaggaggaga tggtggagga ggctgaagcc ttacatgcct ctgggaatga ggtgcccaga      2520
ggggaatgca gtggcccagc cactgtcaac aacagctcag acaccgagag catccccttct      2580 cctcacactg aggccgccaa ggacacaggg cagaatgggc caagcccccc agccaccctg      2640
ggcgccgacg ggccaccccc agggccaccc accccaccac cggaggacat cccggcccc        2700 actgagccca cccggcctc tgaagccacc ggagcccta cgcccccacc agcaccccca        2760
tcgccctctg cacctcctcc tgtggtcccc aaggaggaga aggaggagga gaccgcagca       2820
gcgcccccag tggaggaggg ggaggagcag aagcccccccg cggctgagga gctggcagtg     2880
gacacaggga aggccgagga gcccgtcaag agcgagtgca cggaggaagc cgaggagggg     2940
ccggccaagg gcaaggacgc ggaggccgct gaggccacgg ccgaggggc gctcaaggca       3000 gagaagaagg agggcgggag cggcagggcc accacagcca agagctcggg cgcccccag       3060 gacagcgact ccagtgctac ctgcagtgca gacgaggtgg atgaggccga gggcggcgac      3120
aagaaccggc tgctgtcccc caaggcccagc ctcctcaccc cgactggcga ccccggggcc     3180
aatgcctcac cccagaagcc actggacctg aagcagctga agcagcgagc ggctgccatc     3240 cccccccatcc aggtcaccaa agtccatgag ccccccgggg aggacgcagc tcccaccaag     3300 ccagctccc cagccccacc gccaccgcaa aacctgcagc cggagagcga cgcccctcag       3360
cagcctggca gcagccccg gggcaagagc aggagcccgg cacccccgc cgacaaggag       3420 gccttcgcag ccgaggccca gaagctgcct ggggacccc cttgctggac ttccggcctg       3480 cccttcccg tgcccccccg tgaggtgatc aaggcctccc cgcatgcccc ggaccctcta       3540
```

```
gccttctcct acgctccacc tggtcaccca ctgccctgg gcctccatga cactgcccgg    3600
cccgtcctgc cgcgcccacc caccatctcc aacccgcctc ccctcatctc ctctgccaag    3660
caccccagcg tcctcgagag gcaaataggt gccatctccc aaggaatgtc ggtccagctc    3720
cacgtcccgt actcagagca tgccaaggcc ccggtgggcc ctgtcaccat ggggctgccc    3780
ctgcccatgg accccaaaaa gctggcaccc ttcagcggag tgaagcagga gcagctgtcc    3840
ccacggggcc aggctgggcc accggagagc ctggggtgc ccacagccca ggaggcgtcc    3900
gtgctgagag ggacagctct gggctcagtt ccggcggaa gcatcaccaa aggcattccc    3960
agcacacggg tgccctcgga cagcgccatc acataccgcg gctccatcac ccacggcacg    4020
ccagctgacg tcctgtacaa gggcaccatc accaggatca tcggcgagga cagcccgagt    4080
cgcttggacc gcgccggga ggacagcctg cccaagggcc acgtcatcta cgaaggcaag    4140
aagggccacg tcttgtccta tgagggtggc atgtctgtga cccagtgctc caaggaggac    4200
ggcagaagca gctcaggacc cccccatgag acggccgccc caagcgcac ctatgacatg    4260
atggagggcc gcgtgggcag agccatctcc tcagccagca tcgaaggtct catgggccgt    4320
gccatcccgc cggagcgaca cagccccac cacctcaaag agcagcacca catccgcggg    4380
tccatcacac aagggatccc tcggtcctac gtggaggcac aggaggacta cctgcgtcgg    4440
gaggccaagc tcctaaagcg ggagggcacg cctccgcccc caccgccctc acggacctg    4500
accgaggcct acaagacgca ggccctgggc ccctgaagc tgaagccggc ccatgagggc    4560
ctggtggcca cggtgaagga ggcgggccgc tccatccatg agatcccgcg cgaggagctg    4620
cggcacacgc ccgagctgcc cctggccccg cggccgctca aggagggctc catcacgcag    4680
ggcacccgc tcaagtacga caccggcgcg tccaccactg gctccaaaaa gcacgacgta    4740
cgctccctca tcggcagccc cggccggacg ttcccacccg tgcacccgct ggatgtgatg    4800
gccgacgccc gggcactgga acgtgcctgc tacgaggaga gcctgaagag ccggccaggg    4860
accgccagca gctcgggggg ctccattgcg cgcggcgccc cggtcattgt gcctgagctg    4920
ggtaagccgc ggcagagccc cctgacctat gaggaccacg gggcacccct tgccggccac    4980
ctcccacgag gttcgcccgt gaccacgcgg gagcccacgc cgcgcctgca ggagggcagc    5040
ctttcgtcca gcaaggcatc ccaggaccga aagctgacgt cgacgcctcg tgagatcgcc    5100
aagtccccgc acagcaccgt gcccgagcac caccacacc ccatctcgcc ctatgagcac    5160
ctgcttcggg gcgtgagtgg cgtggacctg tatcgcagcc acatccccct ggccttcgac    5220
cccacctcca taccccgcgg catccctctg gacgcagccg ctgcctacta cctgcccga    5280
cacctggccc ccaaccccac ctacccgcac ctgtacccac cctacctcat ccgcggctac    5340
cccgacacgg cggcgctgga gaaccggcag accatcatca tgactacat cacctcgcag    5400
cagatgcacc acaacgcggc caccgccatg gcccagcgag ctgatatgct gaggggcctc    5460
tcgccccgca gtcctcgct ggcactcaac tacgctgcgg gtccccgagg catcatcgac    5520
ctgtcccaag tgccacacct gcctgtgctc gtgccccga caccaggcac cccagccacc    5580
gccatggacc gccttgccta cctccccacc gcgcccccagc ccttcagcag ccgccacagc    5640
agctccccac tctccccagg aggtccaaca cacttgacaa aaccaaccac cacgtcctcg    5700
tccgagcggg agcgagaccg ggatcgagag cgggaccggg atcgggagcg ggaaaagtcc    5760
atcctcacgt ccaccacgac ggtggagcac gcacccatct ggagacctgg tacagagcag    5820
agcagcggca gcagcggcgg gggtgggggc agcagcagcc gccccgcctc ccactcccat    5880
```

```
gcccaccagc actcgcccat ctcccctcgg acccaggatg ccctccagca gagacccagt    5940
gtgcttcaca acacaggcat gaagggtatc atcaccgctg tggagcccag cacgcccacg    6000
gtcctgaggt ccacctccac ctcctcaccc gttcgcccgg ctgccacatt cccacctgcc    6060
acccactgcc cactgggcgg caccctcgat ggggtctacc ctaccctcat ggagcccgtc    6120
ttgctgccca aggaggcccc ccgggtcgcc cggccagagc ggccccgagc agacaccggc    6180
catgccttcc tcgccaagcc cccagcccgc tccgggctgg agcccgcctc ctcccccagc    6240
aagggctcgg agccccggcc cctagtgcct cctgtctctg gccacgccac catcgcccgc    6300 accccctgcga gaaccctcgc acctcaccac gccagcccgg acccgccggc gccacctgcc    6360
tcggcctcgg acccgcaccg ggaaaagact caaagtaaac ccttttccat ccaggaactg    6420
gaactccgtt ctctgggtta ccacggcagc agctacagcc cgaaggggg ggagcccgtc    6480 agccctgtga gctcacccag tctgacccac gacaaggggc tccccaagca cctggaagag    6540
ctcgacaaga gccacctgga gggggagctg cggcccaagc agccaggccc cgtgaagctt    6600
ggcggggagg ccgcccacct cccacacctg cggccgctgc ctgagagcca gccctcgtcc    6660
agcccgctgc tccagaccgc ccaggggtc aaggtcacc agcgggtggt caccctggcc    6720
cagcacatca gtgaggtcat cacacaggac tacacccggc accacccaca gcagctcagc    6780
gcacccctgc ccgcccccct ctactccttc cctggggcca gctgcccgt cctggacctc    6840 cgccgcccac ccagtgacct ctacctcccg ccccccggacc atggtgcccc ggcccgtggc    6900
tcccccacca gcgaagggg caagaggtct ccagagccaa acaagacgtc ggtcttgggt    6960
ggtggtgagg acggtattga acctgtgtcc ccaccggagg gcatgacgga gccagggcac    7020
tcccggagtg ctgtgtaccc gctgctgtac cgggatgggg aacagacgga gcccagcagg    7080
atgggctcca agtctccagg caacaccagc cagccgccag ccttcttcag caagctgacc    7140
gagagcaact ccgccatggt caagtccaag aagcaagaga tcaacaagaa gctgaacacc    7200
cacaaccgga atgagcctga atacaatatc agccagcctg gacgagagat cttcaatatg    7260
cccgccatca ccggaacagg ccttatgacc tatagaagcc aggcggtgca ggaacatgcc    7320
agcaccaaca tggggctgga ggccataatt agaaaggcac tcatgggtaa atatgaccag    7380
tgggaagagt ccccgccgct cagcgccaat gcttttaacc ctctgaatgc cagtgccagc    7440
ctgcccgctg ctatgcccat aaccgctgct gacggacgga gtgaccacac actcacctcg    7500
ccaggtggcg gcgggaaggc caaggtctct ggcagaccca gcagccgaaa agccaagtcc    7560 ccggcccccgg gcctggcatc tggggaccgg ccaccctctg tctcctcagt gcactcggag    7620
ggagactgca accgccggac gccgctcacc aaccgcgtgt gggaggacag gccctcgtcc    7680
gcaggttcca cgccattccc ctacaacccc ctgatcatgc ggctgcaggc gggtgtcatg    7740
gcttccccac ccccaccggg cctccccgcg ggcagcgggc ccctcgctgg cccccaccac    7800
gcctgggacg aggagcccaa gccactgctc tgctcgcagt acgagacact ctccgacagc    7860
gagtgactca gaacagggcg ggggggggg cggtgtcagg tccagcgag ccacaggaac    7920 ggccctgcag gagcagggcg gctgccgact cccccaacca aggaaggagc cctgagtcc    7980 gcctgcgcct ccatccatct gtccgtccag agccggcatc cttgcctgtc taaagcctta    8040
actaagactc ccgccccggg ctggccctgt gcagaccta ctcaggggat gtttacctgg    8100
tgctcgggaa gggagggaa gggccggg aggggcacg gcaggcgtgt ggcagccaca    8160
cgcaggcggc cagggcggcc agggacccaa agcaggatga ccacgcacct ccacgccact    8220
gcctcccccg aatgcatttg gaaccaaagt ctaaactgag ctcgcagccc ccgcgccctc    8280
```

```
cctccgcctc ccatcccgct tagcgctctg gacagatgga cgcaggccct gtccagcccc    8340
cagtgcgctc gttccggtcc ccacagactg ccccagccaa cgagattgct ggaaaccaag    8400
tcaggccagg tgggcggaca aaagggccag gtgcggcctg gggggaacgg atgctccgag    8460
gactggactg tttttttcac acatcgttgc cgcagcggtg ggaaggaaag gcagatgtaa    8520
atgatgtgtt ggtttacagg gtatattttt gataccttca atgaattaat tcagatgttt    8580
tacgcaagga aggacttacc cagtattact gctgctgtgc ttttgatctc tgcttaccgt    8640
tcaagaggcg tgtgcaggcc gacagtcggt gaccccatca ctcgcaggac caaggggcg    8700 gggactgctg gctcacgccc cgctgtgtcc tccctccctc ccttccttgg gcagaatgaa    8760
ttcgatgcgt attctgtggc cgccatctgc gcagggtggt ggtattctgt catttacaca    8820
cgtcgttcta attaaaaagc gaattatact ccagtta                              8857
```

<210> SEQ ID NO 7
<211> LENGTH: 2514
<212> TYPE: PRT
<213> ORGANISM: Homo sapiens

<400> SEQUENCE: 7

```
Met Ser Gly Ser Thr Gln Pro Val Ala Gln Thr Trp Arg Ala Thr Glu
1               5                   10                  15

Pro Arg Tyr Pro Pro His Ser Leu Ser Tyr Pro Val Gln Ile Ala Arg
            20                  25                  30

Thr His Thr Asp Val Gly Leu Leu Glu Tyr Gln His His Ser Arg Asp
        35                  40                  45

Tyr Ala Ser His Leu Ser Pro Gly Ser Ile Ile Gln Pro Gln Arg Arg
    50                  55                  60

Arg Pro Ser Leu Leu Ser Glu Phe Gln Pro Gly Asn Glu Arg Ser Gln
65                  70                  75                  80

Glu Leu His Leu Arg Pro Glu Ser His Ser Tyr Leu Pro Glu Leu Gly
                85                  90                  95

Lys Ser Glu Met Glu Phe Ile Glu Ser Lys Arg Pro Arg Leu Glu Leu
            100                 105                 110

Leu Pro Asp Pro Leu Leu Arg Pro Ser Pro Leu Leu Ala Thr Gly Gln
        115                 120                 125

Pro Ala Gly Ser Glu Asp Leu Thr Lys Asp Arg Ser Leu Thr Gly Lys
    130                 135                 140

Leu Glu Pro Val Ser Pro Pro Ser Pro Pro His Thr Asp Pro Glu Leu
145                 150                 155                 160

Glu Leu Val Pro Pro Arg Leu Ser Lys Glu Glu Leu Ile Gln Asn Met
                165                 170                 175

Asp Arg Val Asp Arg Glu Ile Thr Met Val Glu Gln Gln Ile Ser Lys
            180                 185                 190

Leu Lys Lys Lys Gln Gln Gln Leu Glu Glu Ala Ala Lys Pro Pro
        195                 200                 205

Glu Pro Glu Lys Pro Val Ser Pro Pro Ile Glu Ser Lys His Arg
    210                 215                 220

Ser Leu Val Gln Ile Ile Tyr Asp Glu Asn Arg Lys Lys Ala Glu Ala
225                 230                 235                 240

Ala His Arg Ile Leu Glu Gly Leu Gly Pro Gln Val Glu Leu Pro Leu
                245                 250                 255

Tyr Asn Gln Pro Ser Asp Thr Arg Gln Tyr His Glu Asn Ile Lys Ile
            260                 265                 270
```

```
Asn Gln Ala Met Arg Lys Lys Leu Ile Leu Tyr Phe Lys Arg Arg Asn
        275                 280                 285

His Ala Arg Lys Gln Trp Glu Gln Lys Phe Cys Gln Arg Tyr Asp Gln
        290                 295                 300

Leu Met Glu Ala Trp Glu Lys Lys Val Glu Arg Ile Glu Asn Asn Pro
305                 310                 315                 320

Arg Arg Arg Ala Lys Glu Ser Lys Val Arg Glu Tyr Tyr Glu Lys Gln
                325                 330                 335

Phe Pro Glu Ile Arg Lys Gln Arg Glu Leu Gln Glu Arg Met Gln Ser
                340                 345                 350

Arg Val Gly Gln Arg Gly Ser Gly Leu Ser Met Ser Ala Ala Arg Ser
        355                 360                 365

Glu His Glu Val Ser Glu Ile Ile Asp Gly Leu Ser Glu Gln Glu Asn
        370                 375                 380

Leu Glu Lys Gln Met Arg Gln Leu Ala Val Ile Pro Pro Met Leu Tyr
385                 390                 395                 400

Asp Ala Asp Gln Gln Arg Ile Lys Phe Ile Asn Met Asn Gly Leu Met
                405                 410                 415

Ala Asp Pro Met Lys Val Tyr Lys Asp Arg Gln Val Met Asn Met Trp
                420                 425                 430

Ser Glu Gln Glu Lys Glu Thr Phe Arg Glu Lys Phe Met Gln His Pro
        435                 440                 445

Lys Asn Phe Gly Leu Ile Ala Ser Phe Leu Glu Arg Lys Thr Val Ala
        450                 455                 460

Glu Cys Val Leu Tyr Tyr Tyr Leu Thr Lys Lys Asn Glu Asn Tyr Lys
465                 470                 475                 480

Ser Leu Val Arg Arg Ser Tyr Arg Arg Gly Lys Ser Gln Gln Gln
                485                 490                 495

Gln Gln Gln Gln Gln Gln Gln Gln Gln Gln Gln Gln Pro Met
        500                 505                 510

Pro Arg Ser Ser Gln Glu Glu Lys Asp Glu Lys Glu Lys Glu
        515                 520                 525

Ala Glu Lys Glu Glu Glu Lys Pro Glu Val Glu Asn Asp Lys Glu Asp
        530                 535                 540

Leu Leu Lys Glu Lys Thr Asp Asp Thr Ser Gly Glu Asp Asn Asp Glu
545                 550                 555                 560

Lys Glu Ala Val Ala Ser Lys Gly Arg Lys Thr Ala Asn Ser Gln Gly
                565                 570                 575

Arg Arg Lys Gly Arg Ile Thr Arg Ser Met Ala Asn Glu Ala Asn Ser
                580                 585                 590

Glu Glu Ala Ile Thr Pro Gln Gln Ser Ala Glu Leu Ala Ser Met Glu
        595                 600                 605

Leu Asn Glu Ser Ser Arg Trp Thr Glu Glu Met Glu Thr Ala Lys
        610                 615                 620

Lys Gly Leu Leu Glu His Gly Arg Asn Trp Ser Ala Ile Ala Arg Met
625                 630                 635                 640

Val Gly Ser Lys Thr Val Ser Gln Cys Lys Asn Phe Tyr Phe Asn Tyr
                645                 650                 655

Lys Lys Arg Gln Asn Leu Asp Glu Ile Leu Gln Gln His Lys Leu Lys
                660                 665                 670

Met Glu Lys Glu Arg Asn Ala Arg Arg Lys Lys Lys Ala Pro Ala
        675                 680                 685
```

```
Ala Ala Ser Glu Glu Ala Ala Phe Pro Pro Val Val Glu Asp Glu Glu
690                 695                 700
Met Glu Ala Ser Gly Val Ser Gly Asn Glu Glu Glu Met Val Glu Glu
705                 710                 715                 720
Ala Glu Ala Leu His Ala Ser Gly Asn Glu Val Pro Arg Gly Glu Cys
            725                 730                 735
Ser Gly Pro Ala Thr Val Asn Asn Ser Ser Asp Thr Glu Ser Ile Pro
            740                 745                 750
Ser Pro His Thr Glu Ala Ala Lys Asp Thr Gly Gln Asn Gly Pro Lys
            755                 760                 765
Pro Pro Ala Thr Leu Gly Ala Asp Gly Pro Pro Gly Pro Pro Thr
770                 775                 780
Pro Pro Pro Glu Asp Ile Pro Ala Pro Thr Glu Pro Thr Pro Ala Ser
785                 790                 795                 800
Glu Ala Thr Gly Ala Pro Thr Pro Pro Ala Pro Ser Pro Ser
            805                 810                 815
Ala Pro Pro Pro Val Val Pro Lys Glu Glu Lys Glu Glu Glu Thr Ala
            820                 825                 830
Ala Ala Pro Pro Val Glu Glu Gly Glu Glu Gln Lys Pro Ala Ala
            835                 840                 845
Glu Glu Leu Ala Val Asp Thr Gly Lys Ala Glu Glu Pro Val Lys Ser
850                 855                 860
Glu Cys Thr Glu Glu Ala Glu Glu Gly Pro Ala Lys Gly Lys Asp Ala
865                 870                 875                 880
Glu Ala Ala Glu Ala Thr Ala Glu Gly Ala Leu Lys Ala Glu Lys Lys
            885                 890                 895
Glu Gly Gly Ser Gly Arg Ala Thr Thr Ala Lys Ser Ser Gly Ala Pro
            900                 905                 910
Gln Asp Ser Asp Ser Ser Ala Thr Cys Ser Ala Asp Glu Val Asp Glu
            915                 920                 925
Ala Glu Gly Gly Asp Lys Asn Arg Leu Leu Ser Pro Arg Pro Ser Leu
            930                 935                 940
Leu Thr Pro Thr Gly Asp Pro Arg Ala Asn Ala Ser Pro Gln Lys Pro
945                 950                 955                 960
Leu Asp Leu Lys Gln Leu Lys Gln Arg Ala Ala Ala Ile Pro Pro Ile
            965                 970                 975
Gln Val Thr Lys Val His Glu Pro Pro Arg Glu Asp Ala Ala Pro Thr
            980                 985                 990
Lys Pro Ala Pro Pro Ala Pro Pro Pro Gln Asn Leu Gln Pro Glu
            995                 1000                1005
Ser Asp Ala Pro Gln Gln Pro Gly Ser Ser Pro Arg Gly Lys Ser
    1010                1015                1020
Arg Ser Pro Ala Pro Pro Ala Asp Lys Glu Ala Phe Ala Ala Glu
    1025                1030                1035
Ala Gln Lys Leu Pro Gly Asp Pro Pro Cys Trp Thr Ser Gly Leu
    1040                1045                1050
Pro Phe Pro Val Pro Pro Arg Glu Val Ile Lys Ala Ser Pro His
    1055                1060                1065
Ala Pro Asp Pro Ser Ala Phe Ser Tyr Ala Pro Pro Gly His Pro
    1070                1075                1080
Leu Pro Leu Gly Leu His Asp Thr Ala Arg Pro Val Leu Pro Arg
    1085                1090                1095
Pro Pro Thr Ile Ser Asn Pro Pro Pro Leu Ile Ser Ser Ala Lys
```

-continued

```
                1100                1105                1110

His Pro Ser Val Leu Glu Arg Gln Ile Gly Ala Ile Ser Gln Gly
    1115                1120                1125

Met Ser Val Gln Leu His Val Pro Tyr Ser Glu His Ala Lys Ala
    1130                1135                1140

Pro Val Gly Pro Val Thr Met Gly Leu Pro Leu Pro Met Asp Pro
    1145                1150                1155

Lys Lys Leu Ala Pro Phe Ser Gly Val Lys Gln Glu Gln Leu Ser
    1160                1165                1170

Pro Arg Gly Gln Ala Gly Pro Pro Glu Ser Leu Gly Val Pro Thr
    1175                1180                1185

Ala Gln Glu Ala Ser Val Leu Arg Gly Thr Ala Leu Gly Ser Val
    1190                1195                1200

Pro Gly Gly Ser Ile Thr Lys Gly Ile Pro Ser Thr Arg Val Pro
    1205                1210                1215

Ser Asp Ser Ala Ile Thr Tyr Arg Gly Ser Ile Thr His Gly Thr
    1220                1225                1230

Pro Ala Asp Val Leu Tyr Lys Gly Thr Ile Thr Arg Ile Ile Gly
    1235                1240                1245

Glu Asp Ser Pro Ser Arg Leu Asp Arg Gly Arg Glu Asp Ser Leu
    1250                1255                1260

Pro Lys Gly His Val Ile Tyr Glu Gly Lys Lys Gly His Val Leu
    1265                1270                1275

Ser Tyr Glu Gly Gly Met Ser Val Thr Gln Cys Ser Lys Glu Asp
    1280                1285                1290

Gly Arg Ser Ser Ser Gly Pro Pro His Glu Thr Ala Ala Pro Lys
    1295                1300                1305

Arg Thr Tyr Asp Met Met Glu Gly Arg Val Gly Arg Ala Ile Ser
    1310                1315                1320

Ser Ala Ser Ile Glu Gly Leu Met Gly Arg Ala Ile Pro Pro Glu
    1325                1330                1335

Arg His Ser Pro His His Leu Lys Glu Gln His His Ile Arg Gly
    1340                1345                1350

Ser Ile Thr Gln Gly Ile Pro Arg Ser Tyr Val Glu Ala Gln Glu
    1355                1360                1365

Asp Tyr Leu Arg Arg Glu Ala Lys Leu Leu Lys Arg Glu Gly Thr
    1370                1375                1380

Pro Pro Pro Pro Pro Ser Arg Asp Leu Thr Glu Ala Tyr Lys
    1385                1390                1395

Thr Gln Ala Leu Gly Pro Leu Lys Leu Lys Pro Ala His Glu Gly
    1400                1405                1410

Leu Val Ala Thr Val Lys Glu Ala Gly Arg Ser Ile His Glu Ile
    1415                1420                1425

Pro Arg Glu Glu Leu Arg His Thr Pro Glu Leu Pro Leu Ala Pro
    1430                1435                1440

Arg Pro Leu Lys Glu Gly Ser Ile Thr Gln Gly Thr Pro Leu Lys
    1445                1450                1455

Tyr Asp Thr Gly Ala Ser Thr Thr Gly Ser Lys Lys His Asp Val
    1460                1465                1470

Arg Ser Leu Ile Gly Ser Pro Gly Arg Thr Phe Pro Pro Val His
    1475                1480                1485

Pro Leu Asp Val Met Ala Asp Ala Arg Ala Leu Glu Arg Ala Cys
    1490                1495                1500
```

Tyr Glu Glu Ser Leu Lys Ser Arg Pro Gly Thr Ala Ser Ser Ser
    1505                1510                1515

Gly Gly Ser Ile Ala Arg Gly Ala Pro Val Ile Val Pro Glu Leu
    1520                1525                1530

Gly Lys Pro Arg Gln Ser Pro Leu Thr Tyr Glu Asp His Gly Ala
    1535                1540                1545

Pro Phe Ala Gly His Leu Pro Arg Gly Ser Pro Val Thr Thr Arg
    1550                1555                1560

Glu Pro Thr Pro Arg Leu Gln Glu Gly Ser Leu Ser Ser Ser Lys
    1565                1570                1575

Ala Ser Gln Asp Arg Lys Leu Thr Ser Thr Pro Arg Glu Ile Ala
    1580                1585                1590

Lys Ser Pro His Ser Thr Val Pro Glu His His Pro His Pro Ile
    1595                1600                1605

Ser Pro Tyr Glu His Leu Leu Arg Gly Val Ser Gly Val Asp Leu
    1610                1615                1620

Tyr Arg Ser His Ile Pro Leu Ala Phe Asp Pro Thr Ser Ile Pro
    1625                1630                1635

Arg Gly Ile Pro Leu Asp Ala Ala Ala Tyr Tyr Leu Pro Arg
    1640                1645                1650

His Leu Ala Pro Asn Pro Thr Tyr Pro His Leu Tyr Pro Pro Tyr
    1655                1660                1665

Leu Ile Arg Gly Tyr Pro Asp Thr Ala Ala Leu Glu Asn Arg Gln
    1670                1675                1680

Thr Ile Ile Asn Asp Tyr Ile Thr Ser Gln Gln Met His His Asn
    1685                1690                1695

Ala Ala Thr Ala Met Ala Gln Arg Ala Asp Met Leu Arg Gly Leu
    1700                1705                1710

Ser Pro Arg Glu Ser Ser Leu Ala Leu Asn Tyr Ala Ala Gly Pro
    1715                1720                1725

Arg Gly Ile Ile Asp Leu Ser Gln Val Pro His Leu Pro Val Leu
    1730                1735                1740

Val Pro Pro Thr Pro Gly Thr Pro Ala Thr Ala Met Asp Arg Leu
    1745                1750                1755

Ala Tyr Leu Pro Thr Ala Pro Gln Pro Phe Ser Ser Arg His Ser
    1760                1765                1770

Ser Ser Pro Leu Ser Pro Gly Gly Pro Thr His Leu Thr Lys Pro
    1775                1780                1785

Thr Thr Thr Ser Ser Ser Glu Arg Glu Arg Asp Arg Asp Arg Glu
    1790                1795                1800

Arg Asp Arg Asp Arg Glu Arg Glu Lys Ser Ile Leu Thr Ser Thr
    1805                1810                1815

Thr Thr Val Glu His Ala Pro Ile Trp Arg Pro Gly Thr Glu Gln
    1820                1825                1830

Ser Ser Gly Ser Ser Gly Gly Gly Gly Ser Ser Ser Arg Pro
    1835                1840                1845

Ala Ser His Ser His Ala His Gln His Ser Pro Ile Ser Pro Arg
    1850                1855                1860

Thr Gln Asp Ala Leu Gln Gln Arg Pro Ser Val Leu His Asn Thr
    1865                1870                1875

Gly Met Lys Gly Ile Ile Thr Ala Val Glu Pro Ser Thr Pro Thr
    1880                1885                1890

-continued

| | | | | | | | | | | | |
|---|---|---|---|---|---|---|---|---|---|---|---|
| Val | Leu | Arg | Ser | Thr | Ser | Thr | Ser | Ser | Pro | Val | Arg | Pro | Ala | Ala |
| | 1895 | | | | 1900 | | | | | 1905 | | | | |
| Thr | Phe | Pro | Pro | Ala | Thr | His | Cys | Pro | Leu | Gly | Gly | Thr | Leu | Asp |
| 1910 | | | | | 1915 | | | | | 1920 | | | | |
| Gly | Val | Tyr | Pro | Thr | Leu | Met | Glu | Pro | Val | Leu | Leu | Pro | Lys | Glu |
| 1925 | | | | | 1930 | | | | | 1935 | | | | |
| Ala | Pro | Arg | Val | Ala | Arg | Pro | Glu | Arg | Pro | Arg | Ala | Asp | Thr | Gly |
| 1940 | | | | | 1945 | | | | | 1950 | | | | |
| His | Ala | Phe | Leu | Ala | Lys | Pro | Pro | Ala | Arg | Ser | Gly | Leu | Glu | Pro |
| 1955 | | | | | 1960 | | | | | 1965 | | | | |
| Ala | Ser | Ser | Pro | Ser | Lys | Gly | Ser | Glu | Pro | Arg | Pro | Leu | Val | Pro |
| 1970 | | | | | 1975 | | | | | 1980 | | | | |
| Pro | Val | Ser | Gly | His | Ala | Thr | Ile | Ala | Arg | Thr | Pro | Ala | Lys | Asn |
| 1985 | | | | | 1990 | | | | | 1995 | | | | |
| Leu | Ala | Pro | His | His | Ala | Ser | Pro | Asp | Pro | Pro | Ala | Pro | Pro | Ala |
| 2000 | | | | | 2005 | | | | | 2010 | | | | |
| Ser | Ala | Ser | Asp | Pro | His | Arg | Glu | Lys | Thr | Gln | Ser | Lys | Pro | Phe |
| 2015 | | | | | 2020 | | | | | 2025 | | | | |
| Ser | Ile | Gln | Glu | Leu | Glu | Leu | Arg | Ser | Leu | Gly | Tyr | His | Gly | Ser |
| 2030 | | | | | 2035 | | | | | 2040 | | | | |
| Ser | Tyr | Ser | Pro | Glu | Gly | Val | Glu | Pro | Val | Ser | Pro | Val | Ser | Ser |
| 2045 | | | | | 2050 | | | | | 2055 | | | | |
| Pro | Ser | Leu | Thr | His | Asp | Lys | Gly | Leu | Pro | Lys | His | Leu | Glu | Glu |
| 2060 | | | | | 2065 | | | | | 2070 | | | | |
| Leu | Asp | Lys | Ser | His | Leu | Glu | Gly | Glu | Leu | Arg | Pro | Lys | Gln | Pro |
| 2075 | | | | | 2080 | | | | | 2085 | | | | |
| Gly | Pro | Val | Lys | Leu | Gly | Gly | Glu | Ala | Ala | His | Leu | Pro | His | Leu |
| 2090 | | | | | 2095 | | | | | 2100 | | | | |
| Arg | Pro | Leu | Pro | Glu | Ser | Gln | Pro | Ser | Ser | Ser | Pro | Leu | Leu | Gln |
| 2105 | | | | | 2110 | | | | | 2115 | | | | |
| Thr | Ala | Pro | Gly | Val | Lys | Gly | His | Gln | Arg | Val | Val | Thr | Leu | Ala |
| 2120 | | | | | 2125 | | | | | 2130 | | | | |
| Gln | His | Ile | Ser | Glu | Val | Ile | Thr | Gln | Asp | Tyr | Thr | Arg | His | His |
| 2135 | | | | | 2140 | | | | | 2145 | | | | |
| Pro | Gln | Gln | Leu | Ser | Ala | Pro | Leu | Pro | Ala | Pro | Leu | Tyr | Ser | Phe |
| 2150 | | | | | 2155 | | | | | 2160 | | | | |
| Pro | Gly | Ala | Ser | Cys | Pro | Val | Leu | Asp | Leu | Arg | Arg | Pro | Pro | Ser |
| 2165 | | | | | 2170 | | | | | 2175 | | | | |
| Asp | Leu | Tyr | Leu | Pro | Pro | Pro | Asp | His | Gly | Ala | Pro | Ala | Arg | Gly |
| 2180 | | | | | 2185 | | | | | 2190 | | | | |
| Ser | Pro | His | Ser | Glu | Gly | Gly | Lys | Arg | Ser | Pro | Glu | Pro | Asn | Lys |
| 2195 | | | | | 2200 | | | | | 2205 | | | | |
| Thr | Ser | Val | Leu | Gly | Gly | Gly | Glu | Asp | Gly | Ile | Glu | Pro | Val | Ser |
| 2210 | | | | | 2215 | | | | | 2220 | | | | |
| Pro | Pro | Glu | Gly | Met | Thr | Glu | Pro | Gly | His | Ser | Arg | Ser | Ala | Val |
| 2225 | | | | | 2230 | | | | | 2235 | | | | |
| Tyr | Pro | Leu | Leu | Tyr | Arg | Asp | Gly | Glu | Gln | Thr | Glu | Pro | Ser | Arg |
| 2240 | | | | | 2245 | | | | | 2250 | | | | |
| Met | Gly | Ser | Lys | Ser | Pro | Gly | Asn | Thr | Ser | Gln | Pro | Pro | Ala | Phe |
| 2255 | | | | | 2260 | | | | | 2265 | | | | |
| Phe | Ser | Lys | Leu | Thr | Glu | Ser | Asn | Ser | Ala | Met | Val | Lys | Ser | Lys |
| 2270 | | | | | 2275 | | | | | 2280 | | | | |
| Lys | Gln | Glu | Ile | Asn | Lys | Lys | Leu | Asn | Thr | His | Asn | Arg | Asn | Glu |

-continued

| | | | | | | 2285 | | | 2290 | | | 2295 | | |
|---|---|---|---|---|---|---|---|---|---|---|---|---|---|---|

Pro Glu Tyr Asn Ile Ser Gln Pro Gly Thr Glu Ile Phe Asn Met
    2300                         2305                       2310

Pro Ala Ile Thr Gly Thr Gly Leu Met Thr Tyr Arg Ser Gln Ala
    2315                         2320                       2325

Val Gln Glu His Ala Ser Thr Asn Met Gly Leu Glu Ala Ile Ile
    2330                         2335                       2340

Arg Lys Ala Leu Met Gly Lys Tyr Asp Gln Trp Glu Glu Ser Pro
    2345                         2350                       2355

Pro Leu Ser Ala Asn Ala Phe Asn Pro Leu Asn Ala Ser Ala Ser
    2360                         2365                       2370

Leu Pro Ala Ala Met Pro Ile Thr Ala Ala Asp Gly Arg Ser Asp
    2375                         2380                       2385

His Thr Leu Thr Ser Pro Gly Gly Gly Gly Lys Ala Lys Val Ser
    2390                         2395                       2400

Gly Arg Pro Ser Ser Arg Lys Ala Lys Ser Pro Ala Pro Gly Leu
    2405                         2410                       2415

Ala Ser Gly Asp Arg Pro Pro Ser Val Ser Ser Val His Ser Glu
    2420                         2425                       2430

Gly Asp Cys Asn Arg Arg Thr Pro Leu Thr Asn Arg Val Trp Glu
    2435                         2440                       2445

Asp Arg Pro Ser Ser Ala Gly Ser Thr Pro Phe Pro Tyr Asn Pro
    2450                         2455                       2460

Leu Ile Met Arg Leu Gln Ala Gly Val Met Ala Ser Pro Pro Pro
    2465                         2470                       2475

Pro Gly Leu Pro Ala Gly Ser Gly Pro Leu Ala Gly Pro His His
    2480                         2485                       2490

Ala Trp Asp Glu Glu Pro Lys Pro Leu Leu Cys Ser Gln Tyr Glu
    2495                         2500                       2505

Thr Leu Ser Asp Ser Glu
    2510

```
<210> SEQ ID NO 8
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: a, c, t, g, unknown or other

<400> SEQUENCE: 8
rgktcanrgk tca                                                        13

<210> SEQ ID NO 9
<211> LENGTH: 5530
<212> TYPE: DNA
<213> ORGANISM: Homo sapiens

<400> SEQUENCE: 9
ttgttgggcg acttttgcaa caactcgccg cgccgcggcc tccgcgcgcc gccgccgcca     60
ccgcagccgc cggctccccg ccgcccgggc ccgggccggc ccgcgccgggg gccgccgcgc   120 ccgccgcccc tgcctgcgc cgccggccgg gcatgagtta gtcgcagaca tggacaccaa    180
acatttcctg ccgctcgatt tctccaccca ggtgaactcc tccctcacct ccccgacggg   240
```

```
gcgaggctcc atggctgccc cctcgctgca cccgtccctg gggcctggca tcggctcccc    300
gggacagctg cattctccca tcagcaccct gagctccccc atcaacggca tgggcccgcc    360
tttctcggtc atcagctccc ccatgggccc ccactccatg tcggtgccca ccacacccac    420
cctgggcttc agcactggca gcccccagct cagctcacct atgaacccg  tcagcagcag    480
cgaggacatc aagccccccc tgggcctcaa tggcgtcctc aaggtccccg cccacccctc    540
aggaaacatg gcttccttca ccaagcacat ctgcgccatc tgcggggacc gctcctcagg    600
caagcactat ggagtgtaca gctgcgaggg gtgcaagggc ttcttcaagc ggacggtgcg    660
caaggacctg acctacacct gccgcgacaa caaggactgc ctgattgaca gcggcagcg    720
gaaccggtgc cagtactgcc gctaccagaa gtgcctggcc atgggcatga gcgggaagc    780
cgtgcaggag gagcggcagc gtggcaagga ccggaacgag aatgaggtgg agtcgaccag    840
cagcgccaac gaggacatgc cggtggagag gatcctggag gctgagctgg ccgtggagcc    900
caagaccgag acctacgtgg aggcaaacat ggggctgaac cccagctcgc cgaacgaccc    960
tgtcaccaac atttgccaag cagccgacaa acagcttttc accctggtgg agtgggccaa    1020
gcggatccca cacttctcag agctgccc ct ggacgaccag gtcatcctgc tgcgggcagg    1080
ctggaatgag ctgctcatcg cctccttctc ccaccgctcc atcgccgtga aggacgggat    1140
cctcctggcc accgggctgc acgtccaccg gaacagcgcc cacagcgcag gggtgggcgc    1200
catctttgac agggtgctga cggagcttgt gtccaagatg cgggacatgc agatggacaa    1260
gacggagctg ggctgcctgc gcgccatcgt cctctttaac cctgactcca aggggctctc    1320
gaacccggcc gaggtggagg cgctgaggga aaggtctat gcgtccttgg aggcctactg    1380
caagcacaag tacccagagc agccgggaag gttcgctaag ctcttgctcc gcctgccggc    1440
tctgcgctcc atcgggctca aatgcctgga acatctcttc ttcttcaagc tcatcgggga    1500
cacacccatt gacaccttcc ttatggagat gctggaggcg ccgcaccaaa tgacttaggc    1560
ctgcgggccc atcctttgtg cccacccgtt ctggccaccc tgcctggacg ccagctgttc    1620
ttctcagcct gagccctgtc cctgcccttc tctgcctggc ctgtttggac tttggggcac    1680
agcctgtcac tgctctgcct aagagatgtg ttgtcaccct ccttatttct gttactactt    1740
gtctgtggcc cagggcagtg gctttcctga ggcagcagcc ttcgtggcaa gaactagcgt    1800
gagcccagcc aggcgcctcc ccaccgggct ctcaggacac cctgccacac ccacgggc     1860
ttgggcgact acagggtctt cgggcccag  ccctggagct gcaggagttg gaacggggc     1920
ttttgtttcc gttgctgttt atcgatgctg gttttcagaa ttcctgtgtg gcctcctgt     1980
ctggagtgac atcttcatct gctctgaata ctggtgccca ccagcccgt  gacagcttcc    2040
ccctaatcag gaggggacag ctgggggcgc aagctggtgt gtcatcagca aagacctcag    2100
ccgcctcggg gatgagaggg gactcgtggg gcaagcaagc tgccctgtgc tctgagtgag    2160
ggggaaggta gccccttttt ccaaagataa ctcacagttt tgccctcgag ccaatgagaa    2220
catgagctgc cctctgtgca aggtttcggg gccacctcca ggctgcaggg gcgggtcact    2280
cacccccctg ttttctctct gccttggtgt tctggtttca gactcccgac tccccgttca    2340
gaccagagtg ccccggcccc tcccagcct  gagtcttctc cttgctctgc ggggtgggct    2400
gaggcttgtc cttgtttcct gcagggctgg ccctggctcg ggcagggtgg ggcatcacca    2460
cctcactggc cttgctggag gcacagggct ctgcggacct gcagccatct gtgaggcccg    2520
cggggatggg aggggaggag ggtggcctgt tggtttccct cagagggggc aggtggcctg    2580
```

```
gagagagagg ggctcaggaa ctgggagcct cgtgggtggg gcagatgctc cgcggcctgg      2640
agtggctctg ccggggcatt ggtgggaccc ctgctcaggc cttctctctg gctgccagtt      2700
gtgtctaaaa gactcttgga atctgagaac ccggagtcgc agcgccctcg ggcctgggcc      2760
acacgcaggc cctggtggga ccacccagcc tggtattgtc cacggacagc gttgttcacc      2820
cagagcctta cttgggagcc tcactgaacg cctgctctgg ttgaaggtgg ggtgggggcg      2880
gggcttgggg cctccctggc tcagcccagt gcggcctggc gctcctcccg caggctctgc      2940
ccccgggctc cggtggtgcg gggccctctc aggttgaact cgcctctttt gcactggaag      3000
gccctccctt tggcctgagt acttttcccg ttcacgcctc agtcccgtgg acccagcctt      3060
tgtcagtggc aggtgcctga acagagggtg gatggggggg ataccggagg gggtcttgtc      3120
ttcccagccg cagtctagga atgatgcggg ggggtggacg ccttctccat agtctttccc      3180
cacctggagc aggggcttcc tcagtggtga ggggagctgc ctacaggttg gacccgggagg      3240 cagtggcttg gagaggcagc tttccagcct tggtggggaa gaaagtgtcc attctttgcc      3300
ttcctggagc tcccagccag agctgagctt aggcacccga gtggagcctg cagctgagtc      3360
tgtgcccgag acaggctgtc agagattcca gaagcctctc ctccccgccg ccctccaccc      3420 ctgccttttca gcgttgtgga tccctagagg tggcccctg cccgatccac cgtcctgagg      3480
cagagtgttg agcctcatac ctgtaccagg tccccggcca gctgggcccc tcccaggcac      3540
tgccaggaag cccccagctgc ccctggcggg tgtggtggaa atggcaggag ggtgcaggta      3600
ctcttggggc cccagcggtg ggagtgcaaa agacccaacg ccaacacctg gtgccttctg      3660
cagccagcgc ccacccatcc gtgcccggac ccttgggaat gcccgcggct ccagaggaaa      3720
aagcccaggg acggggcctc cgttgcgggg ggtcggctgc ttcttgggaa ctttgtcgtt      3780 tccgcgcgctg gctggctggc tggctggctg taaagcactg aagccccccg gccgccaacc      3840
cctgaaagca gaacctggcc tccctggcca cagcagcctt acccaccgct ctacgtgtcc      3900
cgggcacttc ccgcagcctt cccgtccctt tctcatcggc cttgtagttg tacagtgctg      3960
ttggtttgaa aaggtgatgt gtggggagtg cggctcatca ctgagtagag aggtagaatt      4020
tctatttaac cagacctgta gtagtattac caatccagtt caattaaggt gattttttgt      4080
aattattatt attttggtgg gacaatcttt aattttctaa agatagcact aacatcagct      4140
cattagccac ctgtgcctgt ccccgccttg gccggctgg atgaagcggc ttccccgcag      4200 ggccccccact tcccagtggc tgcttcctgg ggacccaggg caccccggca ccttcaggca      4260
cgctcctcag ctggtcacct cccggctttg ccgttcagat ggggctcctg aggctcagga      4320
gtgaagatgc cacagagccg ggctccccta ggctgcgtcg ggcatgcttg gaagctggcc      4380
tgccaggacc ttccaccctg gggcctgtgt cagccgccgg ccctccgcac cctggaagca      4440
cacggcctct gggaaggaca gccctgacct tcggttttcc gagcacggtg tttcccaaga      4500
attctgggct ggcggcctgg tggcagtgct ggagatgacc ccgagcccct ccccgtgggg      4560
cacccaggag ggccctgccg gaatgtgcag cctgtgggta gtcggctggt gtccctgtcg      4620
tggagctggg gtgcgtgatc tggtgctcgt ccacgcaggt gtgtggtgta aacatgtatg      4680
tgctgtacag agagacgcgt gtggagagag ccgcacacca cgccacccca ggaaaggcgg      4740
agcggttacc agtgtttttgt gtttattttt aatcaagacg tttcccctgt tttcctataa      4800
atttgcttcg tgtaagcaag tacataagga ccctccttttg gtgaaatccg ggttcgaatg      4860
aatatctcaa ggcaggagat gcatctattt taagatgctt tggagcagac agctttagcc      4920
gttcccaatc cttagcaatg ccttagctgg gacgcatagc taatactttta gagaggatga      4980
```

-continued

```
cagatccata aagagagtaa agataagaga aaatgtctaa agcatctgga aaggtaaaaa    5040
aaaaaaatct atttttgtac aaatgtaatt ttatccctca tgtatacttg gatatggcgg    5100
ggggagggct gggactgttt cgtttctgct tctagagatt gaggtgaaag cttcgtccga    5160
gaaacgccag gacagacgat ggcagaggag agggctcctg tgacggcggc gaggcttggg    5220
aggaaaccgc cgcaatgggg gtgtcttccc tcggggcagg agggtgggcc tgaggctttc    5280
aagggttttc ttccctttcg agtaatttttt aaagccttgc tctgttgtgt cctgttgccg    5340
gctctggcct tcctgtgact gactgtgaag tggcttctcc gtacgattgt ctctgaaaca    5400
tcgtggcctc aggtgccagg gtttgatgga cagtagcatt agaattgtgg aaaaggaaca    5460
cgcaaaggga gaagtgtgag aggagaaaca aaatatgagc gtttaaaata catcgccatt    5520
cagttcgttt                                                           5530
```

<210> SEQ ID NO 10
<211> LENGTH: 462
<212> TYPE: PRT
<213> ORGANISM: Homo sapiens

<400> SEQUENCE: 10

```
Met Asp Thr Lys His Phe Leu Pro Leu Asp Phe Ser Thr Gln Val Asn
1               5                   10                  15

Ser Ser Leu Thr Ser Pro Thr Gly Arg Gly Ser Met Ala Ala Pro Ser
            20                  25                  30

Leu His Pro Ser Leu Gly Pro Gly Ile Gly Ser Pro Gly Gln Leu His
        35                  40                  45

Ser Pro Ile Ser Thr Leu Ser Ser Pro Ile Asn Gly Met Gly Pro Pro
    50                  55                  60

Phe Ser Val Ile Ser Ser Pro Met Gly Pro His Ser Met Ser Val Pro
65                  70                  75                  80

Thr Thr Pro Thr Leu Gly Phe Ser Thr Gly Ser Pro Gln Leu Ser Ser
                85                  90                  95

Pro Met Asn Pro Val Ser Ser Ser Glu Asp Ile Lys Pro Pro Leu Gly
            100                 105                 110

Leu Asn Gly Val Leu Lys Val Pro Ala His Pro Ser Gly Asn Met Ala
        115                 120                 125

Ser Phe Thr Lys His Ile Cys Ala Ile Cys Gly Asp Arg Ser Ser Gly
    130                 135                 140

Lys His Tyr Gly Val Tyr Ser Cys Glu Gly Cys Lys Gly Phe Phe Lys
145                 150                 155                 160

Arg Thr Val Arg Lys Asp Leu Thr Tyr Thr Cys Arg Asp Asn Lys Asp
                165                 170                 175

Cys Leu Ile Asp Lys Arg Gln Arg Asn Arg Cys Gln Tyr Cys Arg Tyr
            180                 185                 190

Gln Lys Cys Leu Ala Met Gly Met Lys Arg Glu Ala Val Gln Glu Glu
        195                 200                 205

Arg Gln Arg Gly Lys Asp Arg Asn Glu Asn Glu Val Glu Ser Thr Ser
    210                 215                 220

Ser Ala Asn Glu Asp Met Pro Val Glu Arg Ile Leu Glu Ala Glu Leu
225                 230                 235                 240

Ala Val Glu Pro Lys Thr Glu Thr Tyr Val Glu Ala Asn Met Gly Leu
                245                 250                 255

Asn Pro Ser Ser Pro Asn Asp Pro Val Thr Asn Ile Cys Gln Ala Ala
            260                 265                 270
```

```
Asp Lys Gln Leu Phe Thr Leu Val Glu Trp Ala Lys Arg Ile Pro His
    275                 280                 285

Phe Ser Glu Leu Pro Leu Asp Asp Gln Val Ile Leu Leu Arg Ala Gly
    290                 295                 300

Trp Asn Glu Leu Leu Ile Ala Ser Phe Ser His Arg Ser Ile Ala Val
305                 310                 315                 320

Lys Asp Gly Ile Leu Leu Ala Thr Gly Leu His Val His Arg Asn Ser
            325                 330                 335

Ala His Ser Ala Gly Val Gly Ala Ile Phe Asp Arg Val Leu Thr Glu
        340                 345                 350

Leu Val Ser Lys Met Arg Asp Met Gln Met Asp Lys Thr Glu Leu Gly
            355                 360                 365

Cys Leu Arg Ala Ile Val Leu Phe Asn Pro Asp Ser Lys Gly Leu Ser
        370                 375                 380

Asn Pro Ala Glu Val Glu Ala Leu Arg Glu Lys Val Tyr Ala Ser Leu
385                 390                 395                 400

Glu Ala Tyr Cys Lys His Lys Tyr Pro Glu Gln Pro Gly Arg Phe Ala
                405                 410                 415

Lys Leu Leu Leu Arg Leu Pro Ala Leu Arg Ser Ile Gly Leu Lys Cys
            420                 425                 430

Leu Glu His Leu Phe Phe Phe Lys Leu Ile Gly Asp Thr Pro Ile Asp
        435                 440                 445

Thr Phe Leu Met Glu Met Leu Glu Ala Pro His Gln Met Thr
450                 455                 460

<210> SEQ ID NO 11
<211> LENGTH: 1284
<212> TYPE: DNA
<213> ORGANISM: Homo sapiens

<400> SEQUENCE: 11
cagagaggct gcagacagag aaggatgatg gcgtctgcgg cagcagcgga ggccgagaag      60
ggatctccag ttgtggtggg cctgctagtt gtgggcaata tcattattct gctgtcaggc     120
ctgtccctgt tgctgagac  catatgggtg acagccgacc agtaccgtgt atacccactg     180
atgggagtct caggcaagga tgacgtcttc gctggtgcct ggattgccat cttctgcggc     240
ttctccttct tcatggtagc cagttttggt gtgggtgccg cactctgccg ccgcggtcc      300 atggtcctca cgtacctggt gctcatgctc atcgtctaca tcttcgagtg cgcctcctgc     360
atcacgtcct acacccaccg tgactacatg gtgtccaacc catccctgat caccaagcag     420
atgctgacct tctacagcgc ggacaccgac cagggccagg agctgacccg cctctgggac     480
cgcgtcatga ttgagcaaga atgctgtggc acatctggtc ccatggactg ggtgaacttc     540
acgtcagcct tccgggcggc cactccggag gtggtgttcc cctggccccc actgtgctgt     600
cgccggacgg gaaacttcat cccctcaac  gaggagggct gccgcctggg gcacatggac     660
tacctgttca ccaagggctg cttcgaacac atcggccacg ccatcgacag ctacacgtgg     720
ggtatctcgt ggtttgggtt tgccatcctg atgtggacgc tcccggtcat gctgatagcc     780
atgtatttct acaccatgct ctgagggaca ggaggggaag gcaacataca caccccggac     840
tcctccgcat cctcctcctg cttcctccgc tgggcctgga tggctgcctc acctctcacc     900
tcccaacgtc cctagccctt acgtccttcc acttccaaga tcttttttcca ggttcctgag     960 ccctactgtg tctcaggtgt gccctgaaac cccagggctt gtgtgcacat atccttagcc    1020
```

```
catctttcaa gggacctctc catgatccca cctcccattc acagatacct ctcttgtagc    1080
tctctgacct cctccttcat ggcaggcatc gccattcttg ctgaaccgtt tgtgattgcc    1140
atttgagctc tggaagcctc tattgccatg agagttctgt cacggtcact ttactgtccc    1200
catcatcacc cagcacgggg ctaagcatat actagatagt caataaataa ataataatg     1260 aatgaatgaa aaaaaaaaaa aaaa                                           1284
```

<210> SEQ ID NO 12
<211> LENGTH: 258
<212> TYPE: PRT
<213> ORGANISM: Homo sapiens

<400> SEQUENCE: 12

```
Met Ala Ser Ala Ala Ala Glu Ala Glu Lys Gly Ser Pro Val Val
1               5                   10                  15

Val Gly Leu Leu Val Val Gly Asn Ile Ile Leu Leu Ser Gly Leu
                20                  25                  30

Ser Leu Phe Ala Glu Thr Ile Trp Val Thr Ala Asp Gln Tyr Arg Val
            35                  40                  45

Tyr Pro Leu Met Gly Val Ser Gly Lys Asp Asp Val Phe Ala Gly Ala
        50                  55                  60

Trp Ile Ala Ile Phe Cys Gly Phe Ser Phe Met Val Ala Ser Phe
65                  70                  75                  80

Gly Val Gly Ala Ala Leu Cys Arg Arg Arg Ser Met Val Leu Thr Tyr
                85                  90                  95

Leu Val Leu Met Leu Ile Val Tyr Ile Phe Glu Cys Ala Ser Cys Ile
            100                 105                 110

Thr Ser Tyr Thr His Arg Asp Tyr Met Val Ser Asn Pro Ser Leu Ile
        115                 120                 125

Thr Lys Gln Met Leu Thr Phe Tyr Ser Ala Asp Thr Asp Gln Gly Gln
    130                 135                 140

Glu Leu Thr Arg Leu Trp Asp Arg Val Met Ile Glu Gln Glu Cys Cys
145                 150                 155                 160

Gly Thr Ser Gly Pro Met Asp Trp Val Asn Phe Thr Ser Ala Phe Arg
                165                 170                 175

Ala Ala Thr Pro Glu Val Val Phe Pro Trp Pro Leu Cys Cys Arg
            180                 185                 190

Arg Thr Gly Asn Phe Ile Pro Leu Asn Glu Glu Gly Cys Arg Leu Gly
        195                 200                 205

His Met Asp Tyr Leu Phe Thr Lys Gly Cys Phe Glu His Ile Gly His
    210                 215                 220

Ala Ile Asp Ser Tyr Thr Trp Gly Ile Ser Trp Phe Gly Phe Ala Ile
225                 230                 235                 240

Leu Met Trp Thr Leu Pro Val Met Leu Ile Ala Met Tyr Phe Tyr Thr
                245                 250                 255

Met Leu
```

<210> SEQ ID NO 13
<211> LENGTH: 2060
<212> TYPE: DNA
<213> ORGANISM: Homo sapiens

<400> SEQUENCE: 13

```
acctgggtcg ggtgcagact gcggagcggg ccctaccgtg tgcgcagaaa gaggaggcgc    60
ttgccttcag cttgtgggaa atcccgaaga tggccaaaga caactcaact gttcgttgct   120
```

```
tccagggcct gctgattttt ggaaatgtga ttattggttg ttgcggcatt gccctgactg      180
cggagtgcat cttctttgta tctgaccaac acagcctcta cccactgctt gaagccaccg      240
acaacgatga catctatggg gctgcctgga tcggcatatt tgtgggcatc tgcctcttct      300
gcctgtctgt tctaggcatt gtaggcatca tgaagtccag caggaaaatt cttctggcgt      360
atttcattct gatgtttata gtatatgcct ttgaagtggc atcttgtatc acagcagcaa      420
cacaacaaga cttttcaca cccaacctct tcctgaagca gatgctagag aggtaccaaa       480
acaacagccc tccaaacaat gatgaccagt ggaaaaacaa tggagtcacc aaaacctggg      540
acaggctcat gctccaggac aattgctgtg gcgtaaatgg tccatcagac tggcaaaaat      600
acacatctgc cttccggact gagaataatg atgctgacta ccctggcct cgtcaatgct       660 gtgttatgaa caatcttaaa gaacctctca acctggaggc ttgtaaacta ggcgtgcctg      720
gtttttatca caatcagggc tgctatgaac tgatctctgg tccaatgaac cgacacgcct      780
ggggggttgc ctggtttgga tttgccattc tctgctggac tttttgggtt ctcctgggta      840
ccatgttcta ctggagcaga attgaatatt aagcataaag tgttgccacc atacctcctt      900
ccccgagtga ctctggattt ggtgctggaa ccagctctct cctaatattc cacgtttgtg      960
ccccacacta acgtgtgtgt cttacattgc caagtcagat ggtacggact tcctttagga     1020
tctcaggctt ctgcagttct catgactcct acttttcatc ctagtctagc attctgcaac     1080
atttatatag actgttgaaa ggagaatttg aaaaatgcat aataactact tccatccctg     1140
cttattttta atttgggaaa ataaatacat tcgaaggaac ctgtgttatc acagtaaccc     1200
agagctgtat ttggctagca atctgcctgt atctctcact attatctaaa agaaaccttc     1260
caatgcttct gttgatctca gtattgtcag gggaacagag aagttgggaa agattactg      1320 aaatatacct tttgcatttc tttctagagt agctcccata tatggagatg ggtgattctc     1380
ttgatgccac cttcagatcc ttttattctc cagaataatt cttaacagtg gttcaaattt     1440
cctttcatac cttgaagtat gtgtttagta gcctcaattc tccattaatt aaaagtgtgg     1500
gctgggcgtg ggggctcatg cctgtaatcc cagcactttg ggaggccgag gtgggcagat     1560
cacctgaggt caggagttca agaccagcct ggccaacatg gtgaaacccc gtctctacaa     1620
aaatacaaaa attagccagg cgtgatggca ggtgcctgta atcctagcta cttggcaggc     1680
taacgcagga gaatcacttg accgggagac agaggttgca gtgagctgag atcgtaccta     1740
ttgcactcca tcctggatga agagccaga ctctgtctca aaacaaacaa aaaagcgtgg      1800
ggacttctgg ggacagacaa ggtgcctgtt atatatttac tcagtctttg ccctgaatgg     1860
tctcagcttg agaccatttc aaactggaga gaagcaagcc agccaataga atggggtgat     1920
ttacagggat ttctgtttac tgtcaaaata tttctcatct gcactatgtt tccatttgtg     1980
gtcctgaagg aaattcttat aactcaacat ttgtctggtc ttataagtaa agacagcttt     2040
aaaatctgtt cactttcaaa                                                 2060
```

<210> SEQ ID NO 14
<211> LENGTH: 260
<212> TYPE: PRT
<213> ORGANISM: Homo sapiens

<400> SEQUENCE: 14

```
Met Ala Lys Asp Asn Ser Thr Val Arg Cys Phe Gln Gly Leu Leu Ile
1               5                   10                  15

Phe Gly Asn Val Ile Ile Gly Cys Cys Gly Ile Ala Leu Thr Ala Glu
```

```
                  20                  25                  30
Cys Ile Phe Phe Val Ser Asp Gln His Ser Leu Tyr Pro Leu Leu Glu
             35                  40                  45
Ala Thr Asp Asn Asp Asp Ile Tyr Gly Ala Ala Trp Ile Gly Ile Phe
         50                  55                  60
Val Gly Ile Cys Leu Phe Cys Leu Ser Val Leu Gly Ile Val Gly Ile
 65                  70                  75                  80
Met Lys Ser Ser Arg Lys Ile Leu Leu Ala Tyr Phe Ile Leu Met Phe
                 85                  90                  95
Ile Val Tyr Ala Phe Glu Val Ala Ser Cys Ile Thr Ala Ala Thr Gln
            100                 105                 110
Gln Asp Phe Phe Thr Pro Asn Leu Phe Leu Lys Gln Met Leu Glu Arg
        115                 120                 125
Tyr Gln Asn Asn Ser Pro Pro Asn Asn Asp Asp Gln Trp Lys Asn Asn
        130                 135                 140
Gly Val Thr Lys Thr Trp Asp Arg Leu Met Leu Gln Asp Asn Cys Cys
145                 150                 155                 160
Gly Val Asn Gly Pro Ser Asp Trp Gln Lys Tyr Thr Ser Ala Phe Arg
                165                 170                 175
Thr Glu Asn Asn Asp Ala Asp Tyr Pro Trp Pro Arg Gln Cys Cys Val
            180                 185                 190
Met Asn Asn Leu Lys Glu Pro Leu Asn Leu Glu Ala Cys Lys Leu Gly
        195                 200                 205
Val Pro Gly Phe Tyr His Asn Gln Gly Cys Tyr Glu Leu Ile Ser Gly
        210                 215                 220
Pro Met Asn Arg His Ala Trp Gly Val Ala Trp Phe Gly Phe Ala Ile
225                 230                 235                 240
Leu Cys Trp Thr Phe Trp Val Leu Leu Gly Thr Met Phe Tyr Trp Ser
                245                 250                 255
Arg Ile Glu Tyr
            260

<210> SEQ ID NO 15
<211> LENGTH: 947
<212> TYPE: DNA
<213> ORGANISM: Homo sapiens

<400> SEQUENCE: 15
acttgcctca ggaaccccag cctgccagca cctattccac ctcccagccc agcatggcac    60
ccctgctgcc catccggacc ttgcccttga tcctgattct gctggctctg ctgtccccag   120
gggctgcaga cttcaacatc tcaagcctct ctggtctgct gtccccggcg ctaacggaga   180
gcctgctggt tgccttgccc cctgtcacc tcacaggagg caatgccaca ctgatggtcc   240
ggagagccaa tgacagcaaa gtggtgacgt ccagctttgt ggtgcctccg tgccgtgggc   300
gcagggaact ggtgagtgtg gtggacagtg gtgctggctt cacagtcact cggctcagtg   360
cataccaggt gacaaacctc gtgccaggaa ccaaattcta catttcctac ctagtgaaga   420
agggacagc cactgagtcc agcagagaga tcccaatgtc cacactccct cgaaggaaca   480
tggaatccat tgggctgggt atgggccgca caggggggcat ggtggtcatc acggtgctgc   540
tctctgtcgc catgttcctg ctggtgctgg gcttcatcat tgccctggca ctgggctccc   600
gcaagtaagg aggtctgccc ggagcagcag cttctccagg aagcccaggg caccatccag   660
ctccccagcc cacctgctcc caggcccag gcctgtggct cccttggtgc cctcgcctcc   720
```

```
tcctcctgcc ctcctctccc ctagagccct ctcctccctc tgtccctctc cttgccccca       780
gtgcctcacc ttccaacact ccattattcc tctcacccca ctcctgtcag agttgacttt       840
cctcccattt taccacttta aacaccccca taacaattcc cccatccttc agtgaactaa       900
gtccctataa taaaggctga ggctgcatct gccaaaaaaa aaaaaaa                     947
```

<210> SEQ ID NO 16
<211> LENGTH: 184
<212> TYPE: PRT
<213> ORGANISM: Homo sapiens

<400> SEQUENCE: 16

```
Met Ala Pro Leu Leu Pro Ile Arg Thr Leu Pro Leu Ile Leu Ile Leu
1               5                   10                  15

Leu Ala Leu Leu Ser Pro Gly Ala Ala Asp Phe Asn Ile Ser Ser Leu
            20                  25                  30

Ser Gly Leu Leu Ser Pro Ala Leu Thr Glu Ser Leu Leu Val Ala Leu
        35                  40                  45

Pro Pro Cys His Leu Thr Gly Gly Asn Ala Thr Leu Met Val Arg Arg
    50                  55                  60

Ala Asn Asp Ser Lys Val Val Thr Ser Ser Phe Val Val Pro Pro Cys
65                  70                  75                  80

Arg Gly Arg Arg Glu Leu Val Ser Val Val Asp Ser Gly Ala Gly Phe
                85                  90                  95

Thr Val Thr Arg Leu Ser Ala Tyr Gln Val Thr Asn Leu Val Pro Gly
            100                 105                 110

Thr Lys Phe Tyr Ile Ser Tyr Leu Val Lys Lys Gly Thr Ala Thr Glu
        115                 120                 125

Ser Ser Arg Glu Ile Pro Met Ser Thr Leu Pro Arg Arg Asn Met Glu
    130                 135                 140

Ser Ile Gly Leu Gly Met Ala Arg Thr Gly Gly Met Val Val Ile Thr
145                 150                 155                 160

Val Leu Leu Ser Val Ala Met Phe Leu Leu Val Leu Gly Phe Ile Ile
                165                 170                 175

Ala Leu Ala Leu Gly Ser Arg Lys
            180
```

<210> SEQ ID NO 17
<211> LENGTH: 1805
<212> TYPE: DNA
<213> ORGANISM: Homo sapiens

<400> SEQUENCE: 17

```
gagacacact ctgccccaac catcctgaag ctacaggtgc tccctcctgg aatctccaat        60
ggatttcagt cgcagaagct tccacagaag cctgagctcc tccttgcagg ccctgtagt       120 cagtacagtg ggcatgcagc gcctcgggac gacacccagc gtttatgggg gtgctggagg      180
ccggggcatc cgcatctcca actccagaca cacggtgaac tatgggagcg atctcacagg      240
cggcggggac ctgtttgttg gcaatgagaa aatggccatg cagaacctaa atgaccgtct      300
agcgagctac ctagaaaagg tgcggaccct ggagcagtcc aactccaaac ttgaagtgca      360
aatcaagcag tggtacgaaa ccaacgcccc gagggctggt cgcgactaca gtgcatatta      420
cagacaaatt gaagagctgc gaagtcagat taaggatgct caactgcaaa atgctcggtg      480
tgtcctgcaa attgataatg ctaaactggc tgctgaggac ttcagactga agtatgagac      540
tgagagagga atacgtctaa cagtggaagc tgatctccaa ggcctgaata aggtctttga      600
```

```
tgacctaacc ctacataaaa cagatttgga gattcaaatt gaagaactga ataaagacct     660
agctctcctc aaaaaggagc atcaggagga agtcgatggc ctacacaagc atctgggcaa     720
cactgtcaat gtggaggttg atgctgctcc aggcctgaac cttggcgtca tcatgaatga     780
aatgaggcag aagtatgaag tcatggccca gaagaacctt caagaggcca agaacagtt      840 tgagagacag actgcagttc tgcagcaaca ggtcacagtg aatactgaag aattaaaagg     900
aactgaggtt caactaacgg agctgagacg cacctcccag agccttgaga tagaactcca     960
gtcccatctc agcatgaaag agtctttgga gcacactcta gaggagacca aggcccgtta    1020
cagcagccca ttagccaacc tccagtcgct gttgagctct ctggaggccc aactgatgca    1080
gattcggagt aacatggaac gccagaacaa cgaataccat atccttcttg acataaagac    1140
tcgacttgaa caggaaattg ctacttaccg ccgccttctg aaggagaag acgtaaaaac     1200 tacagaatat cagttaagca ccctggaaga gagagatata aagaaaacca ggaagattaa    1260
gacagtcgtg caagaagtag tggatggcaa ggtcgtgtca tctgaagtca agaggtgga     1320 agaaaatatc taaatagcta ccagaaggag atgctgctga ggttttgaaa gaaatttggc    1380
tataatctta tctttgctcc ctgcaagaaa tcagccataa gaaagcacta ttaatactct    1440
gcagtgatta gaaggggtgg ggtggcggga atcctattta tcagactctg taattgaata    1500
taaatgtttt actcagagga gctgcaaatt gcctgcaaaa atgaaatcca gtgagcacta    1560
gaatatttaa aacatcatta ctgccatctt tatcatgaag cacatcaatt acaagctgta    1620
gaccacctaa tatcaatttg taggtaatgt tcctgaaaat tgcaatacat ttcaattata    1680
ctaaacctca caaagtagag gaatccatgt aaattgcaaa taaccacctt tctaattttt    1740
tcctgtttct gaattgtaaa acccccttg ggagtccctg gtttcttatt gagccaattt     1800
ctggg                                                                1805
```

<210> SEQ ID NO 18
<211> LENGTH: 424
<212> TYPE: PRT
<213> ORGANISM: Homo sapiens

<400> SEQUENCE: 18

```
Met Asp Phe Ser Arg Arg Ser Phe His Arg Ser Leu Ser Ser Ser Leu
1               5                   10                  15

Gln Ala Pro Val Val Ser Thr Val Gly Met Gln Arg Leu Gly Thr Thr
            20                  25                  30

Pro Ser Val Tyr Gly Gly Ala Gly Gly Arg Gly Ile Arg Ile Ser Asn
        35                  40                  45

Ser Arg His Thr Val Asn Tyr Gly Ser Asp Leu Thr Gly Gly Gly Asp
    50                  55                  60

Leu Phe Val Gly Asn Glu Lys Met Ala Met Gln Asn Leu Asn Asp Arg
65                  70                  75                  80

Leu Ala Ser Tyr Leu Glu Lys Val Arg Thr Leu Glu Gln Ser Asn Ser
                85                  90                  95

Lys Leu Glu Val Gln Ile Lys Gln Trp Tyr Glu Thr Asn Ala Pro Arg
            100                 105                 110

Ala Gly Arg Asp Tyr Ser Ala Tyr Tyr Arg Gln Ile Glu Glu Leu Arg
        115                 120                 125

Ser Gln Ile Lys Asp Ala Gln Leu Gln Asn Ala Arg Cys Val Leu Gln
    130                 135                 140

Ile Asp Asn Ala Lys Leu Ala Ala Glu Asp Phe Arg Leu Lys Tyr Glu
```

```
           145                 150                 155                 160
       Thr Glu Arg Gly Ile Arg Leu Thr Val Glu Ala Asp Leu Gln Gly Leu
                       165                 170                 175

Asn Lys Val Phe Asp Asp Leu Thr Leu His Lys Thr Asp Leu Glu Ile
                       180                 185                 190

Gln Ile Glu Glu Leu Asn Lys Asp Leu Ala Leu Leu Lys Lys Glu His
                       195                 200                 205

Gln Glu Glu Val Asp Gly Leu His Lys His Leu Gly Asn Thr Val Asn
                       210                 215                 220

Val Glu Val Asp Ala Ala Pro Gly Leu Asn Leu Gly Val Ile Met Asn
       225                 230                 235                 240

Glu Met Arg Gln Lys Tyr Glu Val Met Ala Gln Lys Asn Leu Gln Glu
                       245                 250                 255

Ala Lys Glu Gln Phe Glu Arg Gln Thr Ala Val Leu Gln Gln Gln Val
                       260                 265                 270

Thr Val Asn Thr Glu Glu Leu Lys Gly Thr Glu Val Gln Leu Thr Glu
                       275                 280                 285

Leu Arg Arg Thr Ser Gln Ser Leu Glu Ile Glu Leu Gln Ser His Leu
                       290                 295                 300

Ser Met Lys Glu Ser Leu Glu His Thr Leu Glu Thr Lys Ala Arg
       305                 310                 315                 320

Tyr Ser Ser Gln Leu Ala Asn Leu Gln Ser Leu Leu Ser Ser Leu Glu
                       325                 330                 335

Ala Gln Leu Met Gln Ile Arg Ser Asn Met Glu Arg Gln Asn Asn Glu
                       340                 345                 350

Tyr His Ile Leu Leu Asp Ile Lys Thr Arg Leu Glu Gln Glu Ile Ala
                       355                 360                 365

Thr Tyr Arg Arg Leu Leu Glu Gly Glu Asp Val Lys Thr Thr Glu Tyr
                       370                 375                 380

Gln Leu Ser Thr Leu Glu Glu Arg Asp Ile Lys Lys Thr Arg Lys Ile
       385                 390                 395                 400

Lys Thr Val Val Gln Glu Val Val Asp Gly Lys Val Val Ser Ser Glu
                       405                 410                 415

Val Lys Glu Val Glu Glu Asn Ile
                       420

<210> SEQ ID NO 19
<211> LENGTH: 3070
<212> TYPE: DNA
<213> ORGANISM: Homo sapiens

<400> SEQUENCE: 19
ggcgccgtct tgatactttc agaaagaatg cattccctgt aaaaaaaaaa aaaaaatact      60
gagagaggga gagagagaga gaagaagaga gagagacgga gggagagcga gacagagcga     120
gcaacgcaat ctgaccgagc aggtcgtacg ccgccgcctc ctcctcctct ctgctcttcg     180
ctacccaggt gaccccgagga gggactccgc ctccgagcgg ctgaggaccc cggtgcagag     240
gagcctggct cgcagaattg cagagtcgtc gcccctttt acaacctggt cccgttttat     300
tctgccgtac ccagtttttg gattttgtc ttccccttct tctctttgct aaacgacccc     360
tccaagataa ttttaaaaa accttctcct ttgctcacct ttgcttccca gccttcccat     420
ccccccaccg aaagcaaatc attcaacgac cccgaccct ccgacggcag gagccccccg     480
acctcccagg cggaccgccc tccctccccg cgcgcgggtt ccgggcccgg cgagagggcg     540
```

```
cgagcacagc cgaggccatg gaggtgacgg cggaccagcc gcgctgggtg agccaccacc      600
accccgccgt gctcaacggg cagcacccgg acacgcacca cccgggcctc agccactcct      660
acatggacgc ggcgcagtac ccgctgccgg aggaggtgga tgtgcttttt aacatcgacg      720
gtcaaggcaa ccacgtcccg ccctactacg gaaactcggt cagggccacg gtgcagaggt      780
accctccgac ccaccacggg agccaggtgt gccgcccgcc tctgcttcat ggatccctac      840
cctggctgga cggcggcaaa gccctgggca gccaccacac cgcctccccc tggaatctca      900
gccccttctc caagacgtcc atccaccacg gctccccggg gcccctctcc gtctaccccc      960
cggcctcgtc ctcctccttg tcgggggggc acgccagccc gcacctcttc accttcccgc     1020
ccaccccgcc gaaggacgtc tccccggacc catcgctgtc caccccaggc tcggccggct     1080
cggcccggca ggacgagaaa gagtgcctca agtaccaggt gccctgccc gacagcatga     1140 agctggagtc gtcccactcc cgtggcagca tgaccgccct gggtggagcc tcctcgtcga     1200
cccaccaccc catcaccacc tacccgccct acgtgcccga gtacagctcc ggactcttcc     1260
cccccagcag cctgctgggc ggctccccca ccggcttcgg atgcaagtcc aggcccaagg     1320
cccggtccag cacagaaggc agggagtgtg tgaactgtgg ggcaacctcg accccactgt     1380
ggcggcgaga tggcacggga cactacctgt gcaacgcctg cgggctctat cacaaaatga     1440
acggacagaa ccggccctc attaagccca gcgaaggct gtctgcagcc aggagagcag     1500
ggacgtcctg tgcgaactgt cagaccacca caaccacact ctggaggagg aatgccaatg     1560
gggaccctgt ctgcaatgcc tgtgggctct actacaagct tcacaatatt aacagacccc     1620
tgactatgaa gaaggaaggc atccagacca gaaaccgaaa aatgtctagc aaatccaaaa     1680
agtgcaaaaa agtgcatgac tcactggagg acttccccaa gaacagctcg tttaacccgg     1740
ccgccctctc cagacacatg tcctcctga gccacatctc gccttcagc cactccagcc     1800 acatgctgac cacgcccacg ccgatgcacc cgccatccag cctgtccttt ggaccacacc     1860 accctccag catggtcacc gccatgggtt agagccctgc tcgatgctca cagggccccc     1920
agcgagagtc cctgcagtcc ctttcgactt gcattttgc aggagcagta tcatgaagcc     1980
taaacgcgat ggatatatgt ttttgaaggc agaaagcaaa attatgtttg ccactttgca     2040
aaggagctca ctgtggtgtc tgtgttccaa ccactgaatc tggaccccat ctgtgaataa     2100
gccattctga ctcatatccc ctatttaaca gggtctctag tgctgtgaaa aaaaaaatgc     2160
tgaacattgc atataactta tattgtaaga aatactgtac aatgactttta ttgcatctgg     2220 gtagctgtaa ggcatgaagg atgccaagaa gtttaaggaa tatgggagaa atagtgtgga     2280
aattaagaag aaactaggtc tgatattcaa atggacaaac tgccagtttt gtttcctttc     2340
actggccaca gttgtttgat gcattaaaag aaaataaaaa aagaaaaaa gagaaaagaa     2400 aaaaaagaa aaagttgta ggcgaatcat tgttcaaag ctgttggcct ctgcaaagga     2460
aataccagtt ctgggcaatc agtgttaccg ttcaccagtt gccgttgagg gtttcagaga     2520 gccttttct aggcctacat gctttgtgaa caagtccctg taattgttgt ttgtatgtat     2580
aattcaaagc accaaaataa gaaaagatgt agatttattt catcatatta tacagaccga     2640
actgttgtat aaaatttattt actgctagtc ttaagaactg cttctttcg tttgtttgtt     2700 tcaatatttt ccttctctct caattttttgg ttgaataaac tagattacat tcagttggcc     2760
taaggtggtt gtgctcggag ggtttcttgt ttcttttcca ttttgttttt ggatgatatt     2820
tattaaatag cttctaagag tccggcggca tctgtcttgt ccctattcct gcagcctgtg     2880
ctgagggtag cagtgtatga gctaccagcg tgcatgtcag cgaccctggc ccgacaggcc     2940
```

```
acgtcctgca atcggcccgg ctgcctcttc gccctgtcgt gttctgtgtt agtgatcact    3000
gcctttaata cagtctgttg gaataatatt ataagcataa taataaagtg aaatatttt    3060 aaaactacaa                                                           3070
```

<210> SEQ ID NO 20
<211> LENGTH: 444
<212> TYPE: PRT
<213> ORGANISM: Homo sapiens

<400> SEQUENCE: 20

```
Met Glu Val Thr Ala Asp Gln Pro Arg Trp Val Ser His His Pro
1               5                   10                  15

Ala Val Leu Asn Gly Gln His Pro Asp Thr His His Pro Gly Leu Ser
                20                  25                  30

His Ser Tyr Met Asp Ala Ala Gln Tyr Pro Leu Pro Glu Glu Val Asp
            35                  40                  45

Val Leu Phe Asn Ile Asp Gly Gln Gly Asn His Val Pro Pro Tyr Tyr
        50                  55                  60

Gly Asn Ser Val Arg Ala Thr Val Gln Arg Tyr Pro Pro Thr His His
65                  70                  75                  80

Gly Ser Gln Val Cys Arg Pro Pro Leu Leu His Gly Ser Leu Pro Trp
                85                  90                  95

Leu Asp Gly Gly Lys Ala Leu Gly Ser His His Thr Ala Ser Pro Trp
                100                 105                 110

Asn Leu Ser Pro Phe Ser Lys Thr Ser Ile His Gly Ser Pro Gly
            115                 120                 125

Pro Leu Ser Val Tyr Pro Pro Ala Ser Ser Ser Leu Ser Gly Gly
        130                 135                 140

His Ala Ser Pro His Leu Phe Thr Phe Pro Pro Thr Pro Pro Lys Asp
145                 150                 155                 160

Val Ser Pro Asp Pro Ser Leu Ser Thr Pro Gly Ser Ala Gly Ser Ala
                165                 170                 175

Arg Gln Asp Glu Lys Glu Cys Leu Lys Tyr Gln Val Pro Leu Pro Asp
            180                 185                 190

Ser Met Lys Leu Glu Ser Ser His Ser Arg Gly Ser Met Thr Ala Leu
        195                 200                 205

Gly Gly Ala Ser Ser Ser Thr His His Pro Ile Thr Thr Tyr Pro Pro
    210                 215                 220

Tyr Val Pro Glu Tyr Ser Ser Gly Leu Phe Pro Pro Ser Ser Leu Leu
225                 230                 235                 240

Gly Gly Ser Pro Thr Gly Phe Gly Cys Lys Ser Arg Pro Lys Ala Arg
                245                 250                 255

Ser Ser Thr Glu Gly Arg Glu Cys Val Asn Cys Gly Ala Thr Ser Thr
            260                 265                 270

Pro Leu Trp Arg Arg Asp Gly Thr Gly His Tyr Leu Cys Asn Ala Cys
        275                 280                 285

Gly Leu Tyr His Lys Met Asn Gly Gln Asn Arg Pro Leu Ile Lys Pro
    290                 295                 300

Lys Arg Arg Leu Ser Ala Ala Arg Ala Gly Thr Ser Cys Ala Asn
305                 310                 315                 320

Cys Gln Thr Thr Thr Thr Thr Leu Trp Arg Arg Asn Ala Asn Gly Asp
                325                 330                 335

Pro Val Cys Asn Ala Cys Gly Leu Tyr Tyr Lys Leu His Asn Ile Asn
```

```
            340             345             350
Arg Pro Leu Thr Met Lys Lys Glu Gly Ile Gln Thr Arg Asn Arg Lys
        355                 360                 365

Met Ser Ser Lys Ser Lys Lys Cys Lys Lys Val His Asp Ser Leu Glu
    370                 375                 380

Asp Phe Pro Lys Asn Ser Ser Phe Asn Pro Ala Ala Leu Ser Arg His
385                 390                 395                 400

Met Ser Ser Leu Ser His Ile Ser Pro Phe Ser His Ser Ser His Met
                405                 410                 415

Leu Thr Thr Pro Thr Pro Met His Pro Pro Ser Ser Leu Ser Phe Gly
                420                 425                 430

Pro His His Pro Ser Ser Met Val Thr Ala Met Gly
                435                 440

<210> SEQ ID NO 21
<211> LENGTH: 838
<212> TYPE: DNA
<213> ORGANISM: Homo sapiens

<400> SEQUENCE: 21
gggtcacagc accctcctga aaactgcagc ttccttctca ccttgaagaa taatcctaga      60
aaactcacaa aatgtgtgat gcttttgtag gtacctggaa acttgtctcc agtgaaaact    120
ttgatgatta tatgaaagaa gtaggagtgg gctttgccac caggaaagtg gctggcatgg    180
ccaaacctaa catgatcatc agtgtgaatg gggatgtgat caccattaaa tctgaaagta    240
cctttaaaaa tactgagatt tccttcatac tgggccagga atttgacgaa gtcactgcag    300
atgacaggaa agtcaagagc accataacct tagatggggg tgtcctggta catgtgcaga    360
aatgggatgg aaaatcaacc accataaaga gaaaacgaga ggatgataaa ctggtggtgg    420
aatgcgtcat gaaaggcgtc acttccacga gagtttatga gagagcataa gccaagggac    480
gttgacctgg actgaagttc gcattgaact ctacaacatt ctgtgggata tattgttcaa    540
aaagatattg ttgttttcca tgatttagca agcaactaat tttctcccaa gctgatttta    600
ttcaatatgg ttacgttggt taaataaact tttttttagat ttagaaggtg atgtaatgat    660
gtattcattg tgcttatgat gtattcttag tcataactga gtgaaggaaa tgggaaattt    720
gcattatttc tttgttctga tatgaataat aacatatttc ataataattc aaggtaaaaa    780
gggatatcta tggatttccc taggtaggag ataacaagta tgtaccatta ctgaatat       838

<210> SEQ ID NO 22
<211> LENGTH: 132
<212> TYPE: PRT
<213> ORGANISM: Homo sapiens

<400> SEQUENCE: 22

Met Cys Asp Ala Phe Val Gly Thr Trp Lys Leu Val Ser Ser Glu Asn
1               5                   10                  15

Phe Asp Asp Tyr Met Lys Glu Val Gly Val Gly Phe Ala Thr Arg Lys
                20                  25                  30

Val Ala Gly Met Ala Lys Pro Asn Met Ile Ile Ser Val Asn Gly Asp
            35                  40                  45

Val Ile Thr Ile Lys Ser Glu Ser Thr Phe Lys Asn Thr Glu Ile Ser
        50                  55                  60

Phe Ile Leu Gly Gln Glu Phe Asp Glu Val Thr Ala Asp Asp Arg Lys
65                  70                  75                  80
```

Val Lys Ser Thr Ile Thr Leu Asp Gly Gly Val Leu Val His Val Gln
 85                  90                  95

Lys Trp Asp Gly Lys Ser Thr Thr Ile Lys Arg Lys Arg Glu Asp Asp
            100                 105                 110

Lys Leu Val Val Glu Cys Val Met Lys Gly Val Thr Ser Thr Arg Val
        115                 120                 125

Tyr Glu Arg Ala
    130

<210> SEQ ID NO 23
<211> LENGTH: 3396
<212> TYPE: DNA
<213> ORGANISM: Homo sapiens

<400> SEQUENCE: 23

| | | | | | |
|---|---|---|---|---|---|
| gggcttcctc | ttcgcccggg | tggcgttggg | cccgcgcggg | cgctcgggtg | actgcagctg | 60 |
| ctcagctccc | ctccccgcc | ccgcgccgcg | cggccgcccg | tcgcttcgca | cagggctgga | 120 |
| tggttgtatt | gggcagggtg | gctccaggat | gttaggaact | gtgaagatgg | aagggcatga | 180 |
| aaccagcgac | tggaacagct | actacgcaga | cacgcaggag | gcctactcct | ccgtcccggt | 240 |
| cagcaacatg | aactcaggcc | tgggctccat | gaactccatg | aacacctaca | tgaccatgaa | 300 |
| caccatgact | acgagcggca | acatgacccc | ggcgtccttc | aacatgtcct | atgccaaccc | 360 |
| gggcctaggg | gccggcctga | gtccggcgc | agtagccggc | atgccggggg | gctcggcggg | 420 |
| cgccatgaac | agcatgactg | cggccggcgt | gacggccatg | ggtacggcgc | tgagcccgag | 480 |
| cggcatgggc | gccatgggtg | cgcagcaggc | ggcctccatg | aatggcctgg | cccctacgc | 540 |
| ggccgccatg | aacccgtgca | tgagccccat | ggcgtacgcg | ccgtccaacc | tgggccgcag | 600 |
| ccgcgcgggc | ggcggcggcg | acgccaagac | gttcaagcgc | agctaccgc | acgccaagcc | 660 |
| gccctactcg | tacatctcgc | tcatcaccat | ggccatccag | caggcgccca | gcaagatgct | 720 |
| cacgctgagc | gagatctacc | agtggatcat | ggacctcttc | ccctattacc | ggcagaacca | 780 |
| gcagcgctgg | cagaactcca | tccgccactc | gctgtccttc | aatgactgct | tcgtcaaggt | 840 |
| ggcacgctcc | ccggacaagc | cgggcaaggg | ctcctactgg | acgctgcacc | cggactccgg | 900 |
| caacatgttc | gagaacggct | gctacttgcg | ccgccagaag | cgcttcaagt | gcgagaagca | 960 |
| gccgggggcc | ggcggcgggg | cgggagcgg | aagcgggggc | agcggcgcca | agggcggccc | 1020 |
| tgagagccgc | aaggacccct | ctggcgcctc | taaccccagc | gccgactcgc | ccctccatcg | 1080 |
| gggtgtgcac | gggaagaccg | gccagctaga | gggcgcgccg | gccccgggc | cgccgccag | 1140 |
| cccccagact | ctggaccaca | gtggggcgac | ggcgacaggg | ggcgcctcgg | agttgaagac | 1200 |
| tccagcctcc | tcaactgcgc | ccccataag | ctccgggccc | ggggcgctgg | cctctgtgcc | 1260 |
| cgcctctcac | ccggcacacg | gcttggcacc | ccacgagtcc | cagctgcacc | tgaaagggga | 1320 |
| cccccactac | tccttcaacc | acccgttctc | catcaacaac | ctcatgtcct | cctcggagca | 1380 |
| gcagcataag | ctggacttca | aggcatacga | acaggcactg | caatactcgc | cttacggctc | 1440 |
| tacgttgccc | gccagcctgc | ctctaggcag | cgcctcggtg | accaccagga | gccccatcga | 1500 |
| gccctcagcc | ctggagccgg | cgtactacca | aggtgtgtat | tccagacccg | tcctaaacac | 1560 |
| ttcctagctc | ccgggactgg | ggggtttgtc | tggcatagcc | atgctggtag | caagagagaa | 1620 |
| aaaatcaaca | gcaaacaaaa | ccacacaaac | caaaccgtca | acagcataat | aaaatcccaa | 1680 |
| caactatttt | tatttcattt | ttcatgcaca | acctttcccc | cagtgcaaaa | gactgttact | 1740 |
| ttattattgt | attcaaaatt | cattgtgtat | attactacaa | agacaacccc | aaaccaattt | 1800 |

-continued

```
ttttcctgcg aagtttaatg atccacaagt gtatatatga aattctcctc cttccttgcc    1860
cccctctctt tcttccctct ttcccctcca gacattctag tttgtggagg gttatttaaa    1920
aaaacaaaaa aggaagatgg tcaagtttgt aaaatatttg tttgtgcttt ttccccctcc    1980
ttacctgacc ccctacgagt ttacaggtct gtggcaatac tcttaaccat aagaattgaa    2040
atggtgaaga aacaagtata cactagaggc tcttaaaagt attgaaagac aatactgctg    2100
ttatatagca agacataaac agattataaa catcagagcc atttgcttct cagtttacat    2160
ttctgataca tgcagatagc agatgtcttt aaatgaaata catgtatatt gtgtatggac    2220
ttaattatgc acatgctcag atgtgtagac atcctccgta tatttacata acatatagag    2280
gtaatagata ggtgatatac atgatacatt ctcaagagtt gcttgaccga aagttacaag    2340
gaccccaacc cctttgtcct ctctacccac agatggccct gggaatcaat tcctcaggaa    2400
ttgccctcaa gaactctgct tcttgctttg cagagtgcca tggtcatgtc attctgaggt    2460
cacataacac ataaaattag tttctatgag tgtataccat ttaaagaatt ttttttttcag    2520
taaaagggaa tattacaatg ttggaggaga gataagttat agggagctgg atttcaaaac    2580
gtggtccaag attcaaaaat cctattgata gtggccattt taatcattgc catcgtgtgc    2640
ttgtttcatc cagtgttatg cactttccac agttggacat ggtgttagta tagccagacg    2700
ggtttcatta ttatttctct ttgctttctc aatgttaatt tattgcatgg tttattcttt    2760
ttctttacag ctgaaattgc tttaaatgat ggttaaaatt acaaattaaa ttgttaattt    2820
ttatcaatgt gattgtaatt aaaaatattt tgatttaaat aacaaaaata ataccagatt    2880
ttaagccgtg gaaaatgttc ttgatcattt gcagttaagg actttaaata aatcaaatgt    2940
taacaaaaga gcatttctgt tattttttttt cacttaacta aatccgaagt gaatatttct    3000
gaatacgata ttttttcaaat tctagaactg aatataaatg acaaaaatga aaataaaatt    3060
gttttgtctg ttgttataat gaatgtgtag ctagtaaaaa ggagtgaaag aaattcaagt    3120
aaagtgtata agttgatttta atattccaag agttgagatt tttaagattc tttattccca    3180
gtgatgttta cttcattttt ttttttttttt ttgacaccgg cttaagcctt ctgtgtttcc    3240
tttgagcctt ttcactacaa aatcaaatat taatttaact acctttcctc cttccccaat    3300
gtatcacttt tctttatctg agaattcttc caatgaaaat aaaatatcag ctgtggctga    3360
tagaattaag ttgtgtccaa aaaaaaaaaa aaaaaa                              3396
```

<210> SEQ ID NO 24
<211> LENGTH: 472
<212> TYPE: PRT
<213> ORGANISM: Homo sapiens

<400> SEQUENCE: 24

Met Leu Gly Thr Val Lys Met Glu Gly His Glu Thr Ser Asp Trp Asn
1               5                   10                  15

Ser Tyr Tyr Ala Asp Thr Gln Glu Ala Tyr Ser Ser Val Pro Val Ser
            20                  25                  30

Asn Met Asn Ser Gly Leu Gly Ser Met Asn Ser Met Asn Thr Tyr Met
        35                  40                  45

Thr Met Asn Thr Met Thr Thr Ser Gly Asn Met Thr Pro Ala Ser Phe
    50                  55                  60

Asn Met Ser Tyr Ala Asn Pro Gly Leu Gly Ala Gly Leu Ser Pro Gly
65                  70                  75                  80

Ala Val Ala Gly Met Pro Gly Gly Ser Ala Gly Ala Met Asn Ser Met

-continued

```
                85                   90                   95
Thr Ala Ala Gly Val Thr Ala Met Gly Thr Ala Leu Ser Pro Ser Gly
                100                 105                 110
Met Gly Ala Met Gly Ala Gln Gln Ala Ala Ser Met Asn Gly Leu Gly
                115                 120                 125
Pro Tyr Ala Ala Ala Met Asn Pro Cys Met Ser Pro Met Ala Tyr Ala
                130                 135                 140
Pro Ser Asn Leu Gly Arg Ser Arg Ala Gly Gly Gly Asp Ala Lys
145                 150                 155                 160
Thr Phe Lys Arg Ser Tyr Pro His Ala Lys Pro Pro Tyr Ser Tyr Ile
                165                 170                 175
Ser Leu Ile Thr Met Ala Ile Gln Gln Ala Pro Ser Lys Met Leu Thr
                180                 185                 190
Leu Ser Glu Ile Tyr Gln Trp Ile Met Asp Leu Phe Pro Tyr Tyr Arg
                195                 200                 205
Gln Asn Gln Gln Arg Trp Gln Asn Ser Ile Arg His Ser Leu Ser Phe
210                 215                 220
Asn Asp Cys Phe Val Lys Val Ala Arg Ser Pro Asp Lys Pro Gly Lys
225                 230                 235                 240
Gly Ser Tyr Trp Thr Leu His Pro Asp Ser Gly Asn Met Phe Glu Asn
                245                 250                 255
Gly Cys Tyr Leu Arg Arg Gln Lys Arg Phe Lys Cys Glu Lys Gln Pro
                260                 265                 270
Gly Ala Gly Gly Gly Gly Ser Gly Ser Gly Gly Ser Gly Ala Lys
                275                 280                 285
Gly Gly Pro Glu Ser Arg Lys Asp Pro Ser Gly Ala Ser Asn Pro Ser
                290                 295                 300
Ala Asp Ser Pro Leu His Arg Gly Val His Gly Lys Thr Gly Gln Leu
305                 310                 315                 320
Glu Gly Ala Pro Ala Pro Gly Pro Ala Ala Ser Pro Gln Thr Leu Asp
                325                 330                 335
His Ser Gly Ala Thr Ala Thr Gly Gly Ala Ser Glu Leu Lys Thr Pro
                340                 345                 350
Ala Ser Ser Thr Ala Pro Pro Ile Ser Ser Gly Pro Gly Ala Leu Ala
                355                 360                 365
Ser Val Pro Ala Ser His Pro Ala His Gly Leu Ala Pro His Glu Ser
                370                 375                 380
Gln Leu His Leu Lys Gly Asp Pro His Tyr Ser Phe Asn His Pro Phe
385                 390                 395                 400
Ser Ile Asn Asn Leu Met Ser Ser Glu Gln Gln His Lys Leu Asp
                405                 410                 415
Phe Lys Ala Tyr Glu Gln Ala Leu Gln Tyr Ser Pro Tyr Gly Ser Thr
                420                 425                 430
Leu Pro Ala Ser Leu Pro Leu Gly Ser Ala Ser Val Thr Thr Arg Ser
                435                 440                 445
Pro Ile Glu Pro Ser Ala Leu Glu Pro Ala Tyr Tyr Gln Gly Val Tyr
                450                 455                 460
Ser Arg Pro Val Leu Asn Thr Ser
465                 470

<210> SEQ ID NO 25
<211> LENGTH: 4727
<212> TYPE: DNA
<213> ORGANISM: Homo sapiens
```

<400> SEQUENCE: 25

```
ctttcaattc ctctggcaac aaaccacaca ctgggatctg acactgtaga gtgctttctc      60
ttctcttttt ttgggggggg gaggggtgt ggttgcatat ttaaactctc acgcatttat     120
gtactgagga ctgcagtgta ggactttcct gcagaatacc atttgatcct attaagaatt    180
gtccaaatgt tggagcattt gattgaaaaa tccttcttag ccattttaaa gatagctttc    240
caatgattag acgaattgat tctttctgtg actcatcagt tcatttcctg taaaattcat    300
gtcttgctgt tgatttgtga ataagaacca gagcttgtag aaaccacttt aatcatatcc    360
aggagtttgc aagaaacagg tgcttaacac taattcacct cctgaacaag aaaaatgggc    420
tgtgaccgga actgtgggct catcgctggg gctgtcattg gtgctgtcct ggctgtgttt    480
ggaggtattc taatgccagt tggagacctg cttatccaga agacaattaa aaagcaagtt    540
gtcctcgaag aaggtacaat tgcttttaaa aattgggtta aaacaggcac agaagtttac    600
agacagtttt ggatctttga tgtgcaaaat ccacaggaag tgatgatgaa cagcagcaac    660
attcaagtta agcaaagagg tccttatacg tacagagttc gttttctagc caaggaaaat    720
gtaacccagg acgctgagga caacacagtc tctttcctgc agcccaatgg tgccatcttc    780
gaaccttcac tatcagttgg aacagaggct gacaacttca cagttctcaa tctggctgtg    840
gcagctgcat cccatatcta tcaaaatcaa tttgttcaaa tgatcctcaa ttcacttatt    900
aacaagtcaa atcttctat gttccaagtc agaactttga gagaactgtt atgggctat     960
agggatccta ttttgagttt ggttccgtac cctgttacta ccacagttgg tctgttttat   1020
ccttacaaca atactgcaga tggagtttat aaagttttca atggaaaaga taacataagt   1080
aaagttgcca taatcgacac atataaaggt aaaaggaatc tgtcctattg ggaaagtcac   1140
tgcgacatga ttaatggtac agatgcagcc tcatttccac cttttgttga aaaagccag    1200
gtattgcagt tcttttcttc tgatatttgc aggtcaatct atgctgtatt tgaatccgac   1260
gttaatctga aggaatccc tgtgtataga tttgttcttc catccaaggc ctttgcctct   1320
ccagttgaaa acccgacaa ctattgtttc tgcacagaaa aaattatctc aaaaaattgt    1380
acatcatatg gtgtgctaga catcagcaaa tgcaaagaag ggagacctgt gtacatttca   1440
cttcctcatt ttctgtatgc aagtcctgat gtttcagaac ctattgatgg attaaaccca   1500
aatgaagaag aacataggac atacttggat attgaaccta taactggatt cactttacaa   1560
tttgcaaaac ggctgcaggt caacctattg gtcaagccat cagaaaaaat tcaagtatta   1620
aagaatctga gaggaacta tattgtgcct attctttggc ttaatgagac tgggaccatt   1680
ggtgatgaga aggcaaacat gttcagaagt caagtaactg gaaaaataaa cctccttggc   1740
ctgatagaaa tgatcttact cagtgttggt gtggtgatgt tgttgctttt tatgatttca   1800
tattgtgcat gcagatcgaa aacaataaaa taaacctggc tcaagcacaa accaatttgt   1860
gttgttctga ttcaataatt ggtttctggg tggccaattc agaagaagag tgtacatgct   1920
caacaaatcc taggccctgc attcctgtca tcctcatccg ggggaaacac catcatccca   1980
gtagctgccc tattcaactg caacagtctc caggaccatc agtatactgc atttcatgtg   2040
caccaaatat tttgaaagac atttataaat aattggctta tgactcatat ttctctatga   2100
atacttcat acagcaggta taactctttt ctttatgggc ttaaatattt tgtcactgat    2160
cctgcaaatg gacatcattt tagcacacta gcggtttata ttttaaggac cttcattctc   2220
tgttctgcac ctcttctgga aattgagtaa atttttgcttt tttttttta ctcagttgca   2280
```

```
acttacgctt ggcatcttca gaatgctttt ctagcattaa gagatgtaaa tgataaagga    2340
attattgtat gaaatattac aaagcgtaga ctatgcattg ttattcatta taatatttttt   2400 tgctgtcata atcgcctcat aaagacaggt ttcaaccatt aaaatatgtt cttccttaaa    2460
ttcctgtgct ttttctagtt cctcttgtgt cataaaatgt ttatcctaat tttctctctg    2520
aagtatattt tatctgaatc cacatttctt tataaatcca tagtccttgc tgaaatatgc    2580
tttctaaatt tctaccactt tgttctaggc taattttta agctaattgg atgaagaaca     2640
aaaagacatt tggtttcatc ctttacagca gtaggacaat tgcaaaggtt tttcctttt    2700 cataaggaga cacattaata ggtaactctg tttcttgagc aggggttcac ttattctgag    2760
agcattagtt ctcctaaaaa gctccagcat agaaagggaa gataaaccaa attctagctt    2820
gtgttttacc cacagaagga tacaggacaa aggaatagta actggcctgt ttggatacta    2880
aaatcgaaaa taacttttag cctcctcctt atgatagccg ccagagtaaa tgttgagcat    2940
tactacagaa aagccacaaa ccaagaatct acctgtttgg aaagatcttt tgcatctctg    3000
aaggtgctta agcatacttt agtgcctttc cttttaactg ggaagataaa agaagtatct    3060
gtccaagata ttaatatgta agataacatt gtagacatgt tcttctgata atacaaggtt    3120 tattctatttt gcattaggat atttgtggac atgtccatct aatataaagg aaagttttt    3180 aatcattgag gcatgtaggg ctgagttata taatgtagaa acttctaaag ataattggat    3240
gagaatatac atattgaccct gtatattatg actaatcatg actcagatct taatacaggg    3300
atgatctcat agcatttaga tatcagaaaa ggttttgacc tatatgtctt taatattgtt    3360
tgaatacatg tataatcttt atcattcctc agtgtttcat ttctcaaatt ctgtaaaagg    3420
aatataagag gaaagacaat tcatatacaa agacaacgag attaaaaata tgcagtagga    3480
aaaataatta cttaagggga gattttttt acatgaaatc tgggctttgg atgtgtgtgt    3540
gtgtgtgtgt gtgtgtgtgt gtgcacatat gcactgtggt gggagtgggg caacttgggg    3600
aatatgttac atgtgtgact ttgttttgcc ctggcgaagt taatgttgtt cagaaagggt    3660
aaatgtttgg acacttgcaa ttgctcatgg atgaatttat atgtttttagt catagaaaaa    3720 ttgtaccctt tgatagaagc acattttctt tccaaagctg gttattaacc acagaattat    3780
agcaggtatt cataacttaa gttgaaaat caatagcgtc tgcaaatgga ttaacagatt    3840
agagaatcaa cagcatcgga aaataggtta atgcatattg cttctaacaa gtgcatgaag    3900
aaatagaaga agctatgtag ctttcagttc tgacagaaaa gggtgaagga gggtatcatt    3960
tcaagaaaaa aaatagctat cacgcaatgg ttatctctga aaatatttgt attaagatgt    4020
gtatacatgg ccaggcatgg tggctcatgc ctgtaatccc agcactttgg gaggcaggtg    4080
gatcacgagg tcaggagatc aagaccatcc tggccaacat ggtgaaacct catctctact    4140
aaaaatacaa aaatgagcgg ggtgtggtgg cccatgcctg tagtcccagc tgctcgggag    4200
actgaatctc ttgagcctgg gaagcagagg ttgcagtgaa ctgagatcgc gtcactgcac    4260
tccagcctgg tgacagagcg agattccatc tcaaaaaaaa aaaacagtat gcacgtacaa    4320
atttcttaac ctgttatcaa tgtctgagct acataattat cttctctagtt ggagtttgtt   4380 ttaggtgtgt accaactgac atttcagttt ttctgtttga agtccaatgt attagtgact    4440
ctgtggctgc tctcttcacc tgcccttgt ggcctgtcta caattctaaa tggattttga    4500
actcaatgtc gtcgcttctg gtttcctgca tataccaata gcattaccta tgactttttt    4560
tttcctgagc tattttcact gagctgagct aatgaactaa aactgagtta tgtttaatat    4620
ttgtatcaaa tacataaaag gaatactgct ttttcctttt gtggctcaaa ggtagctgca    4680
```
ttttaaaata tttgtgaaaa taaaaacttt tgttattaga aaaatga          4727

<210> SEQ ID NO 26
<211> LENGTH: 472
<212> TYPE: PRT
<213> ORGANISM: Homo sapiens
<400> SEQUENCE: 26

```
Met Gly Cys Asp Arg Asn Cys Gly Leu Ile Ala Gly Ala Val Ile Gly
 1               5                  10                  15

Ala Val Leu Ala Val Phe Gly Gly Ile Leu Met Pro Val Gly Asp Leu
             20                  25                  30

Leu Ile Gln Lys Thr Ile Lys Lys Gln Val Val Leu Glu Glu Gly Thr
         35                  40                  45

Ile Ala Phe Lys Asn Trp Val Lys Thr Gly Thr Glu Val Tyr Arg Gln
     50                  55                  60

Phe Trp Ile Phe Asp Val Gln Asn Pro Gln Glu Val Met Met Asn Ser
 65                  70                  75                  80

Ser Asn Ile Gln Val Lys Gln Arg Gly Pro Tyr Thr Tyr Arg Val Arg
                 85                  90                  95

Phe Leu Ala Lys Glu Asn Val Thr Gln Asp Ala Glu Asp Asn Thr Val
            100                 105                 110

Ser Phe Leu Gln Pro Asn Gly Ala Ile Phe Glu Pro Ser Leu Ser Val
        115                 120                 125

Gly Thr Glu Ala Asp Asn Phe Thr Val Leu Asn Leu Ala Val Ala Ala
    130                 135                 140

Ala Ser His Ile Tyr Gln Asn Gln Phe Val Gln Met Ile Leu Asn Ser
145                 150                 155                 160

Leu Ile Asn Lys Ser Lys Ser Ser Met Phe Gln Val Arg Thr Leu Arg
                165                 170                 175

Glu Leu Leu Trp Gly Tyr Arg Asp Pro Phe Leu Ser Leu Val Pro Tyr
            180                 185                 190

Pro Val Thr Thr Thr Val Gly Leu Phe Tyr Pro Tyr Asn Asn Thr Ala
        195                 200                 205

Asp Gly Val Tyr Lys Val Phe Asn Gly Lys Asp Asn Ile Ser Lys Val
    210                 215                 220

Ala Ile Ile Asp Thr Tyr Lys Gly Lys Arg Asn Leu Ser Tyr Trp Glu
225                 230                 235                 240

Ser His Cys Asp Met Ile Asn Gly Thr Asp Ala Ala Ser Phe Pro Pro
                245                 250                 255

Phe Val Glu Lys Ser Gln Val Leu Gln Phe Phe Ser Ser Asp Ile Cys
            260                 265                 270

Arg Ser Ile Tyr Ala Val Phe Glu Ser Asp Val Asn Leu Lys Gly Ile
        275                 280                 285

Pro Val Tyr Arg Phe Val Leu Pro Ser Lys Ala Phe Ala Ser Pro Val
    290                 295                 300

Glu Asn Pro Asp Asn Tyr Cys Phe Cys Thr Glu Lys Ile Ile Ser Lys
305                 310                 315                 320

Asn Cys Thr Ser Tyr Gly Val Leu Asp Ile Ser Lys Cys Lys Glu Gly
                325                 330                 335

Arg Pro Val Tyr Ile Ser Leu Pro His Phe Leu Tyr Ala Ser Pro Asp
            340                 345                 350

Val Ser Glu Pro Ile Asp Gly Leu Asn Pro Asn Glu Glu Glu His Arg
        355                 360                 365
```

```
Thr Tyr Leu Asp Ile Glu Pro Ile Thr Gly Phe Thr Leu Gln Phe Ala
    370                 375                 380

Lys Arg Leu Gln Val Asn Leu Leu Val Lys Pro Ser Glu Lys Ile Gln
385                 390                 395                 400

Val Leu Lys Asn Leu Lys Arg Asn Tyr Ile Val Pro Ile Leu Trp Leu
                405                 410                 415

Asn Glu Thr Gly Thr Ile Gly Asp Glu Lys Ala Asn Met Phe Arg Ser
                420                 425                 430

Gln Val Thr Gly Lys Ile Asn Leu Leu Gly Leu Ile Glu Met Ile Leu
                435                 440                 445

Leu Ser Val Gly Val Val Met Phe Val Ala Phe Met Ile Ser Tyr Cys
    450                 455                 460

Ala Cys Arg Ser Lys Thr Ile Lys
465                 470

<210> SEQ ID NO 27
<211> LENGTH: 7585
<212> TYPE: DNA
<213> ORGANISM: Homo sapiens

<400> SEQUENCE: 27
aaaaagtgct ttattttccc actccccgga cgcccagcag ggcagtttct tgaccttcgg      60
agccccttc ccgaggatcc gctcgggagc ctccctggc caggagcagg ggattagtct       120
gccccgcgac cggccccagc cacgacgcgg acatcgcccc ctctgtctgg gccgctgtca     180
ctcacgcgcc aaagggccac ggagaaagaa ggggcgggcc ggggcgggcc gggcgagcgg     240
aggcggggac ttgcgccgtc ctgaggctgc ctcctagggt ccggccggcg ctggagctgc     300
ggatttagat tgtcactgcc acctcggtcg gtgcttactt cgctgccagc tggtcgtcgc     360
catgaacccg gacctgcgca gggagcggga ttccgccagc ttcaacccgg agctgcttac     420
acacatcctg gacggcagcc ccgagaaaac ccggcgccgc cgagagatcg agaacatgat     480
cctgaacgac ccagacttcc agcatgagga cttgaacttc ctcactcgca gccagcgtta     540
tgaggtggct gtcaggaaaa gtgccatcat ggtgaagaag atgagggagt ttggcatcgc     600
tgaccctgat gaaattatgt ggtttaaaaa ttttgtgcac cgagggcggc ctgagcctct     660
ggatcttcac ttgggcatgt tcctgcccac cttgcttcac caggcaactg cggagcagca     720
ggagcgcttc ttcatgcccg cctggaactt ggagatcatt ggcacttatg cccagacaga     780
gatgggtcat ggaactcacc ttcgaggctt ggaaaccaca gccacgtatg accctgaaac     840
ccaggagttc attctcaaca gtcctactgt gacctccatt aaatggtggc ctggtgggct     900
tggaaagact tcaaatcatg caatagttct tgcccagctc atcactaagg ggaaatgcta     960
tggattacat gcctttatcg tacctattcg tgaaatcggg acccataagc ctttgccagg    1020
aattaccgtt ggtgacatcg gccccaaatt tggttatgat gagatagaca atggctacct    1080
caaaatggac aaccatcgta ttcccagaga aacatgctg atgaagtatg cccaggtgaa     1140
gcctgatggc catacgtga aaccgctgag taacaagctg acttacggga ccatggtgtt     1200
tgtcaggtcc ttccttgtgg gagaagctgc tcgggtctg tctaaggcgt gcaccattgc     1260
catccgatac agcgctgtga ggcaccagtc tgaaatcaag ccaggtgaac cagaaccaca    1320
gattttggat tttcaaaccc agcagtataa actcttccca ctcctggcca ctgcctatgc     1380
cttccagttt gtgggcgcat acatgaagga gacctatcac cggattaacg aaggcattgg    1440
tcaaggggac ctgagtgaac tgcctgagct tcatgccctc accgctggac tgaaggcttt    1500
```

```
cacctcctgg actgcaaaca ctggcattga agcatgtcgg atggcttgtg gtgggcatgg    1560
ctattctcat tgcagtggtc ttccaaatat ttatgtcaat ttcacctcaa gctgtacctt    1620
tgagggagaa aacactgtca tgatgctcca gacggctagg ttcctgatga aaagttatga    1680
tcaggtgcac tcaggaaagt tggtgtgtgg catggtgtcc tatttgaacg acctgcccag    1740
tcagcgcatc cagccacagc aggtagcagt ctggccaacc atggtggata tcaacagccc    1800
cgaaagccta accgaagcat ataaactccg tgcagccaga ttagtagaaa ttgctgcaaa    1860
aaaccttcaa aaagaagtga ttcacagaaa aagcaaggag gtagcttgga acctaacttc    1920
tgttgacctt gttcgagcaa gtgaggcaca ttgccactat gtggtagtta agctcttttc    1980
agaaaaactc ctcaaaattc aagataaagc cattcaagct gtcttaagga gtttatgtct    2040
gctgtattct ctgtatggaa tcagtcagaa cgcgggggat ttccttcagg ggagcatcat    2100
gacagagcct cagattacac aagtaaacca gcgtgtaaag gagttactca ctctgattcg    2160
ctcagatgct gttgctttgg ttgatgcatt tgattttcag gatgtgacac ttggctctgt    2220
gcttggccgc tatgatggga atgtgtatga aaacttgttt gagtgggcta agaactcccc    2280
actgaacaaa gcagaggtcc acgaatctta caagcacctg aagtcactgc agtccaagct    2340
ctgaagtgtc acaaggacaa gtttaatctg cttcagaaag cgcctgtgtg caactcaaat    2400
tttgtggaat cttttttcgaa ttcaaatagc tatagagcaa atgataaatt gaccccttt    2460
tataaatgga gggaaaaaat gaacagattt cagagattaa atgaaaaaaa gcagatgttt    2520
taagtgcaat taacactgaa agagacctgt taaaccattc agaaaaagct taagaaatgc    2580
gatatgactt cctttttgtaa tgctgctgat cccagtagac tatgacttt gataattagc    2640
agaatttaac tactgagtag ttgattattt tcacatttta attgctaatc actggctata    2700
taagtgtttt taagcaaagg tatttttgaa gtggtgtaga acccttccaa gctttcctgc    2760
tcagtgttct accagactta ccctgggggcc tggcttaaaa gcaggattga agaaaaggga    2820
ctgggggaag gaaacttatt ggaaaacttg atgcgaatga gtttctgctt ggcacagtct    2880
ctgcctgctt gctctccttt gctgatggat tgcatttatc aaactattca tgctagcatt    2940
tttccaacga gggaacttat tccgcacggg cctactgtag gaccattgtc tcgtgtaatt    3000
aggaattttc catttgaagg attgctaaat tgtcacagta gtaggaagta tagggaaacc    3060
tctcagctgt ggcactgttg tagctttgga gtgcagagtg taactctggg acaatcagat    3120
ttcacatatt ctgtcatctt ggcataagcc attaaaagct tggagattac tgtatttggc    3180
attaaaaaaa aatgtcactt aggtcagcac tcccagacga agcacagaaa acccctttga    3240
cacaaaccat gtgttctgat ttttggttca gaaaatattg aaactgtgag ttgtttttt    3300
tttaacaact gggaaaaaac aaaaacaaaa actatagtt agaaaaatgg aagttccata    3360
ggttctatt cttactctat gtatggcttt gttttcagtc tatttctagg agctttctct    3420
gaatcgctaa ttgtcctttc agttgaaatc taatttatac aatcattcta tacttaaagg    3480
ttaaatacat cttaattaat tttttcttaa agtcaatgta agtcactttg ttttgttttt    3540
ttttaatcta cgccatatgc ctcatgaaac cagctgttct agaatcagtc ctgagaatat    3600
ggcttaattc catggaaaca taactcctat cttgggacct gacataatat ctatctatcc    3660
tggggaactg gtaatatgag acttataggt tacagcagaa atgctacatg ttgacaaaag    3720
ccttaatcgt tccactggga gaactaattg ataattgtgt taagattgaa gattaaccct    3780
gtgttaatct cacttgagtc tatcctgaca gtagttcaga ttctgaaaaa tgataaactg    3840
```

```
acctgctaga tgtagaattg tttcaaaatt agtgttgaaa taccttgttc acagatgaat    3900
atctgggcag gatctgaggg tgtttggaat gacacccccc aatccagttg catagatggg    3960
atgtctttgc aggtttgagg agatcatcga cctgcagagc ccccttttgac ccagtacctc   4020
acgttttatt taaaatctaa atctggggcc aggcgtggtg gctcacgcct gtaatccaag    4080
cactttggga ggccgaagcg ggtggatcac ctgaggtcag gagtttgaga ccatcctggc    4140
caacatggtg aaaccccgtc tctactgaaa aaaatacaaa aattagctgg gcatggtggt    4200
agcacgcgcc tgtagtccca gctactcggg aggctgaggc aggataatcg cttgaacttg    4260
gcgggtagag gttgcagtga gccaagatgg tgccactaca ctgcagcctg ggtggctgag    4320
cgagactccg tctcaaaaaa aaaatctaaa tctgacattt gatgctattt ttattaatat    4380
tggaatgttc tgtcttgaac tttattcaat ataatcaaga ataaagatag agtaaacgtc    4440
actgatttgt actattaaga gagaaaaaat atgccacaca actaaacata ggtttaaatt    4500
atgaagaaat ttagaataga ggtttattag atttagggaa cactaagaac aaaaaaggaa    4560
ggagtgatac ctgcctgagt ggacagctgt aaatcagctg taattactgc agttgtacca    4620
atagttgtga gtggctccag tcactttagg agtccttgga agtacttggt acacatttgt    4680
tggctgtacc ttaaaggaag tggcaagtcc agtttgttct ctctaccaca ctagactgcc    4740
actgacaagt ttgggtctgt tggattcaaa attttgtaag ccattttcac aagtacaaag    4800
atacatttta accttgtctt ctccaaaatt actgagtagg aattttattt ttatctttt     4860
gagacagggt atcactgtca cccagactgg agtgcagtgg tgggatcttg cttactgtg     4920
acctctgcct cccgggttca aatggtcctc cctcctcagt ctcctgagta gctgggacga    4980
caggcacgtg ccaccatgcc cagctaattt gttctatttt ttctgtagag acggggtttt    5040
gccatgttgc ccaggctggt ctcagactcc tgggctcaag cgatcatttc gcctcagcct    5100
cccaaagtgc tgagattata ggtgtgagcc acagcatctg gcccagagtg aggagaatta    5160
atgagatttt ttgtgtgtgt tagataatat tgatttaagc ctttttttaa aaagtactct    5220
caaccaaata caaaattgaa aatgtgaggt ttaatagaaa tgtgttggct atttgcaatg    5280
gattttcttc ttgcccaagt gtttggagtt ctactttatg ctctgtattt aaaaattagt    5340
gacctcaaag cagagttgat gacacaggct ttggggcccct catgttcttg tctttagaac   5400
atatcactac taagtatcag cttatcttca gaacattaca acattcaccg tgttcatatg    5460
ctttctgaga agtcaccact tgtaatttca gatcacatac acctgaaggc attttatagt    5520
tcctaaagtt aacatgttag atctttttttt tccacccccat gagggtctca ctctcaccca   5580
ggctggaatg cagtggtgtg attgtagcac actttggcca ccaactcctg ggctcaagtg    5640
atcctcctgc tttggcctcc tctgagaagc tgggattact ggtgcacacc accacacctg    5700
gctaattttt tattttttttt tattttttgga aatagggtat ggctatgttg ccttgggccc   5760
gtcatgaact cctagcctca ggtgacccctc ccacctcagg cctcccaaag ggttgggatt   5820
acaggagtga gctactgcac tgggccaaca tgttaatttt ttttttttttt ttttgagat    5880
ggagtctccc aggcgggaat gcaatggtgc gatctcgact tcactgcaat cttcacctcc    5940
cgggttcgag cgattctccc acctcagcct cctgagtagc tgggattaca ggcacctgcc    6000
atcacgctcg gctaattttt gtattttgag cagagatgga gtttcaccat gttggccagg    6060
tgatctgcac tcccactccc cccacacttc ccaaagtgct gggattacag gcataagcca    6120
caagccacct cacccagcca acatgttaca tcttaattct tggattttct tcactgcagg    6180
gctttgggtg gagaaataaa actcttcaaa tgcatgatct tggagatccc tgtgaatcaa    6240
```

```
taattcttta gacaactgcg gctcaaaatc cctcctttcc cttttccgag ttattccatc   6300
catcttatta gaaaggaagt gaattaggtg taggtggtct gtaacacctg cacatctttt   6360
tatacgtgta gagggtatgc ctgggatata taggttgtct tcaagcagta gctgctacta   6420
cagctagaga gaggaggagt gccaggaaac tgatgacctg agaccaagag tcttgttgat   6480
gttctgactt agataaaggt tttgatcatt ttcatgaaat aatgcaggga agtcatttct   6540
gctgtttctt tactactcca ttcttggagg attagaacaa gtcacactgt aattgactaa   6600
aacgactttt tattttaaaa tattgatggt ggggttttgc tttttttttt tttttttttt   6660
ttgagacgtt gtcttgctct ttcacccagg gtagagtgca gtggcgaaat cttggctcac   6720
tgcaacctct gcctcccggg ttcaagcaat tctctgcctc agcctcctga aagctggga    6780 ttacagcgcc tgccaccatg cctgtctagt ttttttgtat ttttagtaga cagggggtt    6840 tcaccaagtt ggccaggctg gtcttgaact cctgacctcg tgatccaccc acctcggcct   6900
cccaaagtgc tgggattaca ggcgtgagcc accgtgccgg ccagtgtttt ttaactgtcc   6960
acacttacta aattttccag tacttcttcc tatggttcat gatagtaaac acagaaacat   7020
ataaggaaca ttattagagt taccagatgt tagctgttgc atatgtgcac attcctagat   7080
tcaagggtgt ttttgcctta aatttaagtg ggtcattggt tgtcttggga agatcatgga   7140
aaattcggga tttttttagaa ttctgaacca aaatatgttt tgagtgtttc ttagtaaatg   7200
tgtgatcttc caccttccac attcagactg cggactacac ttcataaatg ccttttttatt   7260 tccagttatg gattaacta  aatgactgcc ttgggagcac ataattactt tgctaccttt   7320 ttccccottt gctgttgtgg ctcgagtttg gttctcacct gagaagatgc attgagcata   7380
tgttgttacc cagccctggc ttaatggtgt cctgtggggt aggggtggga ggacgagggg   7440
cacggggcca gagcatgtga atggatcatg gttggacagc tgtgacctgc cagcactgcg   7500
ggtaagcaaa actacaaacc gttctttcct ctgtgacatt gaataaacct taataaaatt   7560
cataattagc acatactaga aaaaa                                        7585
```

<210> SEQ ID NO 28
<211> LENGTH: 660
<212> TYPE: PRT
<213> ORGANISM: Homo sapiens

<400> SEQUENCE: 28

```
Met Asn Pro Asp Leu Arg Arg Glu Arg Asp Ser Ala Ser Phe Asn Pro
1               5                   10                  15

Glu Leu Leu Thr His Ile Leu Asp Gly Ser Pro Glu Lys Thr Arg Arg
            20                  25                  30

Arg Arg Glu Ile Glu Asn Met Ile Leu Asn Asp Pro Asp Phe Gln His
        35                  40                  45

Glu Asp Leu Asn Phe Leu Thr Arg Ser Gln Arg Tyr Glu Val Ala Val
    50                  55                  60

Arg Lys Ser Ala Ile Met Val Lys Lys Met Arg Glu Phe Gly Ile Ala
65                  70                  75                  80

Asp Pro Asp Glu Ile Met Trp Phe Lys Asn Phe Val His Arg Gly Arg
                85                  90                  95

Pro Glu Pro Leu Asp Leu His Leu Gly Met Phe Leu Pro Thr Leu Leu
            100                 105                 110

His Gln Ala Thr Ala Glu Gln Gln Glu Arg Phe Phe Met Pro Ala Trp
        115                 120                 125
```

-continued

```
Asn Leu Glu Ile Ile Gly Thr Tyr Ala Gln Thr Glu Met Gly His Gly
    130                 135                 140

Thr His Leu Arg Gly Leu Glu Thr Thr Ala Thr Tyr Asp Pro Glu Thr
145                 150                 155                 160

Gln Glu Phe Ile Leu Asn Ser Pro Thr Val Thr Ser Ile Lys Trp Trp
                165                 170                 175

Pro Gly Leu Gly Lys Thr Ser Asn His Ala Ile Val Leu Ala Gln
            180                 185                 190

Leu Ile Thr Lys Gly Lys Cys Tyr Gly Leu His Ala Phe Ile Val Pro
        195                 200                 205

Ile Arg Glu Ile Gly Thr His Lys Pro Leu Pro Gly Ile Thr Val Gly
    210                 215                 220

Asp Ile Gly Pro Lys Phe Gly Tyr Asp Glu Ile Asp Asn Gly Tyr Leu
225                 230                 235                 240

Lys Met Asp Asn His Arg Ile Pro Arg Glu Asn Met Leu Met Lys Tyr
                245                 250                 255

Ala Gln Val Lys Pro Asp Gly Thr Tyr Val Lys Pro Leu Ser Asn Lys
            260                 265                 270

Leu Thr Tyr Gly Thr Met Val Phe Val Arg Ser Phe Leu Val Gly Glu
        275                 280                 285

Ala Ala Arg Ala Leu Ser Lys Ala Cys Thr Ile Ala Ile Arg Tyr Ser
    290                 295                 300

Ala Val Arg His Gln Ser Glu Ile Lys Pro Gly Glu Pro Glu Pro Gln
305                 310                 315                 320

Ile Leu Asp Phe Gln Thr Gln Gln Tyr Lys Leu Phe Pro Leu Leu Ala
                325                 330                 335

Thr Ala Tyr Ala Phe Gln Phe Val Gly Ala Tyr Met Lys Glu Thr Tyr
            340                 345                 350

His Arg Ile Asn Glu Gly Ile Gly Gln Gly Asp Leu Ser Glu Leu Pro
        355                 360                 365

Glu Leu His Ala Leu Thr Ala Gly Leu Lys Ala Phe Thr Ser Trp Thr
    370                 375                 380

Ala Asn Thr Gly Ile Glu Ala Cys Arg Met Ala Cys Gly Gly His Gly
385                 390                 395                 400

Tyr Ser His Cys Ser Gly Leu Pro Asn Ile Tyr Val Asn Phe Thr Pro
                405                 410                 415

Ser Cys Thr Phe Glu Gly Glu Asn Thr Val Met Met Leu Gln Thr Ala
            420                 425                 430

Arg Phe Leu Met Lys Ser Tyr Asp Gln Val His Ser Gly Lys Leu Val
        435                 440                 445

Cys Gly Met Val Ser Tyr Leu Asn Asp Leu Pro Ser Gln Arg Ile Gln
    450                 455                 460

Pro Gln Gln Val Ala Val Trp Pro Thr Met Val Asp Ile Asn Ser Pro
465                 470                 475                 480

Glu Ser Leu Thr Glu Ala Tyr Lys Leu Arg Ala Ala Arg Leu Val Glu
                485                 490                 495

Ile Ala Ala Lys Asn Leu Gln Lys Glu Val Ile His Arg Lys Ser Lys
            500                 505                 510

Glu Val Ala Trp Asn Leu Thr Ser Val Asp Leu Val Arg Ala Ser Glu
        515                 520                 525

Ala His Cys His Tyr Val Val Val Lys Leu Phe Ser Glu Lys Leu Leu
    530                 535                 540

Lys Ile Gln Asp Lys Ala Ile Gln Ala Val Leu Arg Ser Leu Cys Leu
```

```
                545                 550                 555                 560
Leu Tyr Ser Leu Tyr Gly Ile Ser Gln Asn Ala Gly Asp Phe Leu Gln
                565                 570                 575

Gly Ser Ile Met Thr Glu Pro Gln Ile Thr Gln Val Asn Gln Arg Val
                580                 585                 590

Lys Glu Leu Leu Thr Leu Ile Arg Ser Asp Ala Val Ala Leu Val Asp
                595                 600                 605

Ala Phe Asp Phe Gln Asp Val Thr Leu Gly Ser Val Leu Gly Arg Tyr
        610                 615                 620

Asp Gly Asn Val Tyr Glu Asn Leu Phe Glu Trp Ala Lys Asn Ser Pro
625                 630                 635                 640

Leu Asn Lys Ala Glu Val His Glu Ser Tyr Lys His Leu Lys Ser Leu
                645                 650                 655

Gln Ser Lys Leu
        660

<210> SEQ ID NO 29
<211> LENGTH: 2477
<212> TYPE: DNA
<213> ORGANISM: Homo sapiens

<400> SEQUENCE: 29
```

| | | | | |
|---|---|---|---|---|
| ataaagtcct gccgggcacc actgggcatc tctttcaagg tttctgctgg gtttctgaac | | | | 60 |
| tgctgggttt ctgcttgctc ctctggagat gcagcgtctg ttgactccag tgaagcgcat | | | | 120 |
| tctgcaactg acaagagcgg tgcaggaaac ctccctcaca cctgctcgcc tgctcccagt | | | | 180 |
| agcccaccaa aggttttcta cagcctctgc tgtccccctg gccaaaacag atacttggcc | | | | 240 |
| aaaggacgtg ggcatcctgg ccctggaggt ctacttccca gcccaatatg tggaccaaac | | | | 300 |
| tgacctggag aagtataaca atgtggaagc aggaaagtat acagtgggct ggggccagac | | | | 360 |
| ccgtatgggc ttctgctcag tccaagagga catcaactcc ctgtgcctga cggtggtgca | | | | 420 |
| acggctgatg gagcgcatac agctcccatg ggactctgtg gcaggctgga agtaggcac | | | | 480 |
| tgagaccatc attgacaagt ccaaagctgt caaaacagtg ctcatggaac tcttccagga | | | | 540 |
| ttcaggcaat actgatattg agggcataga taccaccaat gcctgctacg gtggtactgc | | | | 600 |
| ctccctcttc aatgctgcca actggatgga gtccagttcc tgggatggtc gttatgccat | | | | 660 |
| ggtggtctgt ggagacattg ccgtctatcc cagtggtaat gctcgtccca caggtggggc | | | | 720 |
| cggagctgtg gctatgctga ttgggcccaa ggcccctctg gcctggagc gagggctgag | | | | 780 |
| gggaacccat atggagaatg tgtatgactt ctacaaacca aatttggcct cggagtaccc | | | | 840 |
| aatagtggat gggaagcttt ccatccagtg ctacttgcgg gccttggatc gatgttacac | | | | 900 |
| atcataccgt aaaaaaatcc agaatcagtg aagcaagct ggcagcgatc gacccttcac | | | | 960 |
| ccttgacgat ttacagtaca tgatctttca tacacccttt tgcaagatgg tccagaagtc | | | | 1020 |
| tctggctcgc ctgatgttca atgacttcct gtcagccagc agtgacacac aaaccagctt | | | | 1080 |
| atataagggg ctggaggctt cgggggggct aaagctggaa gacacctaca ccaacaagga | | | | 1140 |
| cctggataaa gcacttctaa aggcctctca ggacatgttc gacaagaaaa ccaaggcttc | | | | 1200 |
| cctttacctc tccactcaca atgggaacat gtacacctca tccctgtacg ggtgcctggc | | | | 1260 |
| ctcgcttctg tcccaccact ctgcccaaga actggctggc tccaggattg gtgccttctc | | | | 1320 |
| ttatggctct ggtttagcag caagtttctt ttcatttcga gtatcccagg atgctgctcc | | | | 1380 |
| aggctctccc ctggacaagt tggtgtccag cacatcagac ctgccaaaac gcctagcctc | | | | 1440 |

-continued

| | |
|---|---|
| ccgaaagtgt gtgtctcctg aggagttcac agaaataatg aaccaaagag agcaattcta | 1500 |
| ccataaggtg aatttctccc cacctggtga cacaaacagc cttttcccag gtacttggta | 1560 |
| cctggagcga gtggacgagc agcatcgccg aaagtatgcc cggcgtcccg tctaaaggtg | 1620 |
| ttctgcagat ccatggaaag cttcctggga acgtatgct agcagagctt ctccccgtga | 1680 |
| atcatatttt taagatccca ctcttagctg gtaaatgaat ttgaatcgac atagtagccc | 1740 |
| cataagcatc agccctgtag agtgaggagc catctctagc gggcccttca ttcctctcca | 1800 |
| tgctgcaatc actgtcctgg gcttatggtg ctatggacta ggggtccttt gtgaaagagc | 1860 |
| aagatggagc aatggagaga agacctcttc ctgaatcact ggactccaga aatgtgcatg | 1920 |
| cagatcagct gttgccttca agatccagat aaactttcct gtcatgtgtt agaactttat | 1980 |
| tattattaat attgttaaac ttctgtgctg ttcctgtgaa tctccaaatt ttgtaccttg | 2040 |
| ttctaagcta atatatagca attaaaaaga gagaaagagg aaatgattcc tgcgtttctt | 2100 |
| ggaacccaga atacaaaccc agcctaacat gcagcaagcc tgctagacct tgtgggtcag | 2160 |
| agggctgggt ccttgcctca caggctgcct ctgtcccctt gcaattccat tctatttctt | 2220 |
| ccacatgcca agtgctatga caggtacaag gcaaataaga acggtagaac acagcttccc | 2280 |
| ccagcccact tccctgttct aaagacacca catagacaga gagcagcaga caggggccag | 2340 |
| caggagctgt agttcagatc ttcttggtca ttccttgccg ctgttatttg aacaaataaa | 2400 |
| cacagcgcaa aggttaacaa gttttgcct tctatagcca aaaataaaaa aataaataaa | 2460 |
| ttttgaaaaa aaaaaaa | 2477 |

```
<210> SEQ ID NO 30
<211> LENGTH: 508
<212> TYPE: PRT
<213> ORGANISM: Homo sapiens

<400> SEQUENCE: 30

Met Gln Arg Leu Leu Thr Pro Val Lys Arg Ile Leu Gln Leu Thr Arg
1               5                   10                  15

Ala Val Gln Glu Thr Ser Leu Thr Pro Ala Arg Leu Leu Pro Val Ala
            20                  25                  30

His Gln Arg Phe Ser Thr Ala Ser Ala Val Pro Leu Ala Lys Thr Asp
        35                  40                  45

Thr Trp Pro Lys Asp Val Gly Ile Leu Ala Leu Glu Val Tyr Phe Pro
    50                  55                  60

Ala Gln Tyr Val Asp Gln Thr Asp Leu Glu Lys Tyr Asn Asn Val Glu
65                  70                  75                  80

Ala Gly Lys Tyr Thr Val Gly Leu Gly Gln Thr Arg Met Gly Phe Cys
                85                  90                  95

Ser Val Gln Glu Asp Ile Asn Ser Leu Cys Leu Thr Val Val Gln Arg
            100                 105                 110

Leu Met Glu Arg Ile Gln Leu Pro Trp Asp Ser Val Gly Arg Leu Glu
        115                 120                 125

Val Gly Thr Glu Thr Ile Ile Asp Lys Ser Lys Ala Val Lys Thr Val
    130                 135                 140

Leu Met Glu Leu Phe Gln Asp Ser Gly Asn Thr Asp Ile Glu Gly Ile
145                 150                 155                 160

Asp Thr Thr Asn Ala Cys Tyr Gly Gly Thr Ala Ser Leu Phe Asn Ala
                165                 170                 175

Ala Asn Trp Met Glu Ser Ser Ser Trp Asp Gly Arg Tyr Ala Met Val
            180                 185                 190
```

```
Val Cys Gly Asp Ile Ala Val Tyr Pro Ser Gly Asn Ala Arg Pro Thr
            195                 200                 205

Gly Gly Ala Gly Ala Val Ala Met Leu Ile Gly Pro Lys Ala Pro Leu
    210                 215                 220

Ala Leu Glu Arg Gly Leu Arg Gly Thr His Met Glu Asn Val Tyr Asp
225                 230                 235                 240

Phe Tyr Lys Pro Asn Leu Ala Ser Glu Tyr Pro Ile Val Asp Gly Lys
                245                 250                 255

Leu Ser Ile Gln Cys Tyr Leu Arg Ala Leu Asp Arg Cys Tyr Thr Ser
            260                 265                 270

Tyr Arg Lys Lys Ile Gln Asn Gln Trp Lys Gln Ala Gly Ser Asp Arg
        275                 280                 285

Pro Phe Thr Leu Asp Asp Leu Gln Tyr Met Ile Phe His Thr Pro Phe
    290                 295                 300

Cys Lys Met Val Gln Lys Ser Leu Ala Arg Leu Met Phe Asn Asp Phe
305                 310                 315                 320

Leu Ser Ala Ser Ser Asp Thr Gln Thr Ser Leu Tyr Lys Gly Leu Glu
                325                 330                 335

Ala Phe Gly Gly Leu Lys Leu Glu Asp Thr Tyr Thr Asn Lys Asp Leu
            340                 345                 350

Asp Lys Ala Leu Leu Lys Ala Ser Gln Asp Met Phe Asp Lys Lys Thr
        355                 360                 365

Lys Ala Ser Leu Tyr Leu Ser Thr His Asn Gly Asn Met Tyr Thr Ser
    370                 375                 380

Ser Leu Tyr Gly Cys Leu Ala Ser Leu Leu Ser His His Ser Ala Gln
385                 390                 395                 400

Glu Leu Ala Gly Ser Arg Ile Gly Ala Phe Ser Tyr Gly Ser Gly Leu
                405                 410                 415

Ala Ala Ser Phe Phe Ser Phe Arg Val Ser Gln Asp Ala Ala Pro Gly
            420                 425                 430

Ser Pro Leu Asp Lys Leu Val Ser Ser Thr Ser Asp Leu Pro Lys Arg
        435                 440                 445

Leu Ala Ser Arg Lys Cys Val Ser Pro Glu Glu Phe Thr Glu Ile Met
    450                 455                 460

Asn Gln Arg Glu Gln Phe Tyr His Lys Val Asn Phe Ser Pro Pro Gly
465                 470                 475                 480

Asp Thr Asn Ser Leu Phe Pro Gly Thr Trp Tyr Leu Glu Arg Val Asp
                485                 490                 495

Glu Gln His Arg Arg Lys Tyr Ala Arg Arg Pro Val
            500                 505

<210> SEQ ID NO 31
<211> LENGTH: 3372
<212> TYPE: DNA
<213> ORGANISM: Homo sapiens

<400> SEQUENCE: 31
taaaaccagg aagtgaagtc cccgagcacg ttagaaagcc tgacatggcc tgactcggga      60
cagctcagag cagggcagaa ctggggacac tctgggccgg ccttctgcct gcatggacgc     120
tctgaagcca ccctgtctct ggaggaacca cgagcgaggg aagaaggaca gggactcgtg     180
tggcaggaag aactcagagc cgggaagccc ccattcacta gaagcactga gagatgcggc     240 ccctcgcag ggtctgaatt tcctgctgct gttcacaaag atgctttta tctttaactt      300
```

-continued

```
tttgttttcc ccacttccga ccccggcgtt gatctgcatc ctgacatttg gagctgccat    360
cttcttgtgg ctgatcacca gacctcaacc cgtcttacct cttcttgacc tgaacaatca    420
gtctgtggga attgagggag gagcacggaa gggggtttcc cagaagaaca atgacctaac    480
aagttgctgc ttctcagatg ccaagactat gtatgaggtt ttccaaagag gactcgctgt    540
gtctgacaat gggccctgct tgggatatag aaaaccaaac cagccctaca gatggctatc    600
ttacaaacag gtgtctgata gagcagagta cctgggttcc tgtctcttgc ataaaggtta    660
taaatcatca ccagaccagt tgtcggcat  ctttgctcag aataggccag agtggatcat    720
ctccgaattg gcttgttaca cgtactctat ggtagctgta cctctgtatg acaccttggg    780
accagaagcc atcgtacata ttgtcaacaa ggctgatatc gccatggtga tctgtgacac    840
accccaaaag gcattggtgc tgataggaa  tgtagagaaa ggcttcaccc cgagcctgaa    900
ggtgatcatc cttatggacc cctttgatga tgacctgaag caaagagggg agaagagtgg    960
aattgagatc ttatccctat atgatgctga gaacctaggc aaagagcact tcagaaaacc   1020
tgtgcctcct agcccagaag acctgagcgt catctgcttc accagtggga ccacaggtga   1080
ccccaaagga gccatgataa cccatcaaaa tattgtttca aatgctgctg cctttctcaa   1140
atgtgtggag catgcttatg agcccactcc tgatgatgtg ccatatcct  acctccctct   1200 ggctcatatg tttgagagga ttgtacaggc tgttgtgtac agctgtggag ccagagttgg   1260
attcttccaa ggggatattc ggttgctggc tgacgacatg aagactttga gcccacatt    1320 gtttcccgcg gtgcctcgac tccttaacag gatctacgat aaggtacaaa atgaggccaa   1380
gacacccttg aagaagttct tgttgaagct ggctgtttcc agtaaattca aagagcttca   1440
aaagggtatc atcaggcatg atagtttctg ggacaagctc atctttgcaa agatccagga   1500
cagcctgggc ggaaggggttc gtgtaattgt cactggagct gcccccatgt ccacttcagt   1560
catgacattc ttccgggcag caatgggatg tcaggtgtat gaagcttatg gtcaaacaga   1620
atgcacaggt ggctgtacat ttacattacc tggggactgg acatcaggtc acgttggggt   1680 gccctggct tgcaattacg tgaagctgga agatgtggct gacatgaact actttacagt    1740
gaataatgaa ggagaggtct gcatcaaggg tacaaacgtg ttcaaaggat acctgaagga   1800
ccctgagaag acacaggaag ccctggacag tgatggctgg cttcacacag agacattgg    1860 tcgctggctc ccgaatggaa ctctgaagat catcgaccgt aaaaagaaca ttttcaagct   1920
ggcccaagga gaatacattg caccagagaa gatagaaaat atctacaaca ggagtcaacc   1980
agtgttacaa atttttgtac acggggagag cttacggtca tccttagtag gagtggtggt   2040
tcctgacaca gatgtacttc cctcatttgc agccaagctt ggggtgaagg gctcctttga   2100
ggaactgtgc caaaaccaag ttgtaaggga agccattta gaagacttgc agaaaattgg   2160
gaaagaaagt ggccttaaaa cttttgaaca ggtcaaagcc attttcttc  atccagagcc   2220 attttccatt gaaaatgggc tcttgacacc aacattgaaa gcaaagcgag gagagctttc   2280
caaatacttt cggacccaaa ttgacagcct gtatgagcac atccaggatt aggataaggt   2340
acttaagtac ctgccggccc actgtgcact gcttgtgaga aaatggatta aaaactattc   2400
ttacatttgt tttgcctttc ctcctatttt tttttaacct gttaaactct aaagccatag   2460
cttttgtttt atattgagac atataatgtg taaacttagt tcccaaataa atcaatcctg   2520 tcttcccat  cttcgatgtt gctaatatta aggcttcagg gctacttta  tcaacatgcc   2580 tgtcttcaag atcccagttt atgttctgtg tccttcctca tgatttccaa ccttaatact   2640
attagtaacc acaagttcaa gggtcaaagg gaccctctgt gccttcttct ttgttttgtg   2700
```

-continued

```
ataaacataa cttgccaaca gtctctatgc ttatttacat cttctactgt tcaaactaag    2760 agattttttaa attctgaaaa actgcttaca attcatgttt tctagccact ccacaaacca    2820
ctaaaatttt agttttagcc tatcactcat gtcaatcata tctatgagac aaatgtctcc    2880
gatgctcttc tgcgtaaatt aaattgtgta ctgaagggaa aagtttgatc ataccaaaca    2940
tttcctaaac tctctagtta gatatctgac ttgggagtat taaaaattgg gtctatgaca    3000
tattgtccaa aaggaatgct gttcttaaag cattatttac agtaggaact ggggagtaaa    3060
tctgttccct acagtttgct gctgagctgg aagctgtggg ggaaggagtt gacaggtggg    3120
cccagtgaac ttttccagta aatgaagcaa gcactgaata aaaacctcct gaactgggaa    3180
caaagatcta caggcaagca agatgcccac acaacaggct tattttctgt gaaggaacca    3240
actgatctcc cccaccccttg gattagagtt cctgctctac cttacccaca gataacacat    3300
gttgtttcta cttgtaaatg taaagtcttt aaaataaact attacagata cttaaaaaaa    3360
aaaaaaaaaa aa                                                        3372
```

<210> SEQ ID NO 32
<211> LENGTH: 739
<212> TYPE: PRT
<213> ORGANISM: Homo sapiens

<400> SEQUENCE: 32

```
Met Asp Ala Leu Lys Pro Pro Cys Leu Trp Arg Asn His Glu Arg Gly
1               5                   10                  15

Lys Lys Asp Arg Asp Ser Cys Gly Arg Lys Asn Ser Glu Pro Gly Ser
            20                  25                  30

Pro His Ser Leu Glu Ala Leu Arg Asp Ala Ala Pro Ser Gln Gly Leu
        35                  40                  45

Asn Phe Leu Leu Leu Phe Thr Lys Met Leu Phe Ile Phe Asn Phe Leu
    50                  55                  60

Phe Ser Pro Leu Pro Thr Pro Ala Leu Ile Cys Ile Leu Thr Phe Gly
65                  70                  75                  80

Ala Ala Ile Phe Leu Trp Leu Ile Thr Arg Pro Gln Pro Val Leu Pro
                85                  90                  95

Leu Leu Asp Leu Asn Asn Gln Ser Val Gly Ile Glu Gly Gly Ala Arg
            100                 105                 110

Lys Gly Val Ser Gln Lys Asn Asn Asp Leu Thr Ser Cys Cys Phe Ser
        115                 120                 125

Asp Ala Lys Thr Met Tyr Glu Val Phe Gln Arg Gly Leu Ala Val Ser
    130                 135                 140

Asp Asn Gly Pro Cys Leu Gly Tyr Arg Lys Pro Asn Gln Pro Tyr Arg
145                 150                 155                 160

Trp Leu Ser Tyr Lys Gln Val Ser Asp Arg Ala Glu Tyr Leu Gly Ser
                165                 170                 175

Cys Leu Leu His Lys Gly Tyr Lys Ser Ser Pro Asp Gln Phe Val Gly
            180                 185                 190

Ile Phe Ala Gln Asn Arg Pro Glu Trp Ile Ile Ser Glu Leu Ala Cys
        195                 200                 205

Tyr Thr Tyr Ser Met Val Ala Val Pro Leu Tyr Asp Thr Leu Gly Pro
    210                 215                 220

Glu Ala Ile Val His Ile Val Asn Lys Ala Asp Ile Ala Met Val Ile
225                 230                 235                 240

Cys Asp Thr Pro Gln Lys Ala Leu Val Leu Ile Gly Asn Val Glu Lys
```

```
            245                 250                 255
Gly Phe Thr Pro Ser Leu Lys Val Ile Ile Leu Met Asp Pro Phe Asp
            260                 265                 270

Asp Asp Leu Lys Gln Arg Gly Glu Lys Ser Gly Ile Glu Ile Leu Ser
            275                 280                 285

Leu Tyr Asp Ala Glu Asn Leu Gly Lys Glu His Phe Arg Lys Pro Val
            290                 295                 300

Pro Pro Ser Pro Glu Asp Leu Ser Val Ile Cys Phe Thr Ser Gly Thr
305                 310                 315                 320

Thr Gly Asp Pro Lys Gly Ala Met Ile Thr His Gln Asn Ile Val Ser
                325                 330                 335

Asn Ala Ala Ala Phe Leu Lys Cys Val Glu His Ala Tyr Glu Pro Thr
                340                 345                 350

Pro Asp Asp Val Ala Ile Ser Tyr Leu Pro Leu Ala His Met Phe Glu
                355                 360                 365

Arg Ile Val Gln Ala Val Val Tyr Ser Cys Gly Ala Arg Val Gly Phe
            370                 375                 380

Phe Gln Gly Asp Ile Arg Leu Leu Ala Asp Asp Met Lys Thr Leu Lys
385                 390                 395                 400

Pro Thr Leu Phe Pro Ala Val Pro Arg Leu Leu Asn Arg Ile Tyr Asp
                405                 410                 415

Lys Val Gln Asn Glu Ala Lys Thr Pro Leu Lys Lys Phe Leu Leu Lys
                420                 425                 430

Leu Ala Val Ser Ser Lys Phe Lys Glu Leu Gln Lys Gly Ile Ile Arg
                435                 440                 445

His Asp Ser Phe Trp Asp Lys Leu Ile Phe Ala Lys Ile Gln Asp Ser
            450                 455                 460

Leu Gly Gly Arg Val Arg Val Ile Val Thr Gly Ala Ala Pro Met Ser
465                 470                 475                 480

Thr Ser Val Met Thr Phe Phe Arg Ala Ala Met Gly Cys Gln Val Tyr
                485                 490                 495

Glu Ala Tyr Gly Gln Thr Glu Cys Thr Gly Gly Cys Thr Phe Thr Leu
                500                 505                 510

Pro Gly Asp Trp Thr Ser Gly His Val Gly Val Pro Leu Ala Cys Asn
            515                 520                 525

Tyr Val Lys Leu Glu Asp Val Ala Asp Met Asn Tyr Phe Thr Val Asn
            530                 535                 540

Asn Glu Gly Glu Val Cys Ile Lys Gly Thr Asn Val Phe Lys Gly Tyr
545                 550                 555                 560

Leu Lys Asp Pro Glu Lys Thr Gln Glu Ala Leu Asp Ser Asp Gly Trp
                565                 570                 575

Leu His Thr Gly Asp Ile Gly Arg Trp Leu Pro Asn Gly Thr Leu Lys
                580                 585                 590

Ile Ile Asp Arg Lys Lys Asn Ile Phe Lys Leu Ala Gln Gly Glu Tyr
            595                 600                 605

Ile Ala Pro Glu Lys Ile Glu Asn Ile Tyr Asn Arg Ser Gln Pro Val
            610                 615                 620

Leu Gln Ile Phe Val His Gly Glu Ser Leu Arg Ser Ser Leu Val Gly
625                 630                 635                 640

Val Val Val Pro Asp Thr Asp Val Leu Pro Ser Phe Ala Ala Lys Leu
                645                 650                 655

Gly Val Lys Gly Ser Phe Glu Glu Leu Cys Gln Asn Gln Val Val Arg
                660                 665                 670
```

```
Glu Ala Ile Leu Glu Asp Leu Gln Lys Ile Gly Lys Glu Ser Gly Leu
            675                 680                 685

Lys Thr Phe Glu Gln Val Lys Ala Ile Phe Leu His Pro Glu Pro Phe
        690                 695                 700

Ser Ile Glu Asn Gly Leu Leu Thr Pro Thr Leu Lys Ala Lys Arg Gly
705                 710                 715                 720

Glu Leu Ser Lys Tyr Phe Arg Thr Gln Ile Asp Ser Leu Tyr Glu His
                725                 730                 735

Ile Gln Asp

<210> SEQ ID NO 33
<211> LENGTH: 2591
<212> TYPE: DNA
<213> ORGANISM: Homo sapiens

<400> SEQUENCE: 33
```

| | | | | | |
|---|---|---|---|---|---|
| ggggccggga | ccggggccag | ggaccagtgg | tgggaggagg | ctgcggcgct | agatgcggac | 60 |
| acctggaccg | ccgcgccgag | gctcccggcg | ctcgctgctc | ccgcggcccg | cgccatgccc | 120 |
| tcctacacgg | tcaccgtggc | cactggcagc | cagtggttcg | ccggcactga | cgactacatc | 180 |
| tacctcagcc | tcgtgggctc | ggcgggctgc | agcgagaagc | acctgctgga | caagcccttc | 240 |
| tacaacgact | cgagcgtgg | cgcggtggat | tcatcgacg | tgactgtgga | cgaggaactg | 300 |
| ggcgagatcc | agctggtcag | aatcgagaag | cgcaagtact | ggctgaatga | cgactggtac | 360 |
| ctgaagtaca | tcacgctgaa | gacgccccac | ggggactaca | tcgagttccc | ctgctaccgc | 420 |
| tggatcaccg | gcgatgtcga | ggttgtcctg | agggatggac | gcgcaaagtt | ggcccgagat | 480 |
| gaccaaattc | acattctcaa | gcaacaccga | cgtaaagaac | tggaaacacg | gcaaaaacaa | 540 |
| tatcgatgga | tggagtggaa | ccctggcttc | cccttgagca | tcgatgccaa | atgccacaag | 600 |
| gatttacccc | gtgatatcca | gtttgatagt | gaaaaaggag | tggactttgt | tctgaattac | 660 |
| tccaaagcga | tggagaacct | gttcatcaac | cgcttcatgc | acatgttcca | gtcttcttgg | 720 |
| aatgacttcg | ccgactttga | gaaaatcttt | gtcaagatca | gcaacactat | ttctgagcgg | 780 |
| gtcatgaatc | actggcagga | agacctgatg | tttggctacc | agttcctgaa | tggctgcaac | 840 |
| cctgtgttga | tccggcgctg | cacagagctg | cccgagaagc | tcccggtgac | cacggagatg | 900 |
| gtagagtgca | gcctggagcg | gcagctcagc | ttggagcagg | aggtccagca | agggaacatt | 960 |
| ttcatcgtgg | actttgagct | gctggatggc | atcgatgcca | acaaaacaga | cccctgcaca | 1020 |
| ctccagttcc | tggccgctcc | catctgcttg | ctgtataaga | acctggccaa | caagattgtc | 1080 |
| cccattgcca | tccagctcaa | ccaaatcccg | ggagatgaga | accctatttt | cctcccttcg | 1140 |
| gatgcaaaat | acgactggct | tttggccaaa | atctgggtgc | gttccagtga | cttccacgtc | 1200 |
| caccagacca | tcacccacct | tctgcgaaca | catctggtgt | ctgaggtttt | tggcattgca | 1260 |
| atgtaccgcc | agctgcctgc | tgtgcacccc | attttcaagc | tgctggtggc | acacgtgaga | 1320 |
| ttcaccattg | caatcaacac | caaggcccgt | gagcagctca | tctgcgagtg | tggcctcttt | 1380 |
| gacaaggcca | acgccacagg | gggcggtggg | cacgtgcaga | tggtgcagag | gccatgaag | 1440 |
| gacctgacct | atgcctccct | gtgctttccc | gaggccatca | ggcccgggg | catggagagc | 1500 |
| aaagaagaca | tccctactac | cttctaccgg | gacgacgggc | tcctggtgtg | ggaagccatc | 1560 |
| aggacgttca | cggccgaggt | ggtagacatc | tactacgagg | gcgaccaggt | ggtgaggag | 1620 |
| gacccggagc | tgcaggactt | cgtgaacgat | gtctacgtgt | acggcatgcg | gggccgcaag | 1680 |

-continued

```
tcctcaggct tccccaagtc ggtcaagagc cgggagcagc tgtcggagta cctgaccgtg      1740
gtgatcttca ccgcctccgc ccagcacgcc gcggtcaact tcggccagta cgactggtgc      1800
tcctggatcc ccaatgcgcc cccaaccatg cgagccccgc caccgactgc caagggcgtg      1860
gtgaccattg agcagatcgt ggacacgctg cccgaccgcg gccgctcctg ctggcatctg      1920
ggtgcagtgt gggcgctgag ccagttccag gaaaacgagc tgttcctggg catgtaccca      1980
gaagagcatt ttatcgagaa gcctgtgaag gaagccatgg cccgattccg caagaacctc      2040
gaggccattg tcagcgtgat tgctgagcgc aacaagaaga agcagctgcc atattactac      2100
ttgtccccag accggattcc gaacagtgtg gccatctgag cacactgcca gtctcactgt      2160
gggaaggcca gctgccccag ccagatggac tccagcctgc ctggcaggct gtctggccag      2220
gcctcttggc agtcacatct cttcctccga ggccagtacc tttccattta ttctttgatc      2280
ttcagggaac tgcatagatt gatcaaagtg taaacaccat agggacccat tctacacaga      2340
gcaggactgc acagcgtcct gtccacaccc agctcagcat ttccacacca agcagcaaca      2400
gcaaatcacg accactgata gatgtctatt cttgttggag acatgggatg attattttct      2460
gttctatttg tgcttagtcc aattccttgc acatagtagg tacccaattc aattactatt      2520
gaatgaatta agaattggtt gccataaaaa taaatcagtt catttaaaat gaaaaaaaaa      2580
aaaaaaaaaa a                                                           2591
```

<210> SEQ ID NO 34
<211> LENGTH: 674
<212> TYPE: PRT
<213> ORGANISM: Homo sapiens

<400> SEQUENCE: 34

```
Met Pro Ser Tyr Thr Val Thr Val Ala Thr Gly Ser Gln Trp Phe Ala
1               5                   10                  15

Gly Thr Asp Asp Tyr Ile Tyr Leu Ser Leu Val Gly Ser Ala Gly Cys
            20                  25                  30

Ser Glu Lys His Leu Leu Asp Lys Pro Phe Tyr Asn Asp Phe Glu Arg
        35                  40                  45

Gly Ala Val Asp Ser Tyr Asp Val Thr Val Asp Glu Glu Leu Gly Glu
    50                  55                  60

Ile Gln Leu Val Arg Ile Glu Lys Arg Lys Tyr Trp Leu Asn Asp Asp
65                  70                  75                  80

Trp Tyr Leu Lys Tyr Ile Thr Leu Lys Thr Pro His Gly Asp Tyr Ile
                85                  90                  95

Glu Phe Pro Cys Tyr Arg Trp Ile Thr Gly Asp Val Glu Val Val Leu
            100                 105                 110

Arg Asp Gly Arg Ala Lys Leu Ala Arg Asp Gln Ile His Ile Leu
        115                 120                 125

Lys Gln His Arg Arg Lys Glu Leu Glu Thr Arg Gln Lys Gln Tyr Arg
    130                 135                 140

Trp Met Glu Trp Asn Pro Gly Phe Pro Leu Ser Ile Asp Ala Lys Cys
145                 150                 155                 160

His Lys Asp Leu Pro Arg Asp Ile Gln Phe Asp Ser Glu Lys Gly Val
                165                 170                 175

Asp Phe Val Leu Asn Tyr Ser Lys Ala Met Glu Asn Leu Phe Ile Asn
            180                 185                 190

Arg Phe Met His Met Phe Gln Ser Ser Trp Asn Asp Phe Ala Asp Phe
        195                 200                 205
```

-continued

```
Glu Lys Ile Phe Val Lys Ile Ser Asn Thr Ile Ser Glu Arg Val Met
    210                 215                 220
Asn His Trp Gln Glu Asp Leu Met Phe Gly Tyr Gln Phe Leu Asn Gly
225                 230                 235                 240
Cys Asn Pro Val Leu Ile Arg Arg Cys Thr Glu Leu Pro Glu Lys Leu
                245                 250                 255
Pro Val Thr Thr Glu Met Val Glu Cys Ser Leu Glu Arg Gln Leu Ser
                260                 265                 270
Leu Glu Gln Glu Val Gln Gln Gly Asn Ile Phe Ile Val Asp Phe Glu
                275                 280                 285
Leu Leu Asp Gly Ile Asp Ala Asn Lys Thr Asp Pro Cys Thr Leu Gln
            290                 295                 300
Phe Leu Ala Ala Pro Ile Cys Leu Leu Tyr Lys Asn Leu Ala Asn Lys
305                 310                 315                 320
Ile Val Pro Ile Ala Ile Gln Leu Asn Gln Ile Pro Gly Asp Glu Asn
                325                 330                 335
Pro Ile Phe Leu Pro Ser Asp Ala Lys Tyr Asp Trp Leu Leu Ala Lys
            340                 345                 350
Ile Trp Val Arg Ser Ser Asp Phe His Val His Gln Thr Ile Thr His
            355                 360                 365
Leu Leu Arg Thr His Leu Val Ser Glu Val Phe Gly Ile Ala Met Tyr
    370                 375                 380
Arg Gln Leu Pro Ala Val His Pro Ile Phe Lys Leu Leu Val Ala His
385                 390                 395                 400
Val Arg Phe Thr Ile Ala Ile Asn Thr Lys Ala Arg Glu Gln Leu Ile
                405                 410                 415
Cys Glu Cys Gly Leu Phe Asp Lys Ala Asn Ala Thr Gly Gly Gly Gly
            420                 425                 430
His Val Gln Met Val Gln Arg Ala Met Lys Asp Leu Thr Tyr Ala Ser
            435                 440                 445
Leu Cys Phe Pro Glu Ala Ile Lys Ala Arg Gly Met Glu Ser Lys Glu
    450                 455                 460
Asp Ile Pro Tyr Tyr Phe Tyr Arg Asp Asp Gly Leu Leu Val Trp Glu
465                 470                 475                 480
Ala Ile Arg Thr Phe Thr Ala Glu Val Val Asp Ile Tyr Tyr Glu Gly
                485                 490                 495
Asp Gln Val Val Glu Glu Asp Pro Glu Leu Gln Asp Phe Val Asn Asp
                500                 505                 510
Val Tyr Val Tyr Gly Met Arg Gly Arg Lys Ser Ser Gly Phe Pro Lys
            515                 520                 525
Ser Val Lys Ser Arg Glu Gln Leu Ser Glu Tyr Leu Thr Val Val Ile
    530                 535                 540
Phe Thr Ala Ser Ala Gln His Ala Ala Val Asn Phe Gly Gln Tyr Asp
545                 550                 555                 560
Trp Cys Ser Trp Ile Pro Asn Ala Pro Pro Thr Met Arg Ala Pro Pro
                565                 570                 575
Pro Thr Ala Lys Gly Val Val Thr Ile Glu Gln Ile Val Asp Thr Leu
            580                 585                 590
Pro Asp Arg Gly Arg Ser Cys Trp His Leu Gly Ala Val Trp Ala Leu
            595                 600                 605
Ser Gln Phe Gln Glu Asn Glu Leu Phe Leu Gly Met Tyr Pro Glu Glu
    610                 615                 620
His Phe Ile Glu Lys Pro Val Lys Glu Ala Met Ala Arg Phe Arg Lys
```

```
                625                 630                 635                 640
Asn Leu Glu Ala Ile Val Ser Val Ile Ala Glu Arg Asn Lys Lys
                    645                 650                 655

Gln Leu Pro Tyr Tyr Tyr Leu Ser Pro Asp Arg Ile Pro Asn Ser Val
                660                 665                 670

Ala Ile

<210> SEQ ID NO 35
<211> LENGTH: 3875
<212> TYPE: DNA
<213> ORGANISM: Homo sapiens

<400> SEQUENCE: 35
```

| | | | | | |
|---|---|---|---|---|---|
| gggcggggcc | gcgggagggc | ggggccggcg | cggcgagcgc | accagcagca | tcctggctca | 60 |
| gccgcggcgg | tggcggggc | gcaaccagcg | ggccgaggcg | gcggcgccag | cggcgcctta | 120 |
| aatagcatcc | agagccggcg | cggggcaggg | agtgggctgc | agtgacagcc | ggcggcggag | 180 |
| cggccggtcc | acggaggaga | attcagctta | gagaactatc | aacacaggac | aatgcaagcc | 240 |
| catgagctgt | tccggtattt | tcgaatgcca | gagctggttg | acttccgaca | gtacgtgcgt | 300 |
| actcttccga | ccaacacgct | tatgggcttc | ggagcttttg | cagcactcac | caccttctgg | 360 |
| tacgccacga | gacccaaacc | cctgaagccg | ccatgcgacc | tctccatgca | gtcagtggaa | 420 |
| gtggcgggta | gtggtggtgc | acgaagatcc | gcactacttg | acagcgacga | gcccttggtg | 480 |
| tatttctatg | atgatgtcac | aacattatac | gaaggtttcc | agaggggaat | acaggtgtca | 540 |
| aataatggcc | cttgtttagg | ctctcggaaa | ccagaccaac | cctatgaatg | ctttcatat | 600 |
| aaacaggttg | cagaattgtc | ggagtgcata | ggctcagcac | tgatccagaa | gggcttcaag | 660 |
| actgccccag | atcagttcat | tggcatcttt | gctcaaaata | gacctgagtg | ggtgattatt | 720 |
| gaacaaggat | gctttgctta | ttcgatggtg | atcgttccac | tttatgatac | ccttggaaat | 780 |
| gaagccatca | cgtacatagt | caacaaagct | gaactctctc | tggttttgt | tgacaagcca | 840 |
| gagaaggcca | aactcttatt | agagggtgta | gaaaataagt | taataccagg | ccttaaaatc | 900 |
| atagttgtca | tggatgccta | cggcagtgaa | ctggtggaac | gaggccagag | gtgtggggtg | 960 |
| gaagtcacca | gcatgaaggc | gatggaggac | ctgggaagag | ccaacagacg | gaagcccaag | 1020 |
| cctccagcac | ctgaagatct | tgcagtaatt | tgtttcacaa | gtggaactac | aggcaacccc | 1080 |
| aaaggagcaa | tggtcactca | ccgaaacata | gtgagcgatt | gttcagcttt | tgtgaaagca | 1140 |
| acagagaata | cagtcaatcc | ttgcccagat | gatactttga | tatctttctt | gcctctcgcc | 1200 |
| catatgtttg | agagagttgt | agagtgtgta | atgctgtgtc | atggagctaa | aatcggattt | 1260 |
| ttccaaggag | atatcaggct | gctcatggat | gacctcaagg | tgcttcaacc | cactgtcttc | 1320 |
| cccgtggttc | caagactgct | gaaccggatg | tttgaccgaa | ttttcggaca | agcaaacacc | 1380 |
| acgctgaagc | gatggctctt | ggactttgcc | tccaagagga | agaagcagaa | gcttcgcagc | 1440 |
| ggcatcatca | gaaacaacag | cctgtgggac | cggctgatct | ccacaaagt | acagtcgagc | 1500 |
| ctgggcggaa | gagtccggct | gatggtgaca | ggagccgccc | cggtgtctgc | cactgtgctg | 1560 |
| acgttcctca | gagcagccct | gggctgtcag | ttttatgaag | gatacggaca | gacagagtgc | 1620 |
| actgccgggt | gctgcctgac | catgcctgga | gactggaccg | caggccatgt | tgggccccg | 1680 |
| atgccgtgca | atttgataaa | acttgttgat | gtggaagaaa | tgaattacat | ggctgccgag | 1740 |
| ggcgagggcg | aggtgtgtgt | gaagggccca | aatgtatttc | agggctactt | gaaggaccca | 1800 |
| gcgaaaacag | cagaagcttt | ggacaaagac | ggctggttac | acacagggga | cattggaaaa | 1860 |

-continued

```
tggttaccaa atggcacctt gaaaattatc gaccggaaaa agcacatatt taagctggca     1920
caaggagaat acatagcccc tgaaaagatt gaaaatatct acatgcgaag tgagcctgtt     1980
gctcaggtgt tgtccacgg agaaagcctg caggcatttc tcattgcaat tgtggtacca      2040
gatgttgaga cattatgttc ctgggcccaa aagagaggat ttgaagggtc gtttgaggaa     2100
ctgtgcagaa ataaggatgt caaaaaagct atcctcgaag atatggtgag acttgggaag     2160
gattctggtc tgaaaccatt tgaacaggtc aaaggcatca cattgcaccc tgaattattt     2220
tctatcgaca atggccttct gactccaaca atgaaggcga aaaggccaga gctgcggaac     2280
tatttcaggt cgcagataga tgacctctat tccactatca aggtttagtg tgaagaagaa     2340
agctcagagg aaatggcaca gttccacaat ctcttctcct gctgatggcc ttcatgttgt     2400
taattttgaa tacagcaagt gtagggaagg aagcgttcgt gtttgacttg tccattcggg     2460
gttcttctca taggaatgct agaggaaaca gaacactgcc ttacagtcac ctcatgttgc     2520
agaccatgtt tatggtaata cacactttcc aaaatgagcc ttaaaaattg taaggggat     2580
actataaatg tgctaagtta tttgagactt cctcagttta aaaagtgggt tttaaatctt     2640
ctgtctccct gtttttctaa tcaaggggtt aggactttgc tatctctgag atgtctgcta     2700
cttgctgcaa attctgcagc tgtctgctgc tctaaagagt acagtgcact agagggaagt     2760
gttcccttta aaaataagaa caactgtcct ggctggagaa tctcacaagc ggaccagaga     2820
tcttttaaa tccctgctac tgtcccttct cacaggcatt cacagaaccc ttctgattcg      2880
taagggttac gaaactcatg ttcttctcca gtcccctgtg gtttctgttg gagcataagg     2940
tttccagtaa gcgggagggc agatccaact cagaaccatg cagataagga gcctctggca     3000
aatgggtgct catcagaacg cgtggattct ctttcatggc agaatgctct tggactcggt     3060
tctccaggcc tgattcccg actccatcct tttttcaggg gttatttaaaa atctgcctta    3120
gattctatag tgaagacaag catttcaaga aagagttacc tggatcagcc atgctcagct     3180
gtgacgcctg aataactgtc tactttatct tcactgaacc actcactctg tgtaaaggcc     3240
aacagatttt taatgtggtt ttcatatcaa aagatcatgt tgggattaac ttgccttttt     3300
ccccaaaaaa taaactctca ggcaagcatt tctttaaagc tattaaggga gtatatactt     3360
gagtacttat tgaaatggac agtaataagc aaatgttctt ataatgctac ctgatttcta     3420
tgaaatgtgt ttgacaagcc aaaattctag gatgtagaaa tctggaaagt tcatttcctg    3480
ggattcactt ctccagggat ttttttaaagt taatttggga aattaacagc agttcacttt    3540
attgtgagtc tttgccacat ttgactgaat tgagctgtca tttgtacatt taaagcagct    3600
gttttggggt ctgtgagagt acatgtatta tatacaagca caacagggct tgcactaaag    3660
aattgtcatt gtaataacac tacttggtag cctaacttca tatatgtatt cttaattgca    3720
caaaaagtca ataatttgtc accttggggt tttgaatgtt tgctttaagt gttggctatt    3780
tctatgtttt ataaaccaaa acaaaatttc caaaaacaat gaaggaaacc aaaataaata    3840
tttctgcatt tcaggtgaaa aaaaaaaaaa aaaaa                               3875
```

<210> SEQ ID NO 36
<211> LENGTH: 698
<212> TYPE: PRT
<213> ORGANISM: Homo sapiens

<400> SEQUENCE: 36

```
Met Gln Ala His Glu Leu Phe Arg Tyr Phe Arg Met Pro Glu Leu Val
1               5                   10                  15
```

```
Asp Phe Arg Gln Tyr Val Arg Thr Leu Pro Thr Asn Thr Leu Met Gly
             20                  25                  30

Phe Gly Ala Phe Ala Ala Leu Thr Thr Phe Trp Tyr Ala Thr Arg Pro
         35                  40                  45

Lys Pro Leu Lys Pro Pro Cys Asp Leu Ser Met Gln Ser Val Glu Val
 50                  55                  60

Ala Gly Ser Gly Gly Ala Arg Arg Ser Ala Leu Leu Asp Ser Asp Glu
 65                  70                  75                  80

Pro Leu Val Tyr Phe Tyr Asp Asp Val Thr Thr Leu Tyr Glu Gly Phe
                 85                  90                  95

Gln Arg Gly Ile Gln Val Ser Asn Asn Gly Pro Cys Leu Gly Ser Arg
             100                 105                 110

Lys Pro Asp Gln Pro Tyr Glu Trp Leu Ser Tyr Lys Gln Val Ala Glu
         115                 120                 125

Leu Ser Glu Cys Ile Gly Ser Ala Leu Ile Gln Lys Gly Phe Lys Thr
130                 135                 140

Ala Pro Asp Gln Phe Ile Gly Ile Phe Ala Gln Asn Arg Pro Glu Trp
145                 150                 155                 160

Val Ile Ile Glu Gln Gly Cys Phe Ala Tyr Ser Met Val Ile Val Pro
                165                 170                 175

Leu Tyr Asp Thr Leu Gly Asn Glu Ala Ile Thr Tyr Ile Val Asn Lys
             180                 185                 190

Ala Glu Leu Ser Leu Val Phe Val Asp Lys Pro Glu Lys Ala Lys Leu
         195                 200                 205

Leu Leu Glu Gly Val Glu Asn Lys Leu Ile Pro Gly Leu Lys Ile Ile
     210                 215                 220

Val Val Met Asp Ala Tyr Gly Ser Glu Leu Val Glu Arg Gly Gln Arg
225                 230                 235                 240

Cys Gly Val Glu Val Thr Ser Met Lys Ala Met Glu Asp Leu Gly Arg
                245                 250                 255

Ala Asn Arg Arg Lys Pro Lys Pro Pro Ala Pro Glu Asp Leu Ala Val
             260                 265                 270

Ile Cys Phe Thr Ser Gly Thr Thr Gly Asn Pro Lys Gly Ala Met Val
         275                 280                 285

Thr His Arg Asn Ile Val Ser Asp Cys Ser Ala Phe Val Lys Ala Thr
     290                 295                 300

Glu Asn Thr Val Asn Pro Cys Pro Asp Asp Thr Leu Ile Ser Phe Leu
305                 310                 315                 320

Pro Leu Ala His Met Phe Glu Arg Val Val Glu Cys Val Met Leu Cys
                325                 330                 335

His Gly Ala Lys Ile Gly Phe Phe Gln Gly Asp Ile Arg Leu Leu Met
             340                 345                 350

Asp Asp Leu Lys Val Leu Gln Pro Thr Val Phe Pro Val Val Pro Arg
         355                 360                 365

Leu Leu Asn Arg Met Phe Asp Arg Ile Phe Gly Gln Ala Asn Thr Thr
     370                 375                 380

Leu Lys Arg Trp Leu Leu Asp Phe Ala Ser Lys Arg Lys Glu Ala Glu
385                 390                 395                 400

Leu Arg Ser Gly Ile Ile Arg Asn Asn Ser Leu Trp Asp Arg Leu Ile
                405                 410                 415

Phe His Lys Val Gln Ser Ser Leu Gly Gly Arg Val Arg Leu Met Val
             420                 425                 430
```

```
Thr Gly Ala Ala Pro Val Ser Ala Thr Val Leu Thr Phe Leu Arg Ala
            435                 440                 445

Ala Leu Gly Cys Gln Phe Tyr Glu Gly Tyr Gln Thr Glu Cys Thr
    450                 455                 460

Ala Gly Cys Cys Leu Thr Met Pro Gly Asp Trp Thr Ala Gly His Val
465                 470                 475                 480

Gly Ala Pro Met Pro Cys Asn Leu Ile Lys Leu Val Asp Val Glu Glu
                485                 490                 495

Met Asn Tyr Met Ala Ala Glu Gly Gly Glu Val Cys Val Lys Gly
        500                 505                 510

Pro Asn Val Phe Gln Gly Tyr Leu Lys Asp Pro Ala Lys Thr Ala Glu
    515                 520                 525

Ala Leu Asp Lys Asp Gly Trp Leu His Thr Gly Asp Ile Gly Lys Trp
530                 535                 540

Leu Pro Asn Gly Thr Leu Lys Ile Ile Asp Arg Lys Lys His Ile Phe
545                 550                 555                 560

Lys Leu Ala Gln Gly Glu Tyr Ile Ala Pro Glu Lys Ile Glu Asn Ile
                565                 570                 575

Tyr Met Arg Ser Glu Pro Val Ala Gln Val Phe Val His Gly Glu Ser
            580                 585                 590

Leu Gln Ala Phe Leu Ile Ala Ile Val Val Pro Asp Val Glu Thr Leu
        595                 600                 605

Cys Ser Trp Ala Gln Lys Arg Gly Phe Glu Gly Ser Phe Glu Glu Leu
            610                 615                 620

Cys Arg Asn Lys Asp Val Lys Ala Ile Leu Glu Asp Met Val Arg
625                 630                 635                 640

Leu Gly Lys Asp Ser Gly Leu Lys Pro Phe Glu Gln Val Lys Gly Ile
                645                 650                 655

Thr Leu His Pro Glu Leu Phe Ser Ile Asp Asn Gly Leu Leu Thr Pro
            660                 665                 670

Thr Met Lys Ala Lys Arg Pro Glu Leu Arg Asn Tyr Phe Arg Ser Gln
        675                 680                 685

Ile Asp Asp Leu Tyr Ser Thr Ile Lys Val
    690                 695

<210> SEQ ID NO 37
<211> LENGTH: 7
<212> TYPE: PRT
<213> ORGANISM: Simian virus 40

<400> SEQUENCE: 37

Pro Lys Lys Lys Arg Lys Val
1               5

<210> SEQ ID NO 38
<211> LENGTH: 16
<212> TYPE: PRT
<213> ORGANISM: Unknown
<220> FEATURE:
<223> OTHER INFORMATION: Description of Unknown:
      Nucleoplasmin bipartite NLS sequence

<400> SEQUENCE: 38

Lys Arg Pro Ala Ala Thr Lys Lys Ala Gly Gln Ala Lys Lys Lys Lys
1               5                   10                  15

<210> SEQ ID NO 39
<211> LENGTH: 9
```

```
<212> TYPE: PRT
<213> ORGANISM: Unknown
<220> FEATURE:
<223> OTHER INFORMATION: Description of Unknown:
      C-myc NLS sequence

<400> SEQUENCE: 39

Pro Ala Ala Lys Arg Val Lys Leu Asp
1               5

<210> SEQ ID NO 40
<211> LENGTH: 11
<212> TYPE: PRT
<213> ORGANISM: Unknown
<220> FEATURE:
<223> OTHER INFORMATION: Description of Unknown:
      C-myc NLS sequence

<400> SEQUENCE: 40

Arg Gln Arg Arg Asn Glu Leu Lys Arg Ser Pro
1               5                   10

<210> SEQ ID NO 41
<211> LENGTH: 38
<212> TYPE: PRT
<213> ORGANISM: Homo sapiens

<400> SEQUENCE: 41

Asn Gln Ser Ser Asn Phe Gly Pro Met Lys Gly Gly Asn Phe Gly Gly
1               5                   10                  15

Arg Ser Ser Gly Pro Tyr Gly Gly Gly Gly Gln Tyr Phe Ala Lys Pro
            20                  25                  30

Arg Asn Gln Gly Gly Tyr
        35

<210> SEQ ID NO 42
<211> LENGTH: 42
<212> TYPE: PRT
<213> ORGANISM: Unknown
<220> FEATURE:
<223> OTHER INFORMATION: Description of Unknown:
      IBB domain from importin-alpha sequence

<400> SEQUENCE: 42

Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
            20                  25                  30

Asp Glu Gln Ile Leu Lys Arg Arg Asn Val
        35                  40

<210> SEQ ID NO 43
<211> LENGTH: 8
<212> TYPE: PRT
<213> ORGANISM: Unknown
<220> FEATURE:
<223> OTHER INFORMATION: Description of Unknown:
      Myoma T protein sequence

<400> SEQUENCE: 43

Val Ser Arg Lys Arg Pro Arg Pro
1               5

<210> SEQ ID NO 44
<211> LENGTH: 8
```

```
<212> TYPE: PRT
<213> ORGANISM: Unknown
<220> FEATURE:
<223> OTHER INFORMATION: Description of Unknown:
      Myoma T protein sequence

<400> SEQUENCE: 44

Pro Pro Lys Lys Ala Arg Glu Asp
1               5

<210> SEQ ID NO 45
<211> LENGTH: 8
<212> TYPE: PRT
<213> ORGANISM: Homo sapiens

<400> SEQUENCE: 45

Pro Gln Pro Lys Lys Lys Pro Leu
1               5

<210> SEQ ID NO 46
<211> LENGTH: 12
<212> TYPE: PRT
<213> ORGANISM: Mus musculus

<400> SEQUENCE: 46

Ser Ala Leu Ile Lys Lys Lys Lys Lys Met Ala Pro
1               5                   10

<210> SEQ ID NO 47
<211> LENGTH: 5
<212> TYPE: PRT
<213> ORGANISM: Influenza virus

<400> SEQUENCE: 47

Asp Arg Leu Arg Arg
1               5

<210> SEQ ID NO 48
<211> LENGTH: 7
<212> TYPE: PRT
<213> ORGANISM: Influenza virus

<400> SEQUENCE: 48

Pro Lys Gln Lys Lys Arg Lys
1               5

<210> SEQ ID NO 49
<211> LENGTH: 10
<212> TYPE: PRT
<213> ORGANISM: Hepatitis delta virus

<400> SEQUENCE: 49

Arg Lys Leu Lys Lys Lys Ile Lys Lys Leu
1               5                   10

<210> SEQ ID NO 50
<211> LENGTH: 10
<212> TYPE: PRT
<213> ORGANISM: Mus musculus

<400> SEQUENCE: 50

Arg Glu Lys Lys Lys Phe Leu Lys Arg Arg
1               5                   10

<210> SEQ ID NO 51
```

```
<211> LENGTH: 20
<212> TYPE: PRT
<213> ORGANISM: Homo sapiens

<400> SEQUENCE: 51

Lys Arg Lys Gly Asp Glu Val Asp Gly Val Asp Glu Val Ala Lys Lys
1               5                   10                  15

Lys Ser Lys Lys
            20

<210> SEQ ID NO 52
<211> LENGTH: 17
<212> TYPE: PRT
<213> ORGANISM: Homo sapiens

<400> SEQUENCE: 52

Arg Lys Cys Leu Gln Ala Gly Met Asn Leu Glu Ala Arg Lys Thr Lys
1               5                   10                  15

Lys

<210> SEQ ID NO 53
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, t, or g
<220> FEATURE:
<221> NAME/KEY: modified_base
<222> LOCATION: (21)..(22)
<223> OTHER INFORMATION: a, c, t, g, unknown or other

<400> SEQUENCE: 53
nnnnnnnnnn nnnnnnnnnn nnagaaw                                           27

<210> SEQ ID NO 54
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(12)
<223> OTHER INFORMATION: a, c, t, or g
<220> FEATURE:
<221> NAME/KEY: modified_base
<222> LOCATION: (13)..(14)
<223> OTHER INFORMATION: a, c, t, g, unknown or other

<400> SEQUENCE: 54
nnnnnnnnnn nnnnagaaw                                                    19

<210> SEQ ID NO 55
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, t, or g
```

```
<220> FEATURE:
<221> NAME/KEY: modified_base
<222> LOCATION: (21)..(22)
<223> OTHER INFORMATION: a, c, t, g, unknown or other

<400> SEQUENCE: 55
nnnnnnnnnn nnnnnnnnnn nnagaaw                                              27

<210> SEQ ID NO 56
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(11)
<223> OTHER INFORMATION: a, c, t, or g
<220> FEATURE:
<221> NAME/KEY: modified_base
<222> LOCATION: (12)..(13)
<223> OTHER INFORMATION: a, c, t, g, unknown or other

<400> SEQUENCE: 56
nnnnnnnnnn nnnagaaw                                                        18

<210> SEQ ID NO 57
<211> LENGTH: 137
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, t, g, unknown or other

<400> SEQUENCE: 57
nnnnnnnnnn nnnnnnnnnn gttttgtac tctcaagatt tagaaataaa tcttgcagaa           60
gctacaaaga taaggcttca tgccgaaatc aacaccctgt catttatgg cagggtgttt          120 tcgttattta attttt                                                         137

<210> SEQ ID NO 58
<211> LENGTH: 123
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, t, g, unknown or other

<400> SEQUENCE: 58
nnnnnnnnnn nnnnnnnnnn gttttgtac tctcagaaat gcagaagcta caaagataag           60
gcttcatgcc gaaatcaaca ccctgtcatt ttatggcagg gtgttttcgt tatttaattt         120
ttt                                                                       123

<210> SEQ ID NO 59
<211> LENGTH: 110
<212> TYPE: DNA
<213> ORGANISM: Artificial Sequence
```

```
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, t, g, unknown or other

<400> SEQUENCE: 59
nnnnnnnnnn nnnnnnnnnn gttttttgtac tctcagaaat gcagaagcta caaagataag      60
gcttcatgcc gaaatcaaca ccctgtcatt ttatggcagg gtgttttttt                 110

<210> SEQ ID NO 60
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, t, g, unknown or other

<400> SEQUENCE: 60
nnnnnnnnnn nnnnnnnnnn gttttagagc tagaaatagc aagttaaaat aaggctagtc      60
cgttatcaac ttgaaaaagt ggcaccgagt cggtgctttt tt                        102

<210> SEQ ID NO 61
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, t, g, unknown or other

<400> SEQUENCE: 61
nnnnnnnnnn nnnnnnnnnn gttttagagc tagaaatagc aagttaaaat aaggctagtc      60
cgttatcaac ttgaaaaagt gtttttt                                          87

<210> SEQ ID NO 62
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, t, g, unknown or other

<400> SEQUENCE: 62
nnnnnnnnnn nnnnnnnnnn gttttagagc tagaaatagc aagttaaaat aaggctagtc      60
cgttatcatt ttttt                                                       75

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 63
gtcttctcag aataataagg                                            20

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
gtttcagaaa tgccttgcag                                            20

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
ggtggtggtg agatgcaggt                                            20

<210> SEQ ID NO 66
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
gatactgctg cattagacca g                                          21
```

What is claimed is:

1. A method of treating a subject diagnosed with a peroxisome proliferator-activated receptor gamma (PPARG) activated cancer, comprising:
    performing an assay to determine the identity of an amino acid at position 447 of PPARG and position 427 of retinoid X receptor alpha (RXRA), wherein a PPARG reference amino acid at position 447 is threonine (T) and a RXRA reference amino acid at position 427 is serine (S);
    detecting the presence of a PPARG amino acid variation relative to the PPARG reference amino acid, wherein the PPARG amino acid variation is methionine (M) and a RXRA amino acid variation relative to the RXRA reference amino acid, wherein the RXRA amino acid variation is phenylalanine (F) or tyrosine (Y); and
    administering a therapeutically effective amount of a PPARG signaling modulator to the subject having a PPARG T447M variation and/or a RXRA S427F/Y variation.

2. The method of claim 1, wherein the PPARG signaling modulator is an antagonist or an inverse-agonist of PPARG signaling.

3. The method of claim 2, wherein administering the inverse-agonist to the subject decreases proliferation of one or more PPARG activated cancer cells within the subject.

4. The method of claim 2, wherein the inverse-agonist is selected from the group consisting of T0070907, T0070907 analogs, SR10221, SR10221 analogs, and combinations thereof.

5. The method of claim 1, wherein the PPARG signaling modulator is an antisense oligonucleotide or RNAi agent.

6. The method of claim 1, wherein the PPARG activated cancer is associated with an up-regulated peroxisome proliferator-activated receptor (PPAR) signaling pathway.

7. The method of claim 6, wherein the up-regulated PPAR signaling pathway is associated with increased expression of one or more genes selected from the group consisting of Uroplakin 1A (UPK1A), Uroplakin 1B (UPK1B), Uroplakin (UPK2), Keratin 20 (KRT20), GATA Binding Protein 3 (GATA3), Nuclear Receptor Corepressor 1 (NCOR1), Nuclear Receptor Corepressor 2 (NCOR2), Fatty Acid Binding Protein 4 (FABP4), Forkhead Box A1 (FOXA1), CD36 Molecule (CD36), Acyl-CoA Oxidase 1 (ACOX1), 3-Hydroxy-3-Methylglutaryl-CoA Synthase 2 (HMGCS2), Acyl-CoA Synthetase Long-Chain Family Member 5 (ACSL5), Arachidonate 5-Lipoxygenase (ALOX5), and Acyl-CoA Synthetase Long-Chain Family Member 1 (ACSL1).

8. The method of claim 1, wherein the PPARG activated cancer is a bladder cancer selected from the group consisting of a luminal or non-luminal bladder cancer, a basal bladder cancer, a muscle-invasive bladder cancer, and a non-muscle-invasive bladder cancer.

9. The method of claim 1, wherein the subject is a human or a non-human mammal.

10. The method of claim 9, wherein the non-human mammal is selected from the group consisting of a bovine, a canine, an equine, a feline, an ovine, and a primate.

11. The method of claim 1, further comprising administering one or more chemotherapeutic agents.

12. The method of claim 11, wherein the chemotherapeutic agent is selected from the group consisting of Atezolizumab, Avelumab, a *Bacillus* Calmette-Guerin (BCG) therapy, Cisplatin, Doxorubicin Hydrochloride, Durvalumab, Nivolumab, Pembrolizumab, Thiotepa, anti-PD-1 antibodies, anti-PD-L1 antibodies, and combinations thereof.

13. The method of claim 12, wherein the BCG therapy is a strain of *Mycobacterium bovis* in a live, attenuated culture preparation.

14. The method of claim 1, wherein the assay is selected from the group consisting of dynamic allele-specific hybridization, molecular beacons, SNP microarrays, PCR, quantitative PCR, Taq-man, SNPlex, and a metabolite assay.

15. The method of claim 1, wherein the expression of two or more gene products is altered or the expression of one or more gene products is decreased.

* * * * *